(12) United States Patent
Rice et al.

(10) Patent No.: US 11,162,146 B2
(45) Date of Patent: Nov. 2, 2021

(54) REAGENTS FOR IMPROVING PCR ACCURACY

(71) Applicant: Brandeis University, Waltham, MA (US)

(72) Inventors: John Rice, Quincy, MA (US); Lawrence Wangh, Auburndale, MA (US); Arthur H. Reis, Jr., Arlington, MA (US); Kenneth Pierce, Natick, MA (US); Cristina Hartshorn, West Roxbury, MA (US); J. Aquiles Sanchez, Framingham, MA (US); Stephen Van Hooser, Sudbury, MA (US); Skye Fishbein, Catonsville, MD (US)

(73) Assignee: Brandeis University, Waltham, MA (US)

( * ) Notice: Subject to any disclaimer, the term of this patent is extended or adjusted under 35 U.S.C. 154(b) by 181 days.

(21) Appl. No.: 16/372,027

(22) Filed: Apr. 1, 2019

(65) Prior Publication Data
US 2019/0292610 A1 Sep. 26, 2019

Related U.S. Application Data

(63) Continuation of application No. 14/162,540, filed on Jan. 23, 2014.

(60) Provisional application No. 61/755,872, filed on Jan. 23, 2013.

(51) Int. Cl.
*C12Q 1/68* (2018.01)
*C12Q 1/70* (2006.01)
*C12Q 1/6848* (2018.01)

(52) U.S. Cl.
CPC .......... *C12Q 1/701* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 7,517,977 B2 | 4/2009 | Wangh et al. | |
| 9,034,605 B2 * | 5/2015 | Wangh | C12Q 1/6806 435/91.2 |
| 10,301,688 B2 | 5/2019 | Rice et al. | |
| 2011/0196130 A1 * | 8/2011 | Lee | C12Q 1/6816 530/358 |
| 2011/0294675 A1 | 12/2011 | Brabetz et al. | |
| 2012/0088275 A1 | 4/2012 | Wangh et al. | |
| 2014/0106362 A1 | 4/2014 | Makrigiorgos | |

FOREIGN PATENT DOCUMENTS

| | | |
|---|---|---|
| EP | 2948564 A1 | 12/2015 |
| WO | WO-2006/044995 A1 | 4/2006 |
| WO | WO-2010/105074 A1 | 9/2010 |
| WO | WO-2011/050173 A1 | 4/2011 |
| WO | WO-2014/116860 A1 | 7/2014 |

OTHER PUBLICATIONS

Allawi et al., "Thermodynamics and NMR of Internal GT Mismatches in DNA," Biochem, 36: 10581-10594 (1997).
International Search Report, International Patent Application No. PCT/US2014/012794, dated May 19, 2014, 9 pages.
Johansson, MK, "Choosing reporter-quencher pairs for efficient quenching through formation of intramolecular dimers," Methods Mol Bio, 335: 17-29 (2006).
Kainz et al., "Specificity-Enhanced Hot-Start PCR: Addition of Double-Stranded DNA Fragments Adapted to the Annealing Temperature," Biotechniques, 28(2): 278-282 (2000).
Marras et al., "Real-time assays with molecular beacons and other fluorescent nucleic acid hybridization probes," Clin Chim Acta, 363(1-2):48-60 (2006).
Pierce et al., "Design and optimization of a novel reverse transcription linear-after-the-exponential PCR for the detection of foot-and-mouth disease virus," J Appl Microbiol, 109: 180-189 (2010).
Rice et al., "Fluorescent signatures for variable DNA sequences," Nucleic Acids Research Advance Access, 40(21): 1-10 (2012).
Rice et al., "Real-time PCR with molecular beacons provides a highly accurate assay for detection of Tay-Sachs alleles in single cells," Prenatal Diagn, 22: 1130-1134 (2002).
Rutledge, R.G.,"Sigmoidal curve-fitting redefines quantitative real-time PCR with the prospective of developing automated high-throughput applications," Nucl Acids Res, 32(22): e178 (2004).
Santalucia, "A unified view of polymer, dumbbell, and oligonucleotide DNA nearest-neighbor thermodynamics," PNAS (USA), 95: 1460-1465 (1998).

* cited by examiner

*Primary Examiner* — Stephanie K Mummert
(74) *Attorney, Agent, or Firm* — Foley Hoag LLP; Brendan T. Jones; Allison Gilder

(57) ABSTRACT

Provided herein are reagents for improving PCR accuracy.

18 Claims, 57 Drawing Sheets
Specification includes a Sequence Listing.

FIG. 9

| PRIMER/TARGET | SEQUENCE | SEQ ID NO. | MEAN TM | MEAN $C_T$ NO REAGENT | REAGENT1 $\Delta C_T$ |
|---|---|---|---|---|---|
| LIMITING PRIMER | 5'-ACCATCACTGAGCTGTTGATCCGCATGAAACG-3' | (47) | | | |
| IND 339-96 | 3'-TGG TAGTGACTCGACAACTAGGGCGTACTTTGC... | (48) | 74.9 | 24.1 | 25.3 1.2 |
| IND 116-90 | 3'-TGGTAGTGACTCGAA<u>A</u>ACTAGGCGTACTTTGC... | (49) | 72.1 | 24.9 | 26.6 1.7 |
| IND 224-98 | 3'-TGGTA<u>A</u>TGACTCGA<u>A</u>AACTAGGCGTACTTTGC... | (50) | 67.9 | 28.0 | 32.1 4.1 |
| IND 82-96 | 3'-TGGTAGTGACTCGA<u>A</u>AACTA<u>A</u>GCGTACTTTGC... | (51) | 67.7 | 27.6 | 33.1 5.5 |
| IND 23-95 | 3'-TGGTAGTGACTCGA<u>A</u>AACTAGGCGTACTT<u>C</u>GC... | (52) | 68.7 | 25.0 | 28.9 3.9 |
| BR/MYANMAR 001 | 3'-<u>T</u>CG TAGTGCCTC<u>A</u>ACAACTAGGGCGTA<u>G</u>TTTGC... | (53) | 58.9 | 32.0 | 41.3 9.3 |

SEQUENCE LISTING

<160> NUMBER OF SEQ ID NOS: 142

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
cattataatg aaattatagt a                                              21

<210> SEQ ID NO 2
<211> LENGTH: 30
<212> TYPE: DNA
<213> ORGANISM: Artificial Sequence
<220> FEATURE:
<223> OTHER INFORMATION: Synthetic

<400> SEQUENCE: 2
cagctgcact gggaagggtg cagtctgacc                                     30

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3
cagctgcact gggaagggtg cagtctgacc                                     30

<210> SEQ ID NO 4
<211> LENGTH: 22

```
<212> TYPE: DNA
<213> ORGANISM: Artificial Sequence
<220> FEATURE:
<223> OTHER INFORMATION: Synthetic

<400> SEQUENCE: 4
ggagcagact agcactgagg ta                                            22

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
ggagcagact agcactgagg ta                                            22

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
gaaataaaat aaaaataaaa ta                                            22

<210> SEQ ID NO 7
<211> LENGTH: 30
<212> TYPE: DNA
<213> ORGANISM: Artificial Sequence
<220> FEATURE:
<223> OTHER INFORMATION: Synthetic

<400> SEQUENCE: 7
cagctgcact gggaagggtg cagtctgacc                                    30

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
ggagcagact agcactgagg ta                                            22

<210> SEQ ID NO 9
<211> LENGTH: 30
<212> TYPE: DNA
<213> ORGANISM: Artificial Sequence
<220> FEATURE:
<223> OTHER INFORMATION: Synthetic

<400> SEQUENCE: 9
cagctgcact gggaagggtg cagtctgacc                                    30

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
```
ggagcagact agcactgagg ta                                                    22

<210> SEQ ID NO 11
<211> LENGTH: 17
<212> TYPE: DNA
<213> ORGANISM: Artificial Sequence
<220> FEATURE:
<223> OTHER INFORMATION: Synthetic

<400> SEQUENCE: 11
ccatgataca agcttcc                                                          17

<210> SEQ ID NO 12
<211> LENGTH: 41
<212> TYPE: DNA
<213> ORGANISM: Artificial Sequence
<220> FEATURE:
<223> OTHER INFORMATION: Synthetic

<400> SEQUENCE: 12
acttagtaat tgggaagctt gtatcatggc acttagaacc t                               41

<210> SEQ ID NO 13
<211> LENGTH: 27
<212> TYPE: DNA
<213> ORGANISM: Artificial Sequence
<220> FEATURE:
<223> OTHER INFORMATION: Synthetic

<400> SEQUENCE: 13
cgtaagatta caatggcagg ctccagt                                               27

<210> SEQ ID NO 14
<211> LENGTH: 24
<212> TYPE: DNA
<213> ORGANISM: Artificial Sequence
<220> FEATURE:
<223> OTHER INFORMATION: Synthetic

<400> SEQUENCE: 14
gcccaagttt tatcgttctt ctca                                                  24

<210> SEQ ID NO 15
<211> LENGTH: 95
<212> TYPE: DNA
<213> ORGANISM: Artificial Sequence
<220> FEATURE:
<223> OTHER INFORMATION: Synthetic

<400> SEQUENCE: 15
cgtaagatta caatggcagg ctccagaagg ttctaagtgc catgatacaa gcttcccaat           60
tactaagtat gctgagaaga acgataaaac ttggg                                      95

<210> SEQ ID NO 16
<211> LENGTH: 98
<212> TYPE: DNA
<213> ORGANISM: Artificial Sequence
<220> FEATURE:
<223> OTHER INFORMATION: Synthetic

<400> SEQUENCE: 16
cgtaagatta caatggcagg ctccagtagg ttctaagtgc catgatacaa gcttcccaat           60
tactaagtat gctgagaaga acgataaaac ttgggcaa                                   98

```
<210> SEQ ID NO 17
<211> LENGTH: 31
<212> TYPE: DNA
<213> ORGANISM: Artificial Sequence
<220> FEATURE:
<223> OTHER INFORMATION: Synthetic

<400> SEQUENCE: 17
ctccagccag gcacgctcac gtgacagacc g                           31

<210> SEQ ID NO 18
<211> LENGTH: 28
<212> TYPE: DNA
<213> ORGANISM: Artificial Sequence
<220> FEATURE:
<223> OTHER INFORMATION: Synthetic

<400> SEQUENCE: 18
acgtggaggc gatcacaccg cagacgtt                               28

<210> SEQ ID NO 19
<211> LENGTH: 150
<212> TYPE: DNA
<213> ORGANISM: Artificial Sequence
<220> FEATURE:
<223> OTHER INFORMATION: Synthetic

<400> SEQUENCE: 19
ccggtggtcg ccgcgatcaa ggagttcttc ggcaccagcc agctgagcca attcatggac    60
cagaacaacc cgctgtcggg gttgacccac aagcgccgac tgtcggcgct ggggcccggc   120
ggtctgtcac gtgagcgtgc ctggctggag                                    150

<210> SEQ ID NO 20
<211> LENGTH: 150
<212> TYPE: DNA
<213> ORGANISM: Artificial Sequence
<220> FEATURE:
<223> OTHER INFORMATION: Synthetic

<400> SEQUENCE: 20
ccggtggtcg ccgcgatcaa ggagttcttc ggcaccagcc agctgagcca attcatggac    60
cagaacaacc cgctgtcggg gttgaccgac aagcgccgac tgtcggcgct ggggcccggc   120
ggtctgtcac gtgagcgtgc ctggctggag                                    150

<210> SEQ ID NO 21
<211> LENGTH: 16
<212> TYPE: DNA
<213> ORGANISM: Artificial Sequence
<220> FEATURE:
<223> OTHER INFORMATION: Synthetic

<400> SEQUENCE: 21
ctggttggtg cagaag                                            16

<210> SEQ ID NO 22
<211> LENGTH: 23
<212> TYPE: DNA
<213> ORGANISM: Artificial Sequence
<220> FEATURE:
<223> OTHER INFORMATION: Synthetic

<400> SEQUENCE: 22
tcaggtccat gaattggctc aga                                    23
```

<210> SEQ ID NO 23
<211> LENGTH: 12
<212> TYPE: DNA
<213> ORGANISM: Artificial Sequence
<220> FEATURE:
<223> OTHER INFORMATION: Synthetic

<400> SEQUENCE: 23
cagcgggttg tt                                                          12

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
atgcgcttgt ggatcaaccc cgat                                             24

<210> SEQ ID NO 25
<211> LENGTH: 23
<212> TYPE: DNA
<213> ORGANISM: Artificial Sequence
<220> FEATURE:
<223> OTHER INFORMATION: Synthetic

<400> SEQUENCE: 25
aagccccagc gccgacagtc gtt                                              23

<210> SEQ ID NO 26
<211> LENGTH: 12
<212> TYPE: DNA
<213> ORGANISM: Artificial Sequence
<220> FEATURE:
<223> OTHER INFORMATION: Synthetic

<400> SEQUENCE: 26
acagaccgcc gg                                                          12

<210> SEQ ID NO 27
<211> LENGTH: 37
<212> TYPE: DNA
<213> ORGANISM: Artificial Sequence
<220> FEATURE:
<223> OTHER INFORMATION: Synthetic

<400> SEQUENCE: 27
agcgcccact cgtagccgta caggatctcg aggaaac                               37

<210> SEQ ID NO 28
<211> LENGTH: 28
<212> TYPE: DNA
<213> ORGANISM: Artificial Sequence
<220> FEATURE:
<223> OTHER INFORMATION: Synthetic

<400> SEQUENCE: 28
tcttgggctg gaagagctcg tatggcac                                         28

<210> SEQ ID NO 29
<211> LENGTH: 139
<212> TYPE: DNA
<213> ORGANISM: Artificial Sequence
<220> FEATURE:
<223> OTHER INFORMATION: Synthetic

<400> SEQUENCE: 29
gcttgggctg aagagctcg tatggcaccg aaccggtaa ggacgcgatc accagcggca    60
tcgaggtcgt atggacgaac accccgacga aatgggacaa cagtttcctc gagatcctgt    120
acggctacga gtgggagct    139

<210> SEQ ID NO 30
<211> LENGTH: 139
<212> TYPE: DNA
<213> ORGANISM: Artificial Sequence
<220> FEATURE:
<223> OTHER INFORMATION: Synthetic

<400> SEQUENCE: 30
gcttgggctg aagagctcg tatggcaccg aaccggtaa ggacgcgatc accaccggca    60
tcgaggtcgt atggacgaac accccgacga aatgggacaa cagtttcctc gagatcctgt    120
acggctacga gtgggagct    139

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
aagtgatcgc gtccttacct t    21

<210> SEQ ID NO 32
<211> LENGTH: 16
<212> TYPE: DNA
<213> ORGANISM: Artificial Sequence
<220> FEATURE:
<223> OTHER INFORMATION: Synthetic

<400> SEQUENCE: 32
gacctcgatg cagctg    16

<210> SEQ ID NO 33
<211> LENGTH: 39
<212> TYPE: DNA
<213> ORGANISM: Artificial Sequence
<220> FEATURE:
<223> OTHER INFORMATION: Synthetic

<400> SEQUENCE: 33
agccgaagtt gttctggtcg tccaccagcg ggtagcgca    39

<210> SEQ ID NO 34
<211> LENGTH: 30
<212> TYPE: DNA
<213> ORGANISM: Artificial Sequence
<220> FEATURE:
<223> OTHER INFORMATION: Synthetic

<400> SEQUENCE: 34
ttgccgagac catgggcaac taccacccgc    30

<210> SEQ ID NO 35
<211> LENGTH: 123
<212> TYPE: DNA
<213> ORGANISM: Artificial Sequence
<220> FEATURE:

<223> OTHER INFORMATION: Synthetic

<400> SEQUENCE: 35
ttgccgagac catgggcaac taccacccgc acggcgacgc gtcgatctac gacagcctgg    60
tgcgcatggc ccagccctgg tcgctgcgct acccgctggt ggacggccag ggcaacttcg   120
gct                                                                123

<210> SEQ ID NO 36
<211> LENGTH: 30
<212> TYPE: DNA
<213> ORGANISM: Artificial Sequence
<220> FEATURE:
<223> OTHER INFORMATION: Synthetic

<400> SEQUENCE: 36
ttgctgccgt agattgtgag gtcgccgtaa                                     30

<210> SEQ ID NO 37
<211> LENGTH: 17
<212> TYPE: DNA
<213> ORGANISM: Artificial Sequence
<220> FEATURE:
<223> OTHER INFORMATION: Synthetic

<400> SEQUENCE: 37
ggctatgagc acaccag                                                   17

<210> SEQ ID NO 38
<211> LENGTH: 124
<212> TYPE: DNA
<213> ORGANISM: Artificial Sequence
<220> FEATURE:
<223> OTHER INFORMATION: Synthetic

<400> SEQUENCE: 38
tgactgggtc ctttcttgga tcaacccgct caatgcctgg agatttgggc gtgccccgc    60 gagactgcta gccgagtagt gttgggtcgc gaaaggcctt gtggtactgc ctgatagggt   120
gctt                                                               124

<210> SEQ ID NO 39
<211> LENGTH: 124
<212> TYPE: DNA
<213> ORGANISM: Artificial Sequence
<220> FEATURE:
<223> OTHER INFORMATION: Synthetic

<400> SEQUENCE: 39
tgactgggtc ctttcttgga taaacccact ctatgtccgg tcatttgggc gtgccccgc    60 aagactgcta gccgagtagc gttgggttgc gaaaggcctt gtggtactgc ctgatagggt   120
gctt                                                               124

<210> SEQ ID NO 40
<211> LENGTH: 25
<212> TYPE: DNA
<213> ORGANISM: Artificial Sequence
<220> FEATURE:
<223> OTHER INFORMATION: Synthetic

<400> SEQUENCE: 40
ccacaaggcc tttcgcgacc caaca                                          25

```
<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
tgactgggtc ctttcttgga                                              20

<210> SEQ ID NO 42
<211> LENGTH: 19
<212> TYPE: DNA
<213> ORGANISM: Artificial Sequence
<220> FEATURE:
<223> OTHER INFORMATION: Synthetic

<400> SEQUENCE: 42
tcggctagta gtcttgtgg                                               19

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
ccttctctct gccccctggt                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
aggggttcca ctacgtagaa                                              20

<210> SEQ ID NO 45
<211> LENGTH: 78
<212> TYPE: DNA
<213> ORGANISM: Artificial Sequence
<220> FEATURE:
<223> OTHER INFORMATION: Synthetic

<400> SEQUENCE: 45
aggggttcca ctatgtagaa atccttccag tcagggccat aggatatacg gttcaggtac   60 caggggcag agagaagg                                                 78

<210> SEQ ID NO 46
<211> LENGTH: 105
<212> TYPE: DNA
<213> ORGANISM: Artificial Sequence
<220> FEATURE:
<223> OTHER INFORMATION: Synthetic

<400> SEQUENCE: 46
agaagaaggg cccagggttg gactctgagt ggtgtcaaga gctagcaaag gcctggggca   60
gtatgtctcc gcgcgtttca tgcggatcaa cagctcagtg atggt                 105

<210> SEQ ID NO 47
<211> LENGTH: 32
<212> TYPE: DNA
```

```
<213> ORGANISM: Artificial Sequence
<220> FEATURE:
<223> OTHER INFORMATION: Synthetic

<400> SEQUENCE: 47
accatcactg agctgttgat ccgcatgaaa cg                                    32

<210> SEQ ID NO 48
<211> LENGTH: 32
<212> TYPE: DNA
<213> ORGANISM: Artificial Sequence
<220> FEATURE:
<223> OTHER INFORMATION: Synthetic

<400> SEQUENCE: 48
gcaaagtacg cctagttgtc gagtcactac ca                                    32

<210> SEQ ID NO 49
<211> LENGTH: 32
<212> TYPE: DNA
<213> ORGANISM: Artificial Sequence
<220> FEATURE:
<223> OTHER INFORMATION: Synthetic

<400> SEQUENCE: 49
gcaaagtacg cctagttttc gagtcactac ca                                    32

<210> SEQ ID NO 50
<211> LENGTH: 32
<212> TYPE: DNA
<213> ORGANISM: Artificial Sequence
<220> FEATURE:
<223> OTHER INFORMATION: Synthetic

<400> SEQUENCE: 50
gcaaagtacg cctagttttc gagtcattac ca                                    32

<210> SEQ ID NO 51
<211> LENGTH: 32
<212> TYPE: DNA
<213> ORGANISM: Artificial Sequence
<220> FEATURE:
<223> OTHER INFORMATION: Synthetic

<400> SEQUENCE: 51
gcaaagtacg cttagttttc gagtcactac ca                                    32

<210> SEQ ID NO 52
<211> LENGTH: 32
<212> TYPE: DNA
<213> ORGANISM: Artificial Sequence
<220> FEATURE:
<223> OTHER INFORMATION: Synthetic

<400> SEQUENCE: 52
gcgaagtacg cctagttttc gagtcactac ca                                    32

<210> SEQ ID NO 53
<211> LENGTH: 32
<212> TYPE: DNA
<213> ORGANISM: Artificial Sequence
<220> FEATURE:
<223> OTHER INFORMATION: Synthetic

<400> SEQUENCE: 53
gcaaactacg cctagttgtt gaggcactac ga                                    32
```

```
<210> SEQ ID NO 54
<211> LENGTH: 22
<212> TYPE: DNA
<213> ORGANISM: Artificial Sequence
<220> FEATURE:
<223> OTHER INFORMATION: Synthetic

<400> SEQUENCE: 54
ggagcagact agcactgagg ta                                              22

<210> SEQ ID NO 55
<211> LENGTH: 28
<212> TYPE: DNA
<213> ORGANISM: Artificial Sequence
<220> FEATURE:
<223> OTHER INFORMATION: Synthetic

<400> SEQUENCE: 55
aaagcggtgt gtgtgtgctg ggtaggat                                        28

<210> SEQ ID NO 56
<211> LENGTH: 27
<212> TYPE: DNA
<213> ORGANISM: Artificial Sequence
<220> FEATURE:
<223> OTHER INFORMATION: Synthetic

<400> SEQUENCE: 56
acttcagggt cataaagcct aaatagc                                         27

<210> SEQ ID NO 57
<211> LENGTH: 31
<212> TYPE: DNA
<213> ORGANISM: Artificial Sequence
<220> FEATURE:
<223> OTHER INFORMATION: Synthetic

<400> SEQUENCE: 57
aatagagggg gtagaggggg tgctataggg t                                    31

<210> SEQ ID NO 58
<211> LENGTH: 28
<212> TYPE: DNA
<213> ORGANISM: Artificial Sequence
<220> FEATURE:
<223> OTHER INFORMATION: Synthetic

<400> SEQUENCE: 58
tccttatctg cttcctagtc ctgtatgc                                        28

<210> SEQ ID NO 59
<211> LENGTH: 37
<212> TYPE: DNA
<213> ORGANISM: Artificial Sequence
<220> FEATURE:
<223> OTHER INFORMATION: Synthetic

<400> SEQUENCE: 59
aacataagaa cagggaggtt agaagtaggg tcttggt                              37

<210> SEQ ID NO 60
<211> LENGTH: 18
<212> TYPE: DNA
<213> ORGANISM: Artificial Sequence
<220> FEATURE:
```

<223> OTHER INFORMATION: Synthetic

<400> SEQUENCE: 60
cgccccgacc ttagctct                                              18

<210> SEQ ID NO 61
<211> LENGTH: 28
<212> TYPE: DNA
<213> ORGANISM: Artificial Sequence
<220> FEATURE:
<223> OTHER INFORMATION: Synthetic

<400> SEQUENCE: 61
tggttagggt tctttatttt ggggttca                                   28

<210> SEQ ID NO 62
<211> LENGTH: 29
<212> TYPE: DNA
<213> ORGANISM: Artificial Sequence
<220> FEATURE:
<223> OTHER INFORMATION: Synthetic

<400> SEQUENCE: 62
aatggcagag atgtctttaa gtgctgttt                                  29

<210> SEQ ID NO 63
<211> LENGTH: 29
<212> TYPE: DNA
<213> ORGANISM: Artificial Sequence
<220> FEATURE:
<223> OTHER INFORMATION: Synthetic

<400> SEQUENCE: 63
aaatgtaatc gcgttcatat cacccagtt                                  29

<210> SEQ ID NO 64
<211> LENGTH: 29
<212> TYPE: DNA
<213> ORGANISM: Artificial Sequence
<220> FEATURE:
<223> OTHER INFORMATION: Synthetic

<400> SEQUENCE: 64
taattgaaca taggtacgat aaataatta                                  29

<210> SEQ ID NO 65
<211> LENGTH: 29
<212> TYPE: DNA
<213> ORGANISM: Artificial Sequence
<220> FEATURE:
<223> OTHER INFORMATION: Synthetic

<400> SEQUENCE: 65
aactgggtga aaagtgacta tgcggactt                                  29

<210> SEQ ID NO 66
<211> LENGTH: 24
<212> TYPE: DNA
<213> ORGANISM: Artificial Sequence
<220> FEATURE:
<223> OTHER INFORMATION: Synthetic

<400> SEQUENCE: 66
aatgtgaaat ctgcttgggc tggt                                       24

```
<210> SEQ ID NO 67
<211> LENGTH: 25
<212> TYPE: DNA
<213> ORGANISM: Artificial Sequence
<220> FEATURE:
<223> OTHER INFORMATION: Synthetic

<400> SEQUENCE: 67
ggctaggagt tggggagggc gggtt                                          25

<210> SEQ ID NO 68
<211> LENGTH: 25
<212> TYPE: DNA
<213> ORGANISM: Artificial Sequence
<220> FEATURE:
<223> OTHER INFORMATION: Synthetic

<400> SEQUENCE: 68
acgagagtac ccaacgcatg gagag                                          25

<210> SEQ ID NO 69
<211> LENGTH: 25
<212> TYPE: DNA
<213> ORGANISM: Artificial Sequence
<220> FEATURE:
<223> OTHER INFORMATION: Synthetic

<400> SEQUENCE: 69
tttagtaaat gtgttcacct gtaat                                          25

<210> SEQ ID NO 70
<211> LENGTH: 25
<212> TYPE: DNA
<213> ORGANISM: Artificial Sequence
<220> FEATURE:
<223> OTHER INFORMATION: Synthetic

<400> SEQUENCE: 70
tgggggaagt ttttcttat tatgt                                           25

<210> SEQ ID NO 71
<211> LENGTH: 29
<212> TYPE: DNA
<213> ORGANISM: Artificial Sequence
<220> FEATURE:
<223> OTHER INFORMATION: Synthetic

<400> SEQUENCE: 71
aaactactcg attatcaacg tcaaggatt                                      29

<210> SEQ ID NO 72
<211> LENGTH: 29
<212> TYPE: DNA
<213> ORGANISM: Artificial Sequence
<220> FEATURE:
<223> OTHER INFORMATION: Synthetic

<400> SEQUENCE: 72
aaaatggggg aagtttgtat gagttgatt                                      29

<210> SEQ ID NO 73
<211> LENGTH: 29
<212> TYPE: DNA
<213> ORGANISM: Artificial Sequence
<220> FEATURE:
<223> OTHER INFORMATION: Synthetic
```

<400> SEQUENCE: 73
aaacgattgg ggactttaat tgggagttt                                              29

<210> SEQ ID NO 74
<211> LENGTH: 29
<212> TYPE: DNA
<213> ORGANISM: Artificial Sequence
<220> FEATURE:
<223> OTHER INFORMATION: Synthetic

<400> SEQUENCE: 74
tttgtaaaga atgcgtagag ataggagaa                                              29

<210> SEQ ID NO 75
<211> LENGTH: 29
<212> TYPE: DNA
<213> ORGANISM: Artificial Sequence
<220> FEATURE:
<223> OTHER INFORMATION: Synthetic

<400> SEQUENCE: 75
tttttatacg tacggcaatt acatctgaa                                              29

<210> SEQ ID NO 76
<211> LENGTH: 24
<212> TYPE: DNA
<213> ORGANISM: Artificial Sequence
<220> FEATURE:
<223> OTHER INFORMATION: Synthetic

<400> SEQUENCE: 76
agtgaccata atatacctcc ggct                                                   24

<210> SEQ ID NO 77
<211> LENGTH: 25
<212> TYPE: DNA
<213> ORGANISM: Artificial Sequence
<220> FEATURE:
<223> OTHER INFORMATION: Synthetic

<400> SEQUENCE: 77
gtcgcaggac gcctagtttt aggaa                                                  25

<210> SEQ ID NO 78
<211> LENGTH: 24
<212> TYPE: DNA
<213> ORGANISM: Artificial Sequence
<220> FEATURE:
<223> OTHER INFORMATION: Synthetic

<400> SEQUENCE: 78
agataagttc gctgtattcg gtgt                                                   24

<210> SEQ ID NO 79
<211> LENGTH: 22
<212> TYPE: DNA
<213> ORGANISM: Artificial Sequence
<220> FEATURE:
<223> OTHER INFORMATION: Synthetic

<400> SEQUENCE: 79
agacgtctta tgttgtaatt at                                                     22

<210> SEQ ID NO 80
<211> LENGTH: 25

<212> TYPE: DNA
<213> ORGANISM: Artificial Sequence
<220> FEATURE:
<223> OTHER INFORMATION: Synthetic

<400> SEQUENCE: 80
gaggcattgt tcacgtcgtt tgtta                                  25

<210> SEQ ID NO 81
<211> LENGTH: 25
<212> TYPE: DNA
<213> ORGANISM: Artificial Sequence
<220> FEATURE:
<223> OTHER INFORMATION: Synthetic

<400> SEQUENCE: 81
tttttaaatt taatatgggg atagc                                  25

<210> SEQ ID NO 82
<211> LENGTH: 25
<212> TYPE: DNA
<213> ORGANISM: Artificial Sequence
<220> FEATURE:
<223> OTHER INFORMATION: Synthetic

<400> SEQUENCE: 82
tcgtatagtg gtcaatgtgg tatgg                                  25

<210> SEQ ID NO 83
<211> LENGTH: 29
<212> TYPE: DNA
<213> ORGANISM: Artificial Sequence
<220> FEATURE:
<223> OTHER INFORMATION: Synthetic

<400> SEQUENCE: 83
aagttcggtt ggttttttgct ggtgtggtt                             29

<210> SEQ ID NO 84
<211> LENGTH: 29
<212> TYPE: DNA
<213> ORGANISM: Artificial Sequence
<220> FEATURE:
<223> OTHER INFORMATION: Synthetic

<400> SEQUENCE: 84
aatatgaaga atagagcgaa gaggcctttt                             29

<210> SEQ ID NO 85
<211> LENGTH: 29
<212> TYPE: DNA
<213> ORGANISM: Artificial Sequence
<220> FEATURE:
<223> OTHER INFORMATION: Synthetic

<400> SEQUENCE: 85
ttaaggttgt agtgatgggg gtgtttaaa                              29

<210> SEQ ID NO 86
<211> LENGTH: 29
<212> TYPE: DNA
<213> ORGANISM: Artificial Sequence
<220> FEATURE:
<223> OTHER INFORMATION: Synthetic

<400> SEQUENCE: 86
aattgatcaa ggggtttggt atagggatt                                          29

<210> SEQ ID NO 87
<211> LENGTH: 29
<212> TYPE: DNA
<213> ORGANISM: Artificial Sequence
<220> FEATURE:
<223> OTHER INFORMATION: Synthetic

<400> SEQUENCE: 87
ttagataaac catagtatgt ccgagggaa                                          29

<210> SEQ ID NO 88
<211> LENGTH: 19
<212> TYPE: DNA
<213> ORGANISM: Artificial Sequence
<220> FEATURE:
<223> OTHER INFORMATION: Synthetic

<400> SEQUENCE: 88
ttcggcaatg tcgagggggg                                                    19

<210> SEQ ID NO 89
<211> LENGTH: 25
<212> TYPE: DNA
<213> ORGANISM: Artificial Sequence
<220> FEATURE:
<223> OTHER INFORMATION: Synthetic

<400> SEQUENCE: 89
gcggcctatt ccatgttgac gcctg                                              25

<210> SEQ ID NO 90
<211> LENGTH: 25
<212> TYPE: DNA
<213> ORGANISM: Artificial Sequence
<220> FEATURE:
<223> OTHER INFORMATION: Synthetic

<400> SEQUENCE: 90
ttataataat ctttgtgttt tcggc                                              25

<210> SEQ ID NO 91
<211> LENGTH: 25
<212> TYPE: DNA
<213> ORGANISM: Artificial Sequence
<220> FEATURE:
<223> OTHER INFORMATION: Synthetic

<400> SEQUENCE: 91
gggaggttta tagtaaaaga gagat                                              25

<210> SEQ ID NO 92
<211> LENGTH: 25
<212> TYPE: DNA
<213> ORGANISM: Artificial Sequence
<220> FEATURE:
<223> OTHER INFORMATION: Synthetic

<400> SEQUENCE: 92
tcatgattgc agtagtggta agagg                                              25

<210> SEQ ID NO 93
<211> LENGTH: 36
<212> TYPE: DNA
<213> ORGANISM: Artificial Sequence

```
<220> FEATURE:
<223> OTHER INFORMATION: Synthetic

<400> SEQUENCE: 93
cacacacatg tgatttcact agaatcagga taacag                                  36

<210> SEQ ID NO 94
<211> LENGTH: 23
<212> TYPE: DNA
<213> ORGANISM: Artificial Sequence
<220> FEATURE:
<223> OTHER INFORMATION: Synthetic

<400> SEQUENCE: 94
ccattcatat catgctcccc ctt                                                23

<210> SEQ ID NO 95
<211> LENGTH: 19
<212> TYPE: DNA
<213> ORGANISM: Artificial Sequence
<220> FEATURE:
<223> OTHER INFORMATION: Synthetic

<400> SEQUENCE: 95
ctgccccttg agtcaagag                                                     19

<210> SEQ ID NO 96
<211> LENGTH: 13
<212> TYPE: DNA
<213> ORGANISM: Artificial Sequence
<220> FEATURE:
<223> OTHER INFORMATION: Synthetic

<400> SEQUENCE: 96
gtcatttagc aag                                                           13

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
ctctcatagt gataattaag                                                    20

<210> SEQ ID NO 98
<211> LENGTH: 518
<212> TYPE: DNA
<213> ORGANISM: Artificial Sequence
<220> FEATURE:
<223> OTHER INFORMATION: Synthetic

<400> SEQUENCE: 98
ccattcatat catgctcccc cttggaatgc agaaccttct tcttgactca agggggccttg        60 ctaaatgaca acattccaa tggaaccatt aaagacagga gcccatatcg aaccctaatg         120
agctgtccta ttggtgaagt tccctctcca tacaactcaa gatttgagtc agtcgcttgg        180
tcagcaagtg cttgtcatga tggcatcaat tggctaacaa ttggaatttc tggcccagac        240
aatggggcag tggctgtgtt aaagtacaac ggcataataa cagacactat caagagttgg        300
agaaacaata tattgagaac acaagagtct gaatgtgcat gtgtaaatgg ttcttgcttt        360
actgtaatga ccgatggacc aagtaatgga caggcctcat acaagatctt cagaatagaa        420
```
aagggaaaga tagtcaaatc agtcgaaatg aatgcccta attatcacta tgaggaatgc    480
tcctgttatc ctgattctag tgaaatcaca tgtgtgtg                            518

<210> SEQ ID NO 99
<211> LENGTH: 27
<212> TYPE: DNA
<213> ORGANISM: Artificial Sequence
<220> FEATURE:
<223> OTHER INFORMATION: Synthetic

<400> SEQUENCE: 99
ccgacctgac gtacggctct catagga                                        27

<210> SEQ ID NO 100
<211> LENGTH: 19
<212> TYPE: DNA
<213> ORGANISM: Artificial Sequence
<220> FEATURE:
<223> OTHER INFORMATION: Synthetic

<400> SEQUENCE: 100
tggttggagt tgcagttcg                                                 19

<210> SEQ ID NO 101
<211> LENGTH: 22
<212> TYPE: DNA
<213> ORGANISM: Artificial Sequence
<220> FEATURE:
<223> OTHER INFORMATION: Synthetic

<400> SEQUENCE: 101
cagtaagcat ctcttatgca tg                                             22

<210> SEQ ID NO 102
<211> LENGTH: 119
<212> TYPE: DNA
<213> ORGANISM: Artificial Sequence
<220> FEATURE:
<223> OTHER INFORMATION: Synthetic

<400> SEQUENCE: 102
tggttggagt tgcagttcgg ttggttacca ctaatgagtg atatccaggg tgcatatgag    60
atgcttacga aggttcacct tcaagagttt cttcctatga gagccgtacg tcaggtcgg    119

<210> SEQ ID NO 103
<211> LENGTH: 28
<212> TYPE: DNA
<213> ORGANISM: Artificial Sequence
<220> FEATURE:
<223> OTHER INFORMATION: Synthetic

<400> SEQUENCE: 103
aaagcggtgt gtgtgtgctg ggtaggat                                       28

<210> SEQ ID NO 104
<211> LENGTH: 27
<212> TYPE: DNA
<213> ORGANISM: Artificial Sequence
<220> FEATURE:
<223> OTHER INFORMATION: Synthetic

<400> SEQUENCE: 104
acttcagggt cataaagcct aaatagc                                        27

```
<210> SEQ ID NO 105
<211> LENGTH: 29
<212> TYPE: DNA
<213> ORGANISM: Artificial Sequence
<220> FEATURE:
<223> OTHER INFORMATION: Synthetic

<400> SEQUENCE: 105
aatggcagag atgtctttaa gtgctgttt                                29

<210> SEQ ID NO 106
<211> LENGTH: 590
<212> TYPE: DNA
<213> ORGANISM: Artificial Sequence
<220> FEATURE:
<223> OTHER INFORMATION: Synthetic

<400> SEQUENCE: 106
gctcgccaca cacacacgac ccatcctacc cgcccccaac ataactactc taatcatcat    60
accctcaccc tccccttta ttacacaatc aaccccccac tgacaatttt cacgtatggc   120
ggttttctat tttaaacttt agaccaatcc gaccacaatc ccaagaaaca aaaccccaa    180 accgtctcta cacaaattca cgacaccggt cttcgccccc tcccccaa accacccttta    240 aaaaacaata ctacagacac acctttcacc gacacgtctg taagttaaca ataataatac   300
aggatgttcg taattaatta attgtgtgaa atcattcata caagcggaca ttataacttg   360
catccacgct atttattatc ctactccgtc cttagtttct gtctatgacg ctgtatccca   420
cgaggccgag gtcgcagagc gttacgatag cgcacgtatg gggggtctgc ttttatggtt   480
tacgtacctc tcgagggcac tcaccaatta tcccactatc tggacactag gtagcactac   540
agaataaatt ccccttgcac acccgataaa tccgaaatac tgggacttca              590

<210> SEQ ID NO 107
<211> LENGTH: 27
<212> TYPE: DNA
<213> ORGANISM: Artificial Sequence
<220> FEATURE:
<223> OTHER INFORMATION: Synthetic

<400> SEQUENCE: 107
cccagaggcc tgtgccaggg accttac                                  27

<210> SEQ ID NO 108
<211> LENGTH: 25
<212> TYPE: DNA
<213> ORGANISM: Artificial Sequence
<220> FEATURE:
<223> OTHER INFORMATION: Synthetic

<400> SEQUENCE: 108
cttgtctctg tgttcttgtc ccccc                                    25

<210> SEQ ID NO 109
<211> LENGTH: 34
<212> TYPE: DNA
<213> ORGANISM: Artificial Sequence
<220> FEATURE:
<223> OTHER INFORMATION: Synthetic

<400> SEQUENCE: 109
ccatggaccc ccacacagca aagcagaaac tcac                          34

<210> SEQ ID NO 110
```

```
<211> LENGTH: 33
<212> TYPE: DNA
<213> ORGANISM: Artificial Sequence
<220> FEATURE:
<223> OTHER INFORMATION: Synthetic

<400> SEQUENCE: 110
gccagttaac gtcttccttc tctctctgtc ata                          33

<210> SEQ ID NO 111
<211> LENGTH: 37
<212> TYPE: DNA
<213> ORGANISM: Artificial Sequence
<220> FEATURE:
<223> OTHER INFORMATION: Synthetic

<400> SEQUENCE: 111
tgggagccaa tattgtcttt gtgttcccgg acatagt                      37

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
gtgcctctcc ctccctccag                                         20

<210> SEQ ID NO 113
<211> LENGTH: 36
<212> TYPE: DNA
<213> ORGANISM: Artificial Sequence
<220> FEATURE:
<223> OTHER INFORMATION: Synthetic

<400> SEQUENCE: 113
aggaaaatgc tggctgacct aaagccacct ccttac                       36

<210> SEQ ID NO 114
<211> LENGTH: 27
<212> TYPE: DNA
<213> ORGANISM: Artificial Sequence
<220> FEATURE:
<223> OTHER INFORMATION: Synthetic

<400> SEQUENCE: 114
ctcacagcag ggtcttctct gtttcag                                 27

<210> SEQ ID NO 115
<211> LENGTH: 40
<212> TYPE: DNA
<213> ORGANISM: Artificial Sequence
<220> FEATURE:
<223> OTHER INFORMATION: Synthetic

<400> SEQUENCE: 115
ggttgatctt tttgaattca gtttccttca agatcctccc                   40

<210> SEQ ID NO 116
<211> LENGTH: 26
<212> TYPE: DNA
<213> ORGANISM: Artificial Sequence
<220> FEATURE:
<223> OTHER INFORMATION: Synthetic

<400> SEQUENCE: 116
```

```
caaagagagc ttggttggga gctttg                                              26

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
ggctccactg ggtgtaagcc                                                     20

<210> SEQ ID NO 118
<211> LENGTH: 14
<212> TYPE: DNA
<213> ORGANISM: Artificial Sequence
<220> FEATURE:
<223> OTHER INFORMATION: Synthetic

<400> SEQUENCE: 118
cggagcccag cact                                                           14

<210> SEQ ID NO 119
<211> LENGTH: 15
<212> TYPE: DNA
<213> ORGANISM: Artificial Sequence
<220> FEATURE:
<223> OTHER INFORMATION: Synthetic

<400> SEQUENCE: 119
aggctccaca agctg                                                          15

<210> SEQ ID NO 120
<211> LENGTH: 26
<212> TYPE: DNA
<213> ORGANISM: Artificial Sequence
<220> FEATURE:
<223> OTHER INFORMATION: Synthetic

<400> SEQUENCE: 120
ggaccttctg ggatccagag tccccc                                              26

<210> SEQ ID NO 121
<211> LENGTH: 23
<212> TYPE: DNA
<213> ORGANISM: Artificial Sequence
<220> FEATURE:
<223> OTHER INFORMATION: Synthetic

<400> SEQUENCE: 121
ccgctttcgg agatgttgct tgg                                                 23

<210> SEQ ID NO 122
<211> LENGTH: 24
<212> TYPE: DNA
<213> ORGANISM: Artificial Sequence
<220> FEATURE:
<223> OTHER INFORMATION: Synthetic

<400> SEQUENCE: 122
ttatcgagga tttccttgtt ggaa                                                24

<210> SEQ ID NO 123
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 123
acgggaattt taactttctc                                                    20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
ctcttaattt cttgatagcg                                                    20

<210> SEQ ID NO 125
<211> LENGTH: 19
<212> TYPE: DNA
<213> ORGANISM: Artificial Sequence
<220> FEATURE:
<223> OTHER INFORMATION: Synthetic

<400> SEQUENCE: 125
gcagataccc agtaggcgg                                                     19

<210> SEQ ID NO 126
<211> LENGTH: 18
<212> TYPE: DNA
<213> ORGANISM: Artificial Sequence
<220> FEATURE:
<223> OTHER INFORMATION: Synthetic

<400> SEQUENCE: 126 ccaggggca gccgaagg                                                       18

<210> SEQ ID NO 127
<211> LENGTH: 18
<212> TYPE: DNA
<213> ORGANISM: Artificial Sequence
<220> FEATURE:
<223> OTHER INFORMATION: Synthetic

<400> SEQUENCE: 127
ctgcatggtg aaggtgag                                                      18

<210> SEQ ID NO 128
<211> LENGTH: 19
<212> TYPE: DNA
<213> ORGANISM: Artificial Sequence
<220> FEATURE:
<223> OTHER INFORMATION: Synthetic

<400> SEQUENCE: 128
gcatgagccg cgtgatgag                                                     19

<210> SEQ ID NO 129
<211> LENGTH: 28
<212> TYPE: DNA
<213> ORGANISM: Artificial Sequence
<220> FEATURE:
<223> OTHER INFORMATION: Synthetic

<400> SEQUENCE: 129
ccacggtccc ccaagtagtt tatgccgg                                           28
```

<210> SEQ ID NO 130
<211> LENGTH: 33
<212> TYPE: DNA
<213> ORGANISM: Artificial Sequence
<220> FEATURE:
<223> OTHER INFORMATION: Synthetic

<400> SEQUENCE: 130
ttaaaatctg tgatcttggc atgctgcggt gaa                    33

<210> SEQ ID NO 131
<211> LENGTH: 30
<212> TYPE: DNA
<213> ORGANISM: Artificial Sequence
<220> FEATURE:
<223> OTHER INFORMATION: Synthetic

<400> SEQUENCE: 131
tttttgtctc ccctgcatg gtattcttaa                         30

<210> SEQ ID NO 132
<211> LENGTH: 24
<212> TYPE: DNA
<213> ORGANISM: Artificial Sequence
<220> FEATURE:
<223> OTHER INFORMATION: Synthetic

<400> SEQUENCE: 132
cccaccagta tgttcctggt tggg                              24

<210> SEQ ID NO 133
<211> LENGTH: 19
<212> TYPE: DNA
<213> ORGANISM: Artificial Sequence
<220> FEATURE:
<223> OTHER INFORMATION: Synthetic

<400> SEQUENCE: 133
ccagcattat ggctcgccc                                    19

<210> SEQ ID NO 134
<211> LENGTH: 14
<212> TYPE: DNA
<213> ORGANISM: Artificial Sequence
<220> FEATURE:
<223> OTHER INFORMATION: Synthetic

<400> SEQUENCE: 134
tctcttctgt accc                                         14

<210> SEQ ID NO 135
<211> LENGTH: 22
<212> TYPE: DNA
<213> ORGANISM: Artificial Sequence
<220> FEATURE:
<223> OTHER INFORMATION: Synthetic

<400> SEQUENCE: 135
ctaggtcttg gtggattgag cg                                22

<210> SEQ ID NO 136
<211> LENGTH: 24
<212> TYPE: DNA
<213> ORGANISM: Artificial Sequence
<220> FEATURE:

```
<223> OTHER INFORMATION: Synthetic

<400> SEQUENCE: 136
ccggtggtcg ccgcgatcaa ggag                                          24

<210> SEQ ID NO 137
<211> LENGTH: 22
<212> TYPE: DNA
<213> ORGANISM: Artificial Sequence
<220> FEATURE:
<223> OTHER INFORMATION: Synthetic

<400> SEQUENCE: 137
ggagcagact agcactgagg ta                                            22

<210> SEQ ID NO 138
<211> LENGTH: 19
<212> TYPE: DNA
<213> ORGANISM: Artificial Sequence
<220> FEATURE:
<223> OTHER INFORMATION: Synthetic

<400> SEQUENCE: 138
ggattatgcc tggcaccat                                                19

<210> SEQ ID NO 139
<211> LENGTH: 24
<212> TYPE: DNA
<213> ORGANISM: Artificial Sequence
<220> FEATURE:
<223> OTHER INFORMATION: Synthetic

<400> SEQUENCE: 139
gctttgatga cgcttctgta tcta                                          24

<210> SEQ ID NO 140
<211> LENGTH: 22
<212> TYPE: DNA
<213> ORGANISM: Artificial Sequence
<220> FEATURE:
<223> OTHER INFORMATION: Synthetic

<400> SEQUENCE: 140
tcatctttgg tgtttcctat ga                                            22

<210> SEQ ID NO 141
<211> LENGTH: 19
<212> TYPE: DNA
<213> ORGANISM: Artificial Sequence
<220> FEATURE:
<223> OTHER INFORMATION: Synthetic

<400> SEQUENCE: 141
agggcccagg gttggactc                                                19

<210> SEQ ID NO 142
<211> LENGTH: 21
<212> TYPE: DNA
<213> ORGANISM: Artificial Sequence
<220> FEATURE:
<223> OTHER INFORMATION: Synthetic

<400> SEQUENCE: 142
atagctcttg acaccactca t                                             21
```

REAGENTS FOR IMPROVING PCR ACCURACY

CROSS-REFERENCE TO RELATED APPLICATION

The present application is a continuation of U.S. patent application Ser. No. 14/162,540, filed Jan. 23, 2014, and claims priority to U.S. Provisional Application 61/755,872, filed Jan. 23, 2013, each of which is herein incorporated by reference in its entirety.

SEQUENCE LISTING

The instant application contains a Sequence Listing which has been submitted electronically in ASCII format and is hereby incorporated by reference in its entirety. Said ASCII copy is named 33107-US-2-0RD ST2S.txt.

FIELD

Provided herein are reagents for improving PCR accuracy.

BACKGROUND

Two different families of reagents that improve primer specificity when added to a PCR amplification have been described by our laboratory. One family of reagents, described in international patent application WO 2006/044995, is hairpin shaped single stranded oligonucleotides modified at both the 3' and 5' ends so that the end of the stem is stabilized relative to a DNA-DNA hybrid, such as by addition of dabcyl moieties, by addition of Black Hole Quencher™ moieties, or by inclusion of 2' O-methyl nucleotides at the end of the stem. The stem-loop oligonucleotides have loops of 3-22 nucleotides and stems having calculated Tms of 50-85° C. An example of such a reagent is

```
dabcyl-
CATTATAATGAAATTATAGTA-dabcyl,    (SEQ ID No. 1)
``` where the complementary nucleotides of the nine-nucleotide-long stem are underlined. Among the molecules tested for activity reported in WO 2006/044995 were hairpin shaped molecules having fluorescent FAM moieties on both the 3' and 5' ends of the stem. These molecules were not active in suppressing mis-priming, even at 1000 nM. It was concluded that "Adding a pair of FAM fluorophores, which are not believed to interact with one another in a stem-stabilizing fashion, was destabilizing, as was adding a single 5' Dabcyl." (WO 2006/044995 at page 31, lines 17-19).

The second family of reagents for suppression of mis-priming, described in international patent application WO 2010/105074, is pairs of complementary or partially complementary oligonucleotides that form a hybrid 6-50 nucleotides long, wherein the oligonucleotides are modified on one or both ends by addition of polycyclic moieties, for example, dabcyl moieties, that do not have bulky portions that are non-planar. Bulky non-planar groups, such as fluorescein (FAM) were tested and judged to be not useful as modifying groups in PCR additives. WO 2010/10507 at [0114]).

SUMMARY

This invention includes PCR methods performed in the presence of an entirely new class of reagent additives (hereinafter "Reagents") that exhibit at least one manifestation of increased polymerase selectivity, as defined below. Preferred Reagents achieve selectivity improvement without significant concentration-dependent inhibition of the primer-independent 5'exonuclease activity of the enzyme, or of the DNA synthetic activity of the enzyme, or both. This invention further includes PCR reaction mixtures and PCR reagent kits that include one or more of such reagent additives.

"PCR", as used herein, refers to the well-known nucleic acid amplification method known as the polymerase chain reaction. This invention applies to PCR methods generally, including, for example, symmetric PCR methods and non-symmetric PCR methods such as asymmetric PCR and LATE-PCR. Reverse transcription can be included (RT-PCR), if the target is RNA. PCR methods may include detection of amplification products, for example, by a dsDNA binding dye such as SYBR Green, that fluoresces when in contact with double-stranded (ds) DNA, and oligonucleotide probes whose hybridization to amplified target leads to a detectable signal, for example, a fluorescent signal.

As used herein, "non-symmetric PCR" means a PCR amplification in which one primer (the Limiting Primer) of a PCR primer pair is included in the amplification reaction mixture in a limiting amount so as to be exhausted during the amplification reaction, which continues utilizing only the other primer (the Excess Primer), producing single-stranded amplification product, or "amplicon". Non-symmetric PCR methods include asymmetric PCR, wherein the concentration of one primer of a symmetric PCR primer pair is reduced, generally by a factor of at least five, and LATE-PCR. As used herein, "LATE-PCR" means a non-symmetric DNA amplification employing the PCR process utilizing one oligonucleotide primer (the "Excess Primer") in at least five-fold excess with respect to the other primer (the "Limiting Primer"), which itself is utilized at low concentration, up to 200 nM, so as to be exhausted in roughly sufficient PCR cycles to produce detectable double-stranded amplicon, wherein the concentration-adjusted melting temperature of the Limiting Primer to its fully complementary sequence is equal to or higher than the concentration-adjusted melting temperature of the Excess Primer at the start of amplification, preferably at least as high and more preferably 3-10° C. higher; and wherein thermal cycling is continued for multiple cycles after exhaustion of the Limiting Primer to produce single-stranded product, namely, the extension product of the Excess Primer, sometimes referred to as the "Excess Primer Strand". Amplification and detection assays utilizing non-symmetric PCR methods may utilize "low-temperature" probes, wherein the Excess Primer is in at least five-fold excess with respect to the limiting primer and the Tm of the detection probe is at least 5 degrees below the Tm of the Limiting Primer.

Reagents according to this invention, as well as primers and probes, are described herein by their melting temperatures (Tm's). The Tm is the temperature at which 50% of an oligonucleotide exists in double-stranded form, and 50% exists in single-stranded form. In this application Tm's of primers are concentration-adjusted values calculated for complementary or mismatched nucleotide sequences using the software program Visual OMP (DNA Software, Ann Arbor, Mich.) which uses a proprietary modification of the "nearest neighbor" method (Santa Lucia, J. (1998), PNAS (USA) 95: 1460-1465; and Allawi, H. T. and Santa Lucia, J. (1997), Biochem. 36: 10581-10594), with salt concentrations typically set to 50 mM monovalent cation and 3 mM divalent cation. For Reagents and probes, Tm's are initially calculated by that method, ignoring covalently bound moieties and secondary structures. Because Reagents and probes include covalently bound moieties such as fluorophores and quenchers, it is understood that the actual Tm's may differ slightly from calculated values due to actions of such moieties. If an amplification reaction mixture containing a Reagent is subjected to a melt analysis (or an anneal analysis), an actual, or "observed" Tm of the Reagent in that reaction mixture is obtained. Actual Tm's of labeled probes can generally be determined empirically, including structured probes such as molecular beacon probes.

References are made to selectivity. By "selectivity" is meant generally the preference of a DNA polymerase to extend recessed 3' ends during the process of DNA synthesis when certain conditions are met. In accord with this understanding, one type of selectivity is the preference of a DNA polymerase to extend a recessed 3' end of a hybrid when the 3' terminal region, particularly including the terminal 3' nucleotide, of the recessed 3' end is perfectly complementary, that is, is hybridized with no mismatch. Stated another way, this type of selectivity is selectivity against a 3' terminal priming sequence that is not perfectly matched to its target. Selectivity against 3' terminal-region mismatches applies to primer-target hybrids, where it signifies the preference of a polymerase for a primer-target hybrid that is perfectly complementary at the 3' end of the primer over a primer-target hybrid having a mismatch at, for example, the 3' terminal nucleotide. Improvement in discriminating against mismatched primers is sometimes referred to as an improvement in polymerase selectivity or an improvement in primer specificity. Selectivity against 3' terminal-region mismatches also applies more generally to hybrids having recessed, extendable 3' ends formed by any two DNA strands in an amplification reaction mixture, such as may occur when one amplicon strand hybridizes to (that is, primes on) another amplicon strand. The measure of selectivity of the foregoing type is the difference ($\Delta C_T$) between the threshold cycle ($C_T$) of the signal from amplification of the non-preferred hybrid, for example the hybrid formed by a primer and a mismatched target and the $C_T$ of the signal from amplification of the preferred hybrid, for example the hybrid formed by a primer and a matched target. Improvement in selectivity due to the use of an additive, such as the Reagents described herein, is the net $C_T$ difference ($\Delta\Delta C_T$) obtained by subtracting the $\Delta C_T$ without any additive from the $\Delta C_T$ that results with the additive. In other words, the value of the threshold cycle, $C_T$, of a perfectly match primer to its template strand is always smaller than the value of the $C_T$ of a mis-matched primer to the template strand, and inclusion of an additive can increase the difference between these $C_T$ values.

Increased polymerase selectivity is manifest in at least one of the following ways: 1) suppression of mis-priming; 2) increased primer specificity for perfectly complementary primer-target hybrids and against hybrids having recessed 3' terminal sequences that are not perfectly complementary; 3) increased polymerase selectivity for primer-target hybrids having recessed 3' terminal sequences that are GC-rich and against hybrids having recessed 3'terminal sequences that are AT-rich; 4) suppression of product evolution; 5) reduced scatter among replicate reactions.

References are made to polymerase efficiency. By "efficiency" is meant the rate of a polymerase activity, either the quantified kinetics of probe cleavage via primer-independent 5'exonuclease activity or the quantified kinetics of product amplification via polymerase activity. The kinetics of primer-independent probe cleavage is manifested as the slope of the curve of production of cleaved fragments. The effect of a Reagent or other additive is evidenced by a change, generally a reduction, in slope. The kinetics of polymerase activity is manifested as the $C_T$ of an amplification reaction. The effect of a Reagent or other additive is evidenced by a change, generally an increase, in $C_T$ between amplification of a perfectly matched target with the Reagent or other additive and without the Reagent or other additive. We sometimes refer to negative kinetic effects as "inhibition". Inhibition is also evidenced by a reduction in the production of amplified products, which may be shown by a reduction in intensity of SYBR or probe signal or by diminution in the magnitudes of peaks and valley in first-derivative curves.

The Reagents, as well as primers and probes, useful in methods, reaction mixtures and kits of this invention are oligonucleotides in the broad sense, by which is meant that they may be DNA, RNA, mixtures of DNA and RNA, and they may include non-natural nucleotides (for example, 2'o-methyl ribonucleotides, and linked nucleotides), non-natural internucleotide linkages (for example, phosphorothioate linkages), and DNA mimics (for example, PNA). Both primers and probes function in part by hybridizing to a sequence of interest in a reaction mixture. In the Examples below we utilize primers, probes and Reagents that are DNA, which we prefer.

A Reagent in PCR reaction mixtures, methods and kits according to some embodiments of this invention comprise two complementary oligonucleotides that form a double-stranded hybrid. In certain embodiments, the Reagent has one or more of the following characteristics:

Length: the two oligonucleotide strands form a hybrid that is at least six nucleotides long, preferably 6-50 nucleotides long.

Tm: the Reagent has a calculated Tm of at least 32° C. A more preferred Reagent has a calculated Tm not more than 5° C. below the primer extension temperature of the PCR reaction, which generally means a calculated Tm of at least 55° C. in a 2-step PCR having a combined annealing and extension step of 60 degrees, or at least 67° C. in a 3-step PCR that includes a 72° C. extension step. A preferred Reagent may have a calculated Tm that is higher than the primer extension temperature of the PCR reaction, which generally means a Tm above 60° C. in a 2-step PCR, or above 72° C. in a 3-step PCR, or in some cases above 75° C. or even above 78° C. In certain preferred embodiments, a preferred Reagent has a calculated Tm that is higher than the highest probe Tm.

Hybrid Structure: in the PCR reaction the Reagent acts to improve polymerase selectivity when it is double stranded. Neither strand of the Reagent acts as a probe on a template strand amplified in the reaction because neither strands is complementary to any template strand amplified in the reaction. Neither strand acts as a primer on a template strand amplified in the reaction, because no 3' end of the Reagent is extendable by the polymerase or because no 3' end of the Reagent is available to contact an amplified template or because neither strand is complementary to any template strand amplified in the reaction.

Labeling: One end of the hybrid includes interacting labels, that is, labels that interact to quench or modify fluorescence of the Reagent when it is double-stranded. A nucleotide on one end of the hybrid in the double-stranded form of the Reagent, preferably a nucleotide within three nucleotides of the hybrid end, more preferably a terminal nucleotide and even more preferably a 5'-terminal nucleotide, has a covalently attached bulky, non-planar fluorescent moiety, preferably a fluorophore; while a nucleotide on the complementary strand, preferably a nucleotide within three nucleotides of the hybrid end, more preferably a terminal nucleotide, and even more preferably a 3'-terminal nucleotide, has either another covalently attached bulky, non-planar moiety, for example a fluorophore, or a covalently attached non-bulky, planar quencher moiety, preferably a non-fluorescent moiety that absorbs light energy but releases energy as heat (a non-fluorescent quencher or, for short, a "quencher"). Said covalently attached labels on the 5' and 3' end of the double-stranded form of the Reagent are positioned such that these labels interact. Interaction is preferably by contact (providing, for example, contact quenching), such contact being enhanced by making the label ends blunt ended in the preferred double-stranded hybrid. When two interacting fluorescent moieties are used, preferably they are distinguishable colors.

Relative Concentrations of Strands: In preferred embodiments that include a fluorophore is added at a concentration that is equal to or greater than, preferably 1.5-10 times and a quencher, the quencher-labeled strand greater than, even more preferably 2-5 times greater than, the concentration of the complementary strand.

In a method, reaction mixture or kit according to this invention, a single Reagent may be the sole selectivity-enhancing component. As an alternative, two Regents may be included, preferably one of which has a Tm at least 5° C. higher than the Tm of the other. Two Reagents may comprise four strands or, by sharing a common strand, only three strands. As a second alternative, a multi-dabcylated double-stranded reagent may also be included with a Reagent, wherein the dabcylated reagent forms a hybrid 6-50 nucleotides long, is not extendable by polymerase, and has three or four terminal dabcyl moieties. The Reagent and the dabcylated reagent may comprise four strands or, if they share a common strand, only three strands. As yet another alternative, a hot-start polymerase or a hot-start enzyme may be included with any of the foregoing as an additional selectivity-enhancing component.

In methods according to this invention, a Reagent is added to the starting PCR reaction mixture at a concentration sufficient to increase polymerase selectivity without increasing the number of thermal cycles needed for the correct product to reach its $C_T$ by more than 10 cycles, preferably by no more than 5 cycles, most preferably by 3 cycles or less. A Reagent is typically added to a PCR reaction mixture at a concentration in the range of 25-800 nM, preferably in the range of 50-800 nM, more preferably in the range of 50-300 nM, and even more preferably in the range of 50-200 nM. In certain methods of this invention, more than one Reagent ("Reagent(s)" signifies generally one or more Reagents) can be added to a single reaction, in which case the concentration ranges cited above are the total concentrations of said added Reagent(s).

Methods of this invention include PCR amplification reactions, including RT-PCR reactions, to produce one or more amplified products, wherein the amplification reaction mixture contains a Reagent to improve polymerase selectivity. Preferred methods further include fluorescence detection of amplified products. For detection of double-stranded products the reaction mixture may contain a DNA dye, for example SYBR Green dye, that fluoresces in the presence of double-stranded DNA, that is a dsDNA dye. A Reagent's fluorophore may emit at the dye's emission wavelength, as Fluorescein emits at the emission wavelength of SYBR Green dye. Alternatively, a Reagent's fluorophore may emit at the dye's emission wavelength when the strands of the Reagent are separated and may quench fluorescence at the wavelength of the SYBR Green dye when the strands of the Regent are double-stranded. In that event detection of dye emission signaling double-stranded product (amplicon) will also detect not only unquenched SYBR emission, if any, emanating from the double-stranded Reagent(s) but also fluorophore emission from the Reagent(s), including unquenched fluorophore emission at temperatures at which the Reagent(s) is at least partially single-stranded. It will be appreciated that as the temperature of the reaction mixture is increased, dye emission will decrease due to strand melting of the amplicon, but fluorophore emission will increase due to strand melting of the Reagent(s). If the melting temperatures (Tm's) of an amplicon and a Reagent are detectably distinct, the first derivative of a melting curve will include separate peaks and/or valleys indicative of their temperature-depend states as double-stranded (dye binding) molecules and single-stranded (not dye binding) molecules. Alternatively, a Reagent(s) may be labeled with a fluorophore that does not emit at the emission wavelength of the dsDNA dye, for example the combination of SYBR Green dye and a Cal Red fluorophore. In that case, detection in the SYBR (or Fluorescein) channel will detect emission from the dye bound to the double-stranded form of the amplicon, and it will detect SYBR quenching from the double-stranded form of the Reagent(s). In addition, detection of the temperature-depending hybridization and separation of the strands of Reagent(s) will be possible in the Cal Red channel, for instance.

Reagents can also be used in combination with one or more fluorescently labeled probes that emit a detectable signal when they hybridize to their targets. Whereas dsDNA dye signals that some double-stranded product has been made, including, for example, primer-dimers, target-specific hybridization probes signal the production of a particular product, namely, the intended product. The Reagent or Reagents in a reaction may be labeled with the same fluorophore or fluorophores as one or more probes, or the Reagent(s) may include a spectrally distinct fluorophore or fluorophores. Here again, if the Tm's of the Reagent(s) and amplicons are different, the first derivative of a melting curve will include separate peaks and valleys indicative of their temperature-depend states as double-stranded molecules and single-stranded molecules.

The Reagents according to this invention generate a fluorescent signal at particular conditions at a known temperature, best viewed as a melting (or annealing) valley (that is, a negative peak) in a first derivative fluorescence curve, hereafter refer to as a "temperature mark." For that reason a Reagent can serve as an internal temperature standard in every reaction. The temperature mark reveals variations and differences among reactions. Such a temperature mark has three, independent values: 1) the depth of its "valley" is characteristic of the amount of the Reagent added to the reaction; 2) the temperature at which its "valley" reaches its lowest value is the observed, empirical Tm of the Reagent; 3) the width of the valley at "half depth," is a measure of the temperature-dependent process of double-strand/single-strand formation and melting of the Reagent.

Each of the above temperature-mark properties is expected to be a constant property of the corresponding Reagent(s) in identical replicate reactions. This is the case because the Reagent(s) is not amplified or degraded during the course of the reaction. Therefore, a difference in one or more temperature-mark properties in replicate reactions provides evidence of non-uniformity among replicates. These temperature mark properties can also be used to mathematically correct for non-uniformities among replicate reactions, as well to quantify amplified products in a reaction relative to the temperature marks of the non-amplified Reagent(s).

As one versed in the art will appreciate, it is also possible to utilize in a PCR amplification reaction two different Reagents having non-cross-hybridizing oligonucleotide sequences for their double-strands that have significantly different Tm's, for instance Reagent2 with a Tm of 71° C. and Reagent3 with a Tm of ~50° C. Said non-cross-hybridizing Reagents can be labeled in the same color or in different colors. It is preferred to label both Reagents in the same color, for instance FAM, so that in the absence of any other probe/target hybrids both are detected in the same color channel and appear on the same curve. Under these circumstances a melt curve over a broad temperature range has two valleys when expressed as a first derivatives and the distance between the lowest points in these two valleys, in this example, is 21° C. (71-50). Construction of two widely different temperature marks is advantageous, because the distance between the two marks is known in advance and can be used to guarantee that every reaction spans the same range of temperatures.

After any number of desired thermal cycles a ratio of fluorescent intensities can be constructed: sample signal/temperature-mark signal. Since the temperature-mark signal is the same in replicate reactions, calculation of the above ratio provides a quantitative measure of the amount of accumulated product after the chosen number of thermal cycles. And, if a standard set of ratio values is first constructed using known numbers of target copies at the start of amplification, the observed ratio from the experimental sample can be used to establish the target copy number in the original sample.

BRIEF DESCRIPTION OF THE DRAWINGS

FIG. 9 is a table presenting the delay in threshold cycle resulting from inclusion of a given concentration of Reagent1 in the assay of Example 9 for a series of targets variously mismatched to the limiting primer used for amplification.

DETAILED DESCRIPTION

Figure 1A:
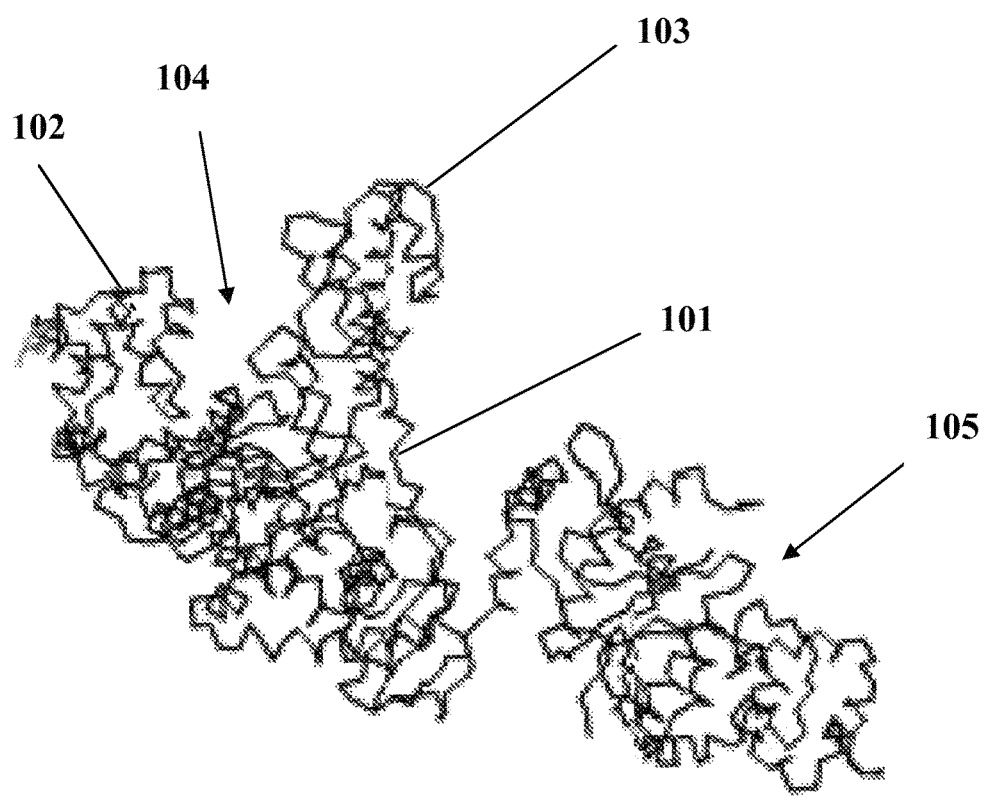
FIG. 1A shows the crystal structure of the Taq polymerase with nothing docked into it.

DNA is a right handed double helix comprised of two oligonucleotides strands that run in opposite, antiparallel, directions, i.e. 3'-to-5' and 5'-to-3'. When DNA is replicated the two strands are temporarily untwisted by DNA topoisomerase and DNA helicase which are part of the Type III DNA polymerase complex. The resulting single strands serve as templates for the synthesis of new base-pair complementary strands. Nucleotide precursors incorporated into new DNA strands during the process of replication are always incorporated in the 3'-to-5' direction because the process of replication is energized during addition of each new nucleoside by cleavage of the 5' pyrophosphates from the triphosphate precursors. As a consequence of these facts, one new strand, the leading strand, grows continuously into the replication fork via the action of DNA polymerase III, while the other strand, the lagging strand, is synthesized discontinuous. Discontinuous synthesis begins by synthesis of an RNA primer by the Primase enzyme. The RNA primer is then extended with deoxynucleotides by the action of Polymerase III. Type III DNA polymerases are dimeric enzymes. Once the resulting Okazaki fragment abuts the 5' end of the adjacent RNA primer that primer is digested by the action of Type I DNA polymerase which also acts to extend the 3' end of the upstream fragment. The resulting gap between the DNA fragments of the lagging strand is closed by the action of DNA ligase.

Taq polymerase and other thermal stable DNA polymerases used in PCR amplification are Type I polymerases. They have a 5' to 3' exonuclease activity in addition to the 3' to 5' DNA synthetic polymerase activity. Xray crystallographic studies of Taq polymerase show this enzyme to be a monomeric molecule comprised of three non-identical domains, shown generally in FIG. 1A. The polymerase domain of the enzyme is described as a having the shape of a right-handed palm 101 with fingers 102 and a thumb 103. The double stranded portion of a replicating DNA template lies across the palm, thereby placing the 3'end of the primer strand at the polymeras-domain catalytic site 104. Binding of the DNA molecule causes the fingers and the catalytic site to move closer to the 3' end where a new nucleotide is added. The extended 5' template strand slips between the fingers and the thumb (into the plane of the page in FIG. 1A). The catalytic site 105 of the 5' exonuclease domain is located on the back side of the domain as viewed in FIG. 1A.

The enzyme exhibits both primer-dependent and primer-independent 5'exonuclease activity but, because the enzyme only binds to double stranded DNA the existence of these two 5'exonuclease activities suggests that it can cut a single-stranded 5' end while approaching such a structure from either direction. The 5' exonuclease domain of the enzyme is thought to either extend below the palm of the polymerase domain as shown in FIG. 1A, or to rotate upward in order to bring the active site of the 5'exonuclease on top of the palm in close proximity to the polymerase catalytic site.

As summarized above international patent application WO2010/105074 describes a class of chemically modified oligonucleotides having 1-4 non-bulky planar moieties (preferably dabcyl moieties, see FIG. 18) on one to four terminal nucleotides that can inhibit the polymerase activity of the enzyme when added to a PCR amplification reactions at a high concentration. However, when the same reagent is added at a lower concentration, it inhibits the 5'exonuclease activity and also increases polymerase selectivity. Increased polymerase selectivity is manifest in at least one of the following ways: 1) suppression of mis-priming; 2) increased primer specificity for perfectly complementary primer-target hybrids and against hybrids having recessed 3' terminal sequences that are not perfectly complementary; 3) increased polymerase selectivity for primer-target hybrids having recessed 3' terminal sequences that are GC-rich and against hybrids having recessed 3' terminal sequences that are AT-rich; 4) suppression of product evolution; 5) reduced scatter among replicate reactions. It is therefore plausible that the added reagent preferentially binds to the 5'exonuclease site of the enzyme and thereby alters polymerase selectivity by an allosteric change in the shape of the polymerase site. It is further plausible that the same reagent binds the polymerase site of the enzyme, but only at higher concentration.

The above line of reasoning is now supported by physical chemical calculation of the probability that dabcyl moieties on the 3' and 5'ends of an oligonucleotide can bind to either or both of the 5'exonuclease catalytic site and the polymerase catalytic site of Taq polymerase. Example 1 describes the computer programs used to make these calculations. The outcome of such a test is called a "glide score". The more negative the glide score, the more likely the chance that the chemical moiety under investigation actually binds to the proposed binding site on the protein. The results in Example 1 generated the following glide scores for the polymerase site: 5'dabcyl interaction=glide score −4.84, 3'dabcyl interaction=−8.08; and for the 5'exonuclease site: 5'dabcyl interaction=glide score −5.33, 3'dabcyl interaction=glide score −10.03. These results indicate that interaction of the 5'exonuclease site with the 3'dabcyl is particularly likely, and examination of a space filling model of the modified oligonucleotide with the surface of the protein confirms a good fit at this site. The evidence for interaction of the dabcyl groups with the polymerase site was not quite as good as for the exonuclease site, since the dabcyl groups entered the palm through the hole between the fingers and the thumb. Taken together, the above evidence suggests a model in which the 5'exonuclease site of a Taq monomer preferentially binds a dabcylated oligonucleotide, and a second dabcylated oligonucleotide binds to the polymerase site at a higher concentration. This model assumes that the binding of the oligonucleotide at the 5'exonuclease site allosterically alters the shape of the polymerase site, making it more selective.

Figure 18:
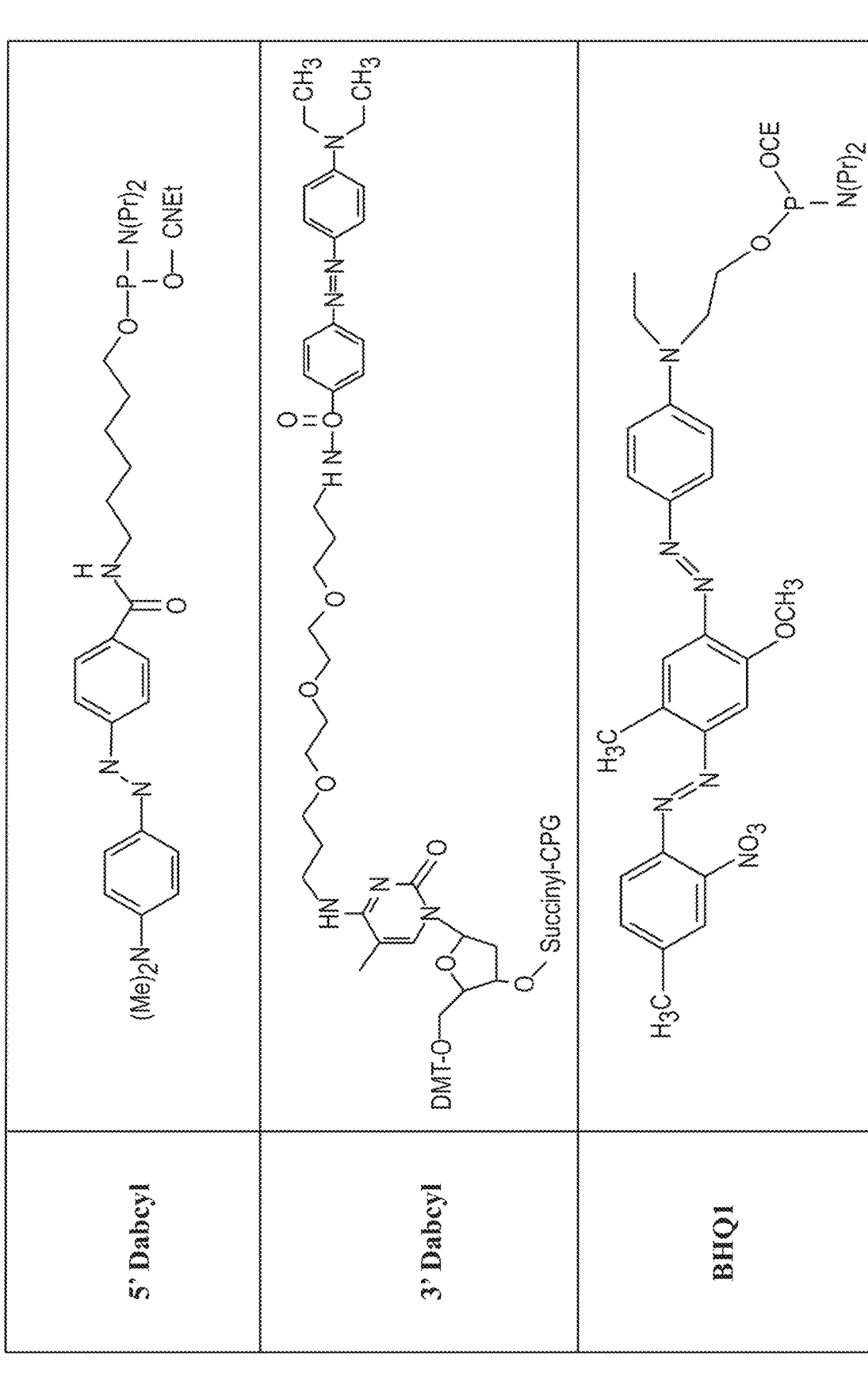
FIG. 18 is a chart showing the chemical structures of various quenching moieties.
Figure 18:
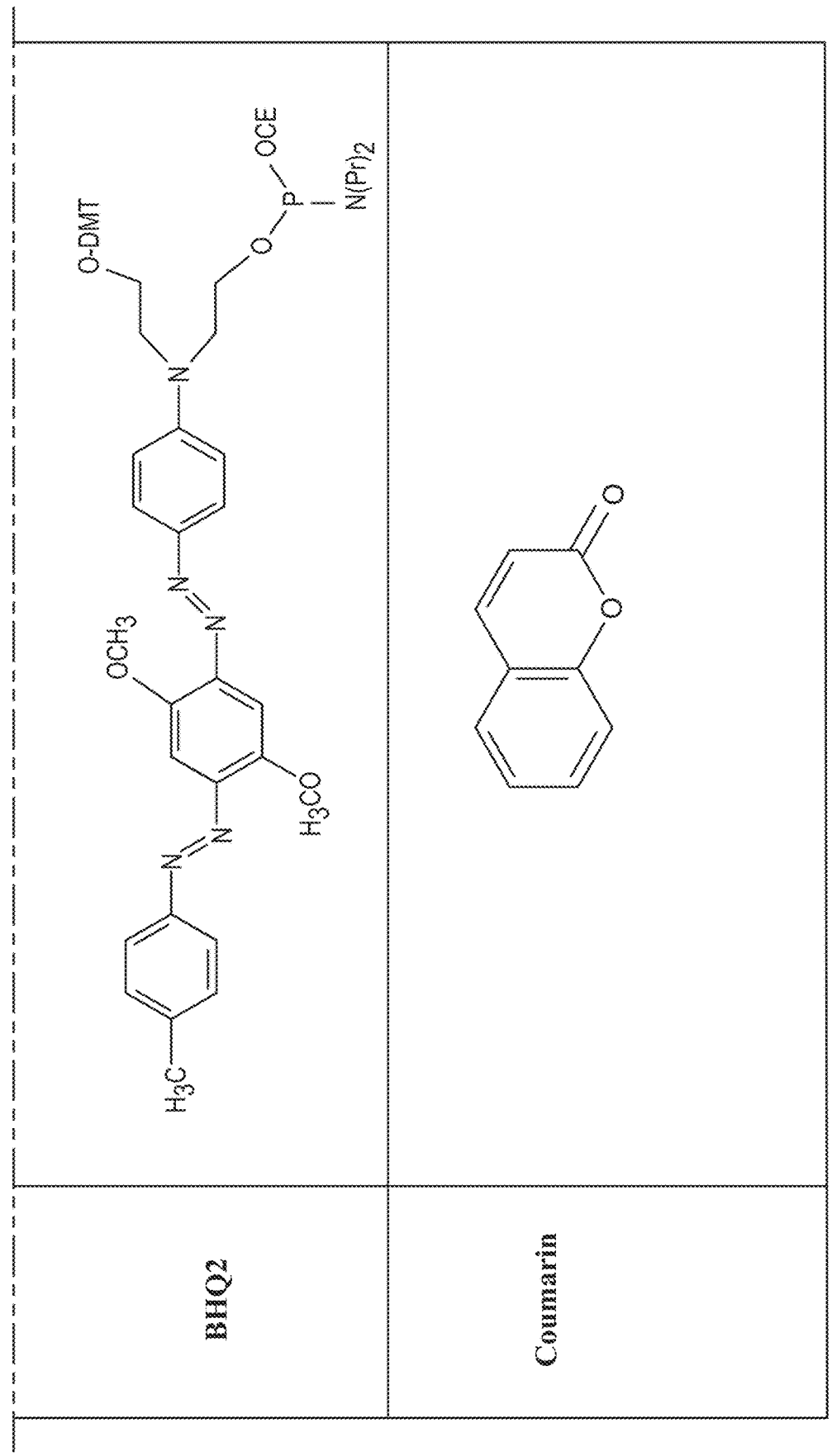
Figure 19:
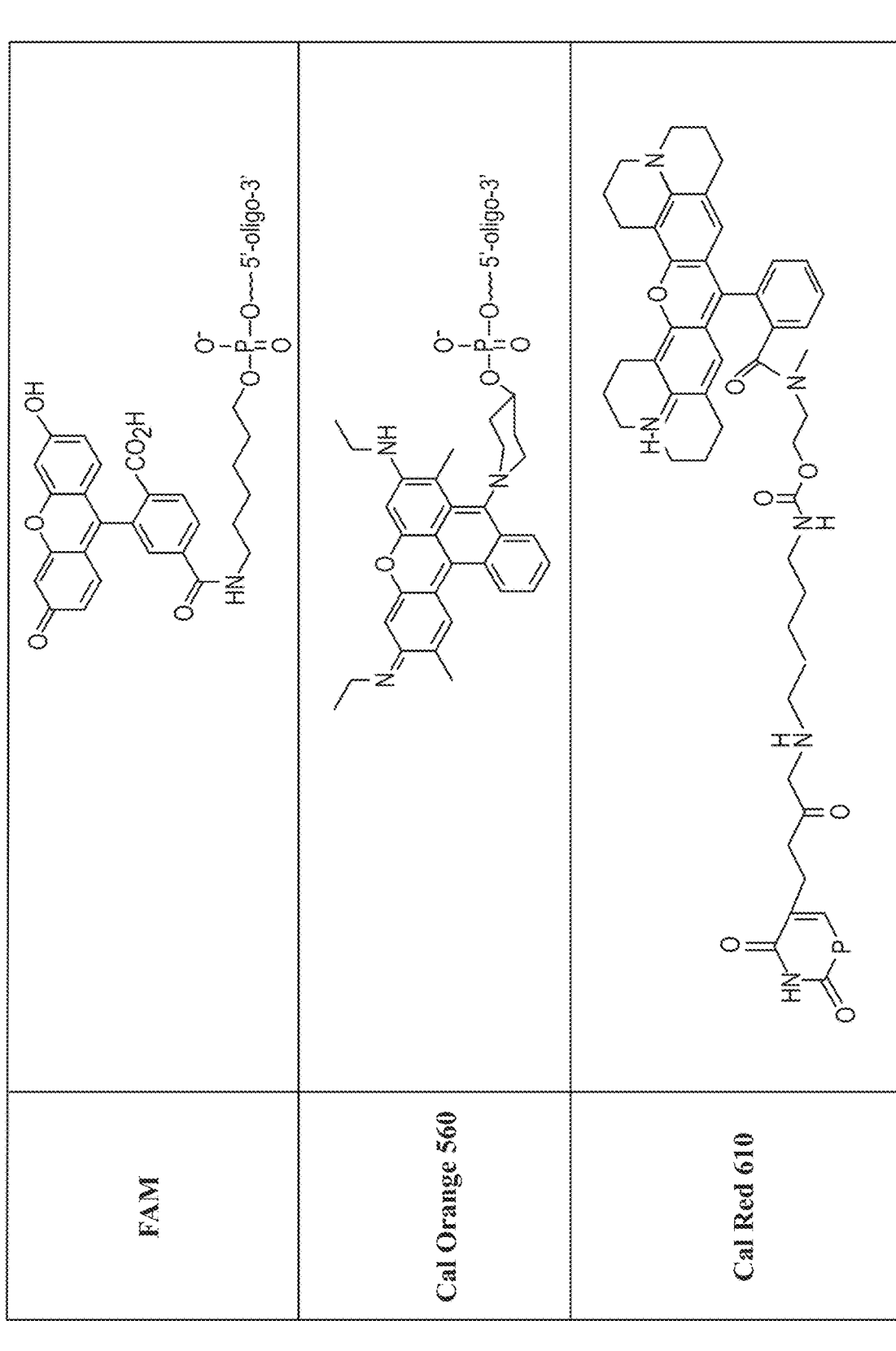
FIG. 19 is a chart showing the chemical structures of various fluorophores.
Figure 19:
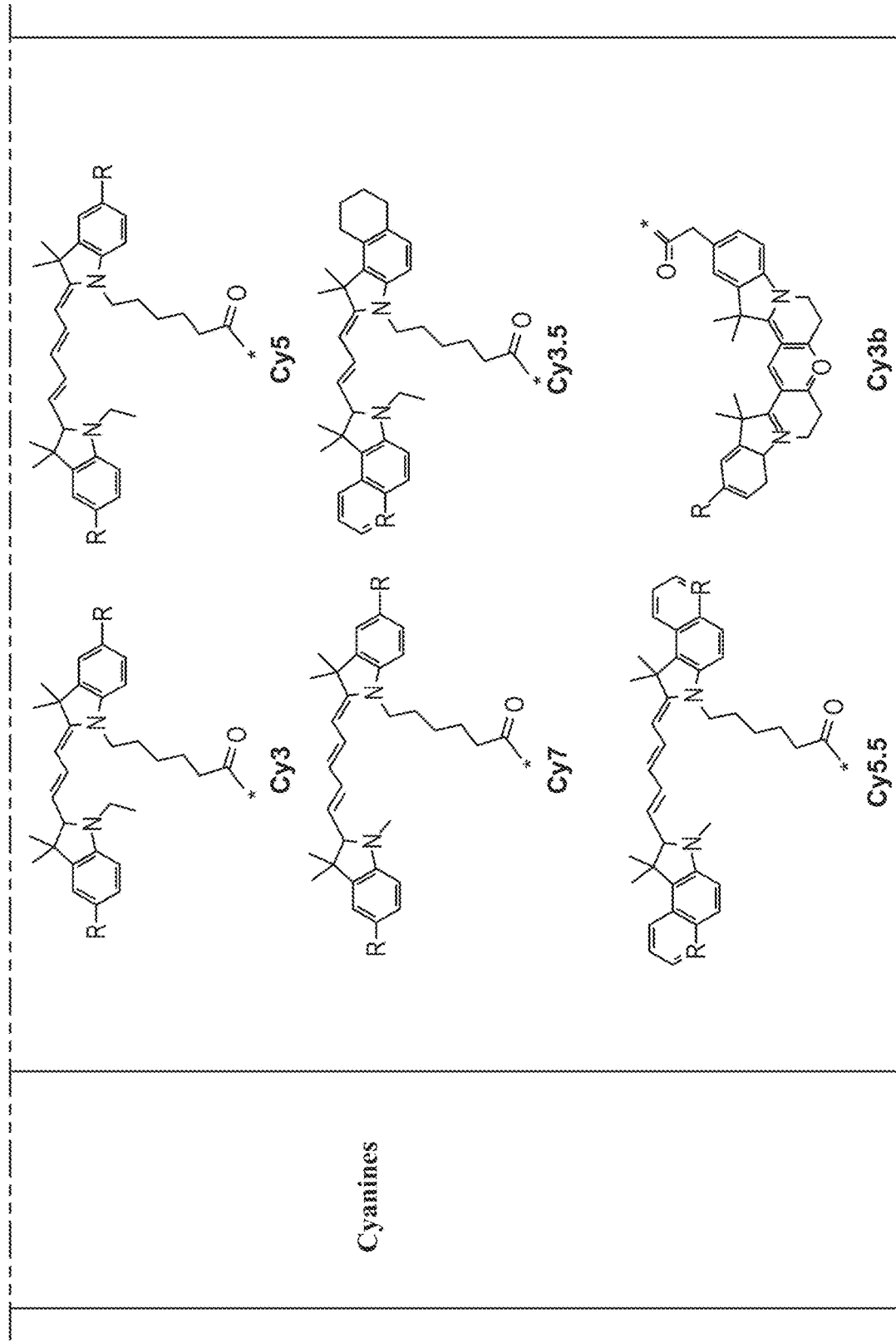
Figure 19:
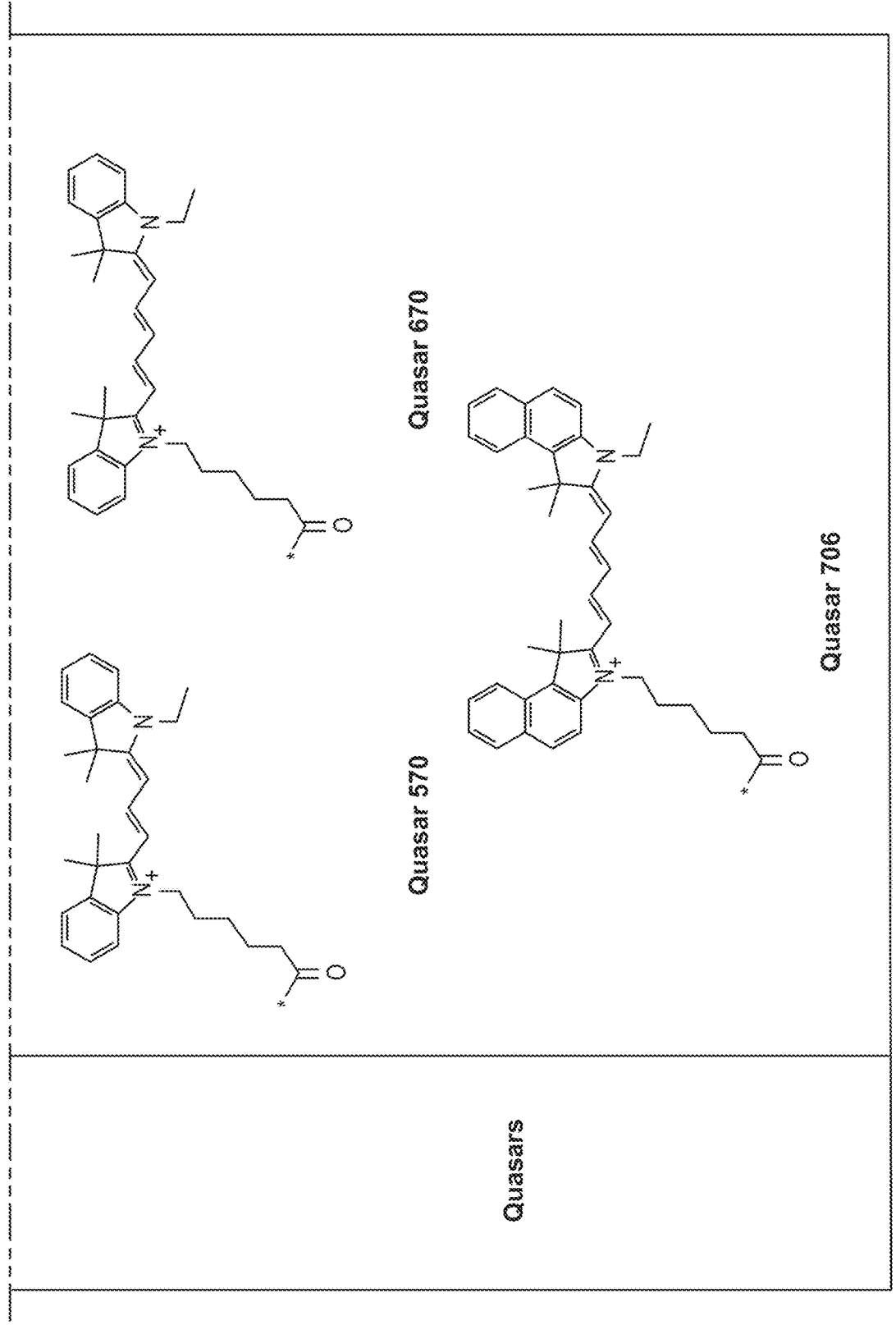

In light of the evidence discussed above, it was surprising to discover an entirely new class of reagents, hereafter referred to as "Reagents" (Reagent1, Reagent2, and so forth). When added to a PCR reaction, Reagents according to this invention exhibit at least one manifestation of increased polymerase selectivity, as defined above, without significant concentration-dependent inhibition of the primer-independent 5'exonuclease activity of the enzyme, or significant concentration-dependent inhibition the polymerase activity. Equally surprising, these Reagents are comprised of two complementary oligonucleotides, at least one of which, contrary to the teaching of international patent application WO 2010/105074, has a moiety that is or includes a bulky non-planar portion. Such a moiety is preferably a fluorophore, on a terminal nucleotide, preferably a 5' nucleotide, and wherein the terminal 3'nucleotide of the complementary strand is modified with either another such bulky moiety, or preferably a planar moiety without a bulky portion, for example, dabcyl or a Black Hole Quencher, both of which are depicted in FIG. 18 and which we refer to as "quenchers" because, rather than emitting absorbed energy as light, they emit absorbed energy as heat. FIG. 19 shows the structures of the bulky fluorophores used in combination with the Reagents herein, but as one versed in the art will appreciate, these particular fluorophores are just a few of many known fluorophores and similar non-fluorescent moieties that are readily attached to an oligonucleotide strand.

In preferred embodiments utilizing a quencher, the strand bearing the quencher moiety is added at a concentration sufficient to reduce fluorescence intensity from the fluorescently labeled strand to an acceptable level through quenching by hybridization. Normally, that concentration at least about equals the concentration of the fluorescently labeled strand. In preferred embodiments the quencher-labeled strand is added at a concentration that is equal to or greater than, preferably 1.5-10 times greater than, most preferably 2-5 times greater than, the concentration of the complementary strand. This guarantees that all of the strands labeled with a covalently linked fluorescent moiety will hybridize to a quencher-labeled strand as temperature is gradually lowered and, as a consequence, fluorescence will be extinguished to its lowest possible level.

Five different embodiments of Reagent according to this invention (Reagent1, Reagent 1', Reagent2, Reagent3 and Reagent4) are employed in the Examples described below. Their oligonucleotide sequences and labeling are summarized in Table 1. In Table 1 "F" denotes an attached fluorescent moiety, preferably a fluorophore (see FIG. 19); "Q" denotes a quencher moiety, preferably a non-fluorescent quencher, and more preferably a Black Hole Quencher (see FIG. 18); "D" denotes the non-fluorescent quencher dabcyl (see FIG. 18); and "$C_3$" denotes a three-carbon linker.

TABLE 1

| Name | Sequence/Labeling |
|---|---|
| Reagent1 | 5' F-CAGCTGCACTGGGAAGGGTGCAGTCTGACC-$C_3$ 3'<br>3' Q-GTCGACGTGACCCTTCCCACGTCAGACTGG 5'<br>(SEQ ID No. 2) |
| Reagent1' | 5' F-CAGCTGCACTGGGAAGGGTGCAGTCTGACC-$C_3$ 3'<br>3' F-GTCGACGTGACCCTTCCCACGTCAGACTGG 5'<br>(SEQ ID No. 3) |

TABLE 1-continued

| Name | Sequence/Labeling |
|---|---|
| Reagent2 | 5' F-GGAGCAGACTAGCACTGAGGTA-$C_3$ 3'<br>3' Q-CCTCGTCTGATCGTGACTCCAT 5'<br>(SEQ ID No. 4) |
| Reagent3 | 5' F-GGAGCAGACTAGCACTGAGGTA-D 3'<br>3' Q-CCTCGTCTGATCGTGACTCCAT-D 5'<br>(SEQ ID No. 5) |
| Reagent4 | 5' F-GAAATAAAATAAAAATAAAATA-D 3'<br>3' Q-CTTTATTTTATTTTTATTTTAT-D 3'<br>(SEQ ID No. 6) |
| reagentA | 5' CAGCTGCACTGGGAAGGGTGCAGTCTGACC-$C_3$ 3'<br>3' $C_3$-GTCGACGTGACCCTTCCCACGTCAGACTGG 5'<br>(SEQ ID No. 7) |
| reagentB | 5' GGAGCAGACTAGCACTGAGGTA-$C_3$ 3'<br>3' $C_3$-CCTCGTCTGATCGTGACTCCAT 5'<br>(SEQ ID No. 8) |
| reagentC | 5' D-CAGCTGCACTGGGAAGGGTGCAGTCTGACC-$C_3$ 3'<br>3' D-GTCGACGTGACCCTTCCCACGTCAGACTGG 5'<br>(SEQ ID No. 9) |
| reagentD | 5' D-GGAGCAGACTAGCACTGAGGTA-$C_3$ 3'<br>3' D-CCTCGTCTGATCGTGACTCCAT 5'<br>(SEQ ID No. 10) |

Reagent1 is comprised of two perfectly complementary strands, each 30 nucleotides in length, plus covalently linked moieties: a 5'-terminal fluorescent moiety on one strand and a 3'-terminal quencher on the other strand, with a resulting melting temperature of approximately 79° C. Reagent 1' is comprised of the same two oligonucleotide strands as Reagent1, but the 3'-terminal quencher is replaced by a fluorescent moiety. Reagent2 is a double-stranded oligonucleotide 22 base pairs long plus covalently linked moieties, again a 5'-terminal fluorescent moiety on one strand and a 3'-terminal quencher on the other strand, with a resulting Tm of approximately 71° C. Reagent3 is a double-stranded oligonucleotide 22 base pairs long plus covalently linked moieties: a 5'-terminal fluorescent moiety and a 3'-terminal dabcyl on one strand, and a 3'-terminal quencher and a 5'-terminal dabcyl on the other strand, with a resulting Tm of approximately 70° C. Reagent4 is a double-stranded oligonucleotide 22 base pairs long plus covalently linked moieties as in Reagent3, with a Tm of approximately 50° C. Table 1 also presents the structure of reagentA, which comprises just the two oligonucleotides strands of Reagent1 capped with three carbon atoms ($C_3$) at both 3' ends. Table 1 also presents the structure of reagentB, which comprises just the two oligonucleotides strands of Reagent2 capped with carbon atoms ($C_3$) at both 3' ends. In addition, Table 1 summarizes reagentC, which comprises the two oligonucleotides strands of Reagent1, one of which is capped with carbon atoms ($C_3$) at its 3' end is also labeled with a dabcyl moiety on its 5' end, and the other of which is labeled with a dabcyl moiety on its 3' end. Thus, double-stranded reagentC has two dabcyl groups on one end. Table 1 also depicts reagentD, which is comprised of the two oligonucleotides strands of Reagent2, one of which is capped with carbon atoms ($C_3$) on its 3' end and is also labeled with a dabcyl moiety on its 5' end, and the other of which is labeled with a dabcyl moiety on its 3' end. As one versed in the art will appreciate, the nucleotide sequences and lengths of the oligonucleotides shown in Table 1 can readily be altered to achieve whatever length and melting temperature is desired or required for the Reagent for use in a particular PCR amplification reaction.

Although the lengths and the sequences of the complementary strands used for Reagent1 and Reagent2 (Table 1) are distinctly different, the structures of these Reagents are similar insofar as they are comprised of natural deoxynucleotides, have fully complementary strands, and have a Black Hole Quencher on a 3'end and a fluorophore on the 5' end of the complementary strand, whose 3'end is capped with a 3-carbon chain.

As one versed in the art can appreciate, formulations of the Reagent can be altered in many ways, and each of the changes can readily be tested for its capacity to enhance polymerase selectivity using the assays described above. A partial list of possible structural changes that can be used to alter the structure of the Reagent includes:

1. The use of two fluorophores rather than a quencher and a fluorophore, as described for Reagent1' in Example 3, FIG. 3. Variants of this design display less enhancement of polymerase selectivity, but generate a temperature-marker at the same Tm in two different colors.
2. Temperature-marks at the same Tm in more than one color and with robust polymerase selectivity can also be achieved by mixing an excess of one strand labeled with a quencher, with a complementary strand labeled with more than one fluorophore.
3. Temperature-marks at different Tm's and labeled in one or more colors and retaining robust polymerase selectivity can be achieved by mixing an excess of one strand labeled with a quencher, with two different complementary strands, one of which is shorter than the other and labeled with the same or a different fluorophore (ref Additive EP042 in Example 10).
4. Using one or both oligonucleotide strands comprised of ribonucleosides rather than deoxyribonucleosides, or using LNAs, or PNAs, or non-natural bases, etc.
5. Using a wide variety of covalently bound quenchers, fluorophores and other properties, provided the resulting double-stranded oligonucleotides display the properties of the Reagents described herein.
6. It is possible to combine the properties of the Reagents with those of reagentC or reagentD shown in Table 1. In this case one end of the double-stranded oligonucleotide is labeled with a fluorophore and a quencher, while the other end of the oligonucleotide is labeled with a 3'dabcyl moiety and a 5'dabcyl moiety. As discussed below, Reagents of this design generate a temperature mark and also inhibit both 5'exonuclease activity and, at a higher concentration, polymerase activity. Table 1 provides two examples of such Reagents, Reagent3 and Reagent4.
7. It is possible to prepare sets of multiple Reagents that share at least one oligonucleotide strand, for example: a) a first long oligonucleotide labeled with a quencher residue on one end; b) a second equally long oligonucleotide that is fully complementary to said first oligonucleotide and has a fluorophore opposite the foregoing quencher; a third oligonucleotide that is shorter than said second oligonucleotide, having been truncated at its unlabeled 3' (or 5') end; a fourth, fifth, etc nucleotides that are progressively shorter than the one before, each having been truncated in a step-wise fashion from the unlabeled 3' (or 5') end. Oligonucleotides from an inventory of the foregoing can be used to construct sets of Reagents having progressively shorter double-stranded regions that are all labeled with the same quencher-fluorophore combination. The Reagents of such a set will have lower and lower temperature-marks as shorter oligonucleotides are included.

8. Sets of Reagents comprised of two different Reagents having measurably different Tm's and distinctly different, non-cross hybridizing sequences, wherein the fluorescent label of said Reagents can be in the same or different colors. Sets of Reagents of this design will generate two different distinctive temperature-marks, reflecting the two different Tm's of the pairs of complementary strands. Melt curves that are marked in this way can be used to construct a standardized "ruler" for empirically comparing and standardizing the number of degrees between the temperature-marks.

9. Yet another Reagent variant type uses one long oligonucleotide strand (for instance 30 nucleotides long) with a 3' fluorophore or, preferably, quencher and one short oligonucleotide strand (for instance 15 nucleotides long) that is complementary to the 3' end of the long strand and is modified on its 5' end with a fluorophore, but is not capped on its 3' end. The long strand is used in excess of the short strand to guarantee hybridization of all molecules of the short strand. The hybrid formed by the two strands will have a first, relatively low, Tm. If such a variant is included in a PCR amplification reaction mixture, the polymerase will extend the 3' end of the shorter strand up to the 5' end of the longer strand. As a result, the Tm of the Reagent will increase significantly. Variants designed in this way provide a convenient way to prove that active polymerase is present in the reaction. This is important for quality control of reagents that are stored for a long time before being used. This method of in-situ construction of the final Reagent is used only in assays in which the fluorescently labeled strand, in both its original short structure and its subsequently extended structure, does not prime any target sequence in the reaction mixture.

10. Yet another variant of the Reagent uses two long strands (for instance 30 nucleotides long) that are fully complementary and one strand is present at a high concentration than the other, wherein the more abundant strand is labeled on its 3' end with a quencher, preferably a Black Hole Quencher, and wherein the less abundant strand is labeled on its 5' end with a bulky moiety that can form a close contact with the quencher moiety but wherein said bulky moiety does not fluoresce in wavelength detected by the device being used for amplification and analysis. Reagents of this design thus separate the Tm marking function of the Reagent from the enhancement of polymerase selectivity. Reagents of this design are useful for designing reactions, assays, or tests that have increased polymerase selectivity, without revealing the presence of the Reagent.

The functionality of a Reagent according to this invention is affected by the PCR method in which it is employed, in particular the temperatures used for thermal cycling. Thus, a designer will consider the intended method. In instances where there is leeway in the particulars of the method, the designer will consider alternatives. As an alternative to changing the Tm or concentration of a Reagent to achieve a desired Reagent functioning, one can sometimes change the thermal-cycling profile. For instance, consider a Reagent with a Tm of 68° C. when added to a reaction mixture at 50 nM concentration, and a thermal-cycling profile that includes an extension step at 72° C. The Reagent will be only partially double-stranded at the extension temperature, so its effective concentration during the extension step will be less than 50 nM. If an effective concentration of 50 nM is desired, any of three things can be done: a) change the structure of the Reagent to increase its Tm to a level such that it is double-stranded at 72° C.; b) increase the concentration of Reagent so that, when partially single-stranded at 72° C., its effective concentration at 72° C. is 50 nM; or c) reduce the PCR extension temperature by several degrees so that the Reagent is double-stranded (or nearly so) at the lower extension temperature. Consider also a Reagent having a Tm of 50° C. at 50 nM concentration, and a thermal-cycling profile that includes a primer-annealing temperature of 50° C. The Reagent will be partially (half, by definition) double-stranded at 50° C. If it is desired that the Reagent act only as a hot-start additive that prevents mis-priming during low-temperature sample preparation but not during temperature cycling, one could change the structure of the Reagent to lower its Tm or, alternatively, one could raise the primer-annealing temperature to a level at which the Reagent is single-stranded (or nearly so).

Example 2 shows the quantified kinetics of probe cleavage via primer-independent 5'exonuclease activity in a set of tests comprising oscillating the temperature of a reaction mixture to induce cleavage of a probe, comparing reaction mixtures having either no added reagent or increasing concentrations of Reagent1, or the equivalent amounts of reagentA or reagentC. Results are presented in FIGS. 2A-2C, which are graphs of fluorescence (due to probe cleavage) versus cycles of temperature oscillation. The results show that: 1) the probe is not cleaved in the absence of a target (curve 201); 2) the probe is maximally cleaved when present with just its target (curve 202); 3) cleavage of the probe is only slightly inhibited by addition of increasing concentrations (50 (curve 203), 100 (curve 204), 150 (curve 205) nM) of reagentA; 4) cleavage of the probe is severely inhibited by addition of 50 nM or more reagentC (curves 206, 207, 208); 5) cleavage of the probe is not much more inhibited by addition of 50 (curve 209), 100 (curve 210) or 150 (curve 211) nM of Reagent1 than it is by addition of the same concentrations of reagentA. For example, the slope with no reagent additive is about 35 degrees, reaching about 3800 fluorescence after 45 cycles; the slope with 50 nM of reagentA is about 25 degrees, reaching about 3300 fluorescence units after 45 cycles; the slope with 50 nM Reagent1 is about 20 degrees, reaching about 3100 fluorescence units after 45 cycles; but the slope with 50 nM of reagentC is only about 10 degrees, reaching only about 2100 fluorescence units after 45 cycles This unexpected result clearly distinguishes Reagent1 from reagentC, and indicates that, unlike reagentC, Reagent1 does not bind to the 5'exonuclease domain of the enzyme.

Both LATE-PCR and symmetric PCR amplifications generate double-stranded DNA amplicons whose kinetics of accumulation can be observed by reading in real time following staining with SYBR Green, a fluorescent intercalating dye. The data in FIGS. 3A-3O, resulting from LATE-PCR reactions described in Example 3, are raw fluorescence plots of double-stranded DNA stained with SYBR Green. It can be seen from FIGS. 3A-C that the reactions receiving increasing concentrations of reagentA have high background levels of SYBR Green staining even prior to amplification, because the DNA of reagentA binds SYBR green and fluoresces. In contrast, reactions receiving Reagent1 labeled with either Cal Orange (FIGS. 3G-I) or Quasar (FIGS. 3J-L) have far lower levels of background fluorescence. The lower level of background fluorescence is due to the covalently linked fluorophore plus the covalently linked Black Hole Quencher of Reagent1, both of which absorb some of the energy from the intercalated SYBR Green dye. The lower level of background fluorescence is desirable, because it increases the signal-over-background resulting from amplification of the double-stranded DNA product.

Figure 3:
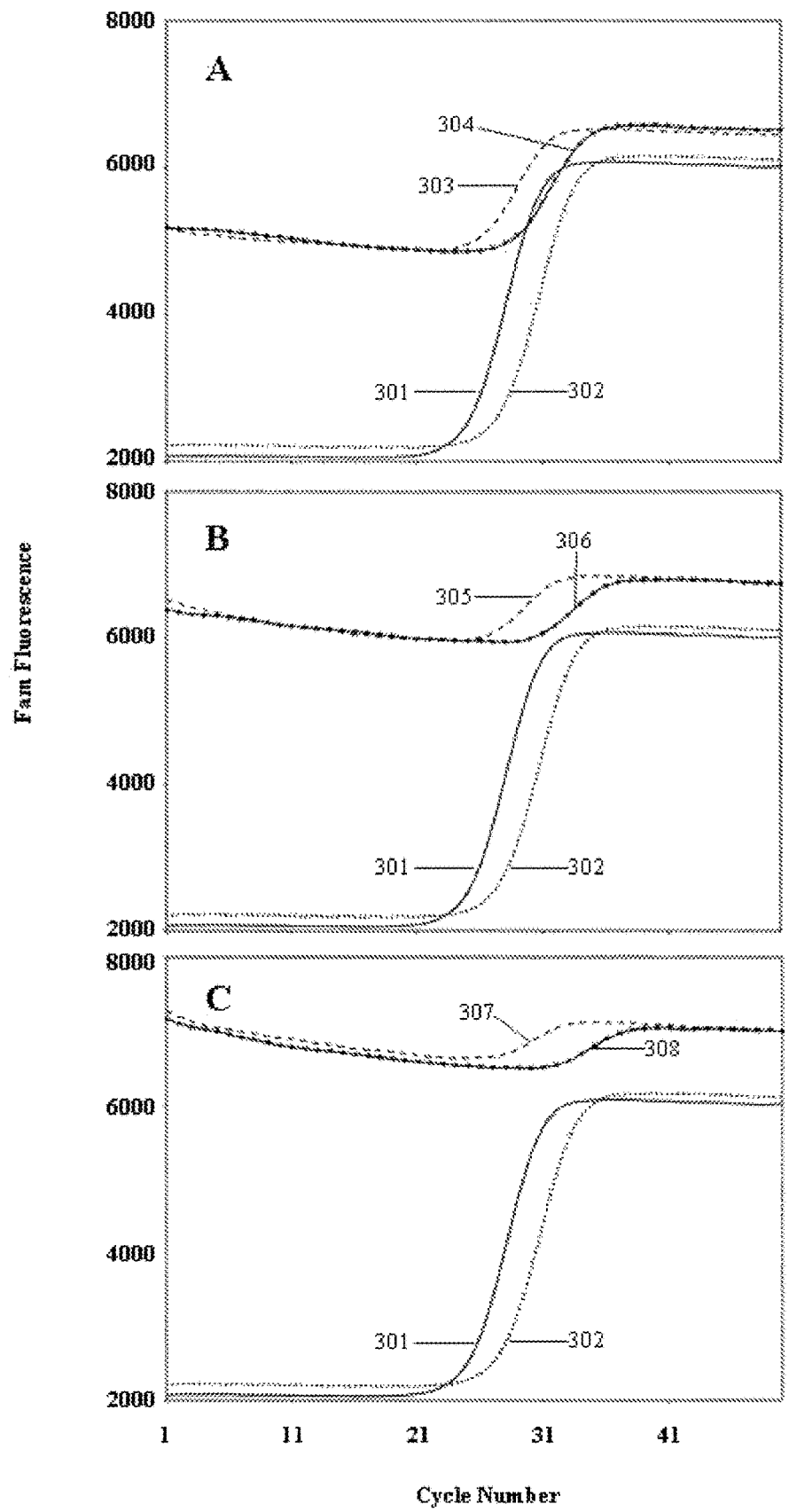
FIG. 3, has 15 panels, A-O, and shows graphs of SYBR Green fluorescence versus cycle number resulting from the primer-specificity assay of Example 3 using no reagent additive or different concentrations of reagentA, reagentC, Reagent or Reagent1'.
Figure 3:
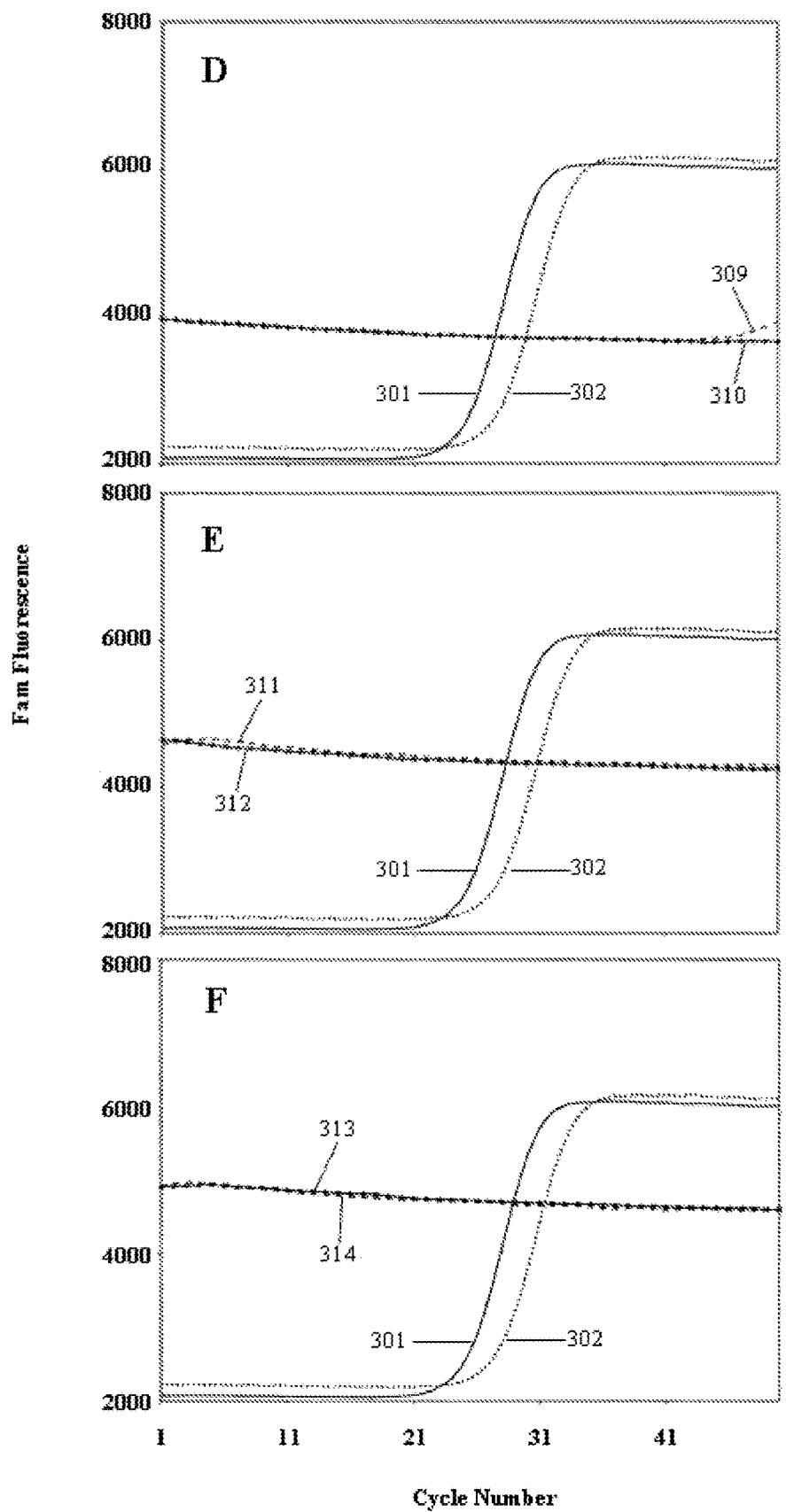
Figure 3:
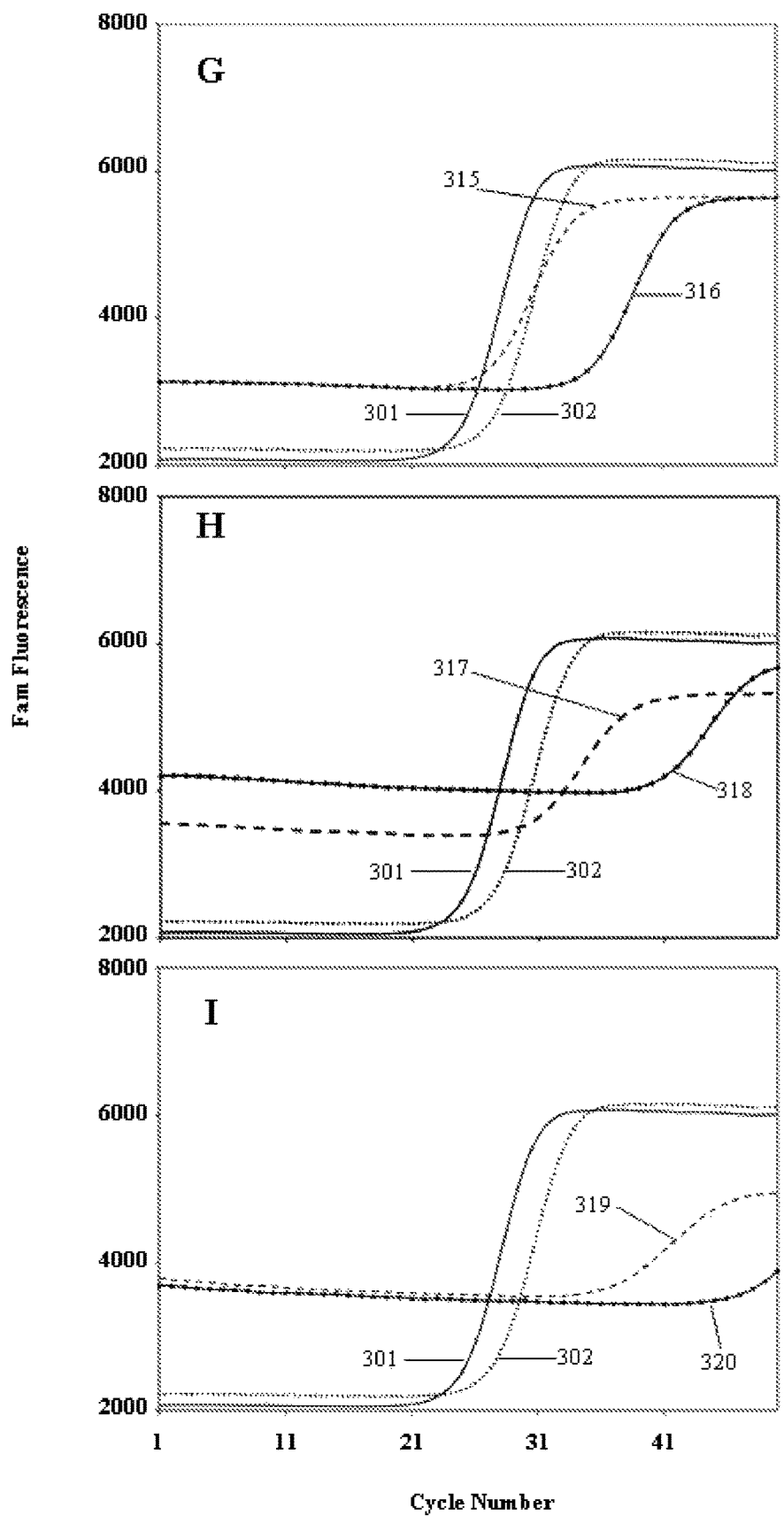
Figure 3:
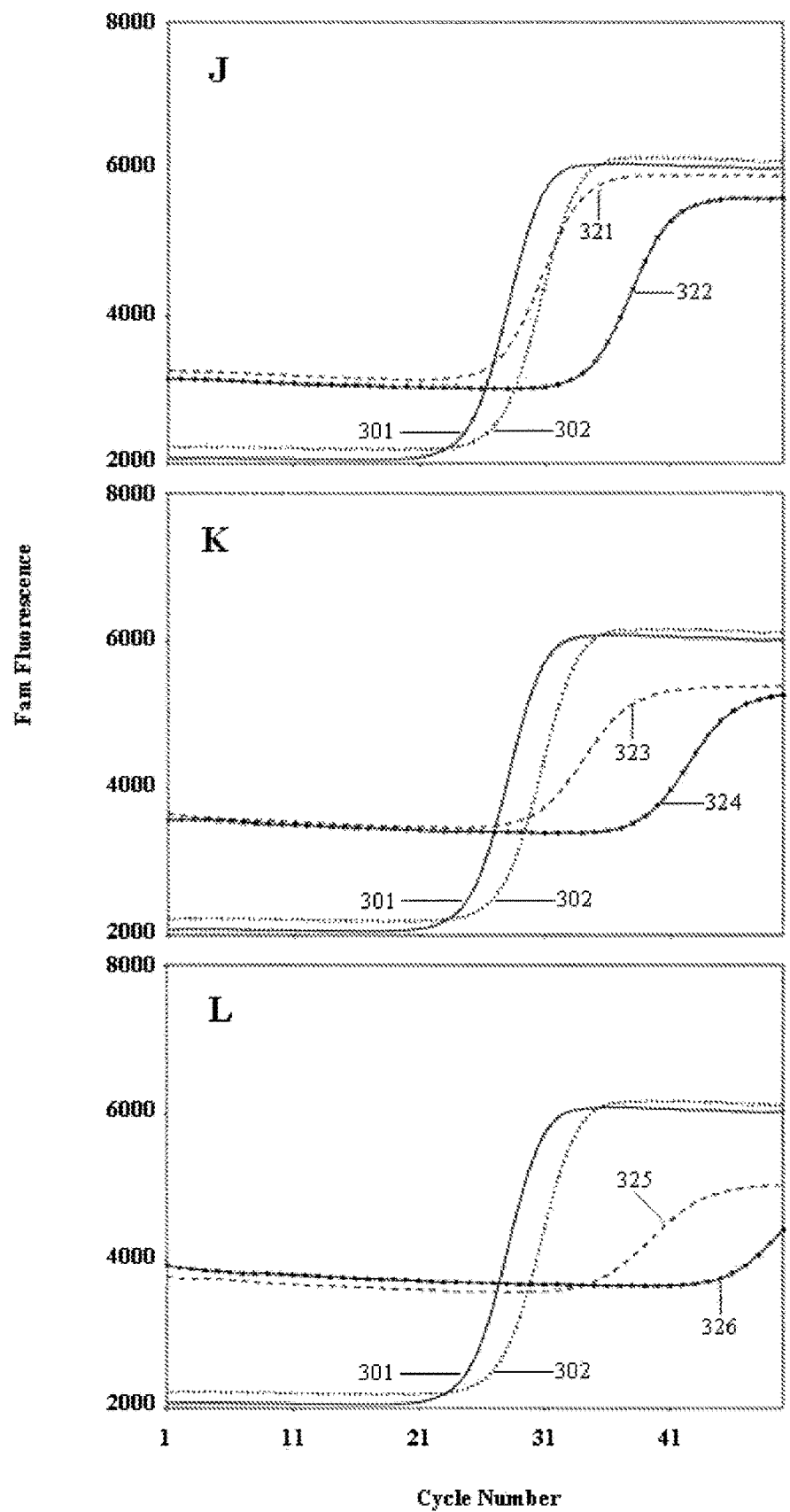
Figure 3:
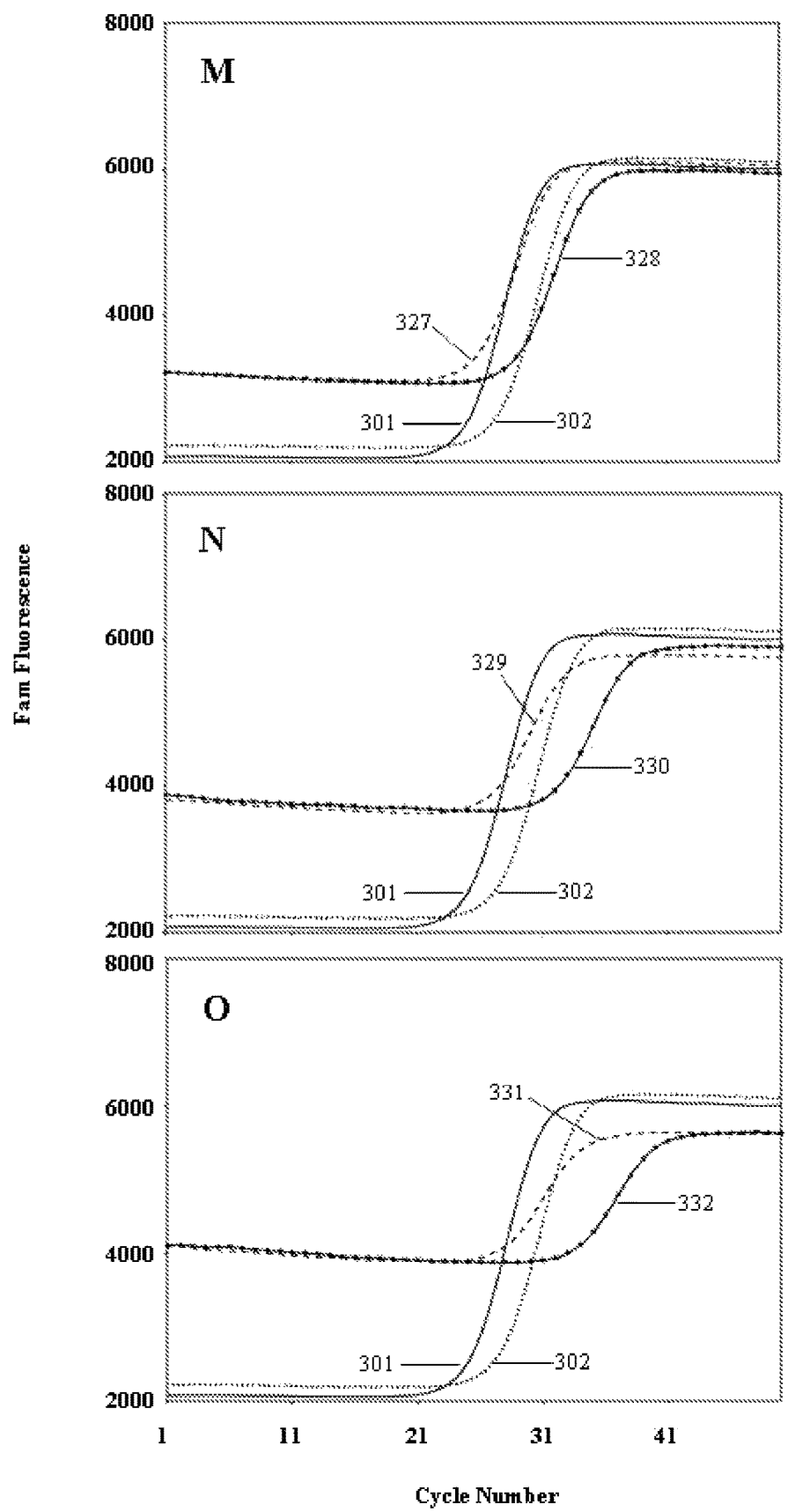

The data in Example 3 also show that both versions of Reagent1 increase primer specificity in contrast to the equivalent concentration of reagentA, the unlabeled double-stranded oligonucleotide. This increase in primer specificity is apparent as the separation between the real-time fluorescence curves from amplification of two equimolar targets, one that is perfectly matched to its primer (odd numbered curves) versus another that is mis-matched to the same primer because of a single nucleotide change at the base complementary to the 3' end of the primer (even numbered curves). This assay measures primer specificity each time the initial template is used to start amplification. Amplicons made from both target strands are identical, because the primer is incorporated into all copies; they have the same sequence, which is perfectly matched to the primer. The results (FIGS. 3G, 3J) clearly show that just 50 nM of Reagent1, labeled with either Cal Orange or Quasar, is sufficient to achieve a significant increase in primer specificity, $\Delta \Delta C_T$, with very little decrease in amplification efficiency as measured by the delay ($\Delta C_T$) in the $C_T$ of the matched target compared to the no-reagent control (FIG. 3, circle 301). In contrast, 50 nM of reagentC labeled with two dabcyl moieties (FIG. 3D, circle 309) causes an increase of about 20 cycles, and at higher concentrations effectively inhibits amplification of both the matched and the mis-matched targets (FIGS. 3E-F). This result also points to the unique nature of these Reagents as class of molecules.

FIGS. 3M-O shows the results of the reaction of Example 3 utilizing a variant of Reagent1, namely, Reagent1' (see Table 1). This variant has no Black Hole Quencher but has two bulky fluorophores on the complementary ends of the double-stranded oligonucleotide, a 3'Cal Orange 560 and a 5'Quasar 670. Comparison of the results in FIGS. 3M-O with FIGS. 3G-I and J-L shows that the background levels of SYBR fluorescence in FIGS. 3M-O are slightly higher than those in FIGS. 3G-I and J-L, in accord with the fact that the two covalently linked fluorophores absorb less energy from the SYBR than do one covalently linked fluorophore and one covalently linked Black Hole Quencher. The results also show that Reagent1' caused a much smaller increase in polymerase selectivity ($\Delta \Delta C_T$) than did either version of Reagent1. In addition, Reagent1' caused no greater decrease in amplification efficiency than reagentA (FIGS. 3A-C). This difference is likely due to the fact that Reagent1' is modified with two bulky fluorophores rather than one fluorophore and one Black Hole Quencher in Reagent1. Black Hole Quenchers and fluorophores are known to interact by contact quenching (Johansson M K. Choosing reporter-quencher pairs for efficient quenching through formation of intramolecular dimers. Methods Mol Biol. 2006; 335:17-29).

Referring to Table 1, Reagent1 is comprised of a double-stranded oligonucleotide that is 30 base-pairs long. It has a Tm of 79° C. Reagent2 is comprised of a double-stranded oligonucleotide that is 22 base-pairs long. It has a Tm of 71° C. Example 4 compares the capacities of Reagent1 and Reagent2 to increase polymerase selectivity when amplifying the perfectly matched target/primer pair and the mis-matched target/primer pair already described in Example 3. Primer extension in this Example was carried out at 72° C. The results demonstrate that Reagent2, like Reagent1, increases polymerase selectivity for the matched target/primer over the mis-matched target/primer ($\Delta \Delta C_T$), but the extent of the improvement was not as great as that observed for the equivalent concentration of Reagent1.

Figure 4:
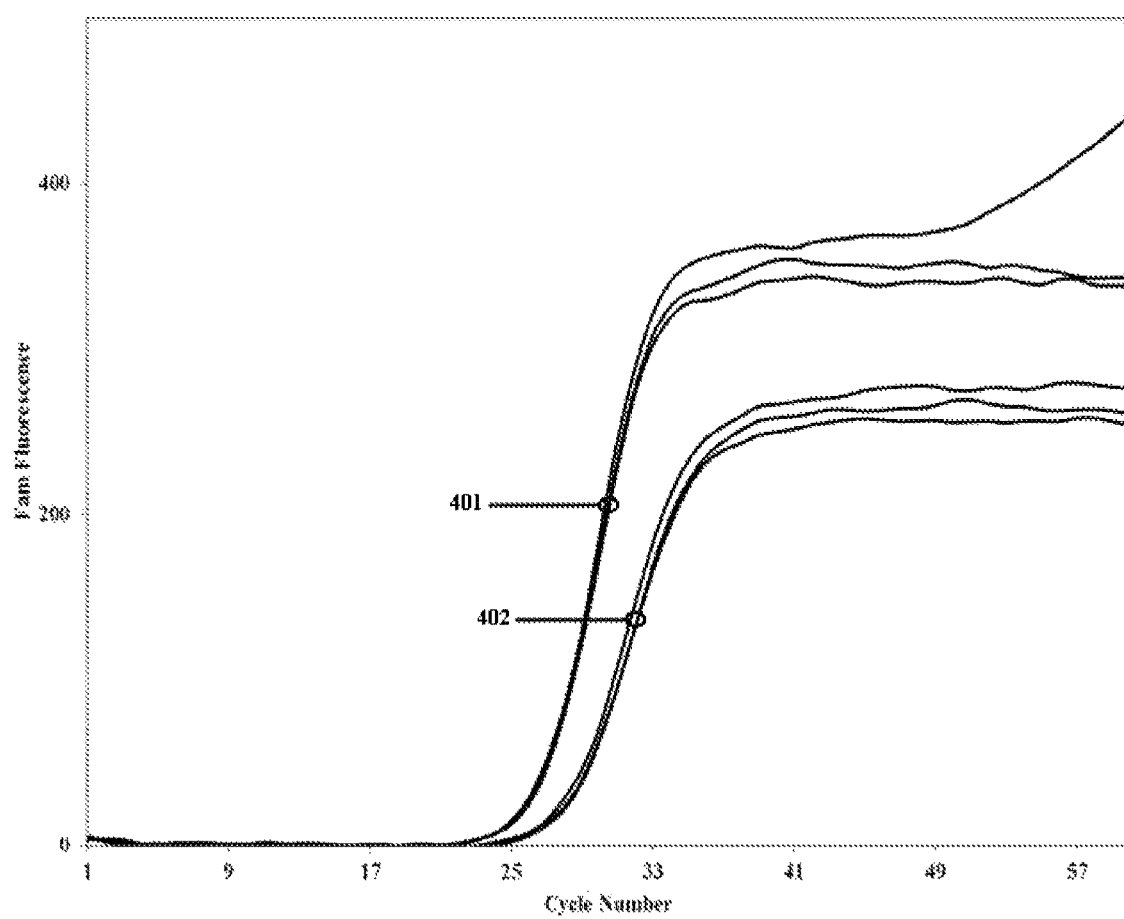
FIG. 4 is a graph of SYBR Green fluorescence versus cycle number resulting from the assay of Example 4 using Reagent1 and Reagent2.

In addition, in the assay of Example 4, Reagent2 was less effective than Reagent1 in enhancing another manifestation of polymerase selectivity—the suppression of product evolution that takes place as a result of unintended interactions between the 3' end of a single-stranded amplicon generated during the linear phase of LATE-PCR amplification and some other single-stranded molecule in the reaction. There are many ways to observe product evolution. Product evolution in Example 4 is shown in FIG. 4, where it is seen as an increase in double-stranded DNA stained with SYBR Green after the reaction has achieved the plateau phase when accumulation of double-stranded DNA is supposed to stop. The results show that Reagent2 did not suppress product evolution as effectively as Reagent1. The likely explanation for this difference is that only approximately 45% of Reagent2 molecules are double-stranded at the extension temperature of 72° C., as compared to approximately 95% of Reagent1 molecules.

Figure 5A:
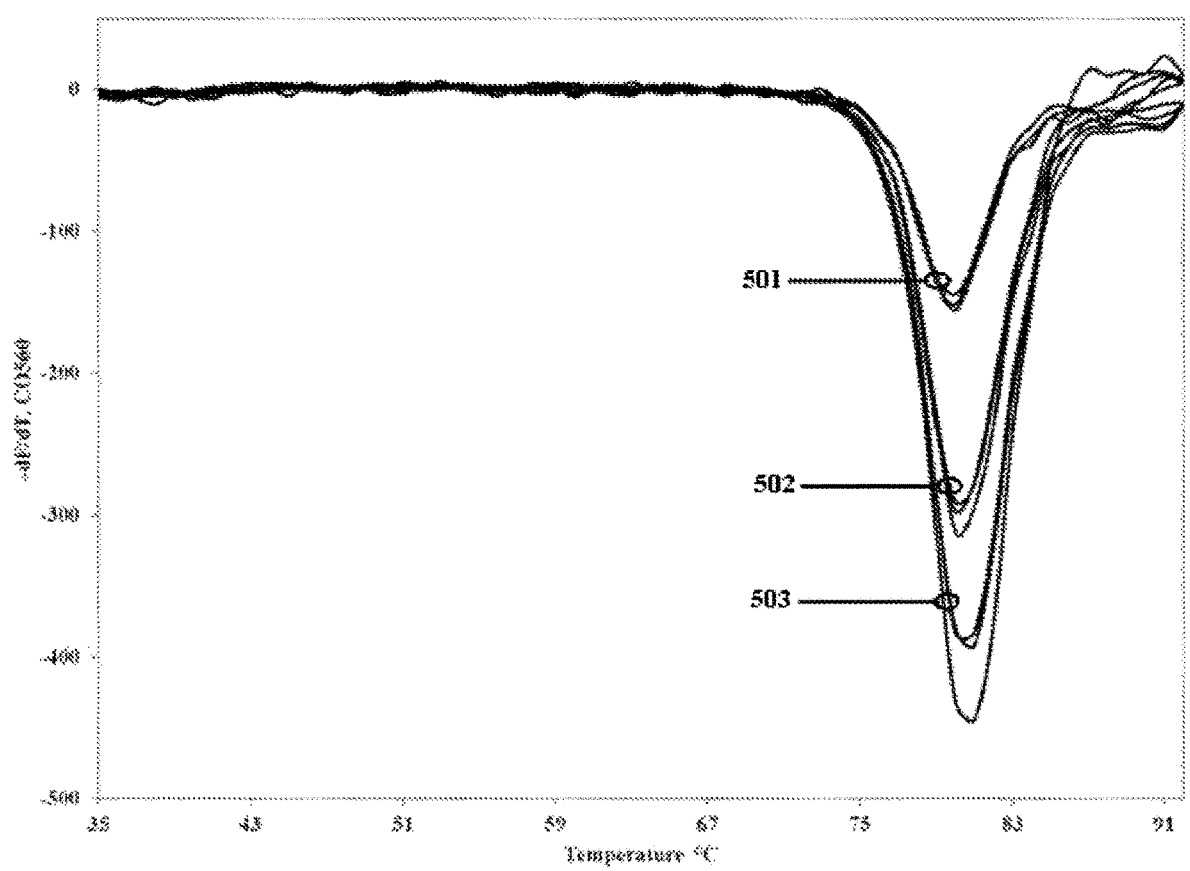
FIG. 5A is a melt curve of Reagent1 at different concentrations.
Figure 5B:
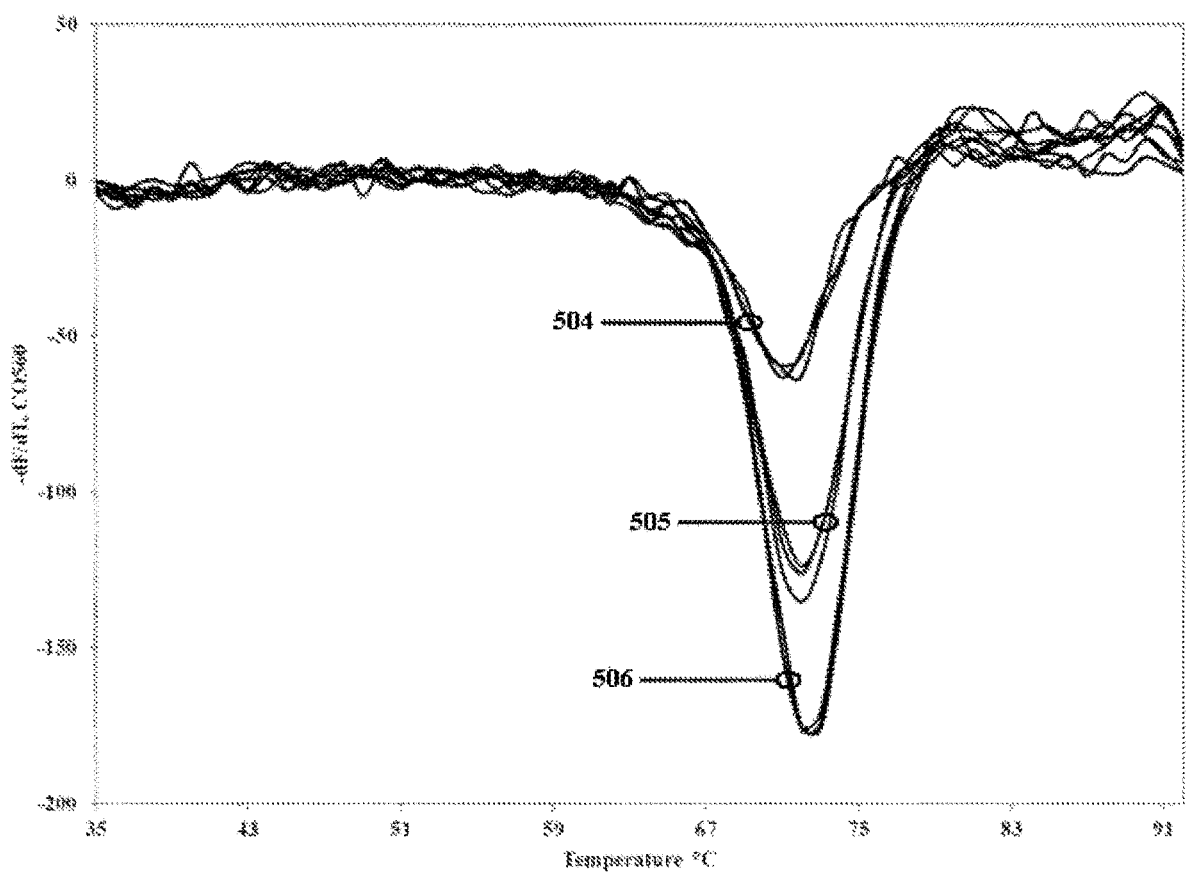
FIG. 5B is a melt curve of Reagent 2 at different concentrations.

Example 5 illustrates yet another property of Reagent1 and Reagent2. While the oligonucleotides of these two Reagents had different sequences, they both have one strand labeled with a 3' Black Hole Quencher and a complementary strand labeled with a 5'fluorophore, Cal Orange with emission maximum of 560 nm. In each case the fluorescent signal from the fluorophore-labeled strand was high at 90° C. and remained at a high level until the temperature of the reaction was lowered to approximately 5° C. above the Tm of the Reagent's double-stranded oligonucleotide. At temperatures below this level the complementary strands hybridize to each other. The fluorescent signal decreases dramatically, because the quencher-labeled strand, which is present in excess of the fluorophore labeled strand, ensures that all of the fluorophore-labeled strands became double-stranded, which in turn brings the fluorophore close to the quencher. When viewed in terms of signal intensity, hybridization of the strands is observed as a sigmoidal decrease from maximum signal to minimum signal at the temperature goes down (not shown). When viewed as the first derivative of the signal intensity, as in FIGS. 5A-B, hybridization of the strands is observed as a negative valley in curves having a slope of zero at temperatures above strand annealing and a slope of zero at temperatures below completion of strand annealing. The temperature at the lowest point of each negative valley is the measured Tm of the Reagent in the reaction mixture, at which 50% of the fluorophore-labeled strands are double-stranded. In accord with their calculated concentration-adjusted Tm's, the empirical Tm of Reagent1 is about 79° C. (FIG. 5A) and the empirical Tm of Reagent 2 is about 71° C. (FIG. 5B). The empirical Tm's are the functional Tm's of Reagents at their stated concentrations in the reaction mixture. But, the results show that the Tm's of both Reagents increase a few degrees as the concentration of the fluorescently labeled strand is increased (tested range 50 nM-150 nM). This concentration-dependent increase in Tm is consistent with the fact that calculated Tm using the nearest neighbor formula includes a correction for concentration (c) of the hybridizing oligonucleotides. Example 5 visually confirms the conclusion reached in Example 4 that only approximately 45% of Reagent2 fluorophore-labeled molecules are double-stranded at 72° C., while approximately 95% of Reagent1 molecules are double-stranded at this temperature.

The functionality of the Reagent in improving polymerase selectivity depends in part on the melting temperatures of PCR amplification products (amplicons), the melting temperature of the Reagent itself, and the particular temperatures used for particular steps in the PCR thermal cycling. For instance, if the extension temperature of reaction is carried out at 72° C., a Reagent having a melting temperature of 79° C. will be approximately 95% double-stranded at 72° C. In contrast, an equivalent amount of a Reagent having a melting temperature of 71° C. will only be approximately 45% double-stranded at 72° C. Since Taq polymerase and related enzymes only bind double-stranded molecules at the polymerase site, the "effective concentration" of Reagent having the lower melting temperature will be lower at 72° C. than that the effective concentration of the Reagent with the high melting temperature. The effective concentration of the Reagent during primer annealing and extension will also be diminished if the Tm's of the primers for their respective template strands are higher than the melting temperature of the Reagent.

Example 6 illustrates such a case. There the amplification was a two-step PCR with a combined annealing-extension step at 75° C. The Limiting Primers used in this example had an initial, concentration-adjusted Tm of about 80° C., while the Excess Primers had an initial, concentration-adjusted Tm of about 78° C. Reagent1 has a Tm of about 79° C., as noted above. Because the Tm's of the primers are so high relative to the Tm of Reagent1, the primers begin to anneal and extend on their template strands before Reagent1 becomes fully effective, as the reaction temperature is lowered from 95° C. to 75° C. during each thermal cycle. Reagent1 is about 80% double stranded at 75° C., the temperature used primer extension in this experiment. Thus, the "effective concentration" of Reagent1 when it is to function during PCR primer annealing and primer extension in Example 6 is lower than its stated concentration.

It could be argued that under these circumstances no benefit is accrued by adding the Reagent in Example 6, but this is not the case for the following reasons: 1) the Reagent can still be used as a temperature-mark (see below) to establish the extent of reproducibility among replicate reactions, and as the basis for mathematically correcting differences among replicate reactions (see below); 2) the amplitude of the Reagent's signal at its Tm still serves as a basis for internal quantitative comparison to any signal generated from any product of amplification; 3) the Reagent still has a fully effective concentration and capacity to increase polymerase selectivity at all temperatures below the temperature at which all molecules are double-stranded (that is, below about 72° C. in the case of Reagent1). This is useful because it makes it possible, for example, to lower the temperature of the reaction at any cycle in order to measure probe hybridization to a target and then, if desired, to resume amplification. In this regard, increasing the concentration of Reagent1 from 50 nM (FIG. 6A) to 100 nM (FIG. 6B) yielded reduced scatter among fluorescence signatures for the rpoB gene at temperatures from about 50° C. to about 75° C., as shown by the curves of circles 604-606 as compared to the curves of circles 601-603. This was achieved without significant inhibition of polymerase activity, as shown by the relative peak/valley heights at about 68 and 56° C. As well, increasing the concentration of Reagent1 from 50 nM (FIG. 6D) to 100 nM (FIG. 6E) yielded reduced scatter among fluorescence signatures for the katG and gyrA genes at temperatures from about 60° C. to about 75° C., as shown by the curves of circles 616-618 as compared to the curves of circles 613-615. This too was achieved without significant inhibition of polymerase activity, as shown by the relative peak/valley heights at about 66 (katG) and 55° C. (gyrA). Further increasing the concentration of Reagent1 to 200 nM increased inhibition of polymerase activity (compare peak/valley heights in FIG. 6C to those in FIG. 6B, and compare the peak/valley heights in FIG. 6F to those in FIG. 6E) without additional reduction in scatter, so we judge 100 nM concentration to be the best of the three tested concentrations.

Figure 6A:
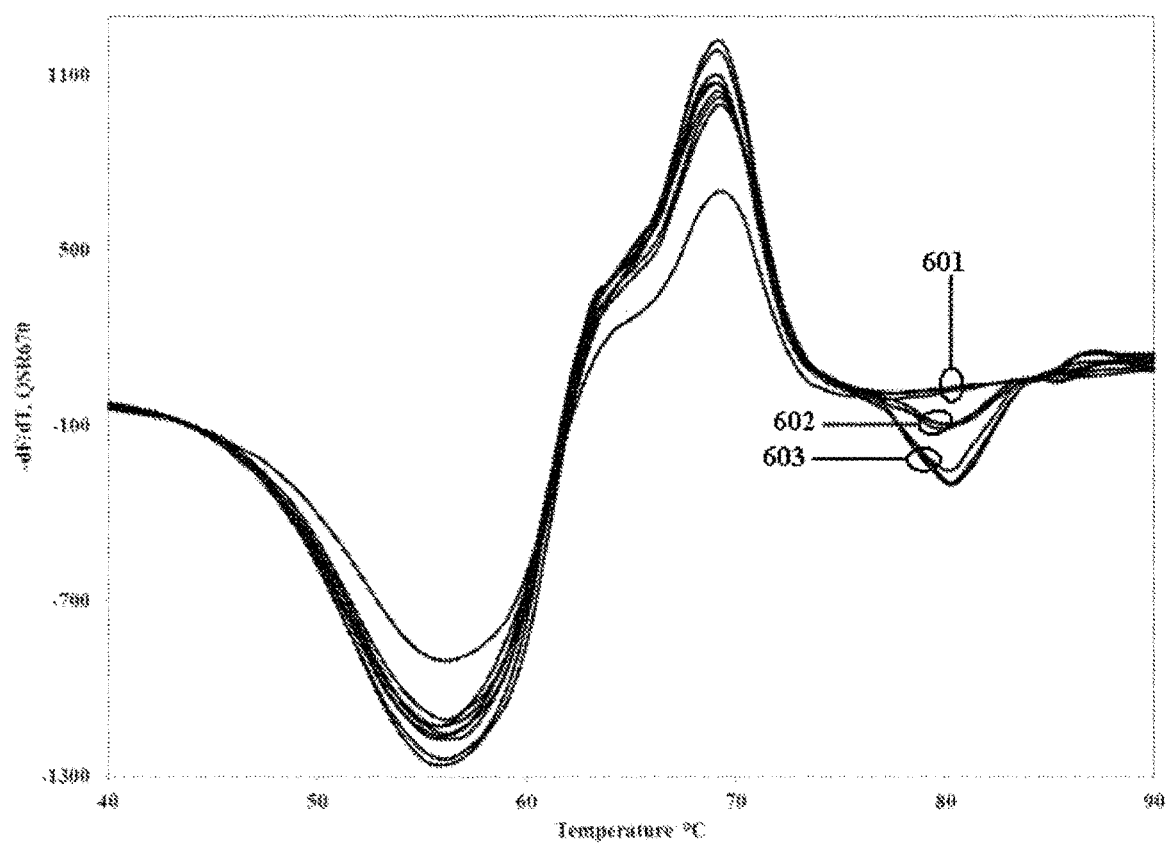
FIG. 6A is a melt profiles, derivative of fluorescence versus temperature, obtained in the multiplex assay of Example 6 with Reagent1, and shows first derivative curves for Quasar fluorescence with sub mixes 1, 2 and 3, each containing a total of 50 nM of the fluorophore strand of Reagent1.
Figure 6B:
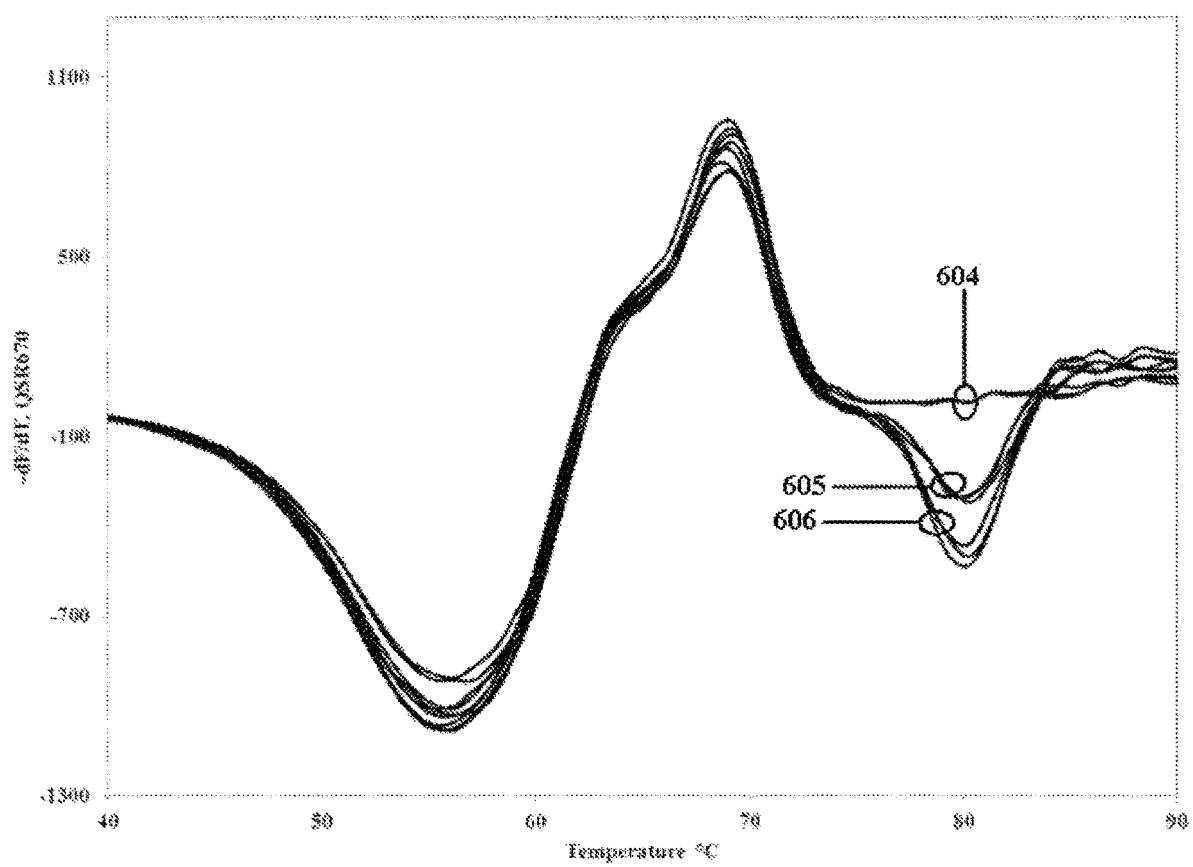
FIG. 6B is a melt profile, derivative of fluorescence versus temperature, obtained in the multiplex assay of Example 6 with Reagent1, and shows the results of sub mixes 4 (circle 604), 5 (line 605), and 6 (line 606), each with 100 nM total of the fluorophore strand of Reagent1.
Figure 6C:
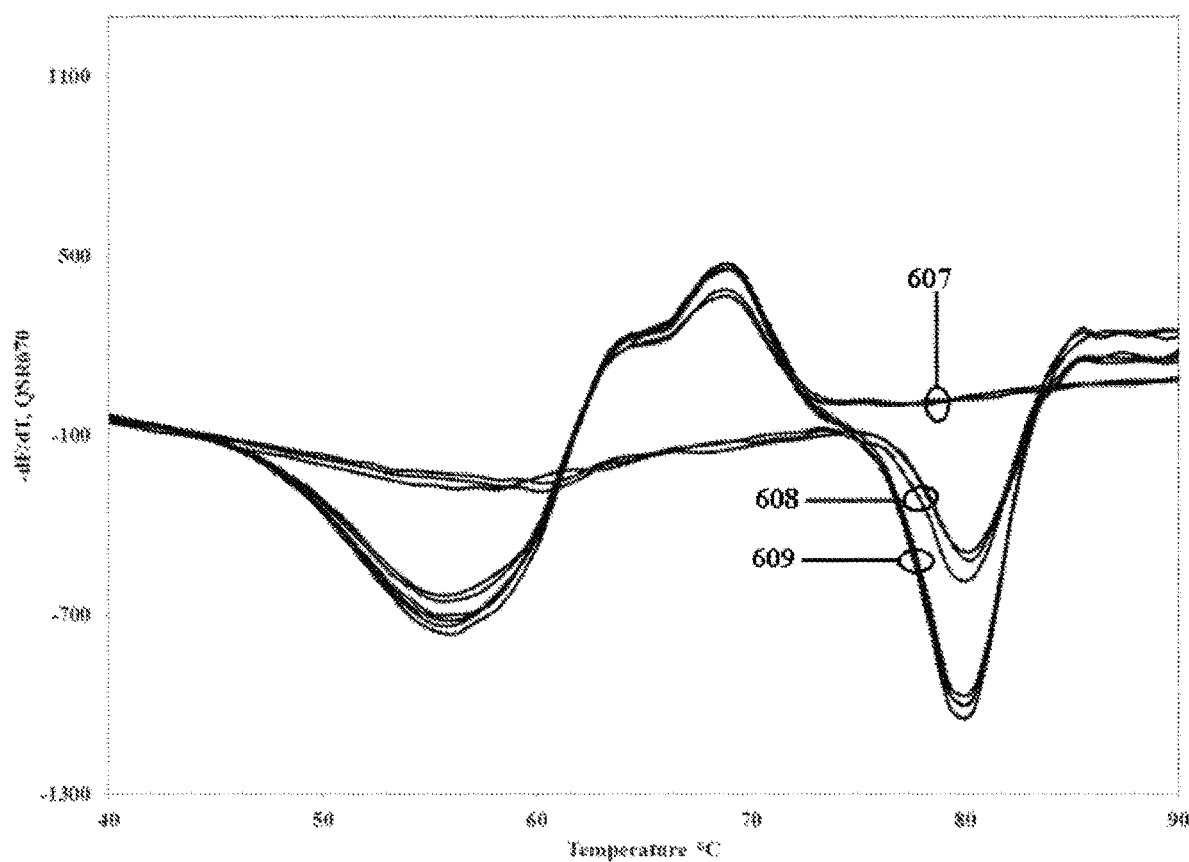
FIG. 6C is a melt profile, derivative of fluorescence versus temperature, obtained in the multiplex assay of Example 6 with Reagent1, and shows results for the highest fluorophore strand concentration (200 nM) with sub mix 7 (circle 607), sub mix 8 (circle 608), and sub mix 9 (circle 609).

Example 6, FIGS. 6A-6C, curves of circles 603, 606, 609 illustrate the use of a Reagent as a temperature marker. Reagent1 has the same fluorophore as the On probes, but it has a Tm above the temperature range of peaks and valleys in the fluorescence signature for the rpoB gene. Thus, melting of the Reagent does not affect the fluorescence signatures. Temperature markers and their use are discussed more fully below in connection with Examples 16 and 17.

The functionality of Taq polymerase and other thermal stable polymerases will also depend on the temperature-dependent properties of the enzyme itself. Thus, two different enzymes having different properties will be impacted differently by the same Reagent at the same temperature. In general, the "effective-concentration" of a particular Reagent will be higher when an enzyme with a lower thermal tolerance is used, because lower cycling temperatures are generally used with such enzymes. Example 7 describes the use of both Reagent1 and Reagent2 an assay in which Tfi (exo-) polymerase was used for amplification rather than Taq polymerase. Tfi (exo-) polymerase is a thermal tolerant polymerase from *Thermus filiformis* that has both a polymerase domain and a 5'exonuclease domain, but has been genetically engineered to have no 5'exonuclease activity. Reactions using Tfi (exo-) are best used with extension temperatures of 68-72° C., because the polymerase activity is inactivated at 75° C. With Taq DNA polymerase, we often use higher extension temperatures, for example 75-81° C.

Figure 7A:
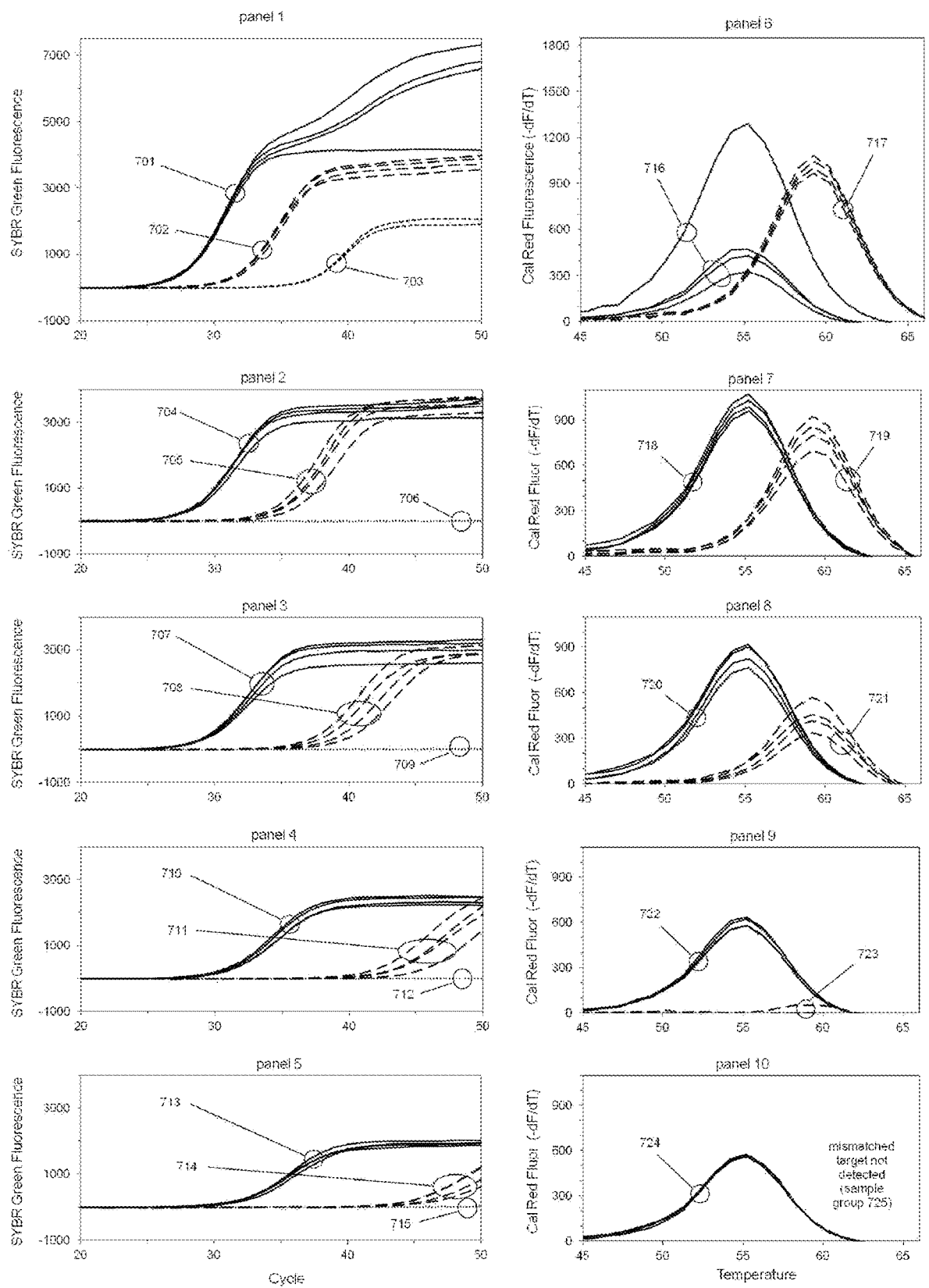
FIG. 7A presents graphs of SYBR Green fluorescence versus cycle number for each of two targets and a quantity of Reagent1 or Reagent2 in the assay of Example 7; plus melt curves of probe fluorescence from that assay.

The results of Example 7 show that addition of increasing concentrations of Reagent2 (100 nM to 150 nM to 200 nM) causes a modest decrease in amplification efficiency but a very significant increase in polymerase selectivity. Addition of 100 nM of Reagent1 achieves a similar increase in polymerase selectivity, but a slightly greater decrease in amplification efficiency. Improvements in polymerase selectivity due to the Reagents are observed in two ways in Example 7. First, addition of the Reagent increases primer specificity each time the initial template is used to start amplification, because both target strands become identical after the primer is incorporated into either initial template. For this reason the primer is perfectly matched to all subsequent copies of the template strand. In Example 7 the mis-matched target is not complementary to the primer at two locations, the nucleotide opposite the 3'end of the primer and the nucleotides opposite position 9 from the 3' end of the primer. The mis-match at the 3'end of the primer dominates primer specificity. Second, addition of the Reagent suppresses product evolution that otherwise occurs toward the end of reactions when the concentration of product strands builds up. Product evolution in LATE-PCR is evident using at least three different metrics: 1) as an unexpected increase in SYBR Green fluorescence after accumulation of double-stranded DNA has begun to plateau at the end of the exponential phase of LATE-PCR amplification; 2) as an increase in the melting temperature of the double-stranded DNA product present at the end of the linear phase of LATE-PCR amplification, visualized using SYBR Green staining; and 3) as a decrease in the amount of single-stranded DNA product present at the end of the linear phase of LATE-PCR amplification, as visualized by hybridization to a sequence specific probe. Product evolution in LATE-PCR also increases scatter among replicate reactions during the linear phase of amplification. As shown in FIG. 7A, panel 1, product evolution in Example 7 is observed in three of four replicates of the matched target/primer pair amplified in the absence of any Reagent. Product evolution is suppressed in all replicates of both targets amplified in the presence of 100-200 nM Reagent2 or 100 nM Reagent1. Product evolution is also suppressed by 50 nM Reagent1 (results not shown).

It is evident from the above discussion that optimization of polymerase selectivity requires both increased primer specificity at the beginning of amplification and suppression of product evolution toward the end of amplification. A feature of Reagents is that a single molecule can accomplish both of these tasks. A hallmark of an optimized reaction is a high level of reproducibility, that is. low scatter among replicate reactions. The data in Example 7 show that both 200 nM Reagent2 and 100 nM Reagent1 exhibit significantly reduced scatter among replicates during the exponential phase of LATE-RCR as judged by the SYBR Green plots of accumulating double-stranded DNA (FIG. 7A, panels 4 and 5). These same two samples also show very little scatter in the level of single-stranded DNA molecules produced during the linear phase of LATE-PCR amplification, as judged by melt curve analysis using a fluorescent probe (FIG. 7A, panels 9 and 10). The fluorescent probe also shows that no molecules of the mis-matched target are present in almost every sample receiving 200 nM Reagent2 or 100 nM Reagent1. The replicates with 100 nM Reagent1 are even more precise than those with 200 nM Reagent2.

Minimum scatter among replicates is a measure of polymerase selectivity and implies that all molecules in a population act in the same manner. While not wishing to be bound by any theory, it is likely in the case described here that "act in the same manner" means that all polymerase molecules bind the Reagent at a higher temperature than they bind-and-extend any mis-matched 3' ends. Because the Tm of a mis-matched primer is always lower than the Tm of the same primer to its perfectly complementary target, and the Tm of the 3' end of a product strand to some other sequence within another strand is also usually lower than the Tm's of the primers used for amplification (if this were not the case product evolution would not be a rare event), it follows that minimum scatter among replicates can best be achieved by ensuring that the concentration of the double-stranded Reagent is sufficient to bind to all the polymerase molecules in the reaction at a temperature just below the Tm of the limiting primer. In Example 7 this condition is met by adding 100 nM Reagent1. Because Reagent1 has a Tm of 79° C., it is approximately 95% double-stranded at 72° C., the Tm of the Limiting primer to its perfectly matched target. Slightly more than 200 nM Reagent2 is required because its Tm is about 71° C., which means that only approximately 45% of the molecules are double-stranded at 72° C.

Figure 8A:
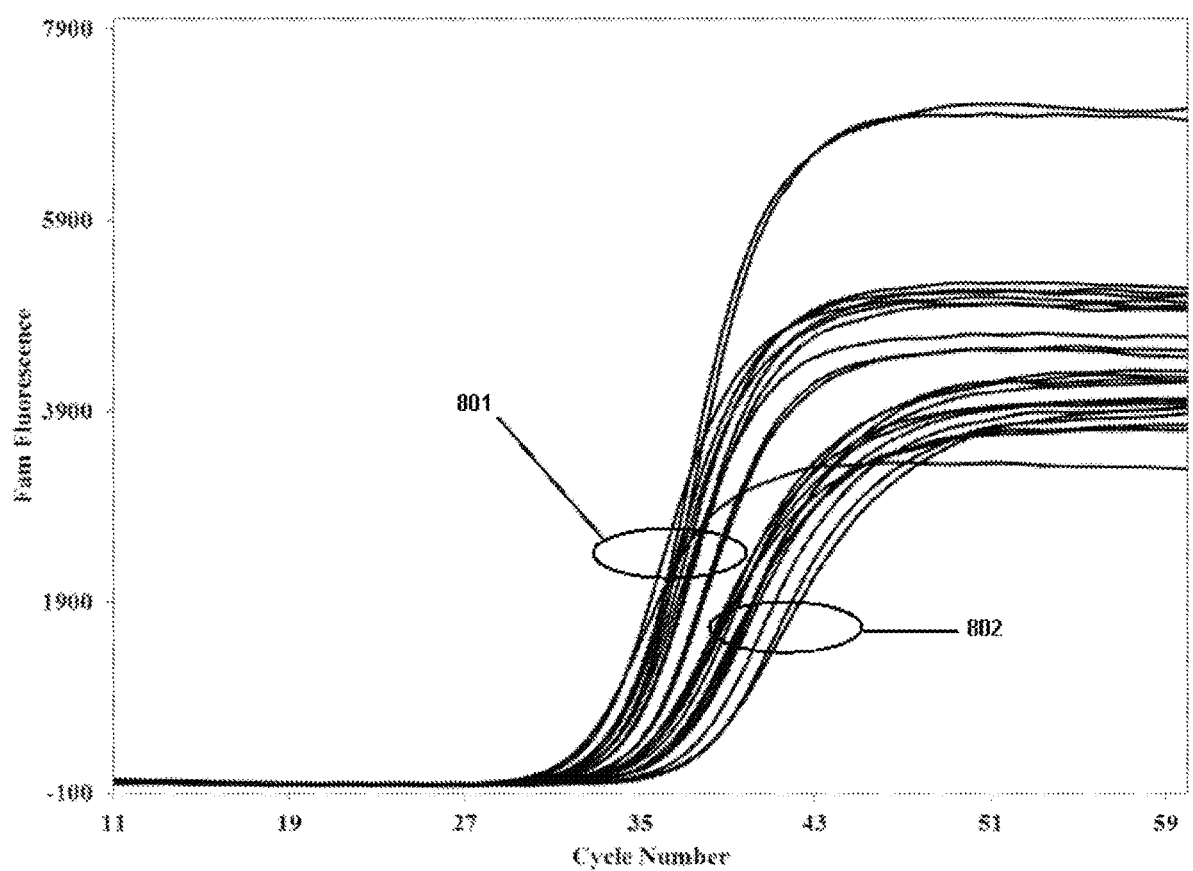
FIG. 8A is a graph of real-time SYBR Green fluorescence of samples with no reagent and samples with Reagent2 in the assay of Example 8.

Scatter among replicates is also a well know phenomenon in symmetric PCR amplifications as they approach the plateau phase of the reaction [R. G. Rutledge, Nucl. Acids Res. (2004) 32 (22): e178. doi: 10.1093/nar/gnh177]. Example 8 and FIG. 8A illustrate scatter among replicate reactions in a symmetric PCR amplification using a pair of primers used to amplify a portion of the gene that causes Tay Sachs disease [J. E. Rice et al. (2002) Prenatal Diagn. 22:1130-1134] in the absence of any added Reagent (FIG. 8A, curves of circle 801) the several samples in a set of 12 plateaued at either much higher or lower levels than most of the samples. In contrast, addition of 100 nM of Reagent2 (FIG. 8A, curves of circle 802) significantly reduced the level of scatter among all of the replicates. Reagent2 was 22 nucleotides long, with a Tm of 68° C. Both sets of reactions were analyzed in real-time using SYBR Green, which stains double-stranded DNA. Approximately 5 copies of human genomic DNA were added to each reaction, and the SYBR Green signals appeared after an average of 33-35 thermal cycles. Plateau was reached after 40 or 45 cycles, depending on whether Reagent2 was added. All of the samples incubated without Reagent2 amplified and plateaued before those incubated with Reagent2, consistent with the possibility that the reactions not containing Reagent2 were comprised of both the intended double-stranded amplicon and additional non-specific double-stranded DNA. Melt curve analysis of all samples was performed after 60 cycles. These results, FIG. 8B and FIG. 8C, confirmed that the samples incubated with Reagent2 were very similar and were free on non-specific double-stranded DNA. In contrast, all of the samples amplified without Reagent2 had some level of higher melting non-specific double-stranded DNA. The replicates amplified in the absence of Reagent2 only diverge from one another as their approached plateau levels. This demonstrates that divergence is a concentration-dependent phenomenon, in other words, it depends on relatively high levels of accumulated product strands. Divergence among replicates is not observed in samples containing Reagent2, even though the concentrations of double-stranded DNA in these samples is higher than those which diverge in the absence of Reagent2. We conclude from these results that Reagent2 increases polymerase selectivity in symmetric PCR and thereby prevents extension of mis-matched 3'ends of product strand interacting with other product strands, that is, product evolution. This result is consistent with those shown earlier for LATE-PCR amplification. We note that product evolution is easier to observe in LATE-PCR, because it causes single-stranded amplicons to become double-stranded. In contrast, in symmetric PCR double-stranded amplicons just become larger double-stranded molecules.

Example 9 demonstrates that the capacity of a Reagent to increase primer specificity depends on the extent of mis-match between the primer and a target. The extent of mis-match varies with the number, identity and location of nucleotide mismatches between the Limiting Primer and various targets. The extent of mismatch is judged using the calculated concentration-adjusted Tm of a primer to a target, based on the nearest neighbor formula. We routinely use Visual OMP (DNA Software) to estimate Tm at the oligo-nucleotide concentrations and salt concentrations of the reaction. The Tm of fluorescently labeled oligonucleotides can be similarly estimated, but preferably are empirically determined. Taq polymerase was used in Example 9, Reagent1 was added at 50 nM, primer annealing was set at 70° C., and primer extension was set at 75° C. The same Limiting Primer and the same Excess Primer were used for all LATE-PCR amplification reactions. Sequence differences among these targets were located in the complement of the Limiting Primer. Nucleotides in the several targets that are mismatched versus the Limiting Primer are underlined in FIG. 9. In reactions of this type where the same Limiting Primer is used to amplify targets having different sequences, the Limiting Primer can either be matched to one of the targets in the set, or it can be a consensus primer that is imperfectly matched to all targets. In either case, each target has its own set of matched or mis-matched bases within its sequence that is the complement of the Limiting Primer, and each imperfectly matched target is amplified less efficiently that it would be using a Limiting Primer perfectly complementary to its own sequence. The results of real-time detection with SYBR Green dye, $C_T$ values, are presented in FIG. 9. The $C_T$ values show that addition of 50 nM Reagent1 increases initial primer specificity in all cases. (In later amplification cycles all targets are amplified with the same efficiency.) Assuming an equal concentration of targets, each target therefore exhibits its own characteristic delay in amplification, which depends on the number, location, and types of base-pair mis-matches with the same Limiting Primer. These combined chemistries can be used for identification of related target variants.

Yet another manifestation of increased polymerase selectivity achieved by addition of the Reagent is enhancement of multiplexing, that is, balanced amplification of multiple products using multiple pairs of primers in the same reaction. Example 10 presents two sets of data from a triplex reaction for three targets in the human mitochondria genome. One set of data was generated in a triplex reactions containing a three-stranded version of the dabcylated reagent described in published international patent application WO 2010/104074. The second set of data was generated in a triplex reaction containing 50 nM of Reagent1. The presence of the Cal Orange version of Reagent1 was observed as a deep valley at 79° C. in the Cal Orange channel. (No such valley is observed in the reactions receiving the dabcylated reagent because this reagent does not fluoresce.) Each of the gene targets is observed as a "fluorescent signature" (see J. E. Rice et al., Fluorescent signatures for variable DNA sequences, Nucleic Acids Research Advance Access, 2012, 1-10 doi: 10.1093/nar/gks731) generated by the binding of a target specific sets of Lights-On/Lights-Off probes labeled with Quasar 670 for the HV2 target, Cal Red 590 for the CO2 target, or Cal Orange 560 for the ND1 target. The fluorescent signatures for the six triplex reactions are presented in FIG. 10, panels 1-6. The enhancement of multiplexing due to Reagent1 is observed as a significant increase in the amplitudes of the peaks and valleys of each of the three fluorescent signatures in panels 2, 4 and 6. The Cal Orange channel (panel 6), in particular, shows a significant increase in the fluorescent signature for the ND1 gene target, because very little of this gene target is generated in the absence of Regent1 or the dabcylated reagent (not shown). The dabcylated reagent only partially overcomes this problem (panel 5). However, improvement in polymerase selectivity due to Reagent1 is not limited to the ND1 gene product and, because the Reagent improves polymerase selectivity in general, it is also observed for the other two gene targets (panels 2 and 4). This overall improvement in target amplification is due to a decrease in mis-priming among the primers. As a result, the primers generate higher levels of the intended double-stranded and single-stranded gene-specific amplicons.

Figure 10:
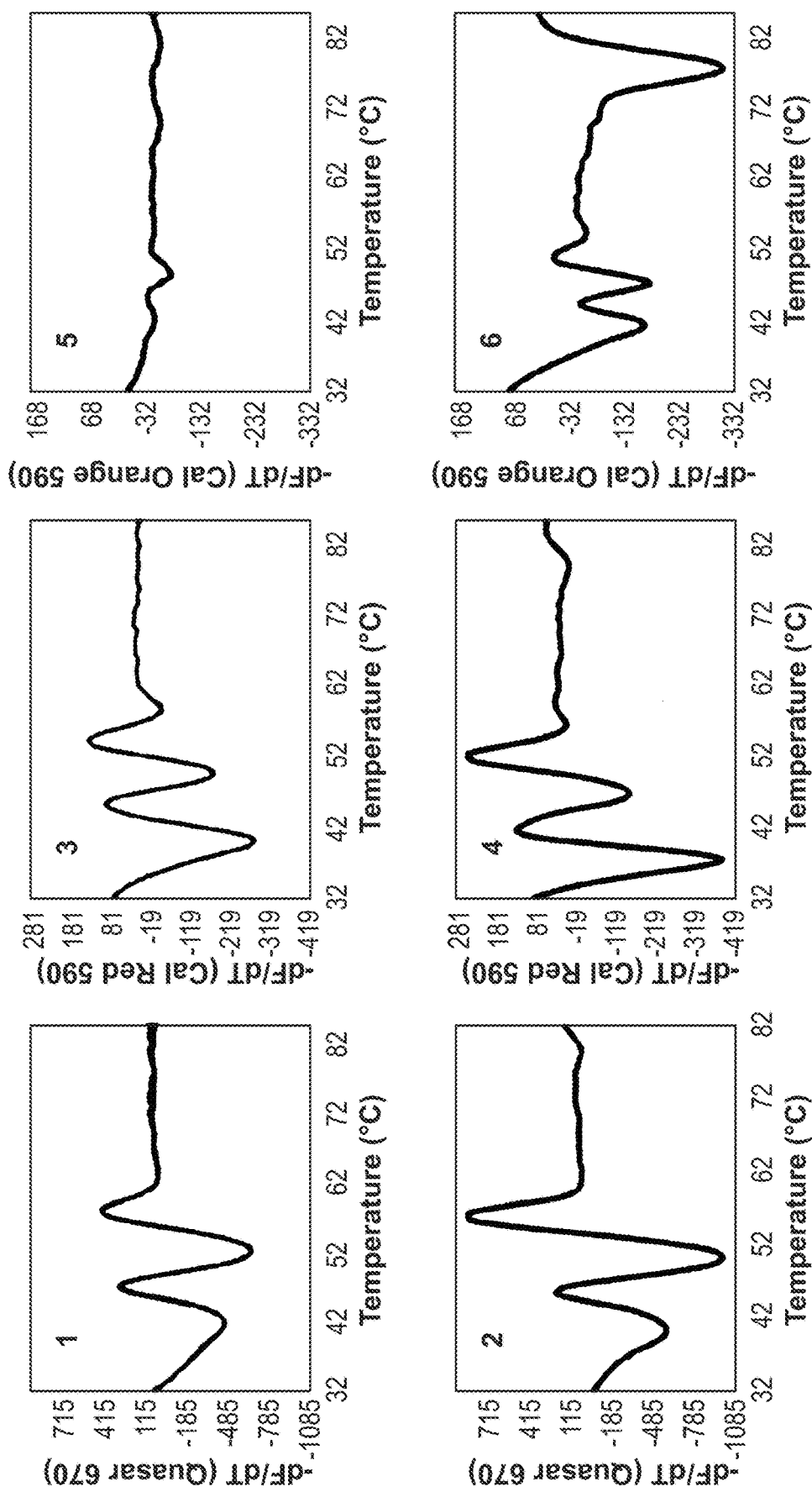
FIG. 10 presents melt profiles from multiple ON/OFF probes in the multiplex assay of Example 10 with the addition of either an additive of the prior art or Reagent1.

FIG. 10, panel 6, illustrates a fluorescent signature curve that includes a valley at about 79° C., the melting of Reagent1 at a temperature above the signature from the probes. The Tm of the Reagent can be used to normalize signature curves among samples.

Example 11 also illustrates improved multiplexing due to addition of the 50 nM of Reagent1. In this case the reaction was a single-tube reverse-transcription/LATE-PCR (RT-LATE-PCR) amplification containing three pairs of primers and probes. Two different RNA targets and a control RNA were multiplexed in the reaction presented in Example 11. The control was derived from a sequence in the bacteria phage MS2. The resulting single-stranded DNA amplicon generated a peak at 50° C. (FIG. 11B) when probed with a Cal Orange probe.

Figure 11A:
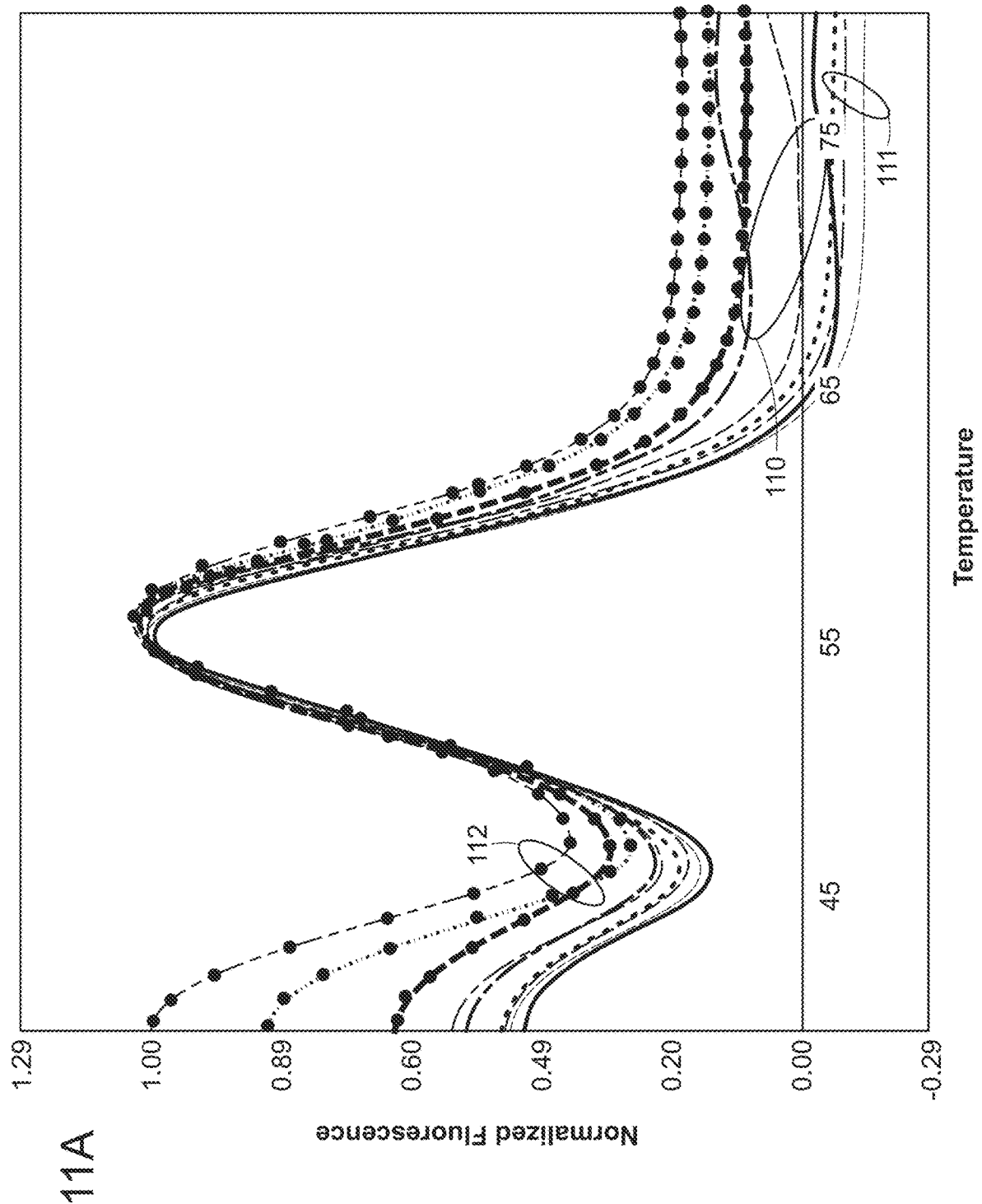
FIG. 11A present melt curves from a triplicate assay of Example 11 with no additive, with a hot-start antibody and with a hot-start antibody plus Reagent1 in the color of ON/OFF probes and in the color of Reagent1.

The target that was the subject of the assay was derived from the neuraminidase gene of human influenza virus. The amplified single-stranded product generated in the RT-LATE-PCR was probed with three probes comprised of a Lights-On/Lights-Off pair that generated a Cal Red 610 peak with a maximum at 55° C. and of another Lights-On probe, the 09N1-Os Probe, that generated a second peak, also in Cal Red, with a maximum of about 42° C. (FIG. 11A). When examined in a monoplex reaction the relative heights of the two peaks were constant, with the 55° C. peak somewhat higher than the 42° C. peak, but when examined in a multiplex the relative height of the 42° C. peak progressively diminished as more and more different primers were added, to the point of disappearing when seven primer pairs were present. Because the peak at 55° C. was always present in the multiplex reaction, the amplicon must have been synthesized. It was concluded that in the multiplex reaction in the absence of any polymerase selectivity enhancement, non-specific products must also be generated which interfere with hybridization of the low-Tm Cal Red probe.

Since the reaction mixture contains both a reverse transcriptase enzyme and a Taq polymerase, a hot-start antibody was added to the reaction mixture to establish whether blocking Taq polymerase activity during the reverse transcription step prior to amplification suppressed mis-priming and thereby increased the low-Tm signal. Addition of antibody (FIG. 11A, curves 111) did not increase the relative strength of the low-Tm signal. But, addition of 50 nM Reagent1 plus the antibody (FIG. 11A, curves 112) did boost the height of the low-Tm peak relative to the height of the high-Tm peak. This result provides additional evidence for improved multiplexing achieved by the Reagent. In this case the improvement in polymerase selectivity was seen in the Cal Red channel while, as expected, the added Reagent1 was observed as sharp negative peak in the Cal Orange channel with its characteristic Tm of 79° C.

As one versed in the art will appreciate, the above discussion assumes that all replicate reaction are homogeneous, closed-tube, and perfectly reproducible. Homogeneous means detection that does not require separation of bound (hybridized to target) fluorescently labeled primers or probes from unbound primers or probes. Closed-tube means, among other things, that the reaction vessel does not experience evaporation over the course of PCR amplification, since evaporation will increase the concentrations of non-volatile ions. Perfectly reproducible means, among other things, that all replicate reactions have the same composition of monovalent and divalent ions, as well as the same levels of other small molecules in the reaction master mix. Ideally, reproducible reaction conditions means, among other things, that the same heating and cooling conditions exist at all positions in a multi-well device.

In reality, some reactions are carried out in multi-chambered devices, including microfluidic devices that allow for changes in chemical compositions during the course of a reaction. Some closed-tube reactions vessels leak or allow evaporation to occur. Many reactions are intentionally or unintentionally prepared using different concentrations of salts, buffers, and other chemical components from time to time. And in reality, not all positions in a multi-vessel device are identical, even in devices that rotate. All of the above variations alter enzyme functions and thereby alter the kinetics of a reaction.

The Reagents according to this invention generate a fluorescent signal at a known temperature, best viewed as a melting (or annealing) valley (negative peak) in a first derivative fluorescence curve, hereafter refer to as a "temperature mark". For that reason a Reagent can serve as an internal temperature standard in every reaction. The temperature mark reveals variations and differences among reactions. Such a temperature mark has three, independent values: 1) the depth of its "valley" is characteristic of the amount of the Reagent added to the reaction; 2) the temperature at which its "valley" reaches its lowest value is the empirical Tm of the Reagent; 3) the width of the valley at "half depth," is a measure of of the temperature-dependent process of double-strand/single-strand formation and melting of the Reagent.

Each of the above temperature-mark properties is expected to be a constant property of the corresponding Reagent(s) in identical replicate reactions. This is the case because the Reagent(s) is not amplified or degraded during the course of the reaction. Therefore, differences in one or more temperature-mark properties in replicate reactions provides evidence of non-uniformity among replicates. These temperature mark properties can also be used to mathematically correct for non-uniformities among replicate reactions, as well to quantify amplified products in a reaction relative to the temperature marks of the non-amplified Reagent(s).

As one versed in the art will appreciate, it is also possible to utilize in a PCR amplification reaction two different Reagents having non-cross-hybridizing oligonucleotide sequences for their double-strands that have significantly different Tm's, for instance Reagent2 with a Tm of 71° C. and Reagent3 with a Tm of ~50° C. Said non-cross-hybridizing Reagents can be labeled in the same color or in different colors. It is preferred to label both Reagents in the same color, for instance FAM, so that in the absence of any other probe/target hybrids the same color. Under these circumstances a melt curve over a broad temperature range has two valleys when expressed as a first derivatives and the distance between the lowest points in these two valleys, in this example, is 21° C. (71-50). Construction of two widely different temperature marks is advantageous, because the distance between the two marks is known in advance and can be used to guarantee that every reaction spans the same range of temperatures.

After any number of desired thermal cycles a ratio of fluorescent intensities can be constructed: sample signal/temperature-mark signal. Since the temperature-mark signal is the same in replicate reactions, calculation of the above ratio provides a quantitative measure of the amount of accumulated product after the chosen number of thermal cycles. And, if a standard set of ratio values is first constructed using known numbers of target copies at the start of amplification, the observed ratio from the experimental sample can be used to establish the target copy number in the original sample.

The Tm of the Reagent is a property of the Reagent, and it is generally known. The observed Tm of the Reagent in an experimental sample can be compared to its Tm in other samples and to the expected Tm of the Reagent. Differences among the Tm's of samples in a set provide evidence of sample-to-sample variation in the system. A consistent difference between the Tm's of all samples in a set and the expected Tm of the Reagent indicates that the composition of the reaction mixture has caused an across-the-board change in the hybridization conditions of the system.

Replicate assays performed at the same time, or at different times in a manner as identical as possible, are nevertheless sometimes observed to be non-identical. This is the case even when a large batch of a particular master mix is prepared, aliquoted, and tested as replicates. Preparation of different batches of the same master mix also can be non-identical, and master mixes having different formulas inevitably display differences. In particular, the concentrations of monovalent and divalent cations, as well as certain polar molecules, are frequently different in different master mixes. Differences among replicates also arise due to machine and tube errors. For instance not all wells in a plate or rotor may be heated and cooled identically and not all tubes in a set may be tightly sealed. Partial evaporation of a sample during repeated cycles of heating and cooling increases the concentrations of all of the non-volatile chemicals in a "closed-tube" reaction. In addition, inclusion of a protein in a reaction mixture, such as a hot start antibody, frequently brings with it unknown amounts of ions and other proprietary chemistries.

The data presented in Example 12 illustrate that the temperature mark of a reagent can be measured repeatedly during the course of an amplification reaction, for instance at the beginning, the middle, and the end. The results show that the temperature-mark is highly reproducible, being the same after 0, 30, and 60 thermal cycles.

Example 13 provides a non-exhaustive set of causes for variations among replicates that we have observed using the temperature mark of at least one Reagent. In most cases variations among replicates are observed as shifts in the temperature mark to either a higher or lower temperature by an amount in excess of 0.5° C. These shifts are in accord with differences in the ionic strength of the reaction mixture. In general, higher ionic strengths stabilize hybridized strands and therefore increase the Tm of the temperature mark. As discussed above in connection with Example 5 and FIGS. 5A-B, 2-3 fold differences in the concentrations of a Reagent alter the temperature mark of that reagent in accord with the nearest neighbor formula for calculating Tm values prior to the start of a reaction, but changes of this nature are usually intentional. In contrast, unintended slight differences in the amounts of a Reagent of known composition to replicate reactions cause slight variations in the amplitude of the signal at a fixed temperature.

Hotstart polymerases, compositions in which a regular polymerase is modified by, for example, antibodies, alkylating groups, or modified trinucleotides, are used in conjunction with all forms of PCR. A hotstart modification blocks or inhibits polymerase activity prior to the first melting step of the first thermal cycle. They thus prevent mis-priming at a time when the reaction mixture is being prepared and the primers are present with the polymerase at a temperature far below their Tm's. All types of hotstart reagents are intentionally irreversibly inactivated during the first one, or first few (in the case of some modified trinucleotides) strand melting steps of PCR thermal cycling. Because the Reagent enhances polymerase selectivity and primer specificity as described above, the Reagent can be used as a substitute for conventional hotstart reagents. In this capacity the Reagent (or combination of Reagents) is not intentionally irreversible inactivated after the start of amplification. Rather it is active or inactive in a temperature-dependent manner corresponding to the extent to which it is double-stranded. Moreover, when used in this capacity, a Reagent (or a combination of Reagents) does not inhibit polymerase activity in the same manner as a traditional hotstart reagent. Rather the Reagent (or combination of Reagents) inhibits 5'exonuclease activity and thereby severely constrains polymerase activity to extension of perfectly matched primer/target interactions, thereby guaranteeing that synthesis of non-specific products is not initiated prior to the first melting step of the first thermal cycle.

Use of a single Reagent as a substitute for hotstart can be bolstered by addition of 100-500 nM of a double-stranded oligonucleotide that is dabcylated on three to four of its terminal nucleotides as describe previously in published international patent application WO 2010/105074. Both of the complementary strand sequences of such a multi-dabcylated molecule are designed to not cross hybridize to any of the primers or Reagents in the reaction. The melting temperature of said multi-dabcylated reagent is set low enough, preferably at least 30° C. but below the primer Tm's and more preferably below the annealing temperature, to guarantee that it does not inhibit primer binding and extension for correctly matched primer/target pairs. Example 14 illustrates such a case in which Reagent1 has been used in combination with 500 nM of a double-stranded oligonucleotide that is 22 nucleotides long, is modified by 4 terminal dabcyl groups, and has a Tm of 67° C., which is below the primer Tm's and 8° C. below the annealing/extension temperature. The amplification reaction contained 10, 100, or 1,000 M. tuberculosis genomes of DNA, along with 20,000 copies of human genomic DNA to increase the possibility of mis-priming if various additives proved unable to prevent mis-priming. One pair of primers for the rpoB gene target in M tuberculosis was used for amplification, together with two pairs of Lights-On/Lights-Off probes.

Figure 14A:
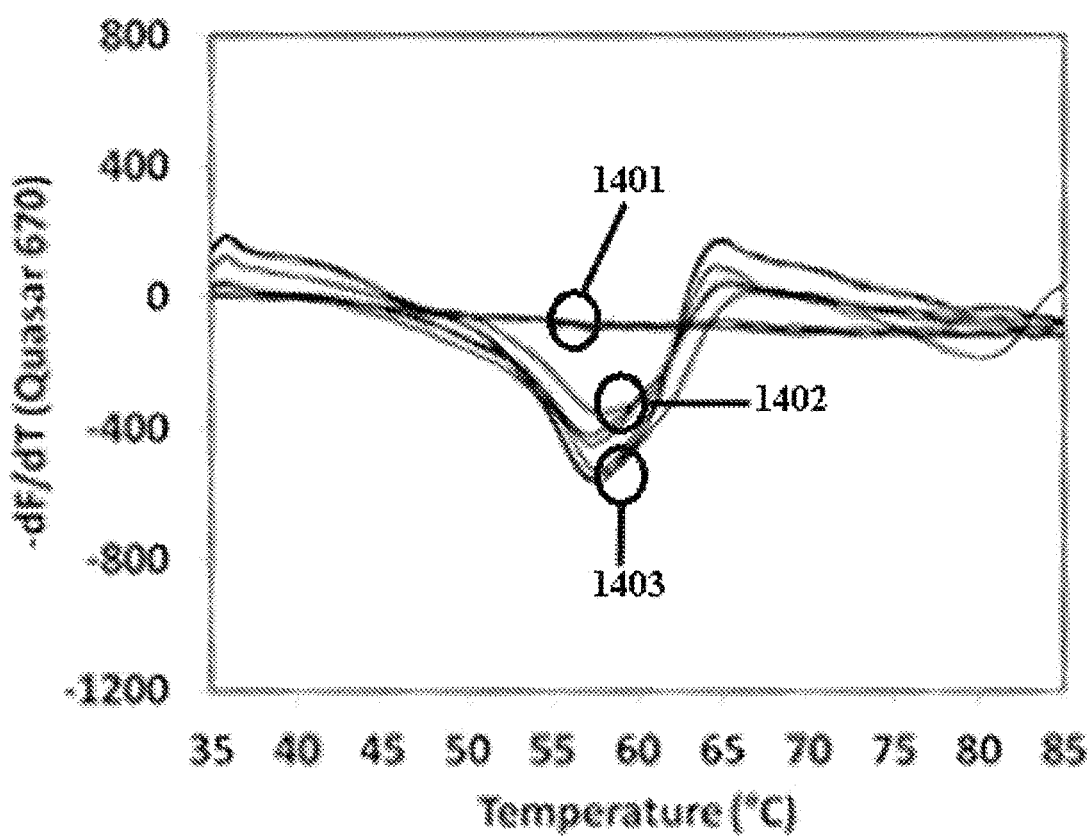
FIG. 14A present melt curves from the assay described in Example 14 for samples with varying amounts of template DNA and either regular Taq polymerase or antibody-Taq polymerase plus either no reagent, a dabcylated, double-stranded additive, or the dabcylated, double-stranded additive and Reagent1.
Figure 14B:
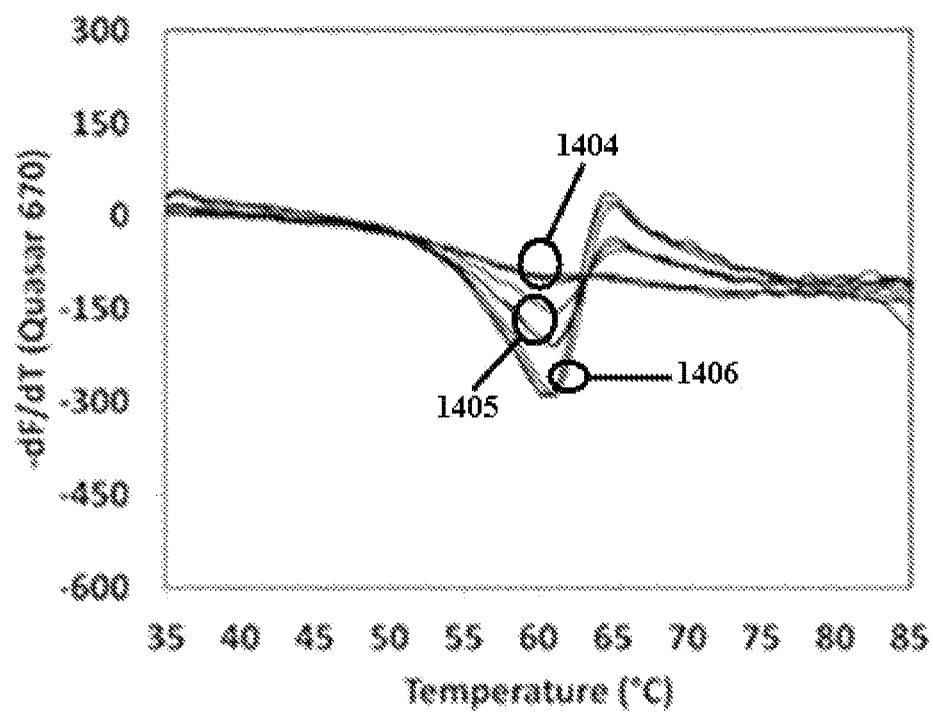
FIG. 14B shows melt curves from the reactions with regular Taq plus the dabcylated additive, where circle 1404 denotes the replicate curves for 10 copies of template DNA, circle 1405 denotes the curves for 100 copies, and circle 1406 denotes the curves for 1000 copies.
Figure 14:
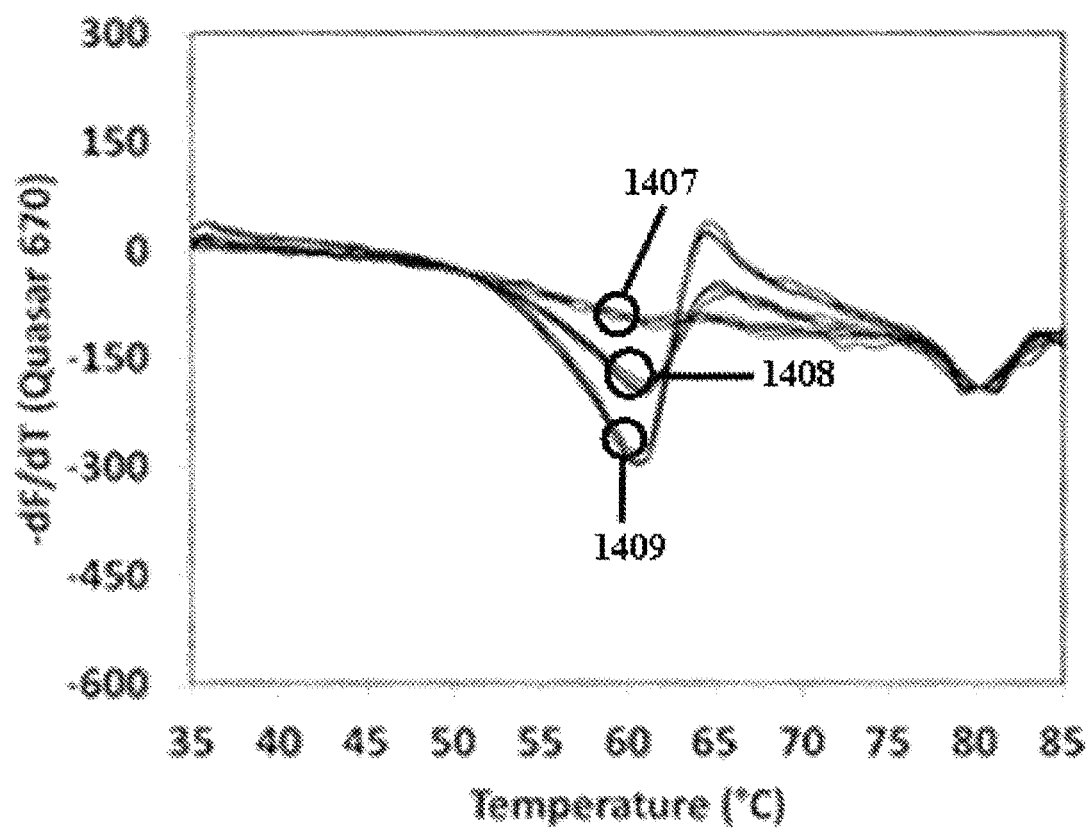
FIG. 14C presents melt curves from the reactions with regular Taq plus both the dabcylated additive and Reagent1, where circle 1407 denotes the replicate curves fo 10 copies of template DNA, circle 1408 denotes the curves for 100 copies, and circle 1409 denotes the curves for 1000 copies.
FIG. 14D presents melt curves from the reactions with antibody Taq and no additive, wherein circle 1410 denotes the replicate curves for 10 copies of template DNA, circle 1411 denotes the curves for 100 copies, and circle 1412 denotes the curves for 1000 copies.
FIG. 14E presents melt curves from the reactions with antibody Taq and no additive.
FIG. 14F presents melt curves from the reactions with antibody Taq plus both the dabcylated additive and Reagent1, where circle 1416 denotes the replicate curves for 10 copies of template DNA, circle 1417 denotes the curves for 100 copies, and circle 1418 denotes the curves for 1000 copies.
Figure 14:
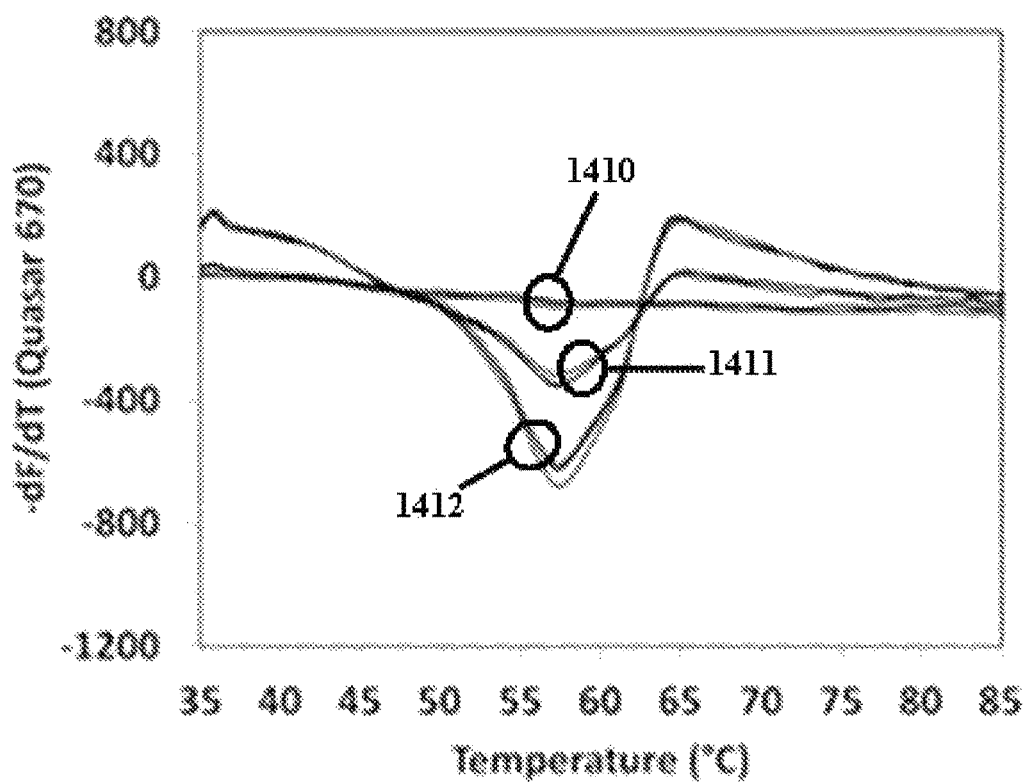

The results in Example 14, FIGS. 14A-C are the products of replicate reactions in which one unit of Taq polymerase per 25 µl was used without a hot start antibody. In contrast, FIGS. 14D-F had an added hot start antibody. FIG. 14A compared to FIG. 14D has more variability among replicate reactions (see region of arrows 1 and 1', 2 and 2') analyzed after 35 cycles of amplification. This variability is due to mis-priming errors prior to the start of amplification in the absence of the antibody. FIGS. 14B and E contained 500 nM of the 22 bp oligonucleotide modified with 4 dabcyl groups but no Reagent1. Comparisons of FIGS. 14B and A, and FIGS. 14E and D illustrate that the presence of the modified oligonucleotide altered the fluorescence pattern of the probe/target hybrid (particularly in the region of arrows 2 and 2'). This shows that the modified oligonucleotide functions to prevent mis-priming prior to and during amplification. FIGS. 14C and F contained 500 nM of the 22 bp oligonucleotide modified with 4 dabcyl groups, plus 75 nM of Reagent1. Comparisons of FIGS. 14B and C, and FIGS. 14E and F illustrate that Reagent1 further reduces scatter among replicate reactions. In addition, comparison of FIGS. 14F and C illustrates that the hot start antibody does not significantly improve the similarity of the replicate reactions at each of the three target levels: 10, 100, and 1000 copies of M tuberculosis genomic DNA. Taken together these results demonstrate that a Reagent combined with a double-stranded oligonucleotide with multiple dabcyls and a Tm below that of the primers exhibit both improved primer selectivity and hot start-like activity.

Example 14 further illustrates the benefit of combining 500 nM of the 22 bp oligonucleotide modified with 4 dabcyl groups with 75 nM Reagent1 after 35 thermal cycles. Comparison of FIGS. 14C and B and FIGS. 14F and E illustrates that the two reagents work together to further improve the accuracy of amplification. Also, the temperature mark at about 80 degrees that is generated by Regent1, FIGS. 14C and F, can be used to normalize the fluorescent signals at all other points.

Example 15 illustrates that Reagent2 used in combination with a hot start antibody improves the reproducibility of replicate reactions as compared to antibody alone. Example 15 also illustrates that Reagent2 used alone is as good as antibody used alone to achieve hot start suppression of mis-priming.

Example 16 illustrates the use of two Reagents having different Tm's. Both Reagents were labeled in the same fluorescent color, and the reaction was carried out in triplicate. The result is generated by plotting the first derivative of fluorescence as a function of temperature and displays two temperature marks in the same fluorescent color. The empirical Tm of the lower temperature mark is about 52° C. and of the higher temperature mark is about 66° C. As one versed in the art will appreciate, the number of degrees C. between these two marks could be increased (or decreased) by altering the base-pair composition of the corresponding Reagents. For instance, the lower temperature mark could remain at 52° C. and the higher temperature mark could be moved to 79° C. by using Reagent1. As one versed in the art will further appreciate, one or more additional fluorescent signals could be added to such a two-mark plot. For instance, an amplifiable target could be probed in the same color, and the probe/target hybrid could be designed to generate a positive first derivative peak between the temperature marks of the two non-amplifiable Reagents. In this case the amplitude of said peak of the amplified target relative to the unchanged depth of the valleys of the two non-amplified Reagents would increase in proportion to the amount of the amplified product. In the case of a LATE-PCR assay this signal would increase as a function of the amount of the single-stranded amplicon generated. Such a signal could be included in a reaction as an internal amplifiable control, as compared to the internal non-amplifiable controls provided by one or more Reagent(s).

Hot-start-like activity can also be achieved using two Reagents, in which case two different temperature marks are also generated over the full temperature range. For instance for 25 µl reactions containing 1.25 units of Taq polymerase, a first combination can be comprised of Reagent3 (Table 1) mixed with Reagent4 (Table 1) to provide a first temperature mark at approximately 67° C. and a second temperature mark at approximately 52° C., depending on the concentration of each Reagent in the range of 50-300 nM. It is preferred that both Reagent3 and Reagent4 be labeled with the same fluorophore, for instance FAM, as illustrated in Example 16. A combination of Reagent3 and Reagent4 can be used with an annealing/extension temperature of, for example, 75° C. A second useful combination of Reagents is comprised of Reagent2 (Table 1) with Reagent4. This combination of Reagents can be used, for example, with an annealing temperature of about 60-65° C. and an extension temperature of 72° C. The Reagent with the lower temperature is designed to have a functional Tm 5° C. or more below the annealing temperature of the reaction and will therefore only become double-stranded below the annealing temperature. It will serve to increase polymerase selectivity and primer specificity, as well as inhibit 5'exonuclease activity at low temperatures, including those used prior to amplification or during low-temperature fluorescence acquisition at any cycle in the course of amplification (for example, detection of a low Tm probe or melt analysis) or at the end of amplification. The two temperature marks generated by the two Reagents can also be used to establish the reproducibility of the thermocycler being used for amplification, as explained below.

Single and double temperature marks provide not only a means for visually adjusting fluorescent signatures of samples for comparison to a library of curves from known samples, but they also provide the starting point for mathematical analysis of melt/anneal curves in all colors in a single sample. A fluorescent signature obtained from an amplified sample using multiple Lights On/Lights-Off probes can be compared by hand to a library of curves obtained from known samples, as disclosed in published international patent application WO 2011/050173. When hand comparison is utilized, variations in the Tm's of peaks and valleys between a reference curve and the curve from a sample containing the same target are easily overcome by sliding one curve to the left or right until they match. For mathematical analysis by a computer, manual sliding of curves is not possible. For mathematical analysis, therefore, use a set of algorithms as illustrated in Example 17 and FIGS. 17A-C. Steps in the analysis are designed to achieve the following: 1) Verify that the shape of the temperature mark "peak" or "valley" (depending upon sign) fits a Gaussian or skewed Gaussian curve in accord with predetermined properties of the Reagent; 2) Establish a calculated temperature mark for the Gaussian curve, which is referred to here as the "observed Tm," OTM, for the empirically measured thermal mark in the particular sample; 3) Develop a temperature-adjustment-value, TAV, which corrects the OTM in each sample to a pre-determined standard-OTM for that Reagent (a TAV can be based on the OTM of a single Reagent, or on a high/low temperature pair of OTM's from two Regents); 4) Use the TAV for a sample to adjust each empirically measured degree of temperature to a corrected temperature. 5) Normalize the fluorescence signals on all channels used to detect probe fluorescence so they are between 0 and 1, using the lowest temperature and highest temperature values as the 0 value and 1 value, respectively, so that we can examine the shape of the melt curves without regard to the abundance of the material; 6) Compute the 1st and 2nd derivatives to highlight the signal pattern or patterns related to the lights ON/lights OFF binding. 7) To evaluate an unknown sample, we calculate the temperature-averaged error (such as the squared error) between the 1st or 2nd derivative, normalized melt curve of the unknown sample and a database of known samples; we consider the known sample with the lowest error to be the best match for the unknown sample.

EXPERIMENTAL

In the Examples that follow, concentrations of reagents and Reagents are sometimes characterized by a single number, for example, 50 nM. When that is done, the concentration number refers to the concentration of the forward strand, meaning the top strand in Table 1. As explained above, the complementary strand (the bottoms strand in Table 1) is often added at a higher concentration, particularly when, as in Reagent1, the forward strand is labeled with a fluorophore and the bottom strand is labeled with a quencher. The concentration of double strands is determined by the lesser concentration of the forward strand, when the reverse-strand concentration is greater.

Example 1

Molecular Modeling of Dabcyl/Taq Interactions

Methods

X-ray crystallography is the method of choice to understand reagentB (no dabcyls) or reagentD (two dabcyls), both shown in Table 1, interactions with Taq polymerase.

Experiments along these lines have not yet yielded crystals. In the interim, we have chosen to use the known crystal structure of Taq polymerase and a docking program to calculate how 3' and 5' dabcyl moieties are best fitted to a portion of the polymerase domain (the polymerase catalytic site, or "poly site", 105 in FIG. 1A) and portion of the 5'exonuclease domain (the 5'exonuclease catalytic site, or "5'exo site", 105 in FIG. 1A) of Taq, The protocol for generating a GLIDE score is a program suite from Schrodinger: a user interface called Maestro, and a specific program used for docking is GLIDE (Grid-based Ligand Docking with Energetics. Glide Score (G Score) is given by:

$$G\ Score = a*vdW + Coul + Lipo + Hbond = Metal + BuryP + RotB + Site,$$

where
vdW=van der Waals energy
Coul=Coulomb energy
Lipo=Lipophilic contact term
HBond=Hydrogen-bonding term
Metal=Metal-binding term
BuryP=Penalty for buried polar groups
RotB=Penalty for freezing rotatable bonds
Site=Polar interactions in the active site'
and the coefficients of vdW and Coul are:
a=0.065, b=0.130 fpr Standard Precision (SP) Glide The GLIDE software essentially looks at all of the interactions between a docking molecule (a dabcyl) and a protein molecule (Taq polymerase), and computes the best interactions that have the lowest interaction energy. Interactions of the protein and the small molecule are defined in a three dimensional docking space and the program computes a GLIDE score based on these interactions. The more negative the GLIDE score the better the interactions between the Taq and the molecule. Unfortunately, in the program GLIDE, the size of the small molecule is limited. Therefore we restricted our analysis to either the 3' or the 5' nucleotide phosphate linked to the corresponding dabcyl moiety. The four GLIDE scores for the best interactions were generated: 3' dabcyl C phosphate at poly site, 5' dabcyl G phosphate at poly site, 3' dabcyl C phosphate at 5'exo site, and 5' dabcyl G phosphate at 5' exo site.

Results

3' Dabcyl C Phosphate at Poly Site

The 3' dabcyl C phosphate docked into the polymerase site of Taq with a docking score of −8.08, which indicates good fit. The 3' dabcyl sticks into the catalytic site, while the C phosphate remains near the entrance to the site. It is also closer to the thumb part of the polymerase.

5' Dabcyl G Phosphate at Poly Site

The 5' dabcyl G phosphate docked into the polymerase site with a GLIDE score of −4.84, indicating moderate binding. The 5' dabcyl sticks into the site while the G phosphate remains near the entrance to the poly site. It is closer to the fingers part of the polymerase 3' Dabcyl C Phosphate at 5'Exo Site The 3' dabcyl C phosphate docked into the 5' exo site with a GLIDE score of 10.03, indicating tight binding. The 3' dabcyl sticks into the site while the C phosphate remains near the entrance to the 5' exo site. The molecule fits within the single strand channel, which lies on the underside (FIG. 1A) of the 5' exo part of the polymerase.

5' Dabcyl G Phosphate at 5' Exo Site

The 5' dabcyl G phosphate docked into the 5' exo site with a GLIDE score of −5.33, which indicates moderate binding. The 5' dabcyl sticks into the site while the G phosphate remains near the entrance to the 5' exo site. The molecule fits within the single strand channel, which lies on the underside (FIG. 1A) of the 5' exo part of the polymerase. Regarding the spatial relationship between the 5' dabcyl G and the 5' exo site of the Taq polymerase, the 5' dabcyl G phosphate is beautifully contoured to the channel in the space-filling structure. Regarding the space-filling structures of the 5'exo site, only one of the 5' dabcyl G phosphate and the 3' dabcyl C phosphate can be bound to the 5' single stranded exo channel at a time.

Discussion

Figure 1B:
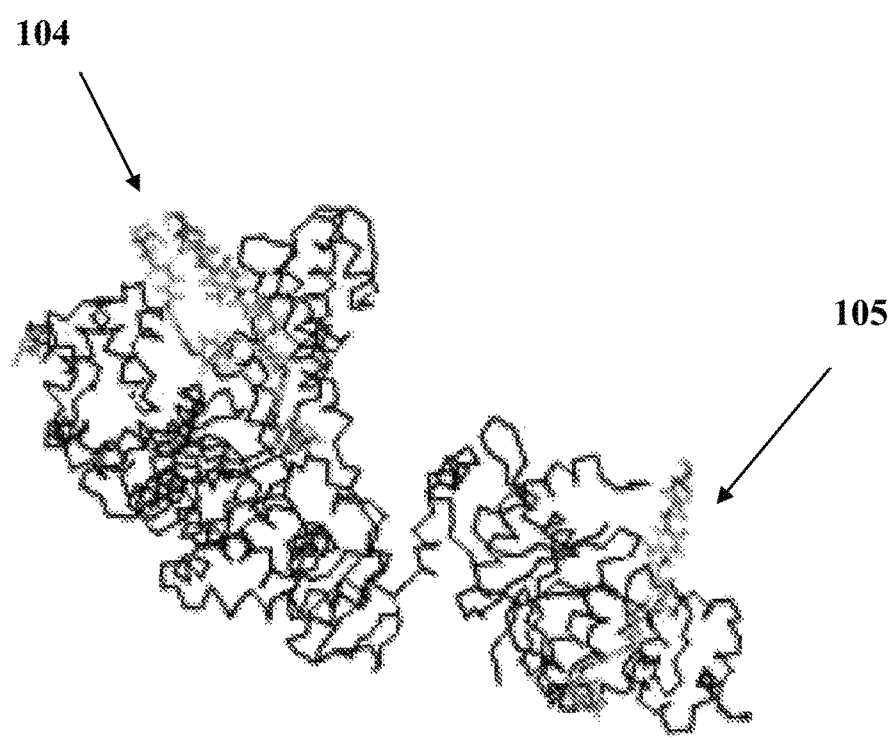
FIG. 1B shows a computer model of that structure wherein both the poly site and the 5' exo site are filled with dabcyl.

The results of the docking program GLIDE show that both the 5' dabcyl G phosphate and the 3' dabcyl C phosphate have reasonable binding GLIDE interaction scores for both the poly and 5' exo sites of Taq polymerase. FIG. 1A shows a structure of the Taq polymerase with nothing docked into it. We note that there is a structure of Taq polymerase with both the 3' dabcyl C phosphate and the 5' dabcyl G phosphate docked into the poly site, since both are able to fit into the double stranded site at the same time, thus completely blocking site. This would occur when there is a very high concentration reagentB or reagentD, thereby shutting down polymerase function. FIG. 1B shows both the poly catalytic site 104 and the 5' exo catalytic site 105 filled with either a 3' dabcyl C phosphate or a 5' dabcyl G phosphate. Both fit well into the 5' exo channel. All of the docking results show that at certain dabcyl concentrations the 5' exo site will be blocked by either a 3' dabcyl C phosphate or a 5' dabcyl G phosphate, which implies that reagentB or reagentD at low concentrations will inhibit the 5' exonuclease activity.

Example 2

A Primer-Independent Oscillating-Temperature Assay for Evaluating Inhibition of 5'Exonuclease Activity Taq DNA polymerase has the capacity to cleave the fluorescently labeled nucleotide on the 5' end of an oligonucleotide probe that is hybridized to its target strand. This 5'exonuclease cleavage even occurs under isothermal conditions in the absence of extension of an upstream primer. It is therefore primer-independent cleavage, in contrast to primer-dependent cleavage that takes place in standard 5' nuclease amplification reactions. We have found that the rate of primer-independent 5'exonuclease cleavage is increased by oscillating the temperature of the reaction mixture over a limited temperature range above and below the Tm of the probe/target hybrid.

Oscillation reactions were carried out in 25 µl volume consisting of 1×PCR buffer (Invitrogen, Carlsbad, Calif.), 3 mM MgCl$_2$, 200 nM dNTPs, 1.25 units of Taq DNA polymerase (Invitrogen, Carlsbad, Calif.), 200 nM of a probe having a 5'FAM and a 3' Black Hole Quencher 1 (BHQ1), and 100 nM of a complementary 41-nucleotide long, perfectly complementary target. This reaction mixture was used without any reagent additive, as well as with varying concentrations (50 nM, 100 nM, 150 nM) of certain reagents identified in Table 1. With reference to Table 1, the reagent additives were: reagentA; reagentC; and Reagent1, wherein the fluorophore, F, was Cal Orange 560 (FIG. 19) and the quencher, Q, was Black Hole Quencher 2 (FIG. 18). Each added reagent was double-stranded and all had the same forward and complimentary reverse nucleotide sequences. As shown in Table 1, reagentA had only 3'-carbon linkers (C3). In this version of reagent A, the reverse strands had concentrations of 150 nM, 300 nM, and 450 nM. As shown in Table 1, reagent C had juxtaposed terminal dabcyl groups. In this version of reagentC the reverse strands had concentrations of 150 nM, 300 nM, and 450 nM. As shown in Table 1, Reagent1 had a terminal quencher on the reverse strand opposite a 5'terminal fluorophore, a bulky moiety, on the forward strand. This example utilized a version of Reagent1 in which the fluorescent moiety, F, was the fluorophore Quasar 670 and the quencher moiety, Q, was Black Hole Quencher 2. In this version of Reagent1, the reverse strands had concentrations of 150 nM, 300 nM, and 450 nM. A control reaction was run with the probe as the only oligonucleotide in the reaction mixture. Reaction mixtures were oscillated using the following thermal profile: 45° C./20s, 60° C./10s for 45 cycles. The FAM fluorescence was acquired during the 45° C. segment of the thermal profile. Results are presented in FIGS. 2A-C, which are graphs of FAM fluorescence intensity versus the number of oscillation cycles.

Sequences for the probe and target were:

```
Probe:
                                        (SEQ ID NO. 11)
5' FAM-CCATGATACAAGCTTCC-BHQ1

Target:
                                        (SEQ ID NO. 12)
5' ACTTAGTAATTGGGAAGCTTGTATCATGGCACTTAGAACCT
```

Figure 2A:
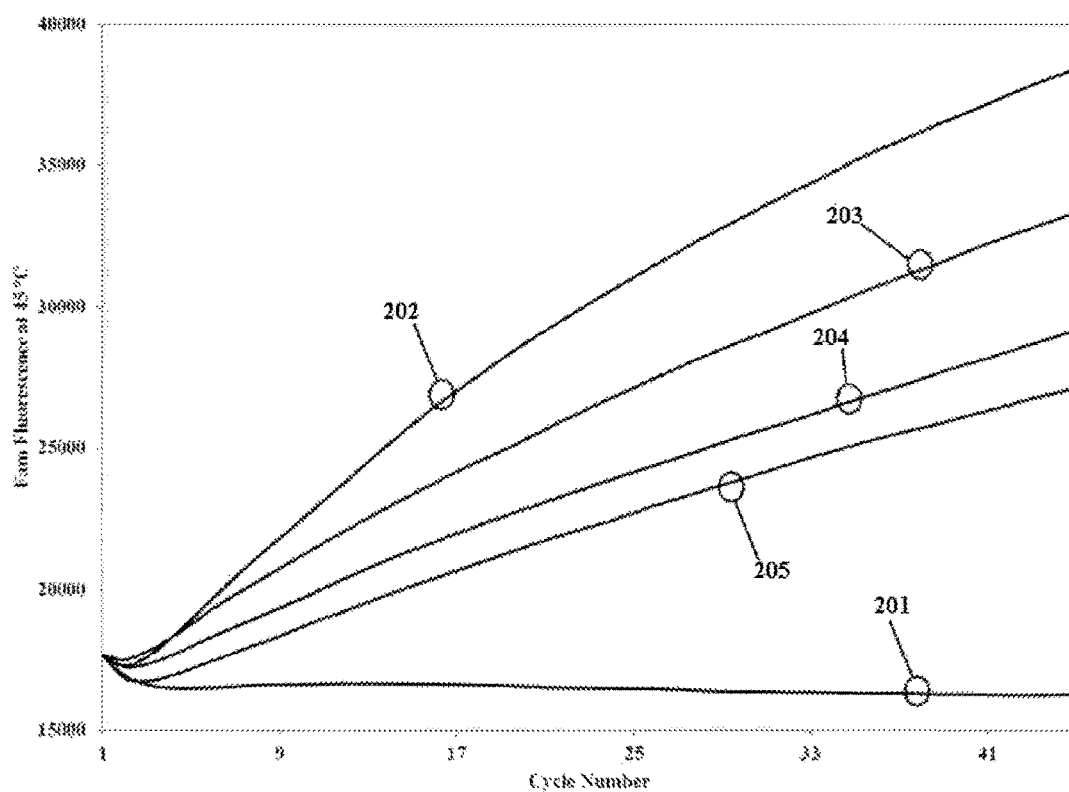
FIG. 2A is a graph of Fam fluorescence versus cycle number resulting from the primer-independent oscillating-temperature assay.
Figure 2B:
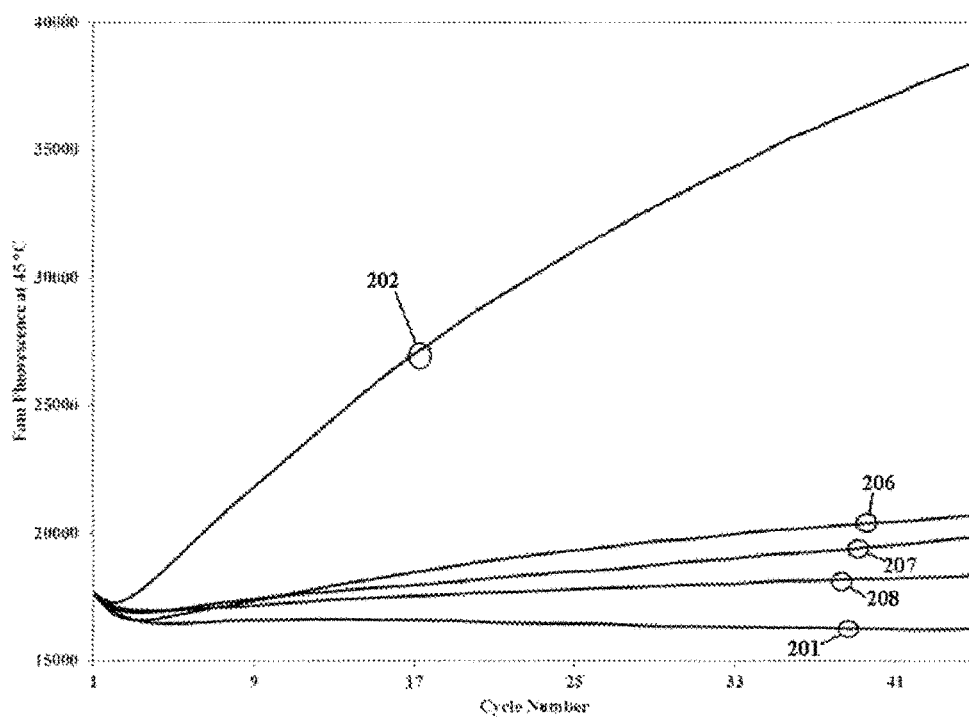
FIG. 2B is a graph of FAM fluorescence versus cycle number resulting from the primer-independent oscillating-temperature assay.
Figure 2C:
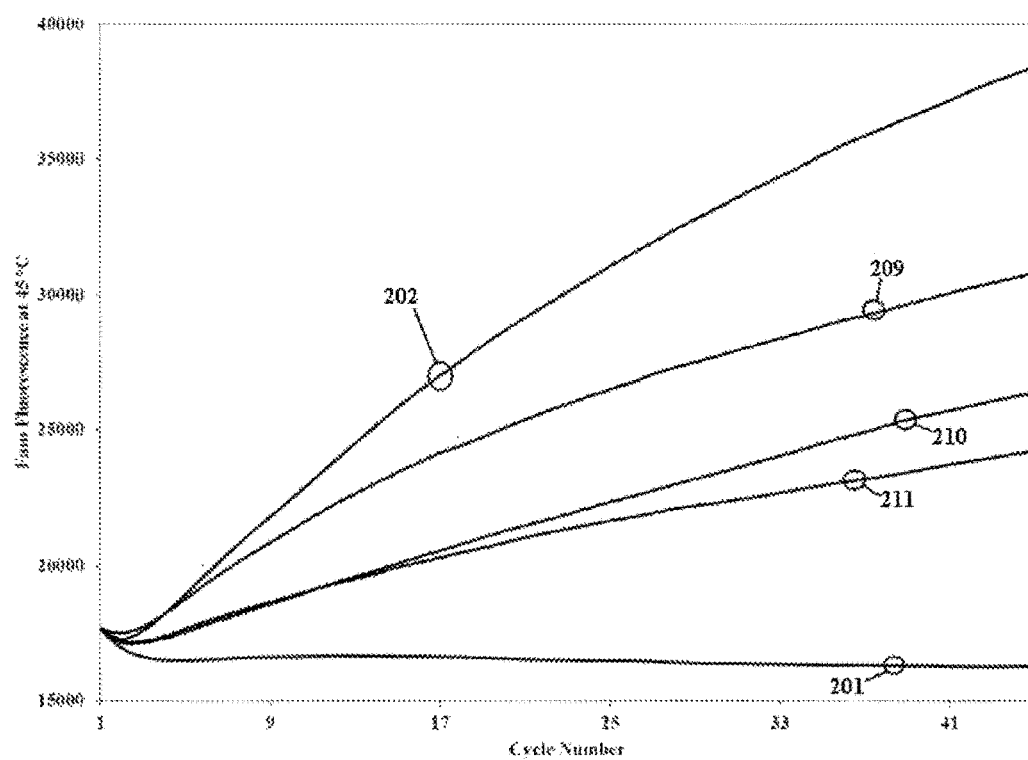
FIG. 2C is a graph of FAM fluorescence versus cycle number resulting from the primer-independent oscillating-temperature assay.

5' Exonuclease cleavage activity separates the probe's fluorophore from the probe, thereby resulting in an increase in fluorescence (FAM). Results reported in FIGS. 2A-C are the average of three replicates with the probe only reactions adjusted up to the lowest fluorescent value at time zero as the probe plus target reactions. In FIG. 2A, curve 201 for the probe-only reaction shows that in the absence of target, the probe is not cleaved. Curve 202 for the reaction containing probe and target but no reagent, shows the highest probe cleavage. Curves 203, 204, and 205 for reactions with reagentA at 50, 100 and 150 nM, respectively, show a gradual decrease in 5'exonuclease activity in a concentration-dependent manner. FIG. 2B shows the results with reagentC (dabcyl/dabcyl), which clearly inhibits 5' exonuclease activity. Curves 206, 207 and 208 are 50, 100 and 150 nM of the reagent. For Reagent1 (CO560/BHQ2), the results are shown in FIG. 2C where curves 210, 211 and 212 are respectively, 50, 100 and 150 nM concentrations. This reagent shows little to no increase of 5' exonuclease inhibition over that of the reagentA without moieties at the 5' and 3' ends.

Example 3

Primer Specificity Assay Using No Reagent Additive, ReagentA, ReagentC, Reagent1 or Reagent1'

We performed a LATE-PCR assay in which we amplified a target that was complementary to both primers (matched target), and in which we separately amplified a target that was complementary to the excess primer but that contained a single mismatch to the 3' terminal nucleotide of the limiting primer. We detected double-stranded product in real time, that is, during the primer extension portion of every PCR cycle, using SYBR Green, a dye that binds to double-stranded DNA. The sequences of the primers and single-stranded targets are as follows:

```
Limiting Primer.
                                    (SEQ ID NO. 13)
5' CGTAAGATTACAATGGCAGGCTCCAGT Excess Primer.
                                    (SEQ ID NO. 14)
5' GCCCAAGTTTTATCGTTCTTCTCA Matched Target (A).
                                    (SEQ ID No. 15)
5' CGTAAGATTACAATGGCAGGCTCCAGAAGGTTCTAA

GTGCCATGATACAAGCTTCCCAATTACTAAGTATGC

TGAGAA GAACGATAAAACTTGGG

Mismatched Target(T).
                                    (SEQ ID No. 16)
5' CGTAAGATTACAATGGCAGGCTCCAGTAGGTTCTAAGTGC

CATGATACAAGCTTCCCAATTACTAAGTATGCTG

AGAAGAACGATAAAACTTGGGCAA
```

The underlined and bolded nucleotide is the nucleotide whose complement in the excess primer strand will either match or mismatch the 3' terminal nucleotide of the limiting primer.

For this assay which contains two targets, we ran a control amplification using the excess primer, which is perfectly complementary to both targets, and a control limiting primer that is also perfectly complementary to both targets, to ensure that the starting copy numbers of both targets are the same, in which case the $C_T$'s for both targets is the same (with <0.5 $C_T$).

The LATE-PCR amplifications were carried out in triplicate (three replicate assays) in 25 μl volume consisting of 1× Invitrogen PCR buffer (Invitrogen, Carlsbad, Calif.), 3 mM MgCl$_2$, 200 nM dNTPs, 50 nM of limiting primer, 1000 nM of excess primer, 0.24×SYBR Green (Invitrogen, Carlsbad, Calif.), 1.25 units of Platinum Taq DNA polymerase (Invitrogen, Carlsbad, Calif.) with approximately 1000 single-stranded target A (matched) or T (mismatched). An exception was reagentB, where two replicate assays were carried out. Reactions additionally contained no added reagent, or various amounts (50 nM, 100 nM or 150 nM) of reagent A, reagentC, Reagent1 with a Cal Orange 560 fluorophore and a Black Hole Quencher 2, Reagent1 with a Quasar 670 fluorophore and a Black Hole Quencher 2, or Reagent1' with a Quasar 670 fluorophore and a Cal Orange 560 fluorophore. For reagentA the concentrations of the reverse strand were 150 nM, 300 nM and 450 nM. For reagentC the concentrations of the reverse strand were 150 nM, 300 nM and 450 nM. For both versions of Reagent1 the concentrations of the reverse strand were 150 nM, 300 nM and 450 nM. For Reagent1' the concentrations of the reverse strand were 150 nM, 300 nM and 450 nM. The thermal profile conditions for these reactions were: 95° C. for 3 minutes followed by 95° C./5s-62° C./20s-72° C./33s for 60 cycles. This was followed by a melt (see Example 5 below) with fluorescent acquisition for Fam, Cal Orange 560 and Quasar 670 at each degree starting at 35° C. with 1° C. increments at 33s intervals to 95° C.

FIGS. 3A-O show the real-time fluorescence curves for SYBR Green dye, which was read in the instrument's FAM channel and so is noted as "FAM Fluorescence". Each figure includes curve 301 for reactions with the matched target and no additive, and curve 302 for reactions with the mismatched target and no additive. FIGS. 3A-C are for reactions with reagentA at concentrations of 50 nM, 100 nM, and 150 nM, respectively. Curves 303, 305 and 307 are for the matched target, and curves 304, 306 and 308 are the mismatched target. FIGS. 3D-F are for reactions with reagentC at concentrations of 50 nM, 100 nM and 150 nM, respectively. Curves 309, 311 and 313 are for the matched target, and curves 310, 312 and 314 are for the mismatched target. FIGS. 3G-I are for reactions with a first version of Reagent1, wherein the fluorescent moiety, F, is Cal Orange 560 and the quencher moiety, Q, is Black Hole Quencher 2. The concentrations of that version of Reagent1 in FIGS. 3G-I are 50 nM, 100 nM and 150 nM, respectively. Curves 315, 317 and 319 are for the matched target, and curves 316, 318 and 320 are for the mismatched target. FIGS. 3J-L are for reactions with a second version of Reagent1, wherein the fluorescent moiety, F, is Quasar 670 and the quencher moiety, Q, is Black Hole Quencher 2. The concentrations of that second version of Reagent1 in FIGS. 3J-L are 50 nM, 100 nM and 150 nM, respectively. Curves 321, 323 and 325 are for the matched target, and curves 322, 324 and 326 are for the mismatched target. FIGS. 3M-O are for reactions with a version of Reagent1', wherein the 5'F is Quasar 670 and the 3'F is Cal Orange 560. The concentrations of that version of Reagent1' are 50 nM, 100 nM and 150 nM, respectively. Curves 327, 329 and 331 are for the matched target, and curves 328, 330 and 332 are for the mismatched target.

Primer extension in favor of matched target/primer versus 3' terminal mismatch target/primer is the difference between the threshold cycle ($C_T$) of the signal from amplification of the mismatched target and the $C_T$ of the signal from amplification of the matched target ($\Delta C_T$). Replicate amplification reactions were run, as stated. The $C_T$ differences were calculated using averages of the replicates. An assay was run without any added reagent or Reagent. SYBR Green signals were detected in real time, that is, during the primer extension portion of all PCR cycles. The fluorescence intensity readings as a function of amplification cycle number show that the enzyme has a modest inherent selectivity for the matched target. The $C_T$ difference between matched and mismatched target sequences (see FIG. 3A, circles 301, 302) was obtained. That A $C_T$ for the two templates with the same limiting primer was 2.1. The effectiveness of a reagent or Reagent to increase primer specificity is the $C_T$ difference ($\Delta C_T$) observed in PCR reactions with the reagent or Reagent minus the A $C_T$ without any reagent or Reagent. Therefore, for each reagent or Reagent, a $\Delta C_T$ was first determined, and then a $\Delta \Delta C_T$ was calculated by subtracting 2.1

Results are reported in Table 2, where the improvement (or, if a minus number, degradation), in the $C_T$ difference resulting from the use of reagent or Reagent versus no reagent is the column headed $\Delta \Delta C_T$.

TABLE 2

| Reagent | Conc. (nM) | $\Delta \Delta C_T$ |
|---------|------------|---------------------|
| none    | —          | —                   |
| reagentA | 50        | −0.35               |
|         | 100        | 1.88                |
|         | 150        | −0.06               |

TABLE 2-continued

| Reagent | Conc. (nM) | $\Delta\Delta C_T$ |
|---|---|---|
| reagentC | 50 | N/A |
| | 100 | (no amplification) |
| | 150 | (no amplification) |
| Reagent1 | 50 | 5.23 |
| (CO 560) | 100 | 7.47 |
| | 150 | 7.74 |
| Reagent1 | 50 | 4.72 |
| (QSR670) | 100 | 6.01 |
| | 150 | 8.02 |
| Reagent1' | 50 | 0.46 |
| | 100 | 2.58 |
| | 150 | 3.34 |

N/A - results are significantly delayed thus not applicable, see FIG. 3D.

Example 4

Type II Mispriming and Polymerase Selectivity

We performed a LATE-PCR assay in which we amplified a target that was complementary to both primers (matched target), and in which we separately amplified a target that was complementary to the excess primer but that contained a single mismatch to the 3' terminal nucleotide of the limiting primer. We detected double-stranded product in real time, that is, during the primer extension portion of every PCR cycle, by a DNA dye, in this case SYBR Green. Selectivity against a 3' terminal mismatch in the presence of reagent at any concentration is the difference between the threshold cycle ($C_T$) of the signal from amplification of the mismatched target and the $C_T$ of the signal from amplification of the matched target ($\Delta C_T$). Amplification reactions were run in triplicate. The $C_T$ differences are calculated using averages of the three replicates. The effectiveness of a reagent for improving selectivity of a DNA polymerase is the $C_T$ difference, $\Delta C_T$, with the reagent minus the $C_T$ difference, $\Delta C_T$, without any reagent, that is, the $\Delta\Delta C_T$. Under the heading "Selectivity" in this example, we report the improvement in the $C_T$ difference, $\Delta\Delta C_T$, resulting from the use of a reagent.

The sequences of the primers and single-stranded targets were the same as in Example 3 For reagentA, the concentrations of the forward strand were 50, 100 and 150 nM; and the concentrations of the reverse strand were 150, 300 and 450 nM, respectively. For Reagent1, wherein the fluorescent moiety, F, on the forward strand was Cal Orange 560 and the quenching moiety, Q, on the reverse strand was Black Hole Quencher 2, the concentrations of the forward strand were 50, 100 and 150 nM; and the concentrations of the reverse strand were 150, 300 and 450 nM, respectively. For Reagent2, wherein the fluorescent moiety, F, on the forward strand was Cal Red 610 and the quenching moiety, Q, on the reverse strand was Black Hole Quencher 2, the concentrations of the forward strand were 50, 100 and 150 nM, and the concentrations of the reverse strand were 150, 300 and 450 respectively.

The LATE-PCR amplifications were carried out in triplicate (three replicate assays) in 25 ul volume consisting of 1× Invitrogen PCR buffer (Invitrogen, Carlsbad, Calif.), 3 mM MgCl$_2$, 200 nM dNTPs, 50 nM of limiting primer, 1000 nM of excess primer, 0.24×SYBR Green (Invitrogen, Carlsbad, Calif.), 1.25 units of Platinum Taq DNA polymerase (Invitrogen, Carlsbad, Calif.) with approximately 10,000 single-stranded target A (matched) or T (mismatched). The thermal profile conditions for these reactions were: 95° C. for 3 minutes followed by 95° C./5s-62° C./20s-72° C./33s for 60 cycles with fluorescence acquisition at each cycle at the 72° C. step. This was followed by a melt with fluorescent acquisition for Fam, Cal Red 610 and Quasar 670 at each degree starting at 35° C. with 1° C. increments at 30s intervals to 95° C. For this assay which contains two targets, we run a control amplification using the excess primer, which is perfectly complementary to both targets, and a control limiting primer that is also perfectly complementary to both targets, to ensure that the starting copy numbers of both targets are the same, in which case the $C_T$'S for both targets is the same (within <0.5 $C_T$). Results are presented in Table 3, where $\Delta C_T$ is the difference between the $C_T$'s for the matched and mismatched targets, and $\Delta\Delta C_T$ is the difference between the $\Delta C_T$'s with and without the Reagent.

TABLE 3

| Reagent | Conc. (nM) | $\Delta C_T$ | $\Delta\Delta C_T$ |
|---|---|---|---|
| none | — | 2.1 | — |
| reagentA | 50 | -0.35 | |
| | 100 | 1.88 | |
| | 150 | -0.06 | |
| Reagent1 | 50 | 6.6 | 4.5 |
| | 100 | 8.6 | 6.5 |
| | 150 | 10.0 | 7.9 |
| Reagent2 | 50 | 3.2 | 1.1 |
| | 100 | 4.3 | 2.2 |
| | 150 | 5.6 | 3.5 |

When a sample with a reagent or Reagent was tested in this assay, a no-reagent control was also included, and the $C_T$ difference between matched and mismatched target sequences for the no-reagent control, generally about 2 $C_T$ cycles, was subtracted from the $C_T$ difference between matched and mismatched target sequences for the reagent to arrive at the selectivity improvement numbers ($\Delta\Delta C_T$) presented in Table 3.

Real-time curves of SYBR Green fluorescence for two of the samples are shown in FIG. 4, where circle 401 denotes the triplicate reactions with 150 nM Reagent2 and the matched target, and circle 402 denotes the triplicate reactions with 150 nM Reagent1 and the matched target. One of the curves of circle 401 shows product evolution, evidenced by a late rise in fluorescence after plateau has been reached. On such evidence of product evolution is seen in any curve of circle 402.

Example 5

Reagent1 and Reagent2 as Temperature Marks

The LATE-PCR amplifications were carried as described in Example 3, with the addition of various amounts (50 nM, 100 nM or 150 nM) of either Reagent1 or shorter Reagent2, wherein in each the fluorescent moiety, F, was Cal Orange 560 or Cal Red 610 and the quenching moiety, Q, was a Black Hole Quencher 2. For both Reagents the reverse strand was added at a concentration three times the forward-strand concentration. The amplification reactions were followed by a melt with fluorescence acquisition for the fluorophore at each degree starting at 35° C. with 1° C. increments at 33s intervals to 95° C. The first derivatives of fluorescence intensity are shown in FIGS. 5A-B. The three sets of curves in FIG. 5A are the different concentrations of Reagent1, and the three sets of curves in FIG. 5B are the different concentrations of Reagent2. For both reagents the concentrations are 50 nM/150 nM (fluorophore strand/ quencher strand), curves 501 and 504. Curves 502 and 505 are 100 nM/300 nM (fluorophore strand/quencher strand), while curves 503 and 506 are 150 nM/450 nM (fluorophore strand/quencher strand). FIGS. 5A-B show the melting of the Reagent in the reaction mixture, with Reagent1 having a higher Tm than Reagent2, as expected. The results show that the Tm temperature (nadir value, or negative peak) shifts slightly upward as the concentration of the Reagent increases. This is due to the concentration-dependent nature of hybridization.

Example 6

The Detection of Multi-Drug Resistance in the Genes rpoB, katG, and gyrA for Two Strains of *M. tuberculosis* and the Depth of the Fluorescence Valley as a Function of the Concentration of Reagent1

A multiplex LATE-PCR assay was used to generate multiple single-stranded target nucleic acids that contain sequences that confer either drug sensitivity or drug resistance for the following antibiotics (and their target genes): rifampicin (rpoB), isoniazid (katG), and fluoroquinolone (gyrA) in two strains of *M. tuberculosis*. In this example, hybridizations were characterized by the use of melt profile analysis using sets of On/Off probes as described in international patent application WO 2011/050173. Two versions of Reagent1 (Table 1) were utilized. A first version had the forward strand labeled with Cal Orange 560. A second version had the forward strand labeled with Quasar 670. Both versions had the reverse strand labeled with a Black Hole Quencher 2. Other oligonucleotides in the reactions were as follows:

Primers for rpoB gene target amplification:

```
Limiting Primer:
                                     (SEQ ID No. 17)
5' CTCCAGCCAGGCACGCTCACGTGACAGACCG Excess Primer:
                                     (SEQ ID No. 18)
5' ACGTGGAGGCGATCACACCGCAGACGTT
```

The underline in the sequence of the limiting primer denotes a deliberate change in nucleotide sequence to prevent the formation of an secondary hairpin structure.

```
rpoB Target: Strain 24609
                                     (SEQ ID No. 19)
CCGGTGGTCGCCGCGATCAAGGAGTTCTTCGGCACCAGCCAGCTGAGCCA

ATTCATGGACCAGAACAACCCGCTGTCGGGGTTGACCCACAAGCGCCGAC

TGTCGGCGCTGGGGCCCGGCGGTCTGTCACGTGAGCGTGCCTGGCTGGAG rpoB Target: Strain 4557
                                     (SEQ ID No. 20)
CCGGTGGTCGCCGCGATCAAGGAGTTCTTCGGCACCAGCCAGCTGAGCCA

ATTCATGGACCAGAACAACCCGCTGTCGGGGTTGACCGACAAGCGCCGAC

TGTCGGCGCTGGGGCCCGGCGGTCTGTCACGTGAGCGTGCCTGGCTGGAG rpoB Probe 1 Off:
                                     (SEQ ID No. 21)
5'-BHQ2-CTGGTTGGTGCAGAAG-C₃ rpoB Probe 1 On:
                                     (SEQ ID No. 22)
5'-BHQ2-TCAGGTCCATGAATTGGCTCAGA-Quasar 670 rpoB Probe 2 Off:
                                     (SEQ ID No. 23)
5'-BHQ2-CAGCGGGTTGTT-C₃ rpoB Probe 2 On:
                                     (SEQ ID No. 24)
5'-BHQ2-ATGCGCTTGTGGATCAACCCCGAT-Quasar 670 rpoB Probe 3 On:
                                     (SEQ ID No. 25)
5'-Quasar 670-AAGCCCCAGCGCCGACAGTCGTT BHQ2 rpoB Probe 3 Off:
                                     (SEQ ID No. 26)
5'-ACAGACCGCCGG BHQ2
```

Primers for katG gene target amplification:

```
Limiting Primer:
                                     (SEQ ID No. 27)
5' AGCGCCCACTCGTAGCCGTACAGGATCTCGAGGAAAC Excess Primer:
                                     (SEQ ID No. 28)
5' TCTTGGGCTGGAAGAGCTCGTATGGCAC katG Target: Strain 24609
                                     (SEQ ID No. 29)
5' GCTTGGGCTGGAAGAGCTCGTATGGCACCGGAACCGGTAAGGACGCG

ATCACCAGCGGCATCGAGGTCGTATGGACGAACACCCCGACGAAATGGGA

CAACAGTTTCCTCGAGATCCTGTACGGCTACGAGTGGGAGCT katG Target: Strain 4557
                                     (SEQ ID No. 30)
5' GCTTGGGCTGGAAGAGCTCGTATGGCACCGGAACCGGTAAGGACGCG

ATCACCACCGGCATCGAGGTCGTATGGACGAACACCCCGACGAAATGGGA

CAACAGTTTCCTCGAGATCCTGTACGGCTACGAGTGGGAGCT katG Probe On:
                                     (SEQ ID No. 31)
5' Cal Orange 560-AAGTGATCGCGTCCTTACCTT-BHQ2 katG Probe Off:
                                     (SEQ ID No. 32)
5' GACCTCGATGCAGCTG-BHQ2
```

Primers for gyrA gene target amplification:

```
Limiting Primer:
                                     (SEQ ID No. 33)
5' AGCCGAAGTTGTTCTGGTCGTCCACCAGCGGGTAGCGCA Excess Primer:
                                     (SEQ ID No. 34)
5' TTGCCGAGACCATGGGCAACTACCACCCGC gyrA Target: Strain 4557
                                     (SEQ ID No. 35)
5' TTGCCGAGACCATGGGCAACTACCACCCGCACGGCGACGCGTCGATC

TACGACAGCCTGGTGCGCATGGCCCAGCCCTGGTCGCTGCGCTACCCGCT

GGTGGACGGCCAGGGCAACTTCGGCT
```

-continued gyrA Target: Strain 24609
no sequence available gyrA Probe On:
(SEQ ID No. 36)
5' Cal Orange 560-TTGCTGCCGTAGATTGTGAGGTCGCCGTAA-
BHQ1 gyrA Probe Off:
(SEQ ID No. 37)
5' GGCTATGAGCACACCAG-BHQ1

A three carbon linker is denoted with $C_3$ while a Black Hole Quencher 2 is denoted with BHQ2 (Biosearch Technologies, Novato Calif.). The underline in the sequence of each denotes the location of the nucleotide change from the drug sensitive *M. tuberculosis* sequence.

Triplicate LATE-PCR amplifications were carried out in a 25 µl volume consisting of 1×PCR buffer (Invitrogen, Carlsbad, Calif.), 0.24×SYBR Green, 2 mM MgCl2, 300 nM dNTPs, 50 nM Limiting Primer and 1000 nM Excess Primer for each primer set, 1.5 units of Platinum Taq DNA Polymerase (Invitrogen, Carlsbad, Calif.), 500 nM Off probes, 200 nM On probes, 500 nM of Reagent1 reverse (quencher) strand, and approximately 10,000 genomes of either target strain. This reaction mixture was subdivided into nine sub mixtures containing differing amounts of Reagent1 forward strand, either the version labeled with Cal Orange 560 or the version labeled with Quasar 670, or both, as follows: 1) Sub mix 1 contained 50 nM of the Cal Orange 560 fluorophore strand; 2) Sub mix 2 contained 25 nM of the Cal Orange 560 fluorophore strand and 25 nM of the Quasar 670 fluorophore strand; 3) Sub mix 3 contained 50 nM of Quasar 670 fluorophore strand; 4) Sub mix 4 contained 100 nM of Cal Orange 560 fluorophore strand; 5) Sub mix 5 contained 50 nM of the Cal Orange 560 fluorophore strand and 50 nM of the Quasar 670 fluorophore strand; 6) Sub mix 6 contained 100 nM of the Quasar 670 fluorophore strand; 7) Sub mix 7 contained 200 nM of the Cal Orange 560 fluorophore strand; 8) Sub mix 8 contained 100 nM of the Cal Orange 560 fluorophore strand and 100 nM of the Quasar 670 fluorophore strand; and 9) Sub mix 9 contained 200 nM of the Quasar 670 fluorophore strand. In addition, all amplification reactions contained approximately 20,000 genomes of human genomic DNA (Promega, Madison, Wis.).

The thermal profile for the amplification reaction was as follows: 95° C./3 min for 1 cycle, followed by 98° C./10s-75° C./42s for 60 cycles, followed by a single cycle at 75° C. for 10 minutes, followed by 10 min at 25° C. This was followed by a melt starting at 25° C. with 1° C. increments at 42s intervals to 97° C.

Probe-target hybridizations were analyzed by the melt curve analysis using the first derivative for each fluorophore separately for the temperatures between 25° C. to 95° C.

Figure 6D:
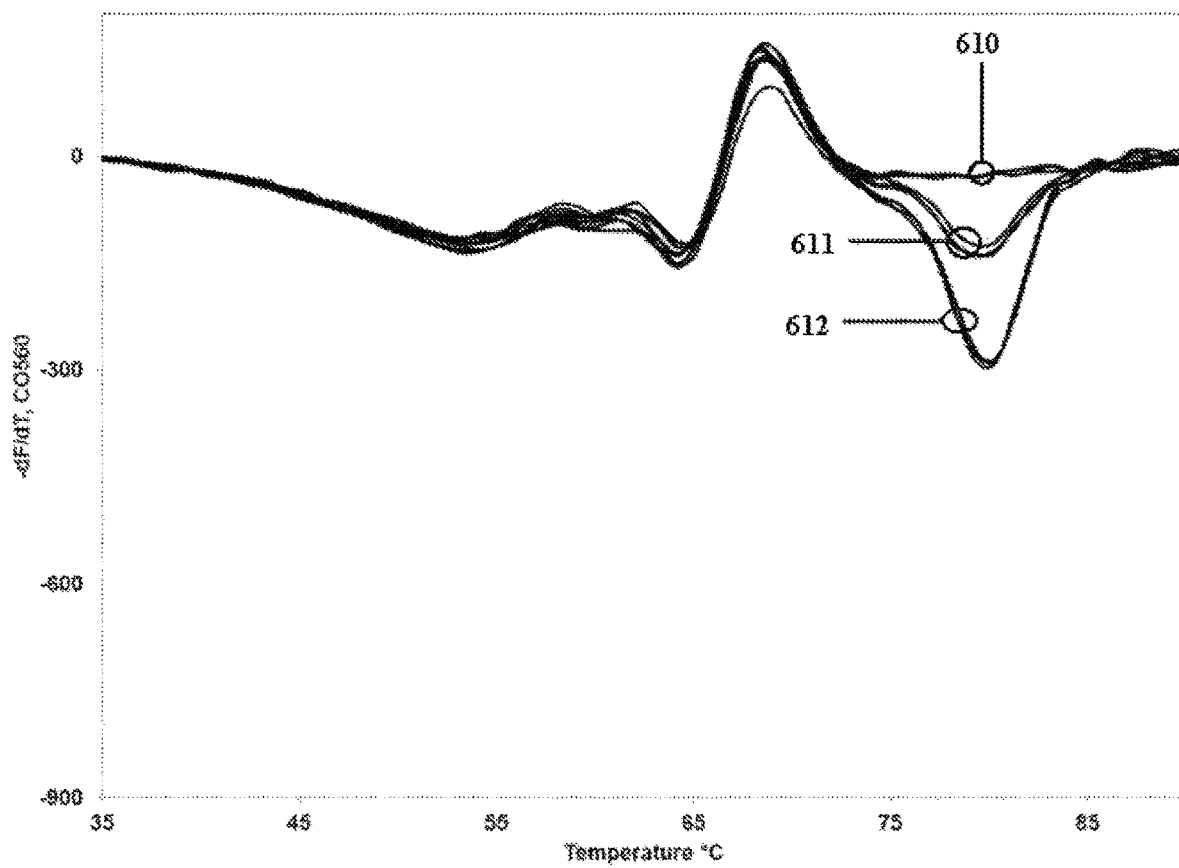
FIG. 6D is a melt profile, derivative of fluorescence versus temperature, obtained in the multiplex assay of Example 6 with Reagent1, and shows the melt derivative results of gyrA (peak at 57° C.) and katG (peak at 66° C.) in the Cal Orange channel using sub mixes 1, 2 and 3.
Figure 6E:
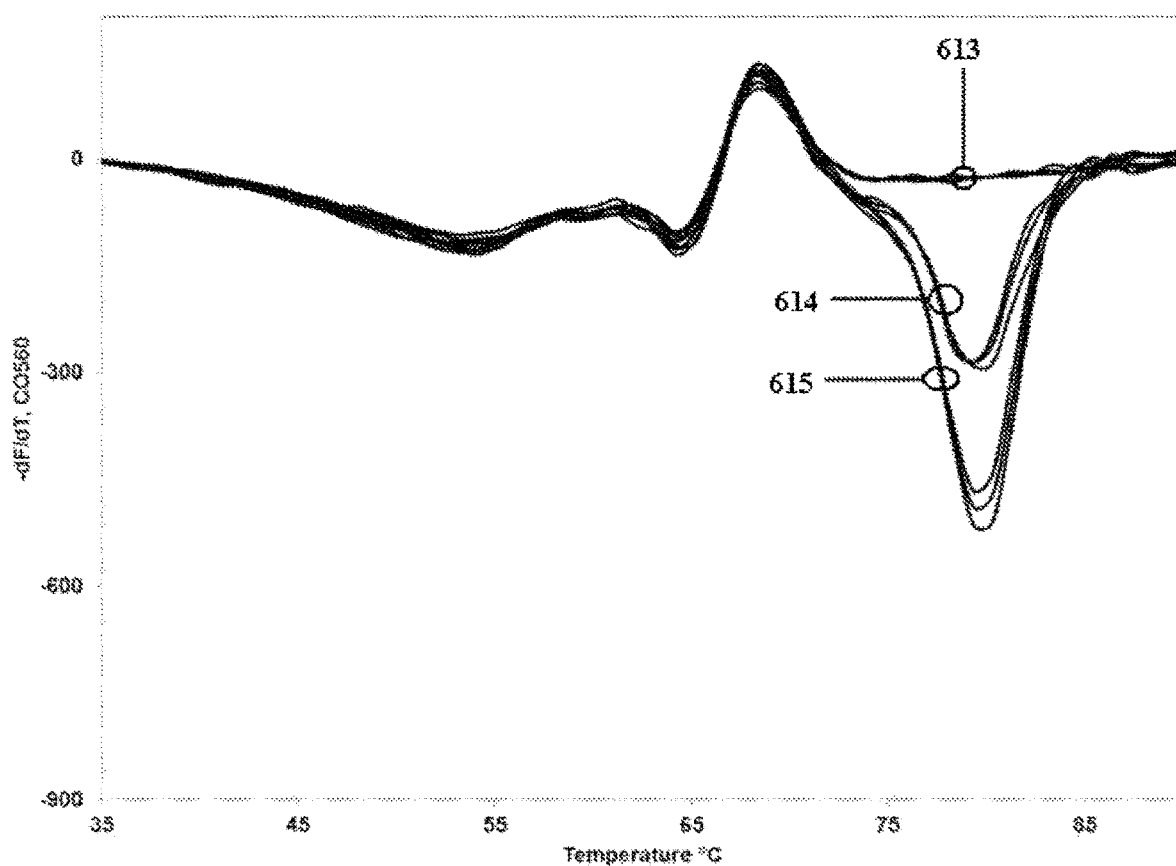
FIG. 6E is a melt profile, derivative of fluorescence versus temperature, obtained in the multiplex assay of Example 6 with Reagent1. These results show sub mixes 6 (circle 613), 5 (circle 614), and sub mix 4 (circle 615), each with 100 nM total of the Reagent1 fluorophore strand.
Figure 6F:
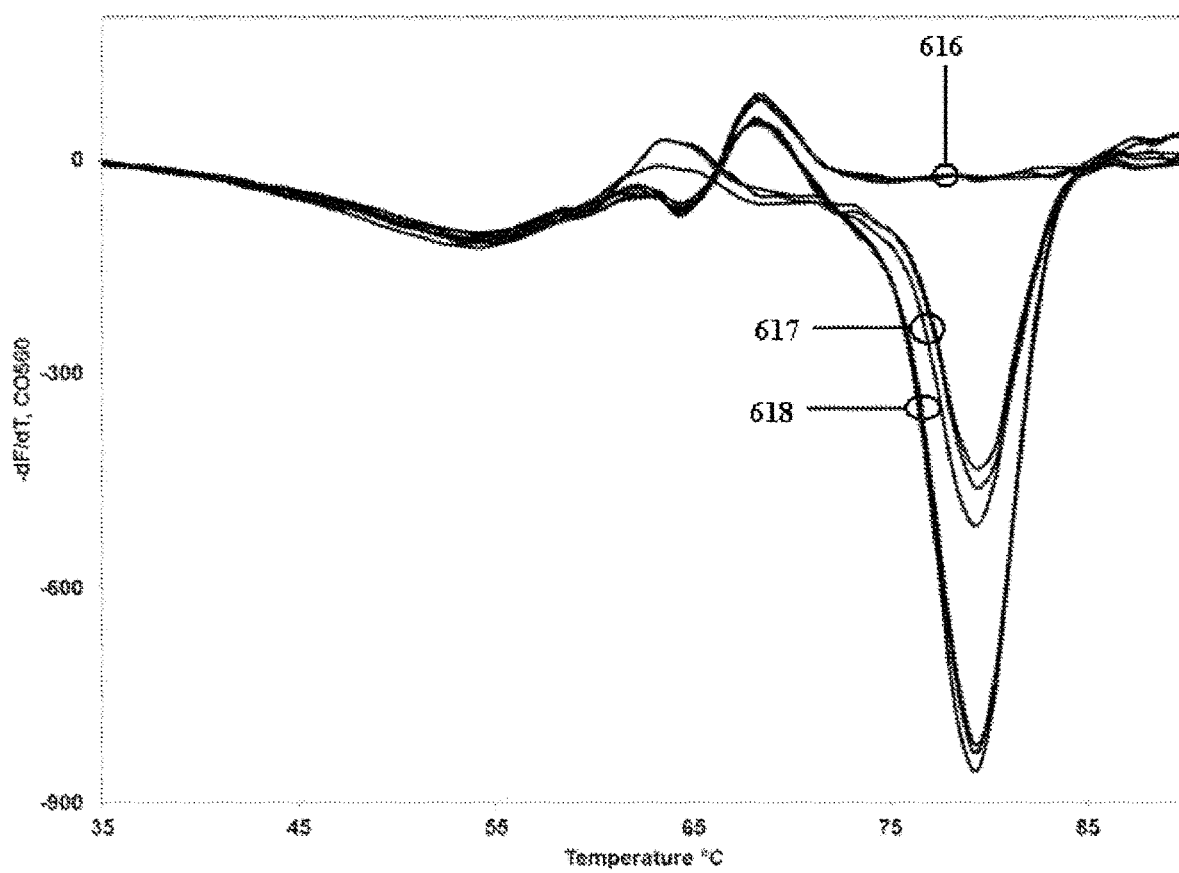
FIG. 6F is a melt profile, derivative of fluorescence versus temperature, obtained in the multiplex assay of Example 6 with Reagent1.

The results in FIGS. 6A-C show the Quasar 670 fluorescent signatures of sensitive strain 24609 for rifampicin (rpoB) with Reagent1 at different concentrations and combinations of the fluorophore strand. FIGS. 6D-F shows the Cal Orange 560 signatures of the resistant strain 4557 for isoniazid (katG) and fluoroquinolone (gyrA). Reagent1 is visible in these melt derivatives as a distinct high temperature valley at 81° C.

FIG. 6A shows first derivative curves for Quasar fluorescence with sub mixes 1, 2 and 3, each containing a total of 50 nM of the fluorophore strand of Reagent1. There are two sources of Quasar fluorescence: Reagent1 and the rpoB gene On probes. Sub mix 1 (replicate curves denoted by circle 601) contains no Quasar fluorophore (only the Cal Orange 560 fluorophore) strand; thus, no distinguishing valley at 81° C. is seen. Sub mix 2 (circle 602) contains only 25 nM of Quasar 670 strand, and shows a moderate valley, while sub mix 3 (circle 603), with 50 nM of Quasar 670 fluorophore strand, has the deepest valley. The results in FIG. 6B are the sub mixes 4 (circle 604), 5 (line 605), and 6 (line 606), each with 100 nM total of the fluorophore strand of Reagent1. The results shown are similar to those in FIG. 6A. The highest fluorophore strand concentration (200 nM) results are shown in FIG. 6C with sub mix 7 (circle 607), sub mix 8 (circle 608), and sub mix 9 (circle 609). Comparing the magnitudes of the peaks and valleys below 75° C. of FIG. 6C with FIG. 6A, the results show that Reagent1 with a combination of the two fluorophores, sub mix 8 (circle 608), inhibited the amplification of rpoB target while Reagent1 with each of the single fluorophores (circles 607, 609) reduced the overall level of fluorescence.

FIG. 6D shows the melt derivative results of gyrA (peak at 57° C.) and katG (peak at 66° C.) in the Cal Orange channel using sub mixes 1, 2 and 3. Reagent1 in sub mix 3 (circle 610) contains only the Quasar 670 fluorophore strand, and, thus, no distinguishing valley is seen at 81° C. Sub mix 2 (circle 611), which contains 25 nM of the Reagent1 Cal Orange strand shows a moderate valley, while sub mix 1 (circle 612), with 50 nM of the Reagent1 Cal Orange strand, has the deepest valley. The results in FIG. 6E are the sub mixes 6 (circle 613), 5 (circle 614), and sub mix 4 (circle 615), each with 100 nM total of the Reagent1 fluorophore strand. The results shown are similar to those in FIG. 6D. The highest fluorophore strand concentration (200 nM) results are shown in FIG. 6F with sub mix 9 (circle 616), sub mix 8 (circle 617), and sub mix 7 (circle 618). The results show that a combination of the fluorophores, sub mix 8, inhibited the amplification of katG target while the single fluorophores reduced the overall level of fluorescence.

Example 7

Reagent1 and Reagent1 Improve Primer Specificity for Amplification of Fully Matched Targets Compared to Those Mismatched to the 3' End of the Limiting Primer This example compares the LATE-PCR amplification and detection assay for two DNA targets with sequences analogous to segments of the 5' Non-Coding Region of Hepatitis C Virus (HCV) genotypes 1b and 2b using a limiting primer that is fully complementary to the HCV 1b target but has a destabilizing mismatch at the 3' end of the primer to the HCV2b target (as well as an additional mismatch at the ninth nucleotide from the 3' end of the limiting primer). Double-stranded DNA targets were generated from HCV 1b and HCV2b Armored RNAs (Asuragen, Austin, Tex., USA) with 1,000 nM excess primer, 50 nM limiting primer and a published RT-PCR protocol (Pierce K E, Mistry R, Reid S M, Bharya S, Dukes J P, Hartshorn C, King D P, Wangh L J: Design and optimization of a novel reverse transcription linear-after-the-exponential PCR for the detection of foot-and-mouth disease virus. J Appl Microbiol 2010, 109: 180-189.). Amplification was stopped after 31 cycles to insure that the majority of the product was double stranded.

For the subsequent amplification of a region of the DNA target thus generated, with detection using a dual-labeled (F/Q) probe in an amplification and detection assay, the DNA target sense strand sequences, primer sequences, and probe sequences were:

```
HCV 1b target:
                                      (SEQ ID No. 38)
5'-TGACTGGGTC CTTTCTTGGA TCAACCCGCT CAATGCCTGG

AGATTTGGGC GTGCCCCGC GAGACTGCTA GCCGAGTAGT

GTTGGGTCGC GAAAGGCCTT GTGGTACTGC CTGATAGGGT

GCTT-3'

HCV 2b target:
                                      (SEQ ID No. 39)
5'-TGACTGGGTC CTTTCTTGGA TAAACCCACT CTATGTCCGG

TCATTTGGGC GTGCCCCGC AAGACTGCTA GCCGAGTAGC

GTTGGGTTGC GAAAGGCCTT GTGGTACTGC CTGATAGGGT

GCTT-3'

Limiting Primer:
                                      (SEQ ID No. 40)
5'-CCACAAGGCCTTTCGCGACCCAACA-3'

Excess Primer:
                                      (SEQ ID No. 41)
5'-TGACTGGGTCCTTTCTTGGA-3'

Probe:
                                      (SEQ ID No. 42)
5'-Cal Red 610-TCGGCTAGTAGTCTTGTGG-BHQ2-3'
```

In the target sequences, the binding sequences for the limiting primer are bolded. In the HCV 2b (mismatched) target, the two mismatched nucleotides in the primer-binding sequence are underlined.

The version of Reagent1 used in this example had a fluorescent moiety, F, that was the fluorophore Cal Orange 560, and it had a quencher moiety, Q, that was a Black Hole Quencher 2. The version of Reagent2 used in this example had a fluorescent moiety, F, that was the fluorophore Cal Red 610, and it had a quencher moiety, Q, that was a Black Hole Quencher 2.

The HCV 1b and HCV 2b DNA targets were amplified and detected in the presence of Reagent1, Reagent2, or no reagent. The limiting primer hybridizes to an internal region of targets (shown in bold above, nucleotides 80 to 104). It is fully complementary to the sense strand of the HCV 1b target. It is partially complementary to the same region in the HCV 2b target, but has a strongly destabilizing mismatch (C with A) at the 3' end of the primer and a weakly destabilizing mismatch (G with T) nine nucleotides from the 3' end of the primer. Based on our previous experience without the Reagents, a G with T mismatch has minimal effect on the PCR cycle at which fluorescence becomes discernable above background, the threshold cycle ($C_T$). Those knowledgeable in the art will understand that the more destabilizing mismatch and the position of a mismatch at the 3' end of the primer will have a much larger effect on initial amplification efficiency and resulting $C_T$ values. All samples contained 1× Platinum Tfi reaction buffer (Invitrogen), 3 mM $MgCl_2$, 0.4 mM of each dNTP, 0.24×SYBR Green, 400 nM probe, 1000 nM excess primer, 50 nM limiting primer, approximately 1,000 copies of one target type, and 2 Units Platinum Tfi exo (−) DNA polymerase (Invitrogen) in a final volume of 25 microliters.

Each target was tested in four replicate amplification reactions without reagent, four replicates with 100 nM Reagent1, four replicates with 100 nM Reagent2, four replicate samples with 150 nM Reagent2, four replicates with 200 nM Reagent2. In each case, the stated concentration is that of the fluorescently labeled strand, and the quencher-labeled strand was used at three times that concentration. A Stratagene Mx30005P Real Time Thermal Cycler was used. The PCR thermal-cycling protocol included initial denaturation at 95° C. for 1 minute, followed by 50 cycles of 95° C. for 10 seconds, 64° C. for 10 seconds, and 72° C. for 60 seconds with fluorescence detection at endpoint of that step. The temperature was then lowered from 72° C. to 40° C. in 1° C. steps every 30 seconds, held for 10 minutes, then raised in 1° C. steps every 30 seconds to a final temperature of 95° C. with fluorescence detection at each step. Real time $C_T$ values for SYBR Green fluorescence were obtained using the Stratagene software adaptive baseline settings. Probe fluorescence values obtained from the post-PCR melt were normalized based on fluorescence at 66° C. Fluorescence signal intensity was calculated by subtracting the average no template control (NTC).

Real time amplification plots of SYBR Green fluorescence versus PCR cycle number are shown in the left side of FIG. 7A, wherein panel 1 is for no reagent, panel 2 is for 100 nM of Reagent2, panel 3 is for 150 nM of Reagent 2, panel 4 is for 200 nM of Reagent 2, and panel 5 is for 100 nM of Reagent1. Solid lines (curves denoted by circles 701, 704, 707, 710 and 713) are for the perfectly matched target, dashed lines (curves denoted by circles 702, 705, 708, 711 and 714) are for the mismatched target, and dotted lines (curves denoted by circles 703, 706, 709, 712 and 715) are for the no-target controls. Mean $C_T$ values for replicates with target are presented in Table 4.

TABLE 4

| Reagent | Target HCV 1b | | Target HCV 2b | | | | Delay |
|---|---|---|---|---|---|---|---|
| | $C_T$ | CR-I | $C_T$ | CR-I | $\Delta C_T$ | $\Delta\Delta C_T$ | $(\Delta C_T)$ |
| no reagent | 24.6 | 4985 | 28.7 | 7441 | 4.1 | — | — |
| Reagent1, 100 nM | 29.4 | 4528 | 42.8 | 32 | 13.4 | 9.3 | 4.8 |
| Reagent2, 100 nM | 25.3 | 7448 | 31.9 | 5478 | 6.6 | 2.5 | 0.7 |
| Reagent2, 150 nM | 26.2 | 6293 | 35.3 | 2998 | 9.1 | 5.0 | 1.6 |
| Reagent2, 200 nM | 28.1 | 4519 | 40.3 | 209 | 12.2 | 8.1 | 3.5 |

Table 4 reports threshold-cycle values, "$C_T$", for SYBR Green fluorescence for the various sample types, with and without a Reagent. Table 4 also reports each sample type the $C_T$ difference "$\Delta C_T$" between matched target HCV 1b and mismatched target HCV 2b. As expected, for samples without reagent, real time fluorescence increase was observed earlier in the fully complementary HCV 1b target (see FIG. 7A, panel 1, circle 701) compared with the mismatched HCV 2b target (see FIG. 7A, panel 1, circle 702). The difference in mean $C_T$ values, ($\Delta C_T$) was 4.1 cycles (Table 4). Table 4 also reports for each sample type the selectivity improvement, that is the $\Delta C_T$ with Reagent minus 4.1, the $\Delta C_T$ with no reagent. Finally, Table 4 also reports for each sample type the difference between the $C_T$ for matched target with the Reagent and 24.6, the $C_T$ without the Reagent, "Delay ($\Delta C_T$)", a measure of inhibition of polymerase activity.

Figure 7B:
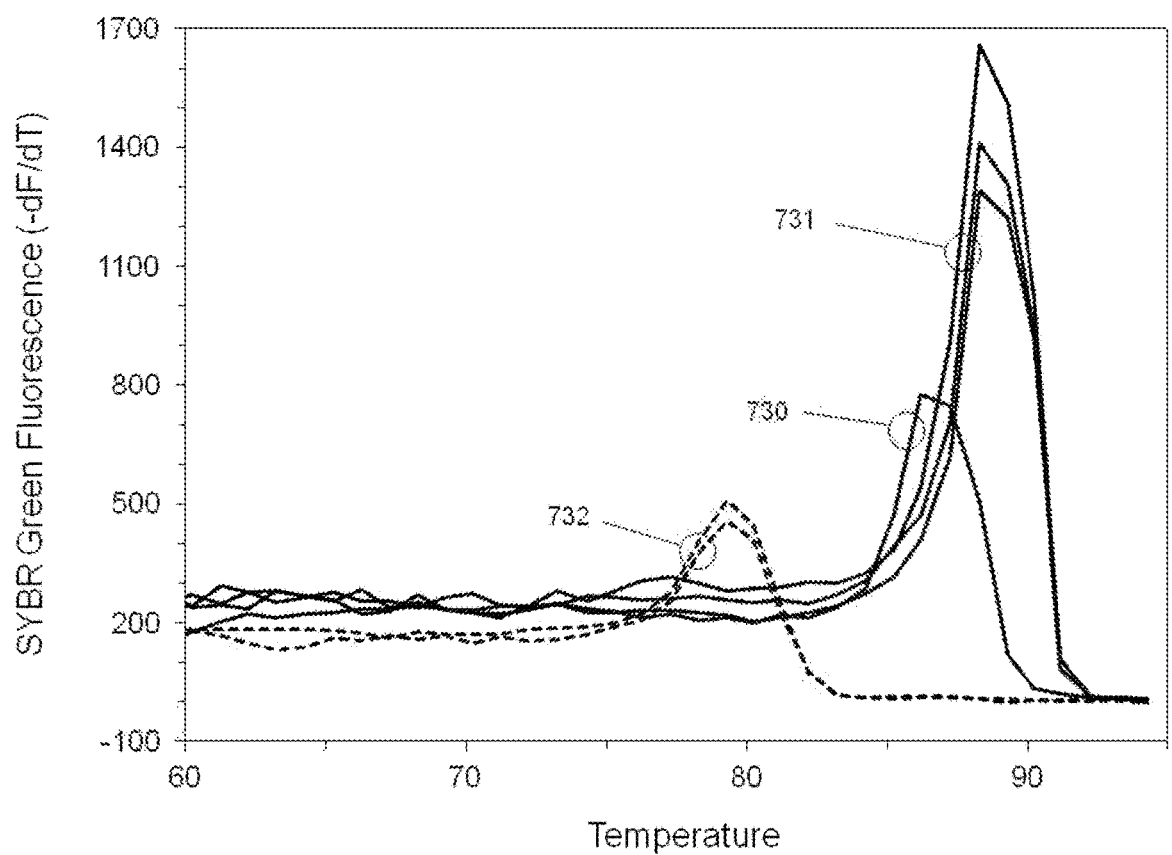
FIG. 7B presents derivative curves of the SYBR Green fluorescence curves of FIG. 7A.

As can be seen in the curves of panel 1, circle 701, three of four replicates for the HCV1b target without reagent showed a secondary rise in fluorescence immediately after reaching typical plateau values, indicating product evolution. (Note also the increase in fluorescence with the no-target control (circle 703.) To investigate product evolution, the samples with no reagent were subjected to melt analysis, along with the no template control. FIG. 7B presents the curves for the first derivative of SYBR Green intensity as a function of temperature. Curve 730 is for the sample that did not show a secondary rise. Curves 731 are for the three samples that did show a secondary rise. Curves 732 are the no template control. Product evolution was confirmed by a SYBR Green-measured melting temperature about 2 degrees higher than the specific product. None of the HCV 2b samples (FIG. 7A, panel 1) had detectable product evolution. Product evolution with the matched target was greatly suppressed at 100 nM Reagent2 (only one sample denoted by circle 704 showed a small secondary fluorescence increase in the last few cycles) and was not detected in any of the samples with higher concentrations of Reagent2 or with 100 nM Reagent1. Here again none of the HCV 2b sample with Reagent (circles 705, 708, 711, 714) had detectable product evolution.

Samples containing the HCV 1b (matched) target and Reagent2 showed a small "Delay" (inhibition measured as an increase in $C_T$ values relative to that matched target without reagent). As shown in Table 4, mean $C_T$ values increased by 0.7 cycles with addition of 100 nM Reagent2, by 1.6 cycles with addition of 150 nM Reagent2, and by 3.5 cycles with addition of 200 nM Reagent2. The mean $C_T$ value for the HCV 1b samples containing 100 nM Reagent1 increased somewhat more, by 4.8 cycles. It is possible that part of these increases was due to reduction in non-specific amplification as compared to amplifications with no reagent, as both specific and non-specific products are detected by the SYBR Green dye. Fluorescence increase due to primer-dimer amplification (FIG. 7A, circle 703, confirmed by melting analysis, FIG. 7B, circle 732) was observed in no-target control samples without reagent. Absence of fluorescence increase in no-target samples with either Reagent1 (circle 715) or Reagent2 (circles 706, 709, 712) provides further evidence that these reagents suppress non-specific amplification.

As reflected in Table 4, amplification was detected after larger $C_T$ delays ($\Delta C_T$) in samples containing the mismatched HCV 2b target versus the matched HCV 1b target with Reagent1 or Reagent2 as compared to samples containing no reagent. The difference in mean $C_T$ values between samples with the matched and mismatched targets increased as the concentration of Reagent2 increased, rising from 6.6 cycles at 100 nM (Panel 2, circles 705, 704), to 9.1 cycles at 150 nM (panel 3, circles 708, 707), and to 12.2 cycles at 200 nM (panel 4, circles 711, 710). That difference was 13.4 cycles with 100 nM Reagent1 (panel 5, circles 714, 713). Improvement is selectivity over samples with no Reagent ($\Delta\Delta C_T$) was less by 4.1 cycles (the $\Delta C_T$ with no Reagent) in each case.

The $C_T$ values from SYBR Green measure combined specific and non-specific amplification. Fluorescent signals from the Cal Red-labeled hybridization probe measure specific amplification. Those signals confirmed a reduction in the amount of specific product from the mismatched target. Maximum intensities from the Cal Red probe (CR-I) are reported in Table 4. FIG. 7A panels 6-10 present the first derivative of probe fluorescence as a function of temperature at temperatures below the Tm of the Reagents. Panel 6 is for no reagent, panel 7 is for 100 nM of Reagent2, panel 8 is for 150 nM of Reagent 2, panel 9 is for 200 nM of Reagent 2, and panel 10 is for 100 nM of Reagent1. Solid lines (circles 716, 718, 720, 722 and 724) are for the perfectly matched target, and dashed lines (circles 717, 719, 721, 723 and 725) are for the mismatched target. Specific product was detectable above background in only one of four samples with the mismatched HCV2b target (panel 9, circle 723) and 200 nM of Reagent2 and was not detected in any sample with the mismatched HCV2b targets and 100 nM of Reagent1 (panel 10). Referring to panel 6, circle(s) 716, it is seen that specific fluorescence was high in the single matched target HCV 1b sample that did not show product evolution, as shown by the greater magnitude of its peak at about 55° C. Also, comparing the curves of panel 6, circle 717 to the curves in panel 7, circle 719 and the curves in panel 8, circle 721, it is seen that the replicates with no Reagent had more variability for the matched HCV 1b target but less variability for the mismatched HCV2b target than the replicates with 100 nM or 150 nM Reagent2. Referring to Table 4, one sees that the mean fluorescent signal (CR-I) declined as the concentration of Reagent2 was increased, but the ratio between the mean signal from the matched and mismatched samples increased. Those knowledgeable in the art will recognize that the greater selectivity achieved by these Reagents can be used in identifying specific gene mutations or nucleotide variations among different strains or species of organisms.

Figure 7C:
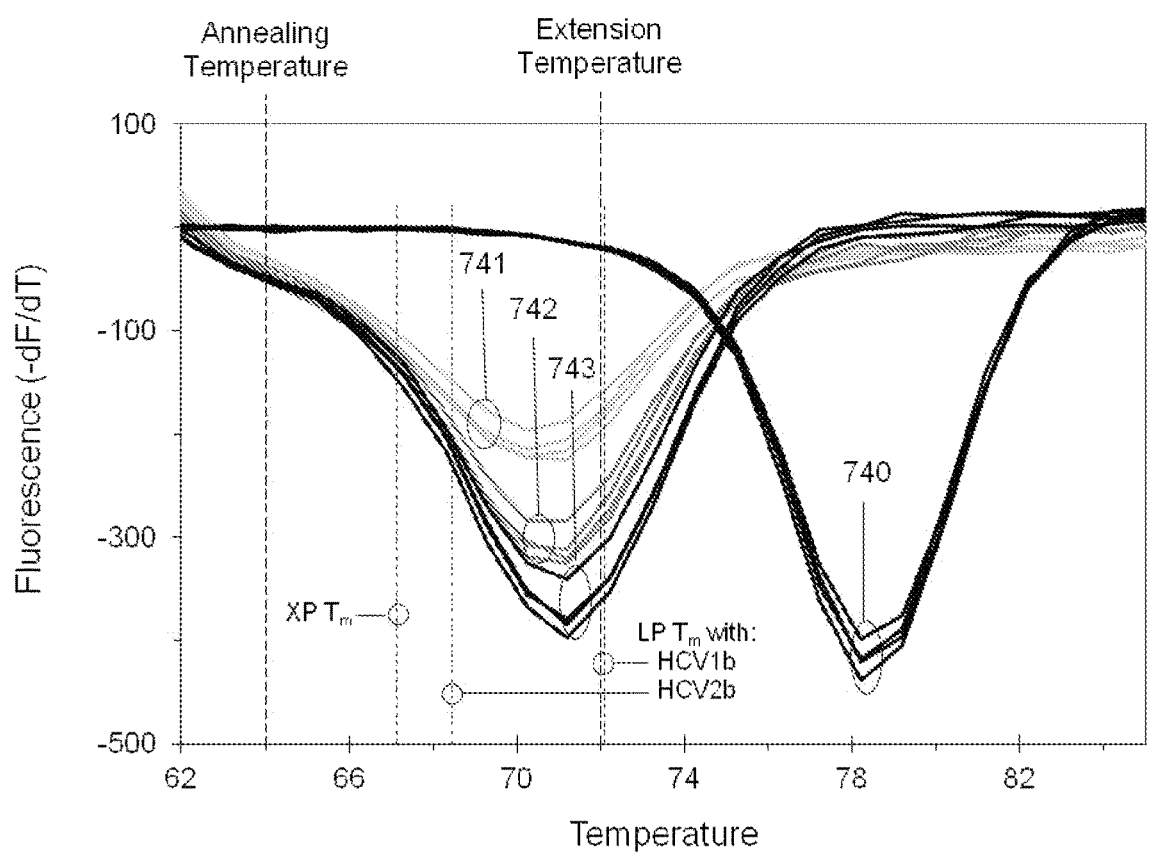
FIG. 7C presents derivative curves of Reagent1 and Reagent2 fluorescence in the assay of Example 7.

The melting of the two strands of the Reagent1 and Reagent2 provides some insight regarding possible differences in action of the two Reagents. As temperature increases, the fluorescently labeled strands (Cal Orange for Reagent1, Cal Red for Reagent2) separate from their complementary strands with the Black Hole Quenchers, and fluorescence increases. The derivative plots of fluorescence intensity versus temperature are shown in FIG. 7C. Circle 740 denotes the curves for Reagent1 at 100 nM. Circle 741 denotes the curves for Reagent2 at 100 nM. Circle 742 denotes the curves for Reagent2 at 150 nM. Circle 743 denotes the curves for Reagent2 at 200 nM. Noted by vertical lines on FIG. 7C are several reference temperatures, including the annealing and extension temperatures, the calculated Tm of the excess primer (denoted XP Tm), the Tm of the limiting primer with target HCV 1b (denoted LP Tm with: HCV1b) and the Tm of the limiting primer with target HCV2b (denoted LP Tm with: HCV2b). Reagent 2 has a Tm of about 71° C. (varying slightly with concentration), which is slightly below the predicted Tm of the limiting primer with the matched HCV 1b target and the 72° C. extension temperature, but above the predicted Tm of that primer with the mismatched HCV2b target. Reagent1 has a Tm of about 78° C. Thus, although both Reagents show selective amplification at the chosen concentrations, Reagent2 shows lower inhibition at 100 nM concentration (shown by the peak height in panel 7, circle 718, as compared to the peak height in panel 10, circle 724), possibly due to the ability of the primer-HCV 1b hybrid to compete more effectively against the Reagent for the available polymerase, particularly during the extension step. Those knowledgeable in the art will recognize that further increases in selectivity between matched and mismatched targets might be achieved by altering the temperature or duration of the thermal cycling steps (for example, decreasing the annealing temperature to provide a higher concentration of Reagent2 to be double stranded during that step, that is, increasing its effective concentration).

Example 8

Reagent2 Functions to Suppress Scatter Among Replicates in a Symmetric PCR Amplification Scatter among replicates is also a well know phenomenon in symmetric PCR amplifications as they approach the plateau phase of the reaction. R. G. Rutledge, Nucl. Acids Res. (2004) 32 (22): e178. doi: 10.1093/nar/gnh177. Example 8 illustrates scatter among replicate reactions in a symmetric PCR amplification using a pair of primers used to amplify a portion of the gene that causes Tay Sachs disease [J. E. Rice et al. (2002) Prenatal Diagn. 22:1130-1134]. The version of Reagent2 (see Table 1) used in this example had Cal Red 610 as the fluorescent moiety, F, and Black Hole Quencher 2 as the quencher, Q. Sequences of the primers and target were as follows:

Primers for TSD gene target amplification:

```
Forward:
                                          (SEQ ID No. 43)
5' CCTTCTCTCTGCCCCCTGGT Reverse:
                                          (SEQ ID No. 44)
5' AGGGGTTCCACTACGTAGAA TSD Target:
                                          (SEQ ID No. 45)
5' AGGGGTTCCACTATGTAGAAATCCTTCCAGTCAGGGCCATAGGATAT
ACGGTTCAGGTACCAGGGGGCAGAGAGAAGG
```

Symmetric amplifications were performed in triplicate carried out in a 25 µl volume consisting of 1×PCR buffer (Invitrogen, Carlsbad, Calif., USA), 0.24×SYBER Green (Invitrogen), 3.0 mM MgCl$_2$, 0.3 mM each dNTP, 300 nM each primer, and 1.25 units Platinum Taq DNA polymerase (Invitrogen), and approximately 5 copies of human genomic DNA. Comparative replicates contained no added reagents. Other replicates contained Reagent2. Reagent2 was added as 100 nM of the forward, fluorophore-containing strand with 300 nM of the reverse, quencher-containing strand. Amplification and fluorescence detection were carried out in a Stratagene MxP 3005P.

The thermal profile for the amplification reaction was as follows: 95° C./3 min for 1 cycle, followed by 95° C./10s, 65° C./30s, and 72° C./15s for 10 cycles, followed by 50 cycles of 95° C./10s, 55° C./30s, and 72° C./30s with fluorescence acquisition during the 72° C. step. This was followed by a melt starting at 43° C. with 1° C. increments at 30s intervals to 97° C.

Figure 8B:
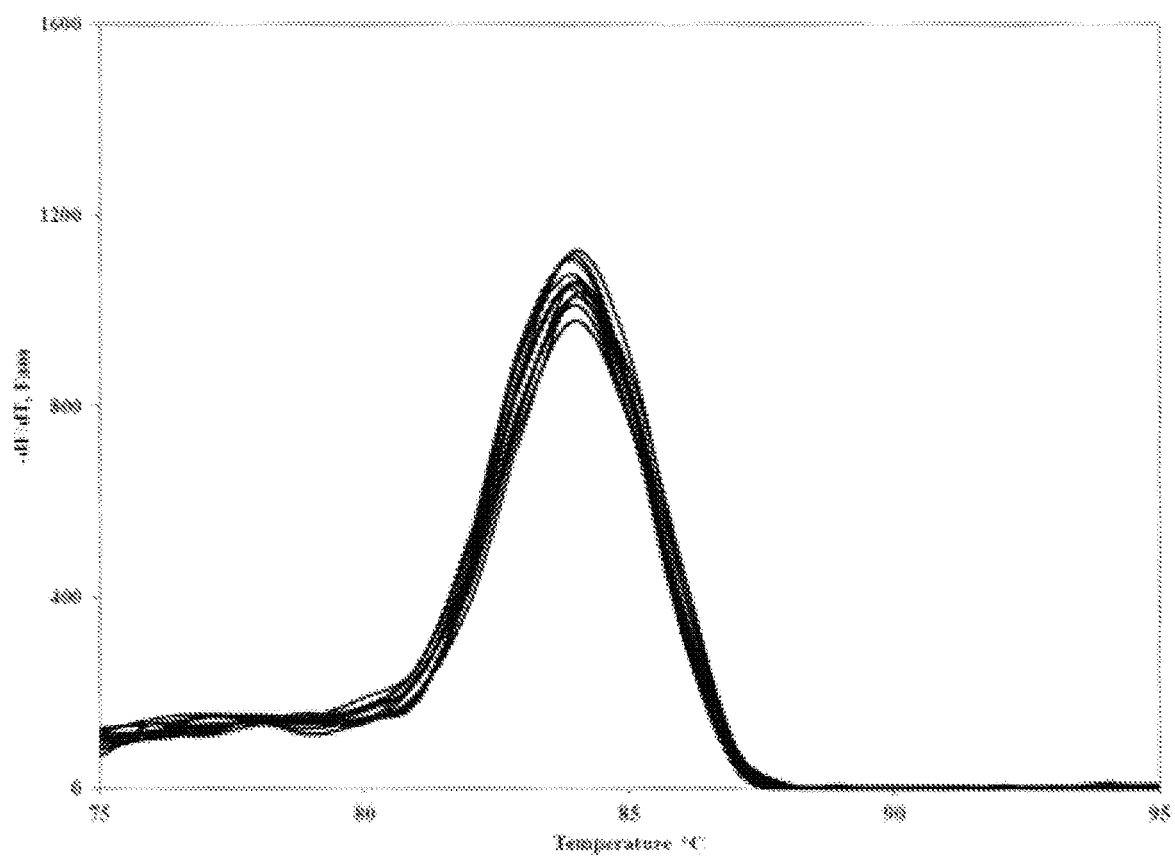
FIGS. 8B and 8C are derivative curves of SYBR Green fluorescence of FIG. 8A for samples with Reagent2 and no reagent, respectively.
Figure 8C:
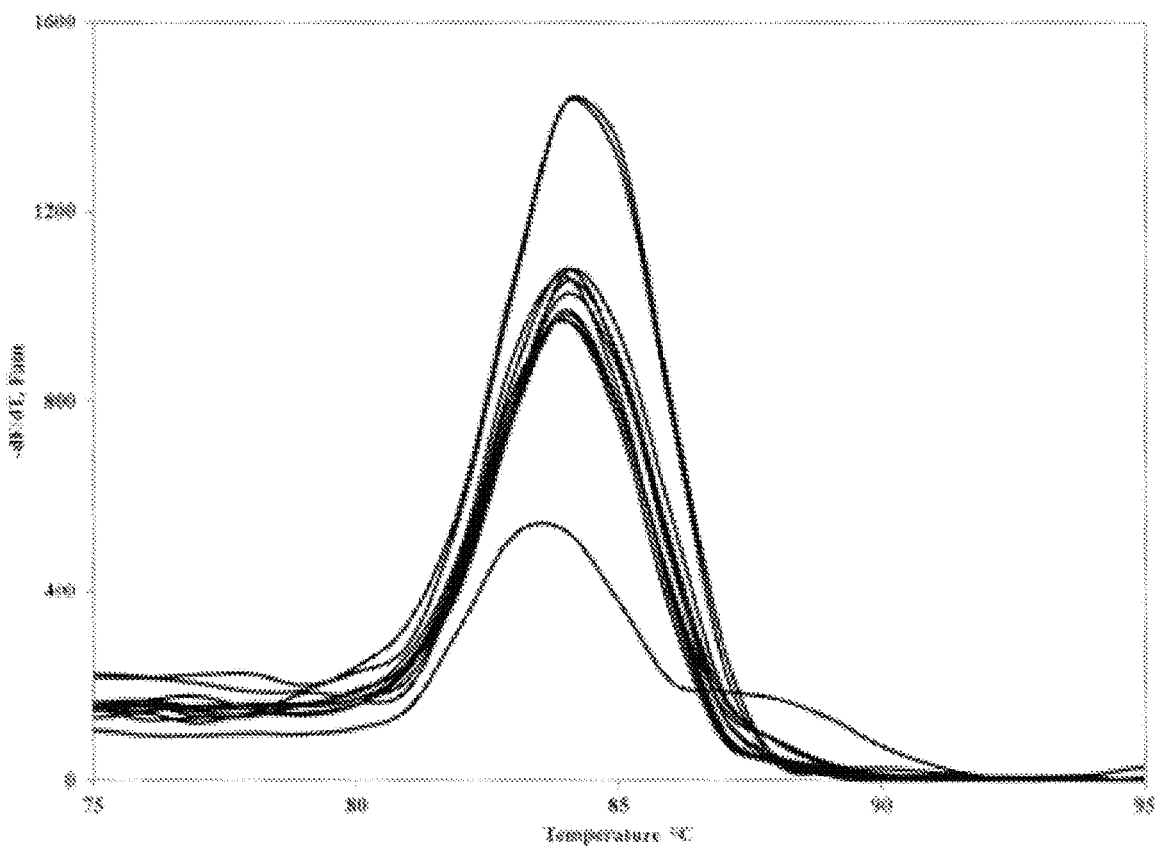

FIG. 8A presents real-time curves of SYBR Green fluorescence intensity, measured in the FAM cannel of the instrument, versus PCR cycle number. FIG. 8B presents derivative curves of SYBR Green fluorescence as a function temperature for samples containing Reagent2. FIG. 8C presents derivative curves of SYBR Green intensity as a function of temperature for samples with no reagent.

Referring to FIG. 8A, twelve replicates with no added reagent are denoted by circle 801, and twelve replicates with 100 nM of Reagent2 are denoted by circle 802. In the absence of any added Reagent (circle 801) several samples in the set of 12 plateaued at either much higher or lower levels than most of the samples. In contrast, addition of 100 nM of Reagent2 (circle 802) significantly reduced the level of scatter among all of the replicates. SYBR Green signals appeared after an average of 33-35 thermal cycles. Plateau was reached after 40 or 45 cycles, depending on whether Reagent2 was added. All of the samples incubated without Reagent2 amplified and plateaued before those incubated with Reagent2, consistent with the possibility that the reactions not containing Reagent2 were comprised of both the intended double-stranded amplicon and additional non-specific double-stranded DNA. Melt curve analysis of all samples was performed after 60 cycles of amplification. These results confirmed that the samples incubated with Reagent2 (FIG. 8B) were very similar and were free from non-specific double-stranded DNA. In contrast, all of the samples amplified without Reagent2 (FIG. 8C) had some level of higher melting non-specific double-stranded DNA. The replicates amplified in the absence of Reagent2 only diverge from one another (FIG. 8A) as their approached plateau levels. This demonstrates that divergence is a concentration-dependent phenomenon. In other words, it depends on relatively high levels of accumulated product strands. Divergence among replicates is not observed in samples containing Reagent2, even though the concentrations of double-stranded DNA in these samples is higher than those which diverge in the absence of Reagent2. We conclude from these results that Reagent2 increases polymerase selectivity in symmetric PCR and thereby prevents extension of mis-matched 3'ends of product strand interacting with other product strands, that is, product evolution. This result is consistent with those shown in previous Examples for LATE-PCR amplification. Product evolution is easier to observe in LATE-PCR, because it causes single-stranded amplicons to become double-stranded. In contrast, in symmetric PCR double-stranded amplicons just become larger double-stranded molecules.

Example 9

Effect of the Reagent1 on the Amplification of Synthetic DNA Targets with Foot-And-Mouth-Disease Virus (FMDV) Sequences that are Fully or Partially Complementary to a Limiting Primer This example compares the amplification of different sequence variants of the FMDV 1D gene targeted by a single limiting primer in the presence or absence of Reagent1. The Cal-Orange-modified strand of Reagent1 (Table 1) was used at 50 nM, and the Black Hole Quencher 2-modified strand was used at 150 nM. Each of several synthetic, single-stranded DNA oligonucleotides was amplified by LATE-PCR using a single limiting primer and a single excess primer. The limiting primer, 5'-ACCATCACTGAGCTGTTGATCCGCATGAAACG-3' (SEQ ID No.) is the DNA sequence analogous to the positive strand RNA of FMDV isolate IND 339-96 and has a predicted Tm of 74.9° C. at 50 nM with the fully complementary target in the PCR reagent mixture described below. The excess primer, 5'-AGGGCCCAGGGTTGGACTC-3' (SEQ ID No.) and has a predicted Tm of 73.7° C. at 1,000 nM with the complementary target. The probe, 5'-Cal Red 610-ATAGCTCTTGACACCACTCAT-Black Hole Quencher 2-3' (SEQ ID No.) was used in all amplifications to confirm specific target amplification and has a predicted Tm of 61.9° C. with each of the targets. Tm was predicted using Visual OMP (DNA Software). One target (shown below and in FIG. 9) contained 105 nucleotides complementary to segments of the positive strand RNA from the FMDV 1D to 2A/B genes of Asia1 serotype isolate IND 339-96. A portion of the FMDV sequence was not included in order to simplify oligonucleotide synthesis.

(SEQ ID No. 46)

5' AGAAGAAGGGCCCAGGGTTGGACTCTGAGTGGTGTCAAGAGCTAGCA

AAGGCCTGGGGCAGTATGTCTCCGCGCGTTTCATGCGGATCAACAGCTCA

GTGATGGT-3'.

In the above target sequence, the region that is the same as the excess-primer sequence is underlined, and the region hybridizing the limiting primer is bolded. Other targets, whose sequences are also given in FIG. 9, contained the same sequence except for variations in the region hybridizing the limiting primer (shown above in bold type). That region of the other targets included nucleotides complementary to different FMDV Asia1 serotype isolates and is shown in FIG. 9. (Targets IND 324-98 and IND 82-96 each have 3 additional nucleotides, GTC, at the 3' end that were included for initial testing with complementary primers, but those nucleotides have minimal effect on hybridization with the limiting primer described above.) Target nucleotides that are mismatched to the limiting primer are shaded in FIG. 9.

Samples included 1× Platinum Taq reaction buffer (Invitrogen), 3 mM $MgCl_2$, 0.4 mM of each dNTP, 250 nM probe, 0.24×SYBR 1000 nM excess primer, 50 nM limiting primer, approximately 10,000 copies of one target type, 1.5 Units Platinum Taq DNA polymerase (Invitrogen), and either no reagent or Reagent1 at 50 nM concentration, in a final volume of 25 microliters. Each target was tested in triplicate with and without Reagent1 using a Stratagene Mx3005P thermal cycler programmed to heat to 95° C. for 1 minute, followed by 60 cycles of 95° C. for 10 seconds, 70° C. for 30 seconds, and 75 degrees for 20 seconds with fluorescence detection. Temperature was lowered in 0.5° C. steps of 30 seconds each from 75° C. to 40° C. (to enable the probe to hybridize with the PCR product), then increased in 0.5° C. steps of 30 seconds from 40° C. to 96° C. with fluorescence detection at each step.

FIG. 9 presents, for each target, fluorescence data from SYBR Green detection, namely, the threshold cycle, $C_T$, of the reactions with no Reagent; the threshold cycle, $C_T$, of the reactions with 50 nM Reagent1, and the delay, A $C_T$, resulting from inclusion of Reagent1 in the reaction mixture. Real-time SYBR Green detection confirmed that amplification was delayed in samples containing targets mismatched to the primer. As reported in FIG. 9, the mean $C_T$ of reactions with no Reagent increased with the number of mismatches, from 24.1 for perfectly matched target to 32.0 for the target with four mismatches. When Reagent1 was present the $C_T$ was delayed in all cases, but the magnitude of the delay, A $C_T$, increased with the number of mismatched nucleotides. For target IND 339-96 (zero mismatched nucleotides) the delay was only 1.2 cycles; for target IND 116-90 (one mismatched nucleotide) the delay increased to 1.7 cycles; for targets IND 224-98, IND 82-96 and IND 23-95 (two mismatched nucleotides) the delay varied with the identity and location of the mixmatches but averaged 4.2 cycles: and for target BR/Myanmar 001 (four mismatches), the delay increased to 9.3 cycles. The $C_T$ with target BR.Myanmar 001 and Reagent1, 41.3, was a full 16 cycles higher than the $C_T$ with matched target IND 339-96 and Reagent1, 25.2, demonstrating the ability of Reagent1 to delay amplification of mismatched targets and thereby improve the selectivity of Taq polymerase for the fully complementary target.

Example 10

Use of the Reagent1 to Enhance Multiplex PCR Amplification

LATE-PCR reactions were used to amplify HV2, CO2 and ND1 sequences from the human mitochondria genome simultaneously in a single reaction mixture utilizing three primer pairs and Lights No/Lights Off probes to generate a fluorescent signature for each target, according to international patent application WO 2011/050173. Amplification products were identified using fluorescent signatures from sets of Lights-On/Lights-Off probes of a unique color that span the length of each amplicon. Reactions were carried out in the presence of either Reagent1 or an additive described in WO 2010/104074 at [0164], where it is denominated "Additive EP042." Additive EP042 is a mixture of two double-stranded reagents having three terminal dabcyl groups each. The two double strands in the mixture are reduced to only three strands by including a common strand, referred to as the "middle strand," in both reagents. The sequences of the three oligonucleotide strands of Additive EP042 are as follows:

```
Upper strand:
3' Dabcyl CCTCGTCTGATCGTGACTCCAT Dabcyl 5'

Middle strand:
5' GGAGCAGACTAGCACTGAGGTA Dabcyl 3'

Lower strand:
                                        (SEQ ID No. 54)
3' Dabcyl CCTGGTCTGATTGTGSCTCCAT Dabcyl 5'
```

Additive EP042 was added to reaction mixtures as follows: 525 nM each of the lower and middle strands and 25 nM upper strand. The version of Reagent1 used here had Cal Orange 560 as the fluorescent moiety, F, and Black Hole Quencher 2 as the quenching moiety, Q. Reagent1 was added to reaction mixtures at a concentration of 50 nM (fluorophore-containing oligonucleotide) with 150 nM of the quencher-containing oligonucleotide.

The primers' sequences used for amplification were as follows (underlined bases in the limiting primers are nucleotides mismatched to the normal target sequence):

```
HV2-Limiting Primer:
                                 (SEQ ID No. 55)
5'-AAAGCGGTGTGTGTGTGCTGGGTAGGAT-3'

HV2-Excess Primer:
                                 (SEQ ID No. 56)
5'-ACTTCAGGGTCATAAAGCCTAAATAGC-3'

CO2-Limiting Primer:
                                 (SEQ ID No. 57)
5'-AATAGAGGGGGTAGAGGGGGTGCTATAGGGT-3'

CO2-Excess Primer:
                                 (SEQ ID No. 58)
5'-TCCTTATCTGCTTCCTAGTCCTGTATGC-3'

ND1-Limiting Primer:
                                 (SEQ ID No. 59)
5'-AACATAAGAACAGGGAGGTTAGAAGTA

GGGTCTTGGT-3'

ND1-Excess Primer:
                                 (SEQ ID No. 60)
5'-CGCCCCGACCTTAGCTCT-3'
```

The sets of Lights-On/Lights Off probes used were as follows (underlined bases in the probes are nucleotides mismatched to the normal target sequence):

```
HV2 Lights-On Probes:
Quasar 670
                                        (SEQ ID No. 61)
5' TGGTTAGGGTTCTTTATTTTGGGGTTCA-3' BHQ-2
```

```
                                              (SEQ ID No. 62)
BHQ-2 5' AATGGCAGAGATGTCTTTAAGTGCTGTTT-3'

Quasar 670
                                              (SEQ ID No. 63)
BHQ-2-5' AAATGTAATCGCGTTCATATCACCCAGTT-3'

Quasar 670
                                              (SEQ ID No. 64)
Quasar 670-

5' TAATTGAACATAGGTACGATAAATAATTA-3' BHQ-2

(SEQ ID No. 65)
Quasar 670-

5' AACTGGGTGAAAAGTGACTATGCGGACTT-3' BHQ-2

HV2 Lights-Off Probes:
                                              (SEQ ID No. 66)
5' AATGTGAAATCTGCTTGGGCTGGT-3' BHQ-2

(SEQ ID No. 67)
BHQ-2-5' GGCTAGGAGTTGGGGAGGGCGGGTT-C3-3'

(SEQ ID No. 68)
BHQ-2-5' ACGAGAGTACCCAACGCATGGAGAG-C3 3'

(SEQ ID No. 69)
5' TTTAGTAAATGTGTTCACCTGTAAT-3' BHQ-2

(SEQ ID No. 70)
5' TGGGGGAAGTTTTTCTTATTATGT-3' BHQ-2

CO2 Lights-On Probes:
                                              (SEQ ID No, 71)
BHQ-2-5' AAACTACTCGATTATCAACGTCAAGGATT-3'

CAL Red 610
                                              (SEQ ID No. 72)
BHQ-2-5' AAAATGGGGAAGTTTGTATGAGTTGATT-3'

Cal Red 610

(SEQ ID No. 73)
Cal Red 610-5' AAACGATTGGGGACTTTAATTGGGAGTTT-3'

BHQ-2

(SEQ ID No, 74)
Cal Red 610-5' TTTGTAAAGAATGCGTAGAGATAGGAGAA-3'

BHQ-2

(SEQ ID No. 75)
BHQ-2-5' TTTTTATACGTACGGCAATTACATCTGAA-3'

Cal Red 610
                                              (SEQ ID No. 76)
BHQ-2-5' AGTGACCATAATATACCTCCGGCT-3' Cal Red 610

CO2 Lights-Off Probes:
                                              (SEQ ID No. 77)
BHQ-2-5' GTCGCAGGACGCCTAGTTTTAGGAA-C3 3'

(SEQ ID No. 78)
BHQ-2-5' AGATAAGTTCGCTGTATTCGGTGT-C3 3'

(SEQ ID No. 79)
5' AGACGTCTTATGTTGTAATTAT-3' BHQ-2

(SEQ ID No. 80)
5' GAGGCATTGTTCACGTCGTTTGTTA-3' BHQ-2

(SEQ ID No. 81)
5' BHQ2-TTTTTAAATTTAATATGGGGATAGC C3 3'

(SEQ ID No. 82)
5' BHQ2-TCGTATAGTGGTCAATGTGGTATGG-C3 3'

ND1 Lights-On Probes:
                                              (SEQ ID No. 83)
Cal Orange 560-

5' AAGTTCGGTTGGTTTTTGCTGGTGTGGTT-3' BHQ-1

(SEQ ID No. 84)
BHQ-1-5' AATATGAAGAATAGAGCGAAGAGGCCTTT-3'

Cal Orange 560
                                              (SEQ ID No. 85)
BHQ-1-5' TTAAGGTTGTAGTGATGGGGGTGTTTAAA-3'

Cal Orange 560
                                              (SEQ ID No. 86)
BHQ-1-5' AATTGATCAAGGGGTTTGGTATAGGGATT-3'

Cal Orange 560
                                              (SEQ ID No. 87)
BHQ-1-5' TTAGATAAACCATAGTATGTCCGAGGGAA-3'

Cal Orange 560

ND1 Lights-Off Probes:
                                              (SEQ ID No. 88)
5' TTCGGCAATGTCGAGGGGG-3' BHQ-1

(53° C.)
                                              (SEQ ID No. 89)
BHQ-1-5' GCGGCCTATTCCATGTTGACGCCTG C3 3'

(SEQ ID No. 90)
BHQ-1-5' TTATAATAATCTTTGTGTTTTCGGC-C3 3'

(SEQ ID No. 91)
BHQ-1-5' GGGAGGTTTATAGTAAAAGAGAGAT-C3 3'

(SEQ ID No. 92)
BHQ-1-5' TCATGATTGCAGTAGTGGTAAGAGG-C3 3'
```

LATE-PCR amplifications were carried out in a 25 µl volume. The reaction mixture consisted of 1×PCR buffer (Invitrogen, Carlsbad, Calif.), 3 mM $MgCl_2$, 250 nM dNTPs, 50 nM HV2 Limiting Primer, 1000 nM HV2 Excess Primer, 100 nM CO2 Limiting Primer, 1000 nM CO2 Excess Primer, 50 nM ND1 Limiting Primer, 1500 nM ND1 Excess Primer, 2.5 units of Platinum Taq DNA Polymerase (Invitrogen, Carlsbad, Calif.), 50 nM of each Lights-On probe, 150 nM of each Lights-Off probes, plus either reagent EP042 or Reagent1 as indicated above. All amplifications were carried out in the Strategene MX3005P (Agilent Technologies, CA). The thermal cycling profile for all amplifications was: 95° C. for 3 minutes; then 75 cycles of 95° C. for 5 seconds, 65° C. for 45 seconds, and 72° C. for 90 seconds; then 75° C. for 10 minutes; then 25° C. for 10 minutes. Post-amplification DNA melts were monitored by probe fluorescence signal as the temperature gradually increased from 25 to 80° C. in 45 second steps at 1° C. per step. The melting data was displayed and analyzed as the negative first derivative of the fluorescent probe signals relative to temperature (fluorescent signature). FIG. 10 presents the fluorescent signatures obtained. FIG. 10, Panel 1 is the signature of the Quasar probe set for the HV2 sequence using Additive EP042. Panel 2 is the signature of the Quasar probe set for the HV2 sequence using Reagent1. Panel 3 is the signature of the Cal Red probe set for the CO2 sequence using Additive EP042. Panel 4 is the signature of the Cal Red probe set for the CO2 sequence using Regaent1. Panel 5 is the signature of the Cal Orange probe set for the ND1 sequence using Additive EP042. Panel 6 is the signature of the Cal Orange probe set for the ND1 sequence using Reagent1.

The ND1 fluorescent signature was barely discernible in the presence of the dabcylated reagent, Additive EP042 (FIG. 10, panel 5). In contrast, replacing the dabcylated reagent with Reagent1 led to a strong ND1 fluorescent signature (FIG. 10, panel 6). Melting of Reagen1, here labeled with a Cal Orange fluorophore, shows up in the signature curve for the ND1 target in panel 6. In panel 6, Reagent1 is visible as a rightmost valley at 79° C. in the ND1 fluorescent signature. Use of Reagent1 also increased the intensities of the HV2 and CO2 fluorescent signatures (compare panel 2 to panel 1, and compare panel 4 to panel 3). Fluorescent signatures were not generated in the absence of either the dabcylated reagent or Reagent1 (data not shown).

Example 11

Mis-Priming Preventing Effect of Reagent1 on Multiplex RT-LATE-PCR of Human Influenza Sequences It was proposed to utilize a sequence of the neuraminidase gene of the pandemic 2009 influenza (09N1) in a highly multiplexed RT-LATE-PCR assay. For development purposes RNAs from human influenza sequences were synthesized by in vitro transcription and used as targets. Commercially available purified genomic RNA from the MS2 phage was also included as a control for RT-PCR efficiency.

In this assay's scheme, the neuraminidase gene of the pandemic 2009 influenza (09N1) is detected by a total of three probes. Two of the probes (ON probes) are conjugated to the CAL Red 610 fluorophore at the 5' end and to a Black Hole Quencher 2 (BHQ2) at the 3' end, and one probe (OFF probe) is conjugated only to a BHQ2 at the 3' end. (See Triplex RT-LATE-PCR Assay section for the probe sequences.) These three probes are designed to have different concentration-adjusted melting temperatures (Tm) to their target sequences, as follows: 09N1-Zan ON Tm>09N1-Zan OFF Tm>09N1-Os Probe Tm.

When probe binding is analyzed over a range of temperatures at the end of LATE-PCR amplification, the CAL Red 610-09N1 probe set produces a combined fluorescence contour as shown in FIG. 11A. As the temperature is decreased from 95° C., the 09N1-Zan ON Probe starts hybridizing to target at 65° C. and reaches maximal fluorescence at 55° C.; binding of the 09N1-Zan OFF Probe at lower temperatures then reduces fluorescence intensity because this probe lies contiguously to the ON probe. Thus, the 09N1-Zan ON+Zan OFF probe pair forms a distinctive peak at 55° C. When the temperature is lowered even further, the 09N1-Os Probe binds to target and CAL Red fluorescence increases again, peaking at about 40° C. (The decline of fluorescence at cooler temperatures is likely due to increased secondary structure of target and/or probe that interferes with probe hybridization.)

This biphasic CAL Red 610 "fluorescent signature" was found to be very consistent in reactions containing a single pair of primers for amplification of the 09N1 target. It was observed, however, that the CAL Red fluorescence shoulder at 40° C. decreased steadily as more primer pairs were added in the reaction, while the peak at 55° C. was always prominently present. The presence of the 55° C. peak proved that the amplicon was generated even in the presence of several primer pairs. It was, hypothesized that interactions among the primers generated non-specific products preventing the 09N1-Os Probe from binding efficiently to target even when the target was present. The efficacy of Reagent1 in reducing this problem was investigated in the work reported in Example 11.

A triplex RT-LATE-PCR assay was chosen as a convenient model to study the effect of Reagent1 on probe binding to the 09N1 amplicon. The assay mixture contained primers and probes for the 09N1 target, the hemagglutinin 09H1 target, and the RT-PCR control MS2 target. In addition to the RNA targets, the reaction mixture contained 16 mM Tris-HCl buffer, pH 8.5, 3.9 mM MgCl$_2$, 50 mM KCl, 0.52 mM dNTPs, 0.5 µl/assay of qScript reverse transcriptase from Quanta Biosciences (concentration undisclosed), 2.5 units/assay of Taq lyophilized on beads (illustra pure Taq Ready-To-Go PCR Beads, GE Healthcare), 100 nM of each limiting primer, and 1 µM of each excess primer. Each excess primer also primed reverse transcription of the respective RNA. The assay mixture also contained 100 nM of each probe, except for the 09N1-ZanOFF Probe, that was used at 300 nM concentration. Assays were run in triplicate with no additional reagent, with 1.5 units/assay of Platinum Taq Antibody (Invitrogen Life Technologies), and with 50 nM Reagent1 plus the same amount of that antibody added to the reaction mixture. Reagent1 was included at a concentration of 50 nM for the fluorophore-containing strand and 150 nM for the quencher-containing strand. The version of Reagent1 used in this assay included Cal Orange 560 as the fluorescent moiety, F, and Black Hole Quencher 2 as the quencher moiety, Q. The 09N1 and 09H1 RNA targets were included in all assays at a 1:1000 dilution from standard stocks, and the MS2 control RNA (Roche Diagnostics) was included at 100,000 copies/assay.

While the reactions contained primers and probes for hemagglutinin 09H1, detection of that target was not the subject of this experiment. As to 09N1 and MS2, whose detection was the subject of this experiment, sequences of the oligonucleotides used for the experiment were:

```
09N1-Limiting Primer:
                                         (SEQ ID No. 93)
5' CACACACATGTGATTTCACTAGAATCAGGATAACAG 09N1-Excess Primer:
                                         (SEQ ID No. 94)
5' CCATTCATATCATGCTCCCCCTT 09N1-ZanON Probe:
                                         (SEQ ID No. 95)
5' CALRed 610-CTGCCCCTTGAGTCAAGAG-BHQ2

09N1-ZanOFF Probe:
                                         (SEQ ID No. 96)
5' GTCATTTAGCAAG-BHQ2

09N1-Os Probe:
                                         (SEQ ID No. 97)
5' CALRed 610-CTCTCATAGTGATAATTAAG-BHQ2

09N1 Target/Amplicon:
                                         (SEQ ID No. 98)
5' CCATTCATATCATGCTCCCCCTTGGAATGCAGAACCTTCTTCTTGAC

TCAAGGGGCCTTGCTAAATGACAAACATTCCAATGGAACCATTAAAGACA

GGAGCCCATATCGAACCCTAATGAGCTGTCCTATTGGTGAAGTTCCCTCT

CCATACAACTCAAGATTTGAGTCAGTCGCTTGGTCAGCAAGTGCTTGTCA

TGATGGCATCAATTGGCTAACAATTGGAATTTCTGGCCCAGACAATGGGG
```

-continued

CAGTGGCTGTGTTAAAGTACAACGGCATAATAACAGACACTATCAAGAGT

TGGAGAAACAATATATTGAGAACACAAGAGTCTGAATGTGCATGTGTAAA

TGGTTCTTGCTTTACTGTAATGACCGATGGACCAAGTAATGGACAGGCCT

CATACAAGATCTTCAGAATAGAAAAGGGAAAGATAGTCAAATCAGTCGAA

ATGAATGCCCCTAATTATCACTAT GAGGAATGCTCCTGTTATCCTGATT

CTAGTGAAATCACATGTGTGTG 3'

MS2-Limiting Primer:
(SEQ ID No. 99)
5' CCGACCTGACGTACGGCTCTCATAGGA

MS2-Excess Primer:
(SEQ ID No. 100)
5' TGGTTGGAGTTGCAGTTCG

MS2-Probe:
(SEQ ID No. 101)
5' CALOrange 560-CAGTAAGCATCTCTTATGCATG-BHQ1

MS2-Amplicon
(SEQ ID No. 102)
5' TGGTTGGAGTTGCAGTTCGGTTGGTTACCACTAATGAGTGATATCCA

GGGTGCATATGAGATGCTTACGAAGGTTCACCTTCAAGAGTTTCTTCCTA

TGAGAGCCGTACGTCAGGTCGG 3'

In order to enhance RT-priming, an initial pre-incubation of the RNA templates with the Excess Primers was carried out in Tris-HCl (10 mM, pH 8.3) for 5 minutes at room temperature, in a final volume of 10 µl/assay. All other reagents were subsequently added to a final volume of 25 µl/assay, and RT-LATE-PCR was performed in an iQ™5 Real-Time PCR Detection System (Bio-Rad). The RT-LATE-PCR thermal profile was: 10 minutes at 50° C. (RT); 3 minutes at 89° C.; 50 cycles comprised of the following three steps: 5 seconds at 95° C., 15 seconds at 62° C. and 30 seconds at 72° C. Amplification was followed by annealing/melting: 3 minutes at 95° C.; annealing from 95 to 25° C. at 1° C./30 seconds-intervals; melting from 25 to 95° C. at 1° C./30 seconds-intervals. Probe fluorescence was acquired at end-point during the annealing and melting steps.

FIG. 11A, shows the first derivative of Cal Red fluorescence, that is, the melting curve of the 09N1-Zan ON+Zan OFF and 09N1-Os probes from the 09N1 amplicon generated in the triplex RT-LATE-PCR assay. Cal Red fluorescence was normalized as follows: first, background fluorescence from averaged No Template Controls (NTCs) was subtracted from the corresponding set of assay. All fluorescence readings from each curve were then divided by the fluorescence reading for that same curve at 55° C., thus assigning the normalized fluorescence value of 1.0 to the 55° C.-peak of all curves. This strategy allowed a direct analysis of fluctuations of fluorescence at 40° C. under different experimental conditions relative to the amplitude of the 55° C. peak. In FIG. 11A, circle 110 denotes the normalized curves for the replicates with no added reagent, circle 111 denotes the replicates for reaction mixtures containing antibody (hot start), and circle 112 denotes the replicates containing antibody and Reagent1. The results in FIG. 11A show that in the absence of a "hot-start" (curves 110) or when only the antibody was present (curves 111) CAL Red 610 fluorescence at 40° C. was considerably lower than fluorescence at 55° C., as shown by the relative peak heights at the two temperatures. In assays also containing Reagent1 (curves 112), however, fluorescence at 40° C. increased considerably when compared to fluorescence at 55° C. This difference shows that Reagent1 suppresses mis-priming and allows a more efficient binding of the 09N1-Os Probe to target in the temperature space between 45 and 25° C.

Figure 11B:
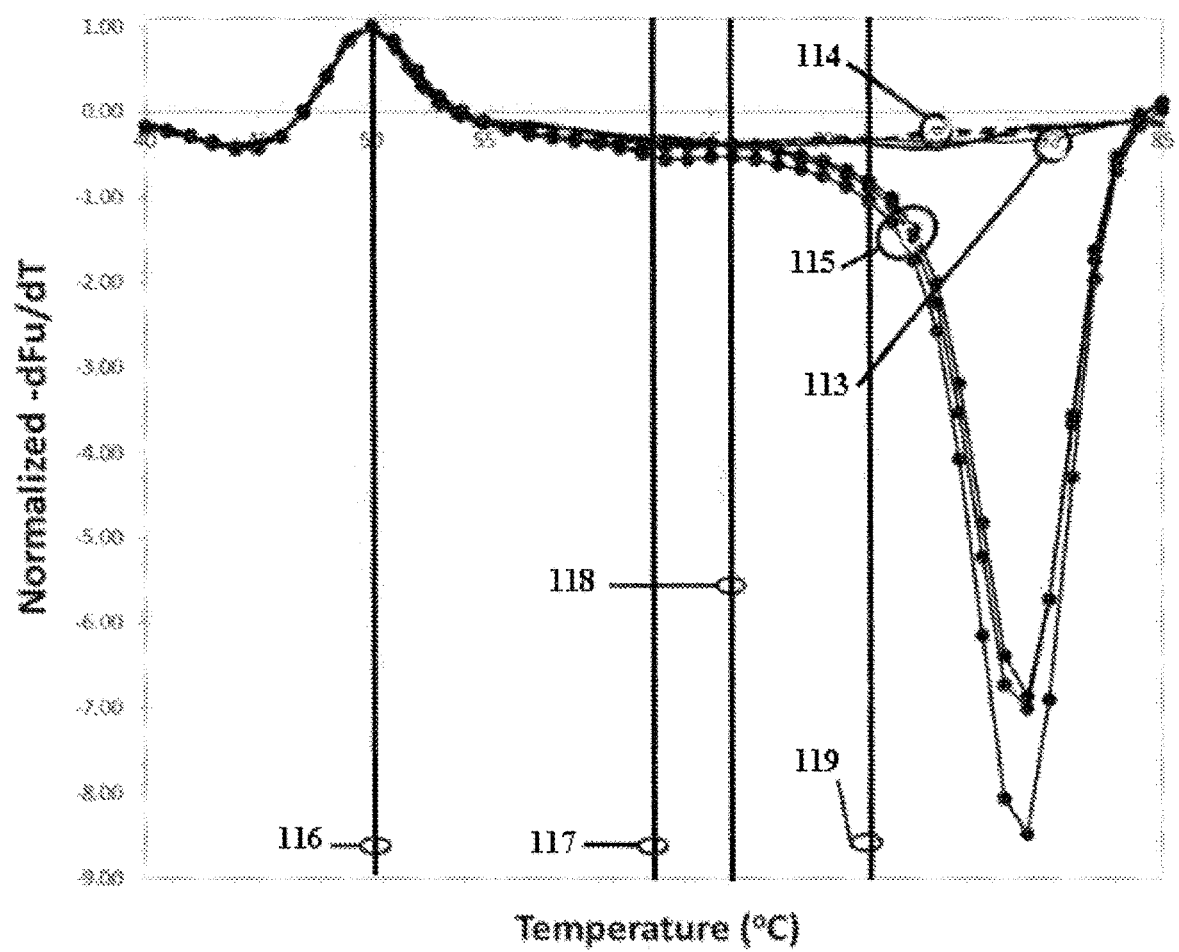
FIG. 11B present melt curves from a triplicate assay of Example 11 with no additive, with a hot-start antibody and with a hot-start antibody plus Reagent1 in the color of ON/OFF probes and in the color of Reagent1.

FIG. 11B presents the negative first derivative of CAL Orange 560 fluorescence during the post-amplification anneal/melt in the same sets of assays shown in FIG. 11A. Circle 113 denotes the curves for the replicates with no added reagent, circle 114 denotes the curves for the reaction mixtures containing antibody, and circle 115 denotes the curves for the replicates containing antibody and Reagent1. Vertical reference lines in FIG. 11B indicate several relevant temperatures. Line 116, at 50° C., is the temperature of reverse transcription; line 117, at 62° C., is the PCR annealing temperature; line 118, at 66° C., is the concentration-adjusted melting temperature of the MS2 excess primer at the start of amplification; and line 119, at 72° C., is both the PCR extension temperature and the concentration-adjusted melting temperature of the MS2 limiting primer at the start of amplification. The valley in curves 115 at about 80° C. indicates the melting temperature of Reagent1, while the positive peak at 50° C. corresponds to the melting temperature of the MS2 probe to its target. (Results were normalized at 50° C., so that the positive peaks had the value of 1.0 for all samples.) The opposite direction of the two peaks is explained by the fact that Reagent1 fluoresces when the sense strand is not bound to the antisense strand, while the MS2 probe fluoresces when it is hybridized to its target.

Example 12

Reagent1 Provides a Stable and Consistent Marker During PCR, Unaffected by Amplicon Generation The LATE-PCR mixture used for this experiment contained, in a final volume of 25 µl/assay, 2.5 units of Platinum Taq DNA polymerase (Invitrogen Life Technologies) and the buffer provided by the manufacturer at 1× final concentration. It also contained 3 mM $MgCl_2$, 0.2 mM dNTPs, Reagent1 at 50 nM concentration for the fluorescently labeled strand and 150 nM for the quencher-labeled strand, 50 nM HV2-Limiting Primer, 1 µM HV2-Excess Primer, 100 nM HV2-Probe and the targets for these primers and probe: 1000 copies of human genomic DNA (Promega Human DNA). It is estimated that 1000 human genomes include approximately 10,000 mitochondrial genomes where the HV2 sequence is located. The variant of Reagent1 used in this example included Cal Orange 560 as the fluorescent moiety, F, and Black Hole Quencher 2 as the quenching moiety, Q. The probe was labeled with a spectrally distinct fluorophore, Quasar 670.

The sequences of the primers, probe and target used for the experiment are listed below.

HV2-Limiting Primer:
(SEQ ID No. 103)
5' AAAGCGGTGTGTGTGTGCTGGGTAGGAT 3'

HV2-Excess Primer:
(SEQ ID No. 104)
5' ACTTCAGGGTCATAAAGCCTAAATAGC 3'

-continued

HV2-Probe:
(SEQ ID No. 105)
5' BHQ2-AATGGCAGAGATGTCTTTAAGTGCTGTTT-Quasar 670 3'

HV2 Amplicon:
(SEQ ID No. 106)
5' GCTCGCCACACACACGACCCATCCTACCCGCCCCCAACATAACTA
CTCTAATCATCATACCCTCACCCTCCCCTTTTATTACACAATCAACCCCC
CACTGACAATTTTCACGTATGGCGGTTTTCTATTTTAAACTTTAGACCAA
TCCGACCACAATCCCAAGAAACAAAAACCCCAAACCGTCTCTACACAAAT
TCACGACACCGGTCTTCGCCCCCTCCCCCCCAAACCACCTTTAAAAACA
ATACTACAGACACACCTTTCACCGACACGTCTGTAAGTTAACAATAATAA
TACAGGATGTTCGTAATTAATTAATTGTGTGAAATCATTCATACAAGCGG
ACATTATAACTTGCATCCACGCTATTTATTATCCTACTCCGTCCTTAGTT
TCTGTCTATGACGCTGTATCCCACGAGGCCGAGGTCGCAGAGCGTTACGA
TAGCGCACGTATGGGGGGTCTGCTTTTATGGTTTACGTACCTCTCGAGGG
CACTCACCAATTATCCCACTATCTGGACACTAGGTAGCACTACAGAATAA
ATTCCCCTTGCACACCCGATAAATCCGAAATACTGGGACTTCA 3'

LATE-PCR was performed in a Mx3005P thermocycler (Stratagene, Agilent Technologies). The LATE-PCR thermal profile was: 3 minutes at 95° C.; a mini-melt of 16 cycles from 70 to 85° C. at 1° C./30 seconds-intervals (this stage was denominated "Time 0" for data analysis); 30 PCR cycles comprised by the following three steps: 5 seconds at 95° C., 20 seconds at 62° C. and 45 seconds at 75° C.; 30 seconds at 95° C.; a mini-melt of 16 cycles from 70 to 85° C. at 1° C./30 seconds-intervals; 30 PCR cycles comprised by the following three steps: 5 seconds at 95° C., 20 seconds at 62° C. and 45 seconds at 75° C.; 30 seconds at 95° C.; a mini-melt of 16 cycles from 70 to 85° C. at 1° C./30 seconds-intervals; a final full melt of 66 cycles from 25 to 90° C. at 1° C./30 seconds-intervals. Fluorescence was acquired at each melting step during all the melts, in both the CAL Orange 560 (Reagent1) and Quasar 670 (Probe) channels.

Figure 12A:
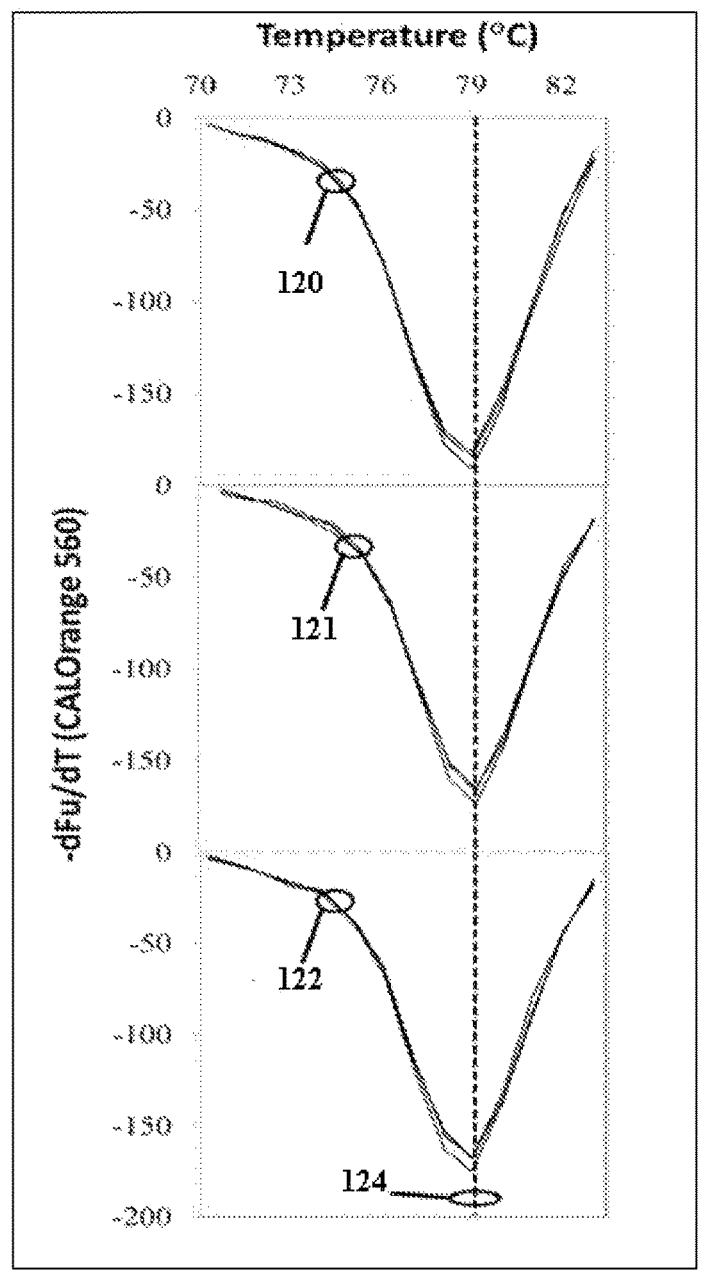
FIG. 12A presents melt curves of Reagent1 at various points during the amplification reaction of Example 12.
Figure 12B:
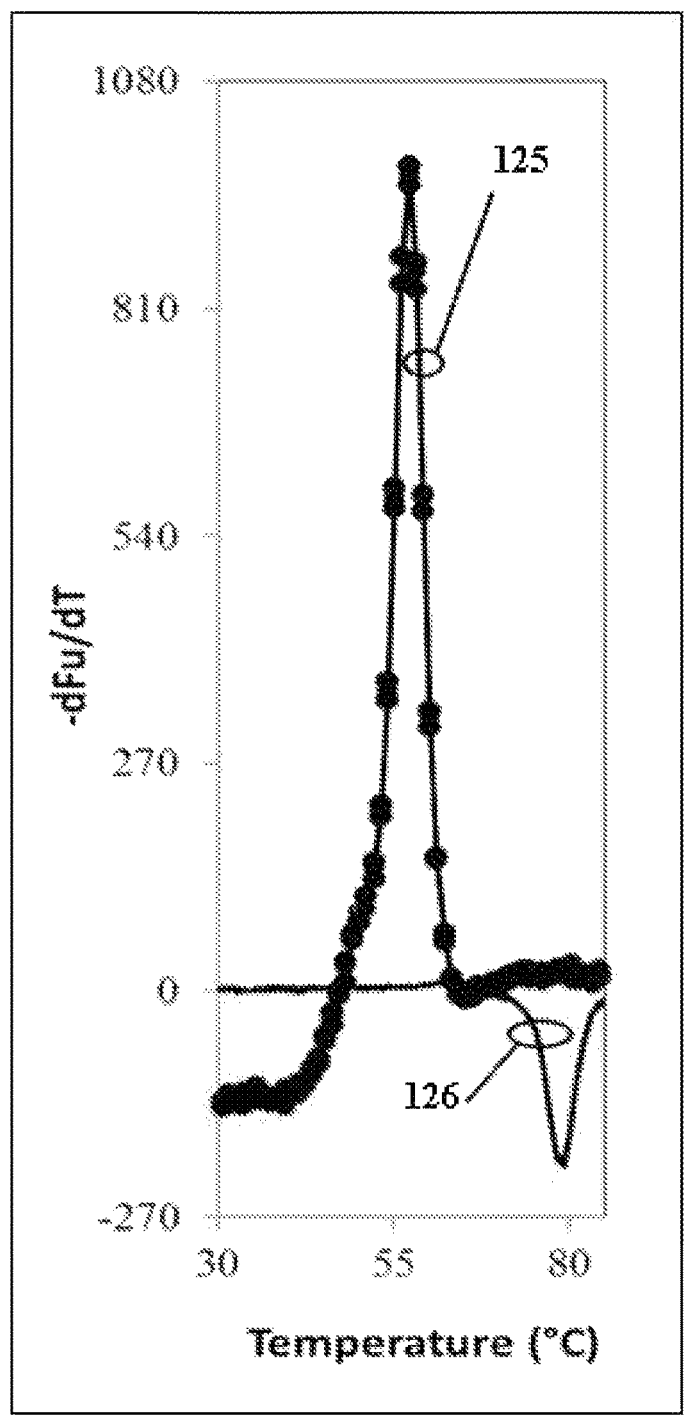
FIG. 12B presents post-amplification melt curves of the probe end of Reagent1 in the assay of Example 12.

FIG. 12A shows the negative first derivative of Cal Orange 560 fluorescence, indicative of Reagent1 melting, at different time points in the course of the experiment. Circle 121 denotes the curves for three replicate assays at Time 0; circle 122 denotes the curves for the three replicates after 30 amplification cycles; and circle 123 denotes the curves for the three replicates after 60 amplification cycles. Vertical line 124 is drawn through the minimums of the valleys in the curves, indicating the Tm of Reagent1. FIG. 12B shows the negative first derivatives of fluorescence during the post-amplification melt. Curve 125 is the Quasar 670 fluorescence from the probe, and curve 126 is the Cal Orange 560 fluorescence from Reagent1. Referring to FIG. 12A, the Tm of Reagent1 remained exactly the same before PCR was started (Time 0), after 30 LATE-PCR cycles and after 60 LATE-PCR cycles. Additionally, the Tm of Reagent1 was unaffected by the progressive accumulation of the HV2 amplicon during the course of PCR. The amplicon was not present at Time 0, because amplification had not started, but it was clearly present after 60 LATE-PCR cycles, as shown by the Quasar 670 peak in FIG. 12B. This peak represents the negative derivative of Quasar 670 fluorescence acquired at end-point and indicates that the HV2 probe has hybridized to its intended target that was generated during PCR. The Tm of Reagent1 was also found to be exactly the same in series of "No Template Control" assays run in parallel to those shown in the figure, either with or without primers and probe for the HV2 amplicon (not shown).

Example 13 Part I

Figure 13A:
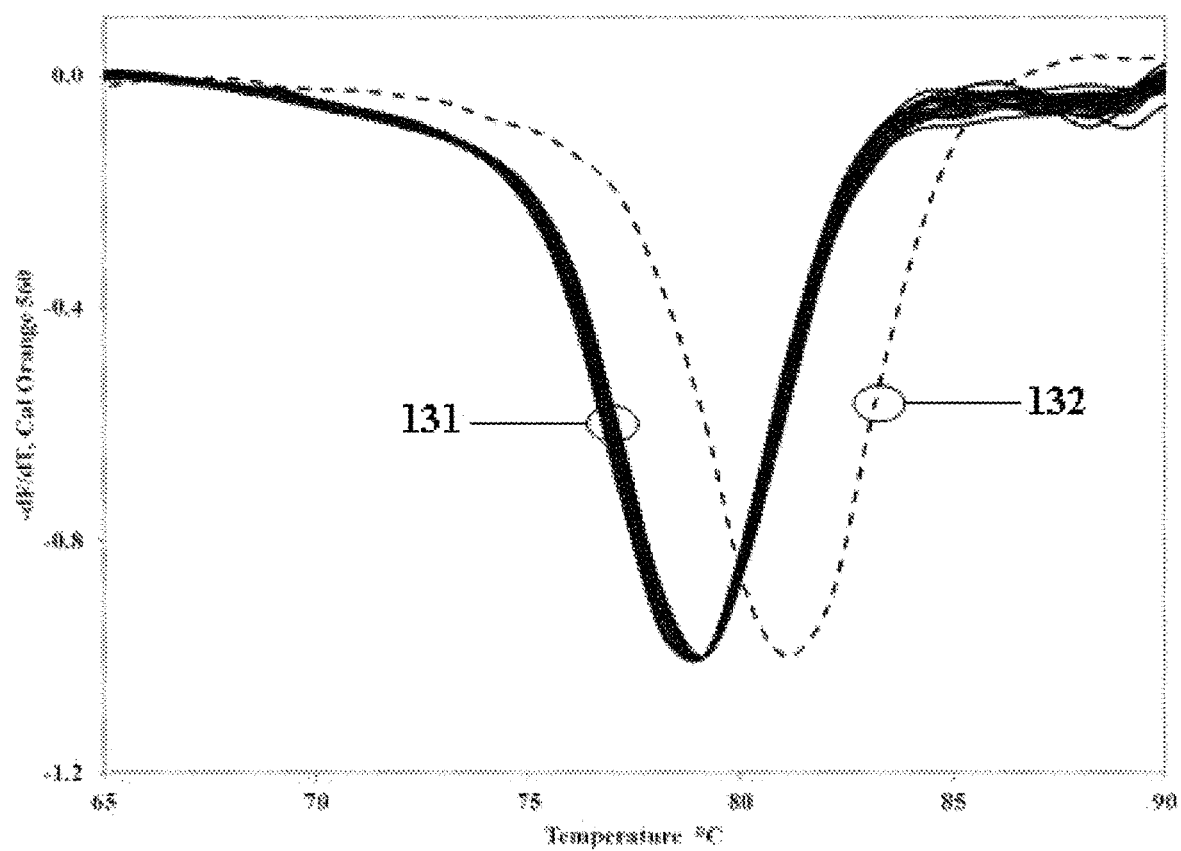
FIG. 13A presents melt curves from Reagent1 in 24 replicates subjected to sixty PCR cycles.

Use of Reagent1 to Identify Partial Evaporation of a Sample During Repeated Cycles of Heating and Cooling in a "Closed-Tube" Reaction A test of partial evaporation was carried out using twenty-four tubes in a 25 µl volume consisting of 1×PCR buffer (Invitrogen, Carlsbad, Calif., USA), 3.0 mM $MgCl_2$, Reagent1 (50 nM of the fluorophore-containing strand with 150 nM of the quencher strand). The thermal profile was as follows: 95° C./3 min for 1 cycle, followed by 98° C./10s-75° C./40s for 60 cycles. This was followed by a melt starting at 45° C. with 1° C. increments at 27s intervals to 97° C. The first derivative results shown in FIG. 13A are normalized to the lowest fluorescent value. The vast majority of replicates (23/24) showed no evaporation (circle 131) while a single replicate (curve 132) had an upward temperature shift indicating a change.

Example 13 Part II

Use of Reagent1 to Identify Temperature Shifts in the Fluorescent Signature as a Result of Sample Evaporation or Changes in Sample Ionic Strength FIGS. 13B-E illustrate the use of Reagent1 to identify artifacts that generate false-positives during mutation analysis using single-tube multiplex LATE-PCR assay and Lights-On/Lights-Off probes. These specific examples show mutational analysis of exons 18-21 from the Epidermal Growth Factor Receptor (EGFR) gene from two lung cancer biopsies. Mutations in these exons define the patient response to cancer therapies with anti-EGFR tyrosine kinase inhibitors. For each of these analyses, EGFR exons 18-21 from the cancer biopsy and from a reference normal sample were amplified in parallel as two separate single-tube multiplex reactions. Individual amplicons from each of these reactions were then interrogated at the end of amplification in the same closed tube using sets of Lights-On/Lights-Off probes that spanned the entire length of each amplicon and that were labeled with a different color for each exon (FAM for exon 18, Cal Red 610 for exon 19, Quasar 670 for exon 20, and Cal Orange 560 for exon 21). The sets of probes for exon 21 included Reagent1 which was also labeled with Cal Orange 560. The resulting fluorescent data were then plotted as the negative first derivative of fluorescent signals as a function of temperature to generate fluorescent signatures. The fluorescent signatures for individual exons from the reference normal and the cancer samples were subsequently compared to identify temperatures shifts indicative of mutations.

The version of Reagent1 used in this example included Cal Orange 560 as the fluorescent moiety, F, and Black Hole Quencher 2 as the quencher moiety, Q.

The primers used for amplification were as follows:

```
Exon 18-Limiting Primer:
                                  (SEQ ID No. 107)
5' CCCAGAGGCCTGTGCCAGGGACCTTAC 3'

Exon 18-Excess Primer:
                                  (SEQ ID No. 108)
5' CTTGTCTCTGTGTTCTTGTCCCCCC 3'

Exon 19-Limiting Primer:
                                  (SEQ ID No. 109)
5' CCATGGACCCCCACACAGCAAAGCAGAAA
CTCAC 3'

Exon 19-Excess Primer:
                                  (SEQ ID No. 110)
5' GCCAGTTAACGTCTTCCTTCTCTCTGTCATA 3'

Exon 20-Limiting Primer:
                                  (SEQ ID No. 111)
5' TGGGAGCCAATATTGTCTTTGTGTTC
CCGGACATAGT 3'

Exon 20-Excess Primer:
                                  (SEQ ID No. 112)
5' GTGCCTCTCCCTCCCTCCAG 3'

Exon 21-Limiting Primer:
                                  (SEQ ID No. 113)
5' AGGAAAATGCTGGCTGACCTAAAGC
CACCTCCTTAC 3'

Exon 21-Excess Primer:
                                  (SEQ ID No. 114)
5' CTCACAGCAGGGTCTTCTCTGTTTCAG 3'
```

The sets of Lights-On/Lights-Off probes used were as follows:

```
Exon 18 Lights-On Probes:
                                  (SEQ ID No. 115)
FAM-5' GGTTGATCTTTTTGAATTCAGTTTCCTTCAAGATCCTCCC
3' BHQ1

(SEQ ID No. 116)
BHQ1-5' CAAAGAGAGCTTGGTTGGGAGCTTTG-3' FAM (SEQ ID. No, 117)
BHQ1-5' GGCTCCACTGGGTGTAAGCC-3' FAM

Exon 18 Lights-Off Probes:
                                  (SEQ ID No. 118)
BHQ1-5' CGGAGCCCAGCACT-3' BHQ1

(SEQ ID No. 119)
BHQ1-5' AGGCTCCACAAGCTG-C3-3'

Exon 19 Lights-On Probes:
                                  (SEQ ID No. 120)
CAL Red 610-5' GGACCTTCTGGGATCCAGAGTCCCCC-3' BHQ2

(SEQ ID No. 121)
BHQ1-5' CCGCTTTCGGAGATGTTGCTTGG-3' CAL Red 610

(SEQ ID No. 122)
BHQ2-5' TTATCGAGGATTTCCTTGTTGGAA-3' CAL Red 610

Exon 19 Lights-Off Probes:
                                  (SEQ ID No. 123)
5' ACGGGAATTTTAACTTTCTC-3' BHQ2

(SEQ ID No. 124)
BHQ2-5' CTCTTAATTTCTTGATAGCG' BHQ2

Exon 20 Lights-On Probes:
                                  (SEQ ID No. 125)
Quasar 670-5' GCAGATACCCAGTAGGCGG-3' BHQ2

(SEQ ID No. 126)
BHQ2-5' CCAGGGGGCAGCCGAAGG-3' Quasar 670

Exon 20 Lights-Off Probes:
                                  (SEQ ID No. 127)
BHQ2-5' CTGCATGGTGAAGGTGAG-3' BHQ2

(SEQ ID No. 128)
BHQ2-5' GCATGAGCCGCGTGATGAG-3' BHQ2

Exon 21 Lights-On Probes:
                                  (SEQ ID No. 129)
CAL Orange 560-5' CCACGGTCCCCCAAGTAGTTTATGCCGG-3'
BHQ1

(SEQ ID No. 130)
CAL Orange 560-5' TTAAAATCTGTGATCTTGGCATGCTGCG
GTGAA-3' BHQ-1

(SEQ ID No. 131)
BHQ1-5' TTTTTGTCTCCCCCTGCATGGTATTCTTAA-3' CAL
Orange 560

(SEQ ID No. 132)
BHQ1-5' CCCACCAGTATGTTCCTGGTTGGG-3' CAL Orange 560

Exon 21 Lights-Off Probes:
                                  (SEQ ID No. 133)
BHQ1-5' CCAGCATTATGGCTCGCCC C3 3'

(SEQ ID No. 134)
BHQ1-5' TCTCTTCTGTACCC-C3 3'

(SEQ ID No. 135)
BHQ1-5' CTAGGTCTTGGTGGATTGAGCG-3' BHQ1
```

In the foregoing sequences, BHQ1 is a Black Hole Quencher 1, BHQ2 is a Black Hole Quencher 2, and $C_3$ dotes a three-carbon linker.

Multiplex LATE-PCR amplifications were carried out in 25 µl reactions and consisted of 1× Platinum Taq buffer (Invitrogen, Carlsbad, Calif.), 3 mM $MgCl_2$, 400 µM deoxynucleotide triphosphates, 50 nM of each limiting primer, 1 µM of each excess primer, 100 nM of each Lights-On probe, 300 nM of each Lights-Off probe, 2.5 units of Platinum Taq DNA polymerase (Invitrogen, Carlsbad, Calif.), 1-1000 copies of genomic DNA and 50 nM Reagent1, wherein the quencher strand was added at 150 nM. Amplification was carried out in a Stratagene MX3500P (Agilent Technologies, Santa Clara, Calif.) for 60-70 thermal cycles. Each thermal cycle consisted of denaturation at 99° C. for 10 seconds, primer annealing at 72° C. for 15 seconds, and primer extension at 75° C. for 30 seconds. At the end of amplification there was a final extension step at 75° C. for 3 minutes. For endpoint analysis, the reaction was slowly cooled down from 85° C. to 35° C. in 1° C. degree decrements every 30 seconds to allow for hybridization of the Lights-On/Lights-Off probes. After 10 minutes incubation at 35° C. to allow for equilibration of the bound probes, the reaction was heated from 35° C. to 85° C. in 1° C. increments every 30 seconds with fluorescence acquisition at every degree. Fluorescent signal signatures were obtained by plotting the negative first derivative of raw fluorescent signals with respect to temperature (−dF/dT) as a function of temperature. Mutations are detected as temperature shifts in the fluorescent signatures from the test sample relative to the reference fluorescent signatures from normal genomes for the corresponding EGFR exon.

Figure 13B:
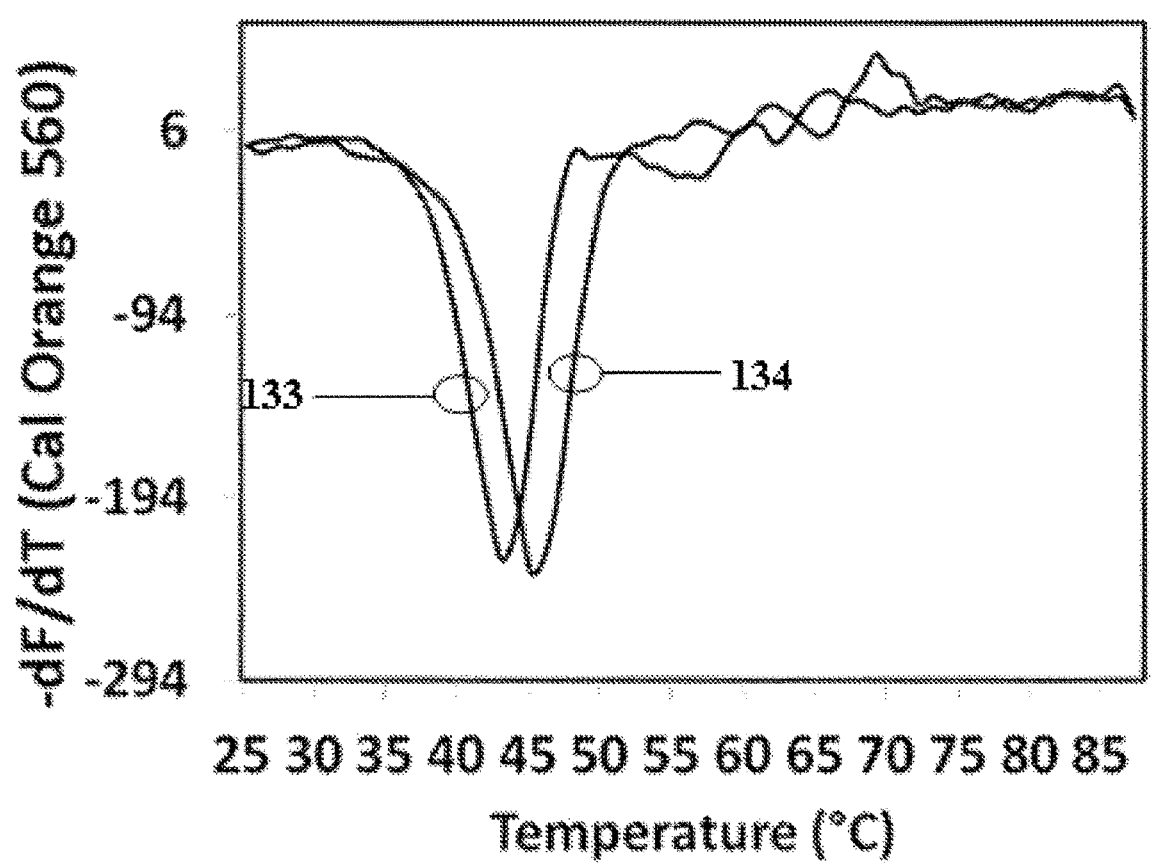
FIG. 13B presents the use of Reagent1 to identify artifacts that generate false-positives during mutation analysis using single-tube multiplex LATE-PCR assay and Lights-On/Lights-Off probes.
Figure 13C:
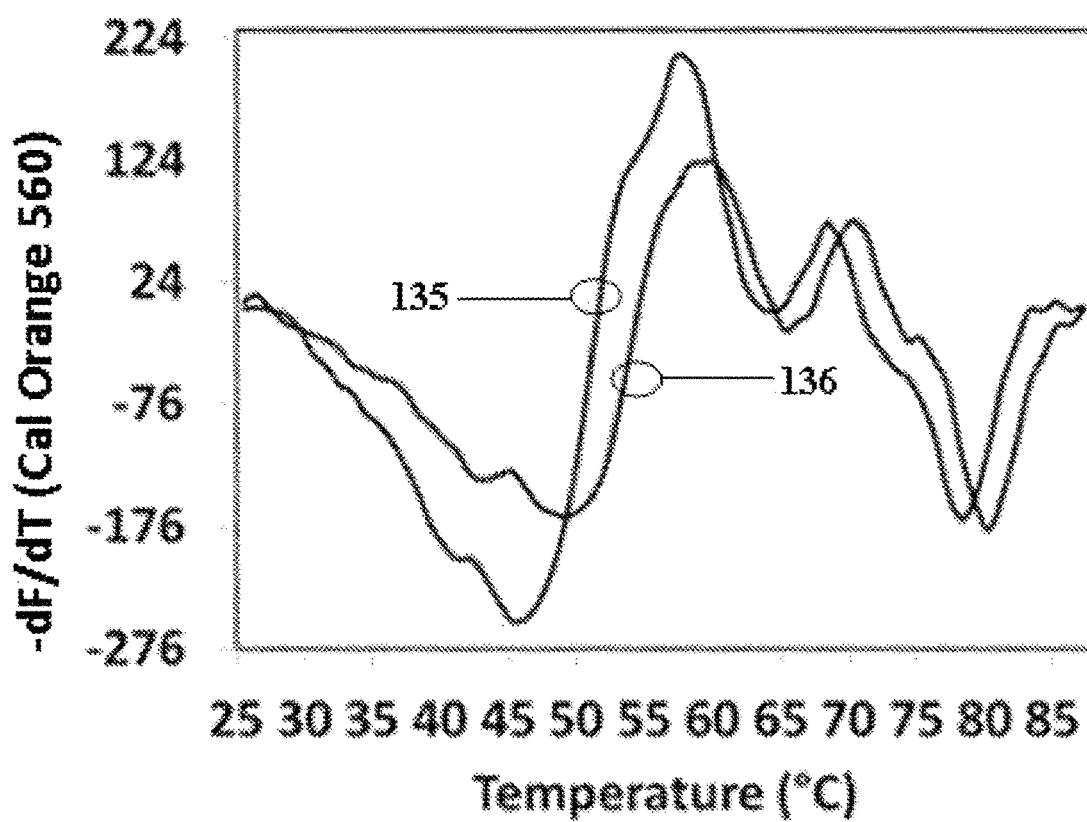
FIG. 13C presents the use of Reagent1 to identify artifacts that generate false-positives during mutation analysis using single-tube multiplex LATE-PCR assay and Lights-On/Lights-Off probes.

FIG. 13B shows a temperature shift to the right between the fluorescent signatures from the reference normal (curve 133) and one of the cancer samples (curve 134) from the FAM fluorescent channel for exon 18. These results suggest that the cancer sample had mutations in exon 18 that provided a better match to the Lights-On/Lights-Off probes used to interrogate this exon (in this particular assay the Lights-On/Lights-Off probes had nucleotide mismatches to their normal target sequences and could have better complementarity to certain mutations). However, analysis of the fluorescent signature from Reagent1 in the Cal Orange 560 channel in the same reactions, shown in FIG. 13C, revealed a similar temperature shift to the right (see rightmost valley in the corresponding fluorescent signatures in FIG. 13C, curves 135 and 136, respectively). This finding demonstrates that the relative changes in the fluorecent signatures between the cancer and the reference normal samples were not the result of mutations but rather were the result of a technical artifact caused by either sample evaporation or by differences in the relative salt concentrations of the cancer and the reference normal DNA samples (these DNA samples were prepared from two different institutions and contributed to almost half of the reaction volume, see details below).

Figure 13D:
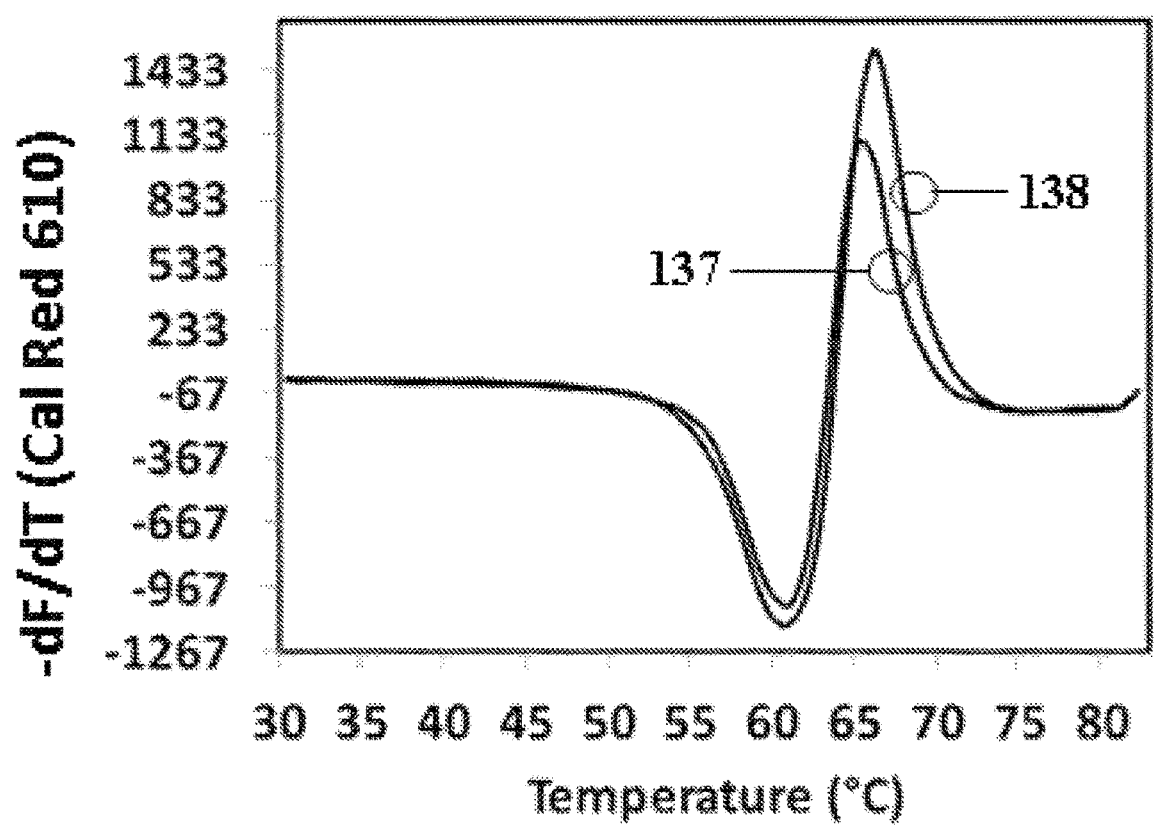
FIG. 13D presents the use of Reagent1 to identify artifacts that generate false-positives during mutation analysis using single-tube multiplex LATE-PCR assay and Lights-On/Lights-Off probes.
Figure 13E:
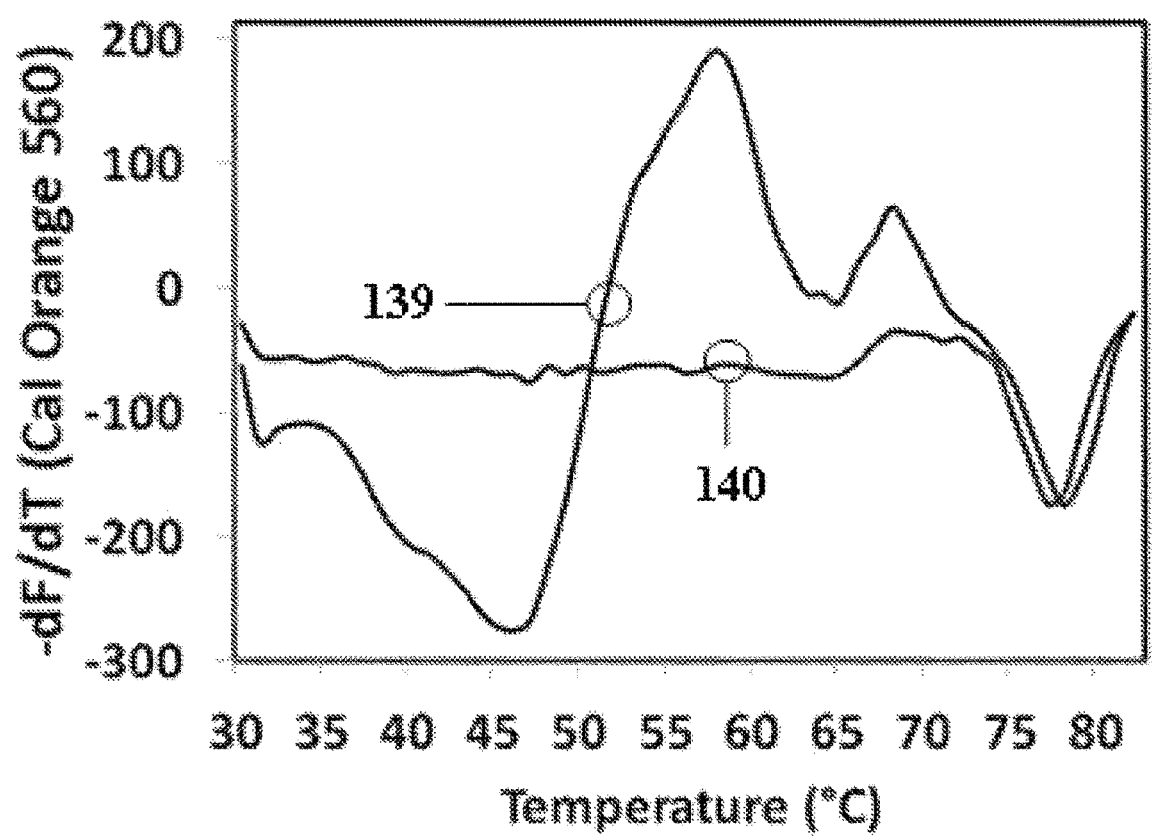
FIG. 13E presents melt curves in Cal Orange showing a shift in the melting temperature of Reagent1 between two mutant samples, one of which did not amplify.

FIG. 13D shows an example of a temperature shift to the left between the Cal Red fluorescent signatures from exon 19 for the reference normal (curve 137) and another cancer biopsy sample (curve 138). Once again, the presence of a similar temperature shift to the left in the fluorescent signature from Reagent1 (FIG. 13E, curves 139 and 140, respectively) demonstrates that the relative changes in fluorescent signatures were not the result of destabilizng mutations but rather were the result of a technical artifact. Such a shift to the left in fluorescent signartures can only be accounted for by a lower ionic strength in the tested cancer DNA. In this example, there were little amplification products from exon 21 from the cancer sample (curve 140).

Example 13 Part III

Sensitivity of Reagent1 to Small Changes in the PCR Mixture

The results illustrated in this part of the example were obtained in the course of the experiment described in Example 11, in parallel sets of assays. All experimental conditions, sequences and reagents, as well as the thermal profile used during RT-LATE-PCR were, thus, the same as described in Example 11.

As reported in Example 11, both sets of assays contained Reagent1 at a concentration of 50 nM for the sense strand and 150 nM for the antisense strand. One set of assays, but not the other, also contained 1.5 units of Platinum Taq Antibody (Invitrogen Life Technologies). Inclusion of this amount of antibody to the RT-PCR mixture implied the addition of the correspondent amount of storage buffer. Thus, the following additional reagents were also added to each of the assays containing the antibody: 0.24 mM Tris-HCl (pH 8.0), 0.48 mM NaCl, 24 mM Sodium Phosphate, 1.2 mM EDTA, 12 mM DTT, 0.6% (v/v) glycerol and stabilizers (concentration and nature undisclosed by the manufacturer). The thermal profile included a period of 3 minutes at 89° C. at the end of reverse transcription and prior to the start of LATE-PCR, intended to denature the antibody and release it from the Taq DNA polymerase; after this step, the antibody was therefore present in each assay as a denatured protein.

As detailed above, the concentrations of the additional reagents present in the assays containing the antibody are very low. Such additions are usually overlooked or ignored even by those skilled in the art. It is generally assumed that the antibody presence does not affect PCR beyond the effect of blocking the DNA polymerase until PCR is started in the thermocycler. The results in this example, however, indicate that a subtle change is also produced in the Tm of the nucleic acid sequences present in the assay. This change is revealed by Reagent1, which provides a very useful tool for the normalization of data when there are slight assay-to-assay differences in the composition of the reaction mixture.

Figure 13F:
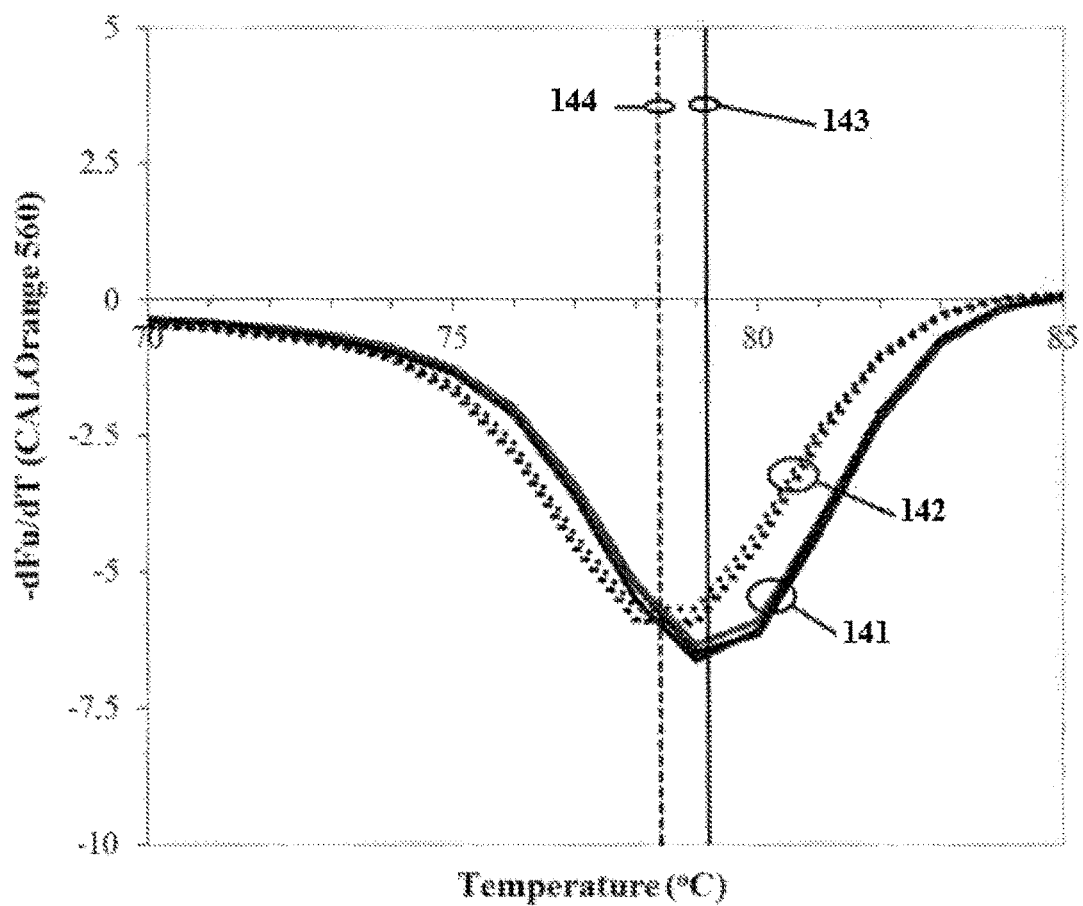
FIG. 13F presents melt curves for Reagent1 in the assay described in Example 11 for samples with Reagent1 and for samples with hot-start antibody plus Reagent1.

FIG. 13F shows the negative derivative of Cal Orange 560 fluorescence at the end of this experiment, in the temperature window where Reagent1 anneals to its anti-sense strand and generates a dip in fluorescence. Reagent1 was present in all six assays whose results are shown in the chart. The antibody was added to three of the assays (curves denoted by circle 142) but not to the other three (curves denoted by circle 141). The resulting Tm's of Reagent1 are indicated by vertical line 143 (no antibody) and 144 (with antibody. Addition of the antibody in its storage buffer slightly but clearly decreases the Tm of Reagent1. This shift could result from a number of factors, including the presence of glycerol and the ability of EDTA to chelate magnesium, both of which are known to decrease the Tm of nucleic acids during PCR.

Example 14

Use of Reagent1 as a Substitute for Hot Start Bolstered by Addition of Double-Stranded Oligonucleotide Dabcylated on Four of its Terminal Nucleotides LATE-PCR assays were carries out for the rpoB gene, similar to the assays for that gene described in Example 6. The version of Reagent1 used in this example had Quasar 670 as the fluorescent moiety, F, and Black Hole Quencher 2 as the quenching moiety, Q. The *M. tuberculosis* rpoB primer sequences and four of the six On/Off probe sequences, namely, Probe 2 Off, Probe 2 On, Probe 3 Off and Probe 3 On, were the same as those listed in Example 6 except that the excess primer sequence was modified to make this primer less specific to non-*M. tuberculosis* mycobacteria:

```
rpoB Modified Excess Primer:
5'-CCGGTGGTCGCCGCGATCAAGGAG-3'    (SEQ. ID No. 136)
```

Dabcyl-modified additive consisted of the following complementary strands:

```
5' Dabcyl-GGAGCAGACTAGCACTGAGGTA-Dabcyl 3'
                                        (SEQ ID No. 137)
3' Dabcyl-CCTCGTCTGATCGTGACTCCAT-Dabcyl 5'
```

The dabcyl-modified oligonucleotide had a Tm below that of the primers to minimize any interference with primer extension.

LATE-PCR amplifications were carried out in 25 μl reactions containing 1×PCR buffer (Invitrogen, Carlsbad, Calif.), 3 mM MgCl$_2$, 250 nM dNTPs, 50 nM rpoB Limiting Primer, 1000 nM rpoB Excess Primer, 50 nM of each of the two Lights-On probes, 150 nM of each of the two Lights-Off probes. One set of reactions had 1 unit Platinum Taq DNA Polymerase, a hot start polymerase with antibody referred to below as "antibody Taq" (Invitrogen, Carlsbad, Calif.). The other had 1 unit recombinant Taq DNA Polymerase, a non-hot start polymerase without antibody, referred to below as "regular Taq" (Invitrogen, Carlsbad, Calif.). A first subset of each of these sets of reactions had no additional component, a second subset was supplemented with 500 nM of the 22 bp modified oligonucleotide with four terminal dabcyls (Tm=67° C.), and a third subset was supplemented with 75 nM Reagent1 (75 nM fluorophore-containing oligonucleotide and 225 nM Reagent1 quencher oligonucleotide) plus 500 nM of the 22 bp modified oligonucleotide with four terminal dabcyls. The individual oligonucleotides comprising Regeant1 and the dabcylated duplex were combined first at their final concentrations and incubated on ice for 5 minutes before being added in. Reactions were started from 10, 100, or 1000 copies of M. tuberculosis genomic DNA in the presence of 20,000 copies of human genomic DNA (Promega, Madison, Wis.). Amplifications were carried out in a Strategene MX3005P (Agilent Technologies, CA). The thermal cycling profile consisted of 30 cycles of 98° C. for 10 seconds, 75° C. for 40 seconds, followed by DNA melts from 30 to 85° C. in 30 second intervals at 1° C. degree per step with fluorescence acquisition from the Quasar 670-laleled On probes. The same thermal cycling profile followed by the same DNA melts was then carried out every five cycles for 60 cycles total.

Figure 14E:
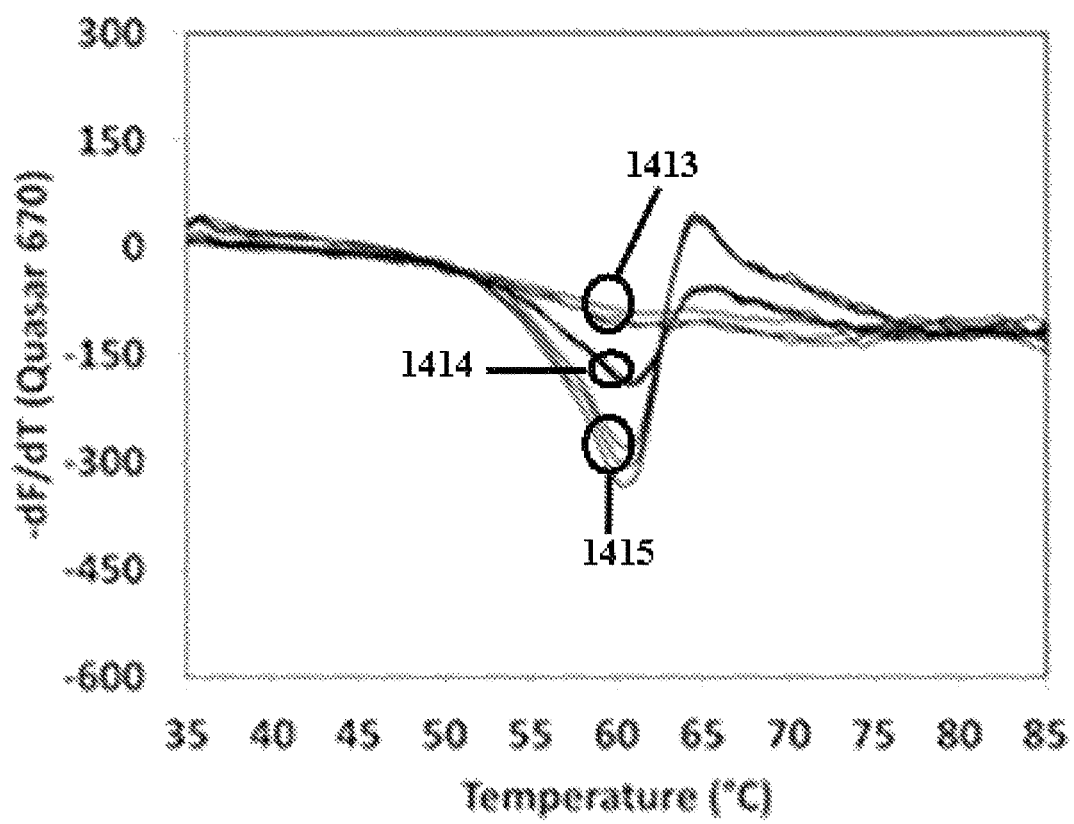
Figure 14F:
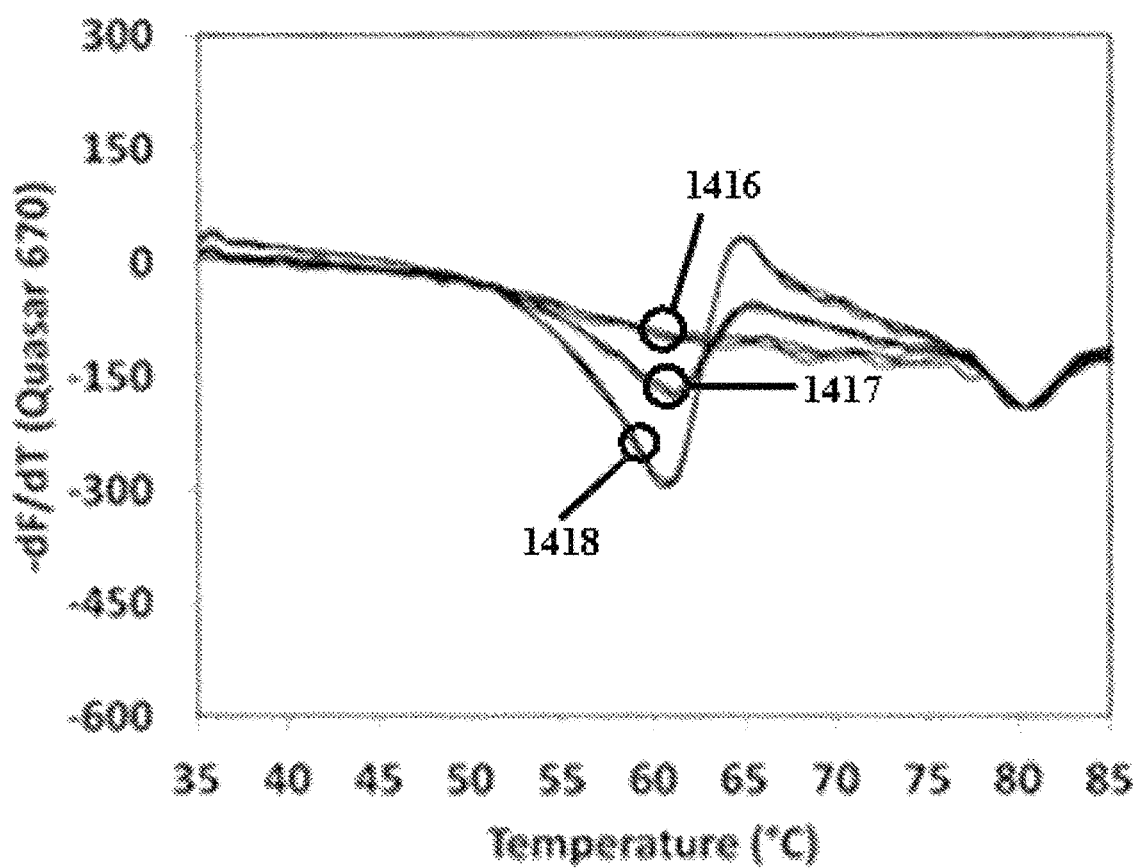

FIGS. 14A-F presents the probe melting results (Quasar 670 channel) after cycle 35 of the 60-cycle amplification reaction. The melting data is displayed as the negative first derivative of the fluorescence signals relative to temperature (fluorescent signature). FIG. 14A is from the reactions with regular Taq and no additive, where circle 1401 denotes the replicate curves for 10 copies of template DNA, circle 1402 denotes the curves for 100 copies of template DNA, and circle 1403 denotes the curves for 1000 copies of template DNA. FIG. 14B is from the reactions with regular Taq plus the dabcylated additive, where circle 1404 denotes the replicate curves for 10 copies of template DNA, circle 1405 denotes the curves for 100 copies, and circle 1406 denotes the curves for 1000 copies. FIG. 14C is from the reactions with regular Taq plus both the dabcylated additive and Reagent1, where circle 1407 denotes the replicate curves fo 10 copies of template DNA, circle 1408 denotes the curves for 100 copies, and circle 1409 denotes the curves for 1000 copies. FIG. 14D is from the reactions with antibody Taq and no additive, wherein circle 1410 denotes the replicate curves for 10 copies of template DNA, circle 1411 denotes the curves for 100 copies, and circle 1412 denotes the curves for 1000 copies. FIG. 14E is from the reactions with antibody Taq plus the dabcylated additive, where circle 1413 denotes the replicate curves for 10 copies of template DNA, circle 1414 denotes the curves for 100 copies, and circle 1415 denotes the curves for 1000 copies. FIG. 14F is from the reactions with antibody Taq plus both the dabcylated additive and Reagent1, where circle 1416 denotes the replicate curves for 10 copies of template DNA, circle 1417 denotes the curves for 100 copies, and circle 1418 denotes the curves for 1000 copies. Fluorescent signals for FIG. 14C and FIG. 14F were normalized to the lowest signal from the Reagent1 duplex acquired at 80° C.

Example 14 illustrates the advantages of replacing the hot start antibody (FIG. 14D) with 75 nM Reagent1 plus 500 nM of a 22 bp oligonucleotide modified with 4 dabcyl groups (FIG. 14C) versus 500 nM of a 22 bp oligonucleotide modified with 4 dabcyl groups alone (FIG. 14B).

FIGS. 14A and D show reactions with no additives in the absence of the presence of the hot start antibody. This data illustrates the increased variability due to mis-priming errors prior to the start of amplification among replicates without antibody (see region of arrows 1 and 1', 2 and 2'). Reactions of FIGS. 14B and E contained 500 nM of the 22 bp oligonucleotide modified with four dabcyl groups. Comparison of FIG. 14B with FIG. 14A, and comparison of FIG. 14E with FIG. 14D shows that the addition of the modified oligonucleotide alone altered the pattern of the probe/target hybrid (particularly in the region of arrows 2 and 2') due to inhibition of mis-priming prior to and during amplification. Reactions of FIGS. 14C and F contained 500 nM of the 22 bp oligonucleotide modified with 4 dabcyl groups, plus 75 nM of Reagent1. Comparison of FIG. 14C with FIG. 14B, and comparison of FIG. 14F with E shows that Reagent1 further reduces scatter among replicate reactions. Comparison of FIG. 14F with FIG. 14C shows that, when Reagent1 is present, the hot start antibody does not significantly improve the similarity of the replicate reactions at any of the three starting target levels (10, 100, 1000 copies of M tuberculosis genomic DNA). These results demonstrate that Reagent1 combined with a double-stranded oligonucleotide with multiple dabcyls and a Tm below that of the primers improves primer selectivity and effectively replaces hot start antibody.

Example 15

Effect of the Reagent2 on Symmetric Amplification of the Cystic Fibrosis Gene (CFTR); Reduction of End-Point Signal Variance and Use as a PCR Hot Start This Example compares symmetric PCR closed-tube amplification and detection of a segment of exon 10 of the CFTR gene in the presence and absence of Reagent2. The version of Reagent2 used in this example had Cal Red 610 as the fluorescent moiety, F, and Black Hole Quencher II as the quencher moiety, Q. Samples included 1× Platinum Taq reaction buffer (Invitrogen), 3 mM $MgCl_2$, 0.2 mM of each dNTP, 0.24×SYBR Green, 300 nM each primer, 300 nM probe, approximately 1,000 copies of human genomic DNA, and 1.25 Units Platinum Taq DNA polymerase (Invitrogen) in a final volume of 25 microliters. The sense primer, 5'-GGATTATGCCTGGCACCAT-3' (SEQ ID No, 138) has a predicted Tm of 66.2° C. at 300 nM and the antisense primer, 5'-GCTTTGATGACGCTTCTGTATCTA-3' (SEQ ID No. 139) and has a predicted Tm of 65.8° C. at 300 nM. The probe, 5'-Quasar 670-TCATCTTTGGTGTTTCCTATGA-Black Hole Quencher 2-3' (SEQ ID No. 140) was used in all amplifications to confirm specific target amplification and has a predicted Tm of 64.1° C. at probe and amplicon concentrations of 300 nM each. Tm's were predicted using Visual OMP (DNA Software). Reaction mixtures either contained no additive or contained 200 nM Reagent2 (quencher strand at 600 nM). Amplification was carried out in a Stratagene Mx3005P thermal cycler programmed to heat to 95° C. for 2 minutes, followed by 60 cycles of 95° C. for 10 seconds, 60° C. for 15 seconds, and 75° C. for 30 seconds. Fluorescence detection was done at 60° C. for the Quasar-labeled probe and at 75° C. for SYBR Green.

Figure 15A:
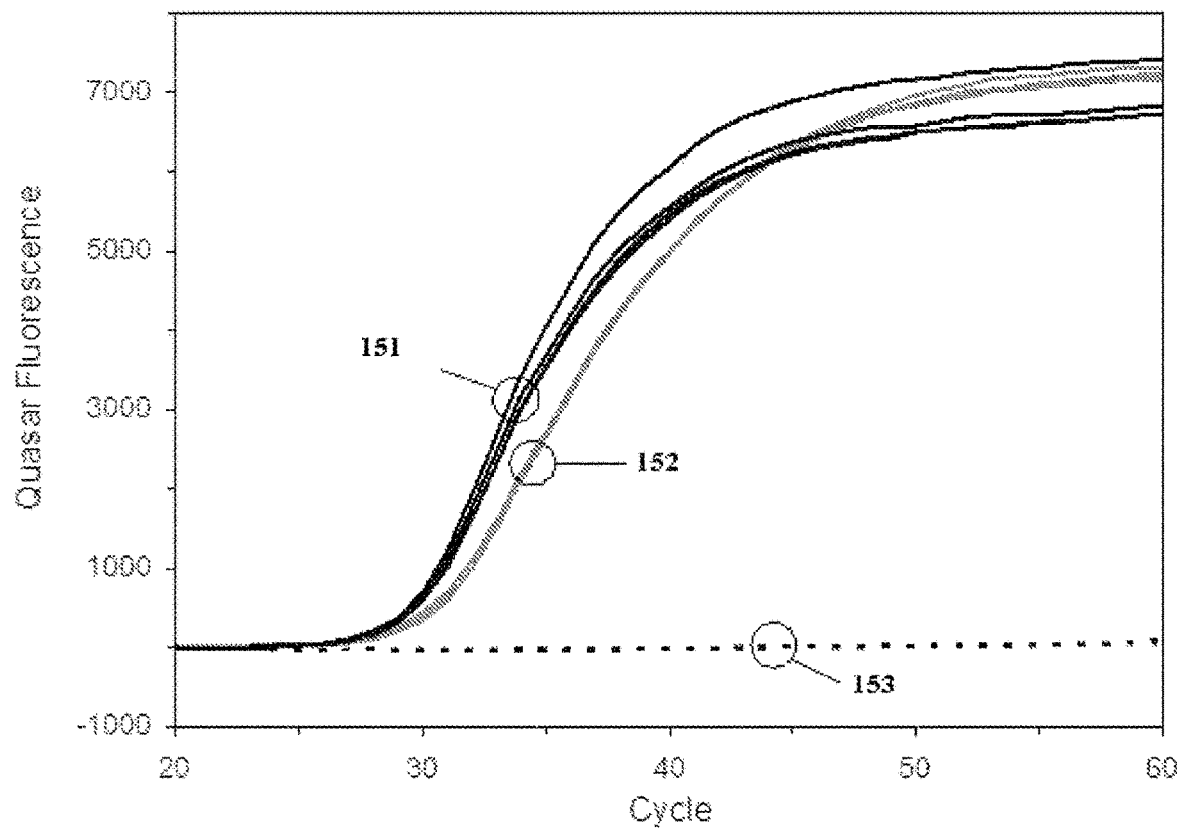
FIG. 15A present real-time curve of probe fluorescence from the assay described in Example 15 for samples containing hot-start Taq polymerase and either no reagent or Reagent2, for samples containing hot-start Taq polymerase with antibody, and for samples containing regular Taq polymerase and Reagent2, respectively.

Real time amplification plots of the probe fluorescence are presented in FIG. 15A, where circle 151 denote the curves for replicate assays (four) containing no added reagent, circle 152 denotes the curves for replicate assays containing 200 nM Reagent2, and circle 153 is for a no-template control. Samples with Reagent2 show a minor delay in fluorescence increase compared to those without Reagent2 (mean $C_T$ value difference of 0.5 cycle). A small variation is observed in the fluorescence increase in samples without Reagent2. Virtually no fluorescence variation is detected up to cycle 45 in samples with Reagent2, and variation remains low through cycle 60. Despite the initial delay, the average fluorescence at end point is higher in samples with Reagent2 than in samples without Reagent2. Also, samples without Reagent2 generated a mean $C_T$ value with SYBR Green (detecting all double-stranded DNA) of 1.3 cycles earlier than those with Reagent2 (plots not shown), indicating a greater level of non-specific amplification in the former. Taken together, these results suggest that Reagent2 reduces non-specific amplification that can increase variation and reduce overall amplification of the intended target. The consistency possible with Reagent2 could be useful in end-point quantification where real-time detection is not possible. It is also likely to improve detection sensitivity at low target concentrations and to provide improved product purity for sequencing reactions.

A separate experiment was conducted to test the ability of Reagent2 to provide a hot start for symmetric amplification of CFTR. Samples were prepared as described above, except that samples with 200 nM Reagent2 contained 1.25 Units of Taq DNA polymerase lacking the antibody to the polymerase present in Platinum Taq. (Both enzymes are recombinant Taq DNA polymerases manufactured by Invitrogen.) All samples were incubated at room temperature for 45 minutes prior to thermal cycling in order to provide a greater challenge for each hot start method.

Figure 15B:
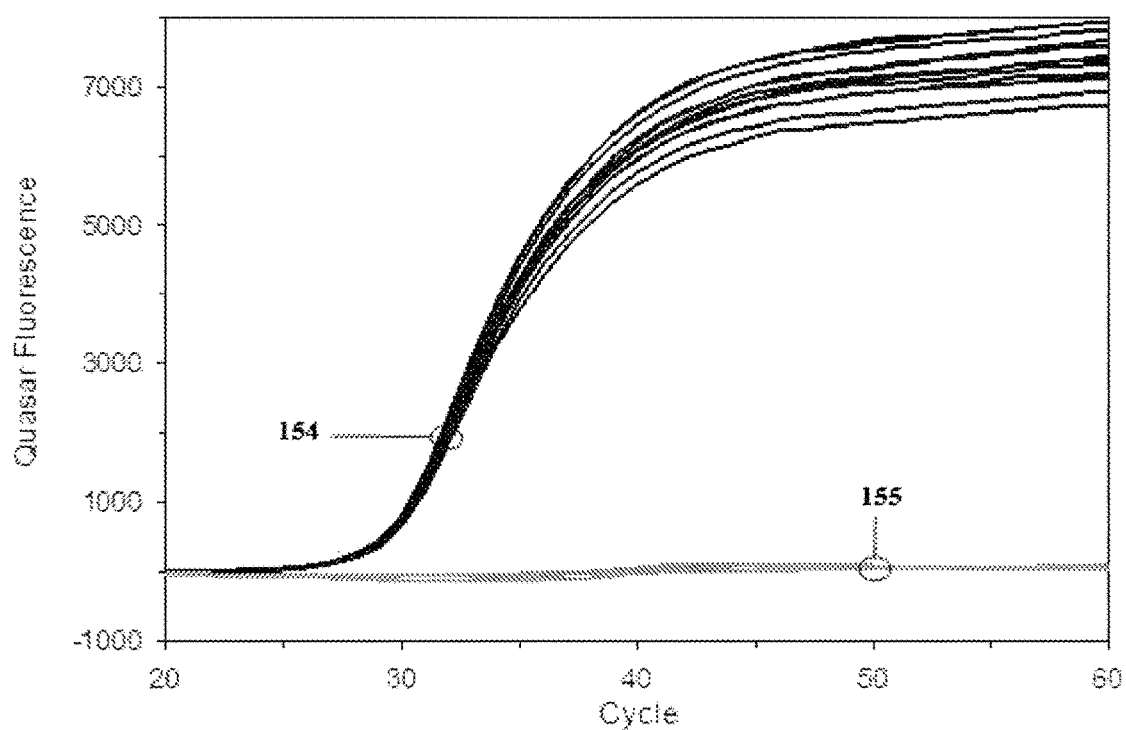
FIG. 15B present real-time curve of probe fluorescence from the assay described in Example 15 for samples containing hot-start Taq polymerase and either no reagent or Reagent2, for samples containing hot-start Taq polymerase with antibody, and for samples containing regular Taq polymerase and Reagent2, respectively.
Figure 15C:
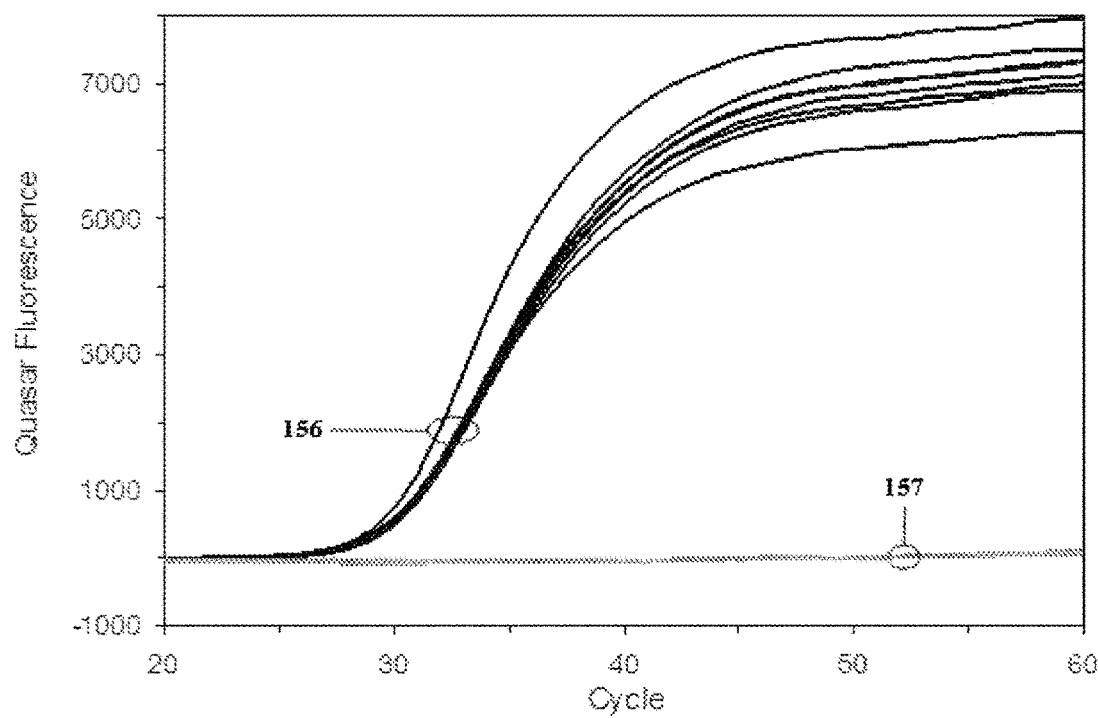
FIG. 15C present real-time curve of probe fluorescence from the assay described in Example 15 for samples containing hot-start Taq polymerase and either no reagent or Reagent2, for samples containing hot-start Taq polymerase with antibody, and for samples containing regular Taq polymerase and Reagent2, respectively.

FIG. 15B shows real time probe fluorescence plots of replicate samples with antibody, circle 154, and no template controls circle 155. FIG. 15C shows real time probe fluorescence plots of replicate samples with Reagent2, circle 156, and no template controls, circle 157. Those groups generated comparable $C_T$ values (delay with Reagent2 was 0.4 cycle). Final fluorescence was similar in the two groups, reaching mean values of 7426±387 with antibody and 7174±490 with Reagent2.

Example 16

Figure 16:
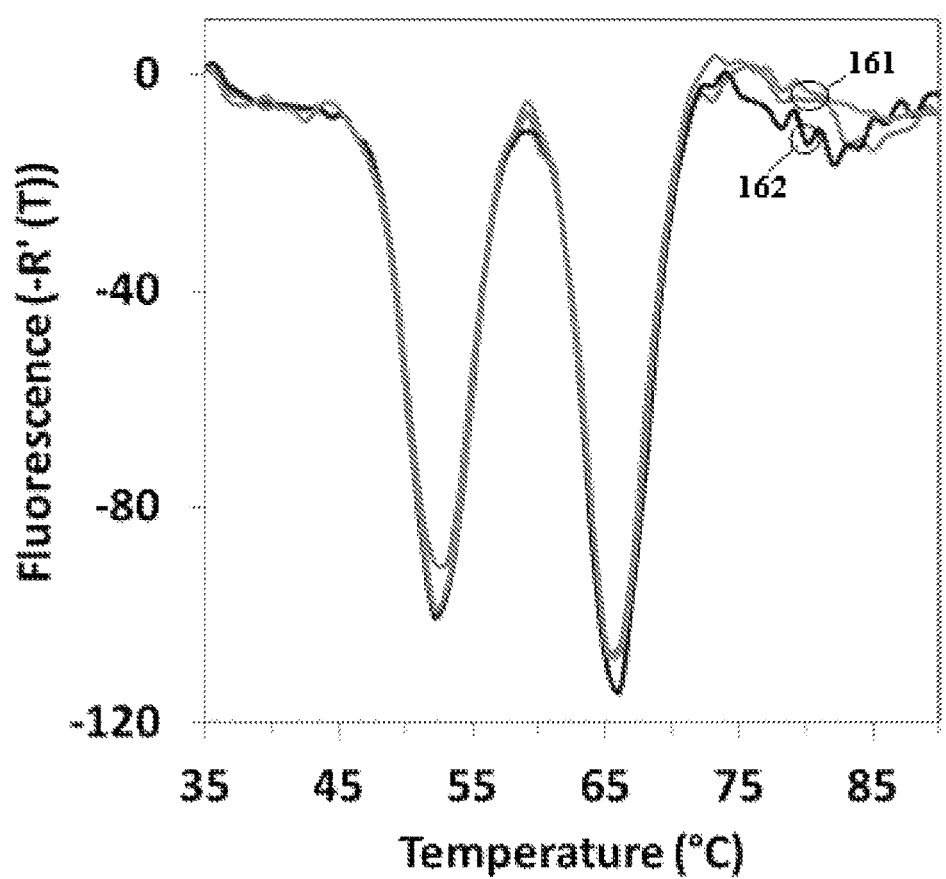
FIG. 16 presents melt curves in PCR reaction mixtures of either Reagent 4 or of a combination of Reagent3 and Reagent4.

Use of Reagent3 and Reagent4 to Generate High Temperature and Low Temperature Marks for Fluorescent Signal Normalization In this example the versions of Reagent3 and Reagent4 (Table 1) had FAM as the fluorescent moiety, F, and Black Hole Quencher 1 as the quencher moiety, Q, along with the two dabcyl labels in each Reagent. A typical PCR reaction mixture was supplemented with 100 nM Reagent3 fluorophore-labeled oligonucleotide and 300 nM Reagent3 quencher-labeled oligonucleotide, plus, 50 nM Reagent4 fluorophore-labeled oligonucleotide and 150 nM Reagent4 quencher-labeled oligonucleotide. FIG. 16 illustrates the fluorescent signatures for Reagent3 and Reagent4 in the FAM channel, where circle 161 denotes the curves for the combination of Reagent3 and Reagent4 and circle 162 denotes the curves for 150 nM Reagent 4. These fluorescent signatures generate both a high temperature and a low temperature mark for normalization of fluorescent probe signatures from probe/target hybrids in either the FAM channel or other fluorescent channels in the reaction. These temperature marks were generated by supplementing the PCR reagent mix with higher concentrations of Reagent3 duplex correct for the temperature-dependency of FAM fluorescent signals and generate fluorescent signature whose depth matches that of the fluorescent signature valley from Reagent4. The greater width of the fluorescent valley signals compared to the fluorescent signals from Reagent1 in other examples in this application is attributed to the known interactions between the extra dabcyl moieties attached to Reagent3 and Reagent4. Such interactions stabilize the fluor-quencher oligonucleotide duplexes in these reagents and result in broader temperature transitions during melting curve analysis.

Example 17

Mathematical Method for Using One or More Temperature Marks to Normalize Fluorescent Data from LATE-PCR Assays that Use Lights-on/Lights-Off Probes PCR assays, including particularly LATE-PCR assays, employing multiple Lights-On/Lights-Off probes are used to generate "fluorescent signatures" that are compared to a library of fluorescent signatures from known samples, as is described I published international patent application WO 2011/050173. Single and double temperature marks provide the starting point for mathematical analysis of melt/anneal curves in all colors in a single sample. Mathematical analysis is accomplished using a series of mathematical procedures or algorithms whose use and outcome is illustrated in the seven Steps of this example. Various of the Steps rely on previously determined standards: first a standard Tm for each Reagent that is used in the assay whose results are being investigated, and, second, a library of fluorescent signatures from known samples, which may be stored in a computer database in a form suitable for comparative purposes, for example, a series of values at several or many temperatures of the normalized first derivative of fluorescence versus temperature for each different probe color.

Figure 17A:
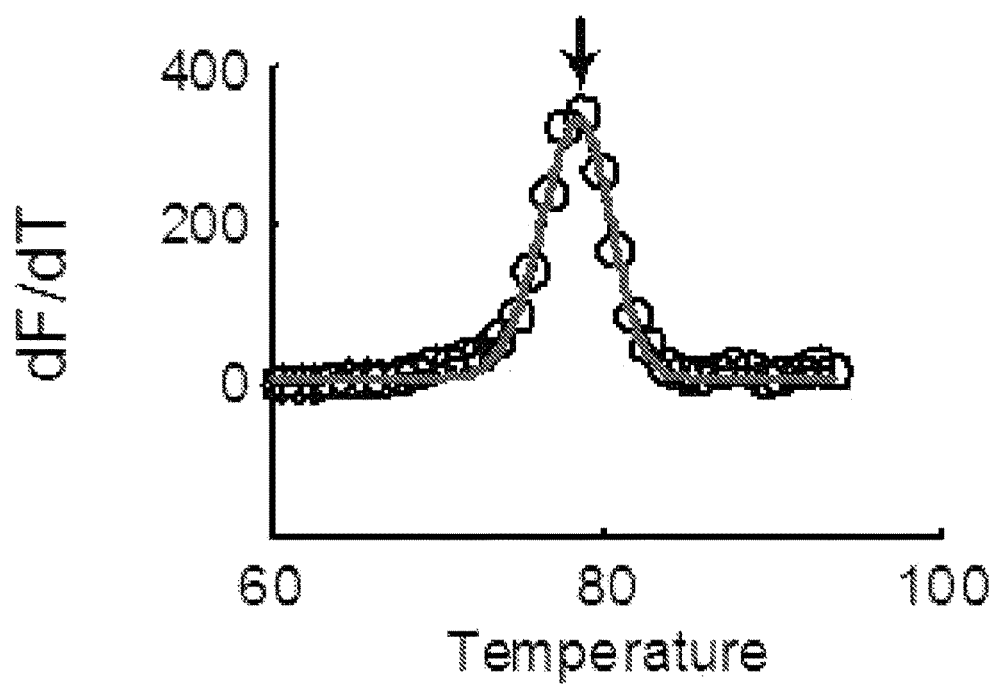
FIG. 17A shows a method for determining such Tm's in two Steps, and presents Reagent melting curves that might be obtained from three replicate samples, each fitted with a Gaussian curve.
Figure 17B:
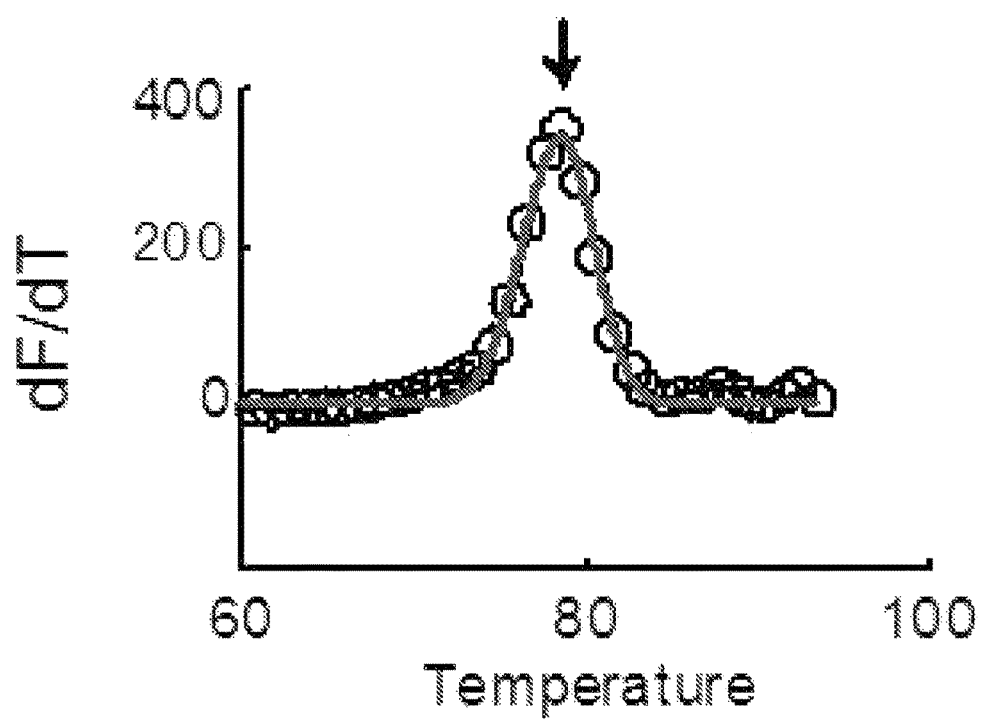
FIG. 17B presents Reagent melting curves that might be obtained from three replicate samples, each fitted with a Gaussian curve.
Figure 17C:
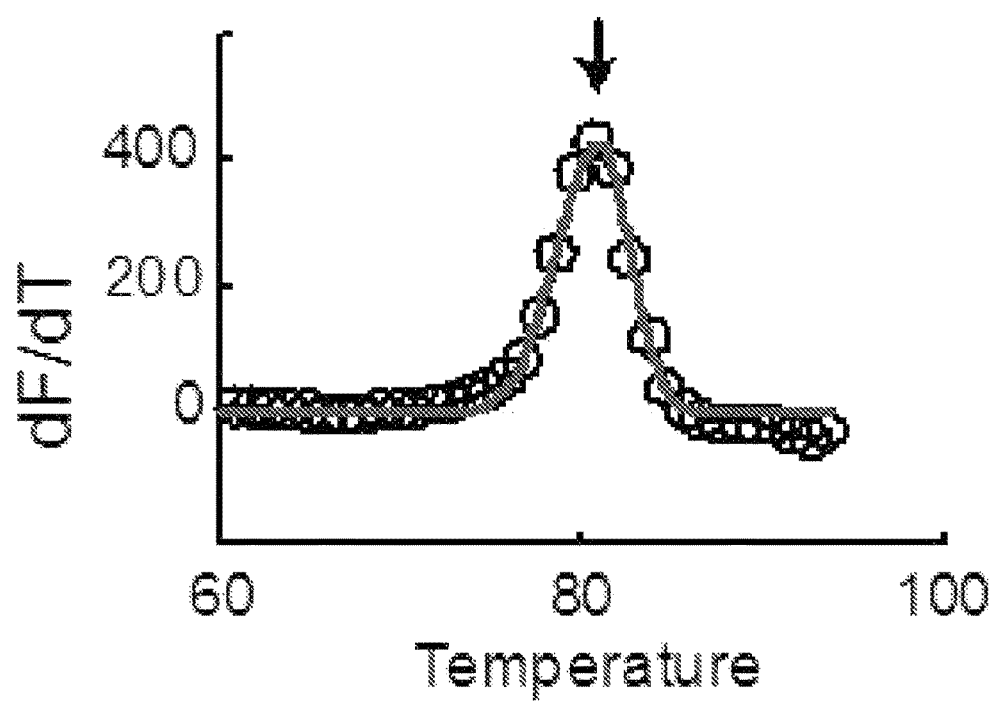
FIG. 17C presents Reagent melting curves that might be obtained from three replicate samples, each fitted with a Gaussian curve.

A first task is to determine if and how the Tm of each Reagent in the sample being investigated differs from the previously determined standard Tm for the Reagent. FIG. 17A shows a method for determining such Tm's in two Steps, here denominated Step 1 and Step 2. In Step 1, the data for a thermal mark "valley" (−dF/dT of a Reagent's fluorophore) is inverted into a "hill" and is plotted as a set of data-points as a function of temperature. FIGS. 17A-C show plots of data points (open circles) from three replicate reactions. Each hill from each replicate sample is treated separately and in Step 2 is fitted with a slightly skewed Gaussian curve (solid lines in FIGS. 17A-C). The peak of the fitted curve for each sample (arrow) is the observed Tm, (OTM), for the temperature mark of that Reagent in a sample.

Figure 17D:
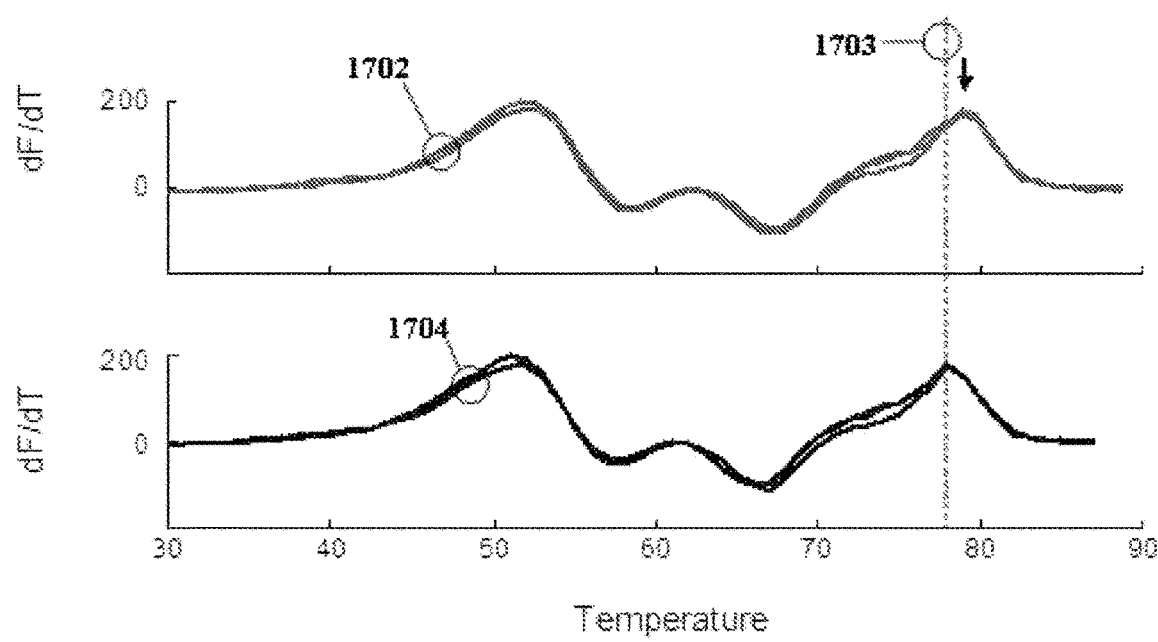
FIG. 17D shows fluorescence signatures that might be obtained from a sample before and after adjustment.

Next, correction is made to align each sample curve with the library of curves using the standard Tm of the Reagent. This is done in two steps, denominated Step 3 and Step 4. FIG. 17D presents two sets of curves. The upper panel shows the derivate curves, circle 1702, for replicates of a sample, wherein the downward arrow indicates the OTM and vertical line 1703 indicates the standard Tm for the Reagent. Step 3 is to determine the difference between the OTM and the standard Tm. We refer to the difference as the temperature-adjustment-value, TAV. As shown in the curves of circle 1702, the OTM differs by some amount from the previously established standard OTM for that Reagent, this difference being the TAV. If two Reagents are used, each with a different Tm, two independent TAV's can be produced, one for the high temperature Reagent and one for the low temperature Reagent. In Example 14, for instance, there was just one Reagent, hence one TAV. The TAV is useful for correcting the OTM in each sample to a pre-determined standard-OTM for that Reagent. Such an adjustment can be based on a single TAV, but it is preferable to base the TAV on a high/low temperature pair of OTM's from two Reagents. In Step 4 the TAV for each sample is used to adjust the sample curves (see FIG. 17D, lower panel, circle 1704) shows curves 1702 so adjusted. In this case the TAV was subtracted from each degree of temperature, thereby shifting the OTM to the left to its "theoretical peak position" and also shifting all other temperatures by the same amount. However, as one skilled in the art will appreciate, a constant shift is not the only way of using the OTM. It could, for instance, be used to shift the OTM to the position of the theoretical peak and then be further used to correct all temperatures above and below the theoretical peak by a scaling factor that is proportional to the number of degrees away from the OTM.

Figure 17E:
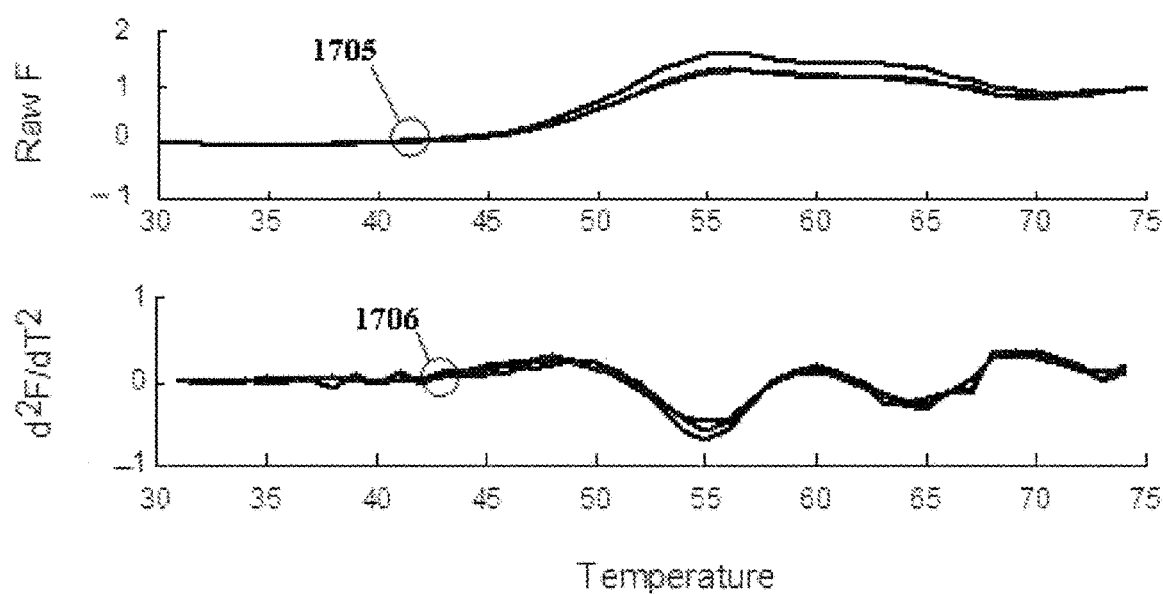
FIG. 17E shows fluorescence signatures that might be obtained from a sample after adjustment, presented both as normalized fluorescence and as a second derivative curve.

It remains to compare sample curves (circle 1704) to the library of possible targets, previously entered into a computer memory as a series of values at a number of temperatures sufficient to distinguish among the possible targets. For we utilize normalized curves for constructing the library and also for the sample curves being compared to the library. Step 5 involves normalization of the fluorescence signals on all channels so they are between 0 and 1, setting the fluorescence value at the lowest temperature of the interrogation range (30° C. in the illustration in FIG. 17E) as 0 and the fluorescence value at the highest temperature of the interrogation range (75° C. in the illustration of FIG. 17E) as 1. FIG. 17E, top panel, circle 1705, shows normalized curves of raw fluorescence data after the adjustment described above in connection with FIG. 17D. Normalization permits examination of the shape of the melt curves without regard to the abundance of the material. Step 6 involves computing the 1st and 2nd derivatives of the normalized raw fluorescence curve to highlight the signals related to the pattern of fluorescent signals as a function of temperature. FIG. 17E, bottom panel, illustrates such second derivative curves, circle 1706.

Step 7 involves evaluating an unknown sample. In this step we calculate the temperature-averaged error (such as the squared error) between the 1st or 2nd derivative of the normalized melt curve of the unknown sample and the same derivatives from a database of known samples. We consider the known sample with the lowest error to be the best match for the unknown sample. Because computers are very fast at making calculations, each data set could be shifted and/or scaled in said proportional manner and then compared to known patterns of fluorescent signals for different relevant targets very rapidly. A best fit target could be identified as the one having total differences below a prescribed amount, or if no best fit target is identified, the computer could make a different proportional adjustment and again compare the empirical pattern of fluorescent signatures to the library of all possible fluorescent signatures.

We claim:

1. A polymerase chain reaction (PCR) amplification reaction mixture comprising in a PCR reaction buffer: at least one nucleic acid strand comprising at least one target sequence, at least one primer pair, a DNA polymerase, dNTPs, and at least one Reagent comprised of at least one pair of complementary oligonucleotide strands, wherein the Reagent comprises the sequence set forth in SEQ ID NO: 2, SEQ ID NO: 4, SEQ ID NO: 5, or SEQ ID NO: 6 with the capacity to form 25-800 nM concentration of a double-stranded hybrid 6-50 base pairs long with a melting temperature (Tm) of at least 32° C., said double-stranded hybrid having an end that includes interacting, covalently attached label moieties, a bulky, non-planar fluorophore on one strand and on the other strand a non-bulky, planar moiety that is a non-fluorescent quencher, wherein neither strand of said at least one Reagent acts as a probe or a primer on a template strand amplified in the reaction.

2. The reaction mixture of claim 1, wherein the Reagent comprises the sequence set forth in SEQ ID NO: 2.

3. The reaction mixture of claim 1, wherein the Reagent comprises the sequence set forth in SEQ ID NO: 4.

4. The reaction mixture of claim 1, wherein the Reagent comprises the sequence set forth in SEQ ID NO: 5.

5. The reaction mixture of claim 1, wherein the Reagent comprises the sequence set forth in SEQ ID NO: 6.

6. The reaction mixture of claim 1 wherein the double-stranded hybrid of the Reagent is blunt ended and the label moieties are attached to terminal nucleotides of the blunt end.

7. The reaction mixture of claim 1 wherein at least one double-stranded oligonucleotide Reagent comprises two double-stranded oligonucleotide Reagents having calculated Tm's differing from one another by at least 10° C.

8. The reaction mixture of claim 7 wherein the two double-stranded oligonucleotide Reagents share a common oligonucleotide strand.

9. The reaction mixture of claim 1, wherein at least the at least one double-stranded oligonucleotide of the Reagent consists of natural nucleotides.

10. The reaction mixture of claim 1 wherein the reaction mixture is a LATE-PCR reaction mixture.

11. The reaction mixture of claim 1, wherein the at least one nucleic acid target sequence is RNA, and the reaction mixture includes reverse transcriptase.

12. The reaction mixture of claim 1 wherein the reaction mixture includes at least one fluorescently labeled probe that is capable of hybridizing to said amplified target sequence and signaling.

13. The reaction mixture of claim 1, wherein the Tm of the at least one Reagent is used as a temperature mark.

14. The reaction mixture of claim 13, wherein at least one Reagent is at least two Reagents whose Tm's provide at least two temperature marks.

15. The reaction mixture of claim 14, wherein said temperature mark is used for mathematical analysis of the probe/target hybridization signals.

16. The reaction mixture of claim 1, wherein the at least one nucleic acid target sequence is RNA, and the reaction mixture includes reverse transcriptase.

17. The reaction mixture of claim 1, wherein one of the strands of the double-stranded hybrid is longer than the other strand, and further wherein the shorter strand has a polymerase-extendable 3' end.

18. A kit of reagents for amplifying at least one DNA target sequence, said kit including the reagents for a reaction mixture according to claim 1.

* * * * *